(12) United States Patent
Donald et al.

(10) Patent No.: US 9,321,718 B2
(45) Date of Patent: Apr. 26, 2016

(54) BENZAMIDE DERIVATIVES AND THEIR USE AS HSP90 INHIBTORS

(75) Inventors: Alastair David Graham Donald, Oxfordshire (GB); Joanne McDermott, Oxfordshire (GB); Sanjay Ratilal Patel, Oxfordshire (GB); David Festus Charles Moffat, Oxfordshire (GB)

(73) Assignee: CHROMA THERAPEUTICS LTD. (GB)

( * ) Notice: Subject to any disclaimer, the term of this patent is extended or adjusted under 35 U.S.C. 154(b) by 0 days.

(21) Appl. No.: 13/703,387

(22) PCT Filed: Jun. 10, 2011

(86) PCT No.: PCT/GB2011/000879
§ 371 (c)(1),
(2), (4) Date: Feb. 25, 2013

(87) PCT Pub. No.: WO2011/154708
PCT Pub. Date: Dec. 15, 2011

(65) Prior Publication Data
US 2013/0143926 A1     Jun. 6, 2013

(30) Foreign Application Priority Data

Jun. 11, 2010 (GB) .................................. 1009853.1

(51) Int. Cl.
| | | |
|---|---|---|
| C07D 211/00 | (2006.01) |
| C07D 295/00 | (2006.01) |
| C07D 209/04 | (2006.01) |
| C07D 207/04 | (2006.01) |
| C07D 207/46 | (2006.01) |
| A61K 31/445 | (2006.01) |
| C07C 235/60 | (2006.01) |
| C07D 207/09 | (2006.01) |
| C07D 209/44 | (2006.01) |
| C07D 211/26 | (2006.01) |
| C07D 211/58 | (2006.01) |
| C07D 207/14 | (2006.01) |

(52) U.S. Cl.
CPC ............ *C07C 235/60* (2013.01); *C07D 207/09* (2013.01); *C07D 207/14* (2013.01); *C07D 209/44* (2013.01); *C07D 211/26* (2013.01); *C07D 211/58* (2013.01); *C07C 2101/08* (2013.01)

(58) Field of Classification Search
None
See application file for complete search history.

(56) References Cited

U.S. PATENT DOCUMENTS

2009/0215742 A1 * 8/2009 Funk et al. .................. 514/211.1

FOREIGN PATENT DOCUMENTS

| EP | 0505321 A2 | 9/1992 |
| WO | 2004024702 A1 | 3/2004 |
| WO | 2006009085 A1 | 1/2006 |
| WO | 2006091963 A1 | 8/2006 |
| WO | 2006109075 A2 | 10/2006 |
| WO | WO 2006/109075 A2 * | 10/2006 |
| WO | WO 2006109075 A2 * | 10/2006 |
| WO | 2006117549 A1 | 11/2006 |
| WO | 2006117567 A2 | 11/2006 |
| WO | 2006117669 A1 | 11/2006 |
| WO | WO 2007/044041 A1 * | 4/2007 |
| WO | 2008024963 A1 | 2/2008 |
| WO | 2008040934 A1 | 4/2008 |
| WO | 2008044029 A1 | 4/2008 |
| WO | 2008044034 A1 | 4/2008 |
| WO | 2008044041 A1 | 4/2008 |
| WO | 2008053319 A1 | 5/2008 |
| WO | 2009106848 A2 | 9/2009 |
| WO | 2009125230 A1 | 10/2009 |

OTHER PUBLICATIONS

Carey, FA. Organic Chemistry 6th Ed. McGraw Hill. 2006, chapter 1, p. 9.*
Greenwald, RB. et al. Drug Delivery Systems: Water Soluble Taxol 2'-Poly(ethylene glycol) Ester Prodrugs-Design and in Vivo Effectiveness. J. Med. Chem. 1996, vol. 39, p. 425.*
Testa, B. et al. Lessons Learned from Marketed and Investigational Prodrugs. J. Med. Chem. 2004, vol. 47(10), p. 2393.*
International Search Report issued Aug. 18, 2011, during prosecution of International Application No. PCT/GB2011/000879.
M.A.Biannonte et al, "Heat Shock Protein 90: Inhibitors in Clinical Trials", Journal of Medicinal Chemistry, Sep. 16, 2009, vol. 53, No. 1, p. 3-17.
Needham et al., "Drug Targeting to Monocytes and Macrophages Using Esterase-Sensitive Chemical Motifs", J Pharmacol Exp Ther., Oct. 2011, vol. 339, No. 1, pp. 132-142.
Hutchinson, Ian, et al., Antitumor Benzothiazoles. 16.1 Synthesis and Pharmaceutical Properties of Antitumor 2-(4-Aminophenyl) Benzothiazole Amino Acid Prodrugs; J. Med. Chem 2002; 45, 755-747.
Quinney, S.K., et al., Hydrolysis of Capecitabine to 5'-Deoxy-5-fluorocytidine by Human Carboxylesterases and Inhibition by Loperamide.

* cited by examiner

*Primary Examiner* — Rita Desai
*Assistant Examiner* — Ben S Michelson
(74) *Attorney, Agent, or Firm* — Norton Rose Fulbright US LLP

(57) ABSTRACT

The invention provides a compound which is (a) a phenylamide derivative of formula (I) or a tautomer thereof, or (b) a pharmaceutically acceptable salt, N-oxide, hydrate, prodrug or solvate thereof: wherein $R^1$, $R^2$, $R^3$, $R^4$, $R^5$, $R^6$ and $R^7$ are as defined herein. The compounds are useful in the treatment of diseases mediated by HSP90.

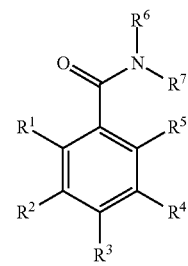

(I)

9 Claims, No Drawings

BENZAMIDE DERIVATIVES AND THEIR USE AS HSP90 INHIBTORS

This application is a 35 USC §371 national phase application of PCT International Application Ser. No. PCT/GB2011/000879, filed Jun. 10, 2011, which claims priority to Great Britain Application Ser. No. 1009853.1, filed Jun. 11, 2010, both of which applications are incorporated by reference herein in their entirety.

This invention relates to a series of amino acid derivatives, to compositions containing them, to processes for their preparation and to their use in medicine as HSP90 inhibitors. The compounds may also be of use in the treatment of cell proliferative diseases such as cancer which are mediated by aberrant HSP90 activity as well as inflammatory and immune disorders such as rheumatoid arthritis, chronic obstructive pulmonary disease (COPD), psoriasis, Crohn's disease, ulcerative colitis, systemic lupus erythematosis, and disorders related to angiogenesis such as age related macular degeneration, diabetic retinopathy and endometriosis. The compounds may also be of use in the protection of normal cells against the action of cytotoxic agents.

BACKGROUND TO THE INVENTION

Cells respond to stress by increasing the synthesis of a number of molecular chaperones: cellular machines that facilitate protein folding. Heat shock proteins (Hsps) are molecular chaperones that assist general protein folding and prevent non-functional side reactions such as non-specific aggregation of misfolded or unfolded proteins, even under normal conditions. They account for 1 to 2% of total protein in unstressed cells. However, their levels of intracellular expression increase in response to protein-denaturing stressors, such as temperature change, as an evolutionarily conserved response to restore the normal protein-folding environment and to enhance cell survival. The essential chaperoning functions of Hsps are subverted during oncogenesis to make malignant transformation possible and to facilitate rapid somatic evolution.

Hsp90 (heat shock protein 90 kDa), one of the most abundant proteins expressed in cells, is a member of the heat shock protein family, up-regulated in response to stress. It has been identified as an important mediator of cancer cell survival. Hsp90 binds to a variety of target or "client" proteins, among them many steroid hormone receptors, protein kinases and transcription factors. It interacts with client-proteins by facilitating their stabilisation and activation or by directing them for proteasomal degradation. Thanks to its multifaceted ability to influence signal transduction, chromatin remodelling and epigenetic regulation, development and morphological evolution, it is considered as a promising target for cancer therapy.

The Hsp90 protein contains three well-defined domains, each of these plays a crucial role in the function of the protein. The N-terminal domain, binding site for ATP, is also the binding site for Geldanamycin, a representative of the ansamycin drugs that specifically target Hsp90. The middle domain completes the ATPase site and binds to client proteins. Finally, at the C-terminal dimerisation domain, Hsp90 forms homo-dimers where the contact sites between subunits are localised within the C-terminus in the open conformation of the dimer. During the ATPase cycle, the three domains of Hsp90 move from an ATP-free "open" state to an ATP-bound "closed" state. The N-termini also come in contact in the closed conformation of the dimer. The functions of Hsp90 include assisting in protein folding, cell signaling, and tumor repression. In unstressed cells, Hsp90 plays a number of important roles, which include assisting in folding, intracellular transport, maintenance, and degradation of proteins as well as facilitating cell signaling.

The majority of known Hsp90 inhibitors, such as the natural products belonging to the ansamycins or radicicol families or synthetic purines, bind at the ATP-site on the N-terminal domain, resulting in client protein deactivation, destabilisation and degradation. However, compounds such as novobiocin and cisplatin have been reported to bind to the C-terminal domain of Hsp90, resulting in an anti-cancer effect as well. Inhibition of Hsp90 can also be a result of inactivation through post-translational modification, typically acetylation or ubiquitinylation. When Hsp90 is inhibited, its regulatory functions are disrupted. As Hsp90 is involved in the regulation of many relevant oncoproteins, it is suggested that its inhibition will result in a broad range of biological activities, hence the Hsp chaperone molecule is an appealing target for cancer. Cancerous cells over-express a number of proteins, including PI3K and AKT and inhibition of these two proteins triggers apoptosis. As Hsp90 stabilizes the PI3K and AKT proteins, its inhibition appears to induce apoptosis through inhibition of the PI3K/AKT signaling pathway. Together with its co-chaperones, Hsp90 modulates tumour cell apoptosis, mediated through effects on AKT, tumor necrosis factor receptors (TNFR) and nuclear factor-KB (NF-κB) function. Finally Hsp90 participates in many key processes in oncogenesis such as self-sufficiency in growth signals, stabilization of mutant proteins, angiogenesis, and metastasis.

Recent studies have shown that Hsp90 also plays an important role in regulating pro-inflammatory signalling pathways. For example, agonists that stimulate NO production were reported to activate a mechanism that recruits Hsp90 to the eNOS. Interaction between Hsp90 and eNOS enhances activation of the enzyme in cells and in intact blood vessels leading to NO production. Following this discovery, Geldanamycin, a known natural inhibitor of Hsp90, was shown to be anti-inflammatory in vivo. Geldanamycin treatment was also shown to induce a significant reduction in IKK protein levels. IKK phosphorylates IκB, marking it for subsequent proteasomal degradation. It is therefore a crucial regulator of the NF-κB pathway, which holds prominent roles in inflammation and cancer. It has been shown that Hsp90 inhibitors prolong survival, reduce or abolish systemic and pulmonary inflammation, and restore normal lung function in a murine model of sepsis. Sepsis is associated with activation of pro-inflammatory mediators, including NF-κB, an important pro-inflammatory transcription factor that mediates up-regulated expression of several pro-inflammatory cytokines and chemokines, such as tumour necrosis factor α (TNF-α), IL-6, IL-8 and IL-1β, critical for amplifying the inflammatory insult. Hsp90-complexing to the glucocorticoid receptor (GR) is necessary to maintain GR in a conformation able to bind hormone. Binding of the hormone to GR causes a conformational change in the complex which results in the interaction between Hsp90 and GR to be disrupted: the receptor then translocates from the cytoplasm to the nucleus, dimerizes and binds to DNA to activate the transcription of the target genes. Hsp90 is also required for the proper functioning of several other steroid receptors, including those responsible for the binding of aldosterone, androgen, estrogen and progesterone.

HSP90 has also been implicated in a number of other conditions, such as viral infection and Alzheimer's Disease.

A group of compounds has now been identified which are potent and selective inhibitors of HSP90 and the isoforms and splice variants thereof. The compounds are characterised by the presence in the molecule of an amino acid motif or an amino acid ester motif which is hydrolysable by intracellular carboxylesterases. Compounds of the invention having lipophilic amino acid ester motifs cross the cell membrane, and are hydrolysed to the acid by said carboxylesterases. The polar hydrolysis product accumulates in the cell since it does not readily cross the cell membrane and hence the Hsp90 inhibitory activity of the compound is prolonged and enhanced. The compounds of the invention are related to the HSP90 inhibitors encompassed by the disclosures in WO2006/109075, WO2006/109085 and WO2006/117669 but differ therefrom in that the present compounds have the amino acid motif referred to above. The compounds are thus of use in medicine, for example in the treatment of a variety of proliferative disease states, where inappropriate action of HSP90 may be involved such as cancer, inflammatory and immune disorders such as rheumatoid arthritis, COPD, psoriasis, Crohn's disease, ulcerative colitis, systemic lupus erythmatosis, and disorders related to angiogenesis such as age related macular degeneration, diabetic retinopathy and endometriosis. Inhibitors of Hsp90 may be useful in the treatment of inflammation. Inflammation is mediated by a variety of soluble factors, including a group of secreted polypeptides known as cytokines. Those which mediate acute inflammation include IL-1, TNF-a, IL-6, IL-11, IL-8, G-CSF, and M-CSF. Cytokines involved in chronic inflammation can be subdivided into cytokines mediating humoral responses such as IL-4, IL-5, IL-6, IL-7, and IL-13, and those mediating cellular responses such as IL-1, IL-2, IL-3, IL-4, IL-7, IL-9, IL-10, IL-12, interferons, transforming growth factor-b, and tumor necrosisfactor a and b. Some cytokines, such as IL-1, significantly contribute to both acute and chronic inflammation. The compounds may also be of use in the protection of normal cells against the action of cytotoxic agents or in the management of viral infection or Alzheimer's Disease.

BRIEF DESCRIPTION OF THE INVENTION

The invention provides a compound which is (a) a phenylamide derivative of formula (I) or a tautomer thereof, or (b) a pharmaceutically acceptable salt, N-oxide, hydrate, prodrug or solvate thereof:

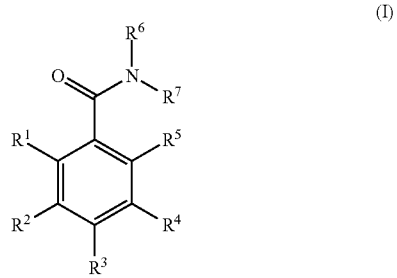

(I)

wherein:
$R^1$ is hydrogen or hydroxy;
$R^2$, $R^3$, $R^4$ and $R^5$ are the same or different and represent hydrogen or halogen atoms or $C_{1-6}$ alkyl, $C_{2-6}$ alkenyl, $C_{2-6}$ alkynyl, $C_{1-6}$ alkoxy, hydroxy, cyano, nitro or —NR'R" groups wherein R' and R" are the same or different and represent hydrogen or unsubstituted $C_{1-4}$ alkyl, and with the proviso that no more than two of $R^2$, $R^3$, $R^4$ and $R^5$ are cyano or nitro;

either:
(i) $R^6$ is selected from $C_{1-4}$ alkyl and $R^7$ represents —$CR^8R^9$-A wherein $R^8$ and $R^9$ are the same or different and represent a hydrogen or halogen atom or a $C_{1-4}$ alkyl, $C_{2-4}$ alkenyl, $C_{1-4}$ alkoxy, hydroxy or —NR'R" group where R' and R" are the same or different and represent hydrogen or unsubstituted $C_{1-4}$ alkyl, and A represents a phenyl ring or a 5- or 6-membered heteroaryl group and is substituted with a group W; or
(ii) $R^6$ and $R^7$, together with the nitrogen atom to which they are bonded, form a 5- or 6-membered heterocyclyl group which is either (a) unfused, or (b) fused to a phenyl ring or a 5- to 6-membered heteroaryl group, and wherein either the heterocyclyl group or, when fused, the heterocyclyl group or the phenyl ring or heteroaryl group to which it is fused, is substituted with a group W;
W represents a group -$Alk^1$-R;
$Alk^1$ represents a bond, a $C_{1-4}$ alkylene group or a group —($C_{1-4}$ alkylene)-NR'—($C_{1-4}$ alkylene)- wherein R' represents hydrogen or $C_{1-4}$ alkyl;
R represents a group of formula (X) or (Y):

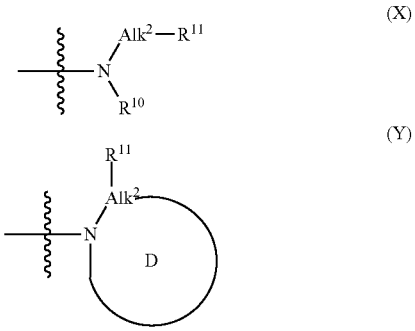

$R^{10}$, where present, represents a hydrogen atom or a $C_{1-4}$ alkyl group;
$Alk^2$ represents a group of formula —$C(R^{12})(R^{13})$— when R is of formula (X) or —$C(R^{12})$— when R is of formula (Y), wherein $R^{12}$ and $R^{13}$ are the same or different and represent hydrogen or the α-substituents of an α-substituted or α,α-disubstituted glycine or glycine ester compound;
ring D, where present, is a 5- to 6-membered heterocyclyl group containing $Alk^2$ and wherein $R^{11}$ is linked to ring D via $Alk^2$, and ring D is optionally fused to a second ring comprising a phenyl, 5- to 6-membered heteroaryl, $C_{3-7}$ carbocylyl or 5- to 6-membered heterocyclyl; and
$R^{11}$ is a group —COOH or an ester group which is hydrolysable by one or more intracellular carboxylesterase enzymes to a —COOH group;
and wherein, unless otherwise stated:
the alkyl, alkenyl and alkynyl groups and moieties in $R^2$, $R^3$, $R^4$, $R^5$, $R^6$, $R^8$, $R^9$, $Alk^1$, $R^{12}$ and $R^{13}$ are unsubstituted or substituted with 1, 2 or 3 unsubstituted substituents which are the same or different and are selected from halogen atoms and $C_{1-4}$ alkyl, $C_{2-4}$ alkenyl, $C_{1-4}$ alkoxy, $C_{2-4}$ alkenyloxy, $C_{1-4}$ haloalkyl, $C_{2-4}$ haloalkenyl, $C_{1-4}$ haloalkoxy, $C_{2-4}$ haloalkenyloxy, hydroxyl, —SR', cyano, nitro, $C_{1-4}$ hydroxyalkyl and —NR'R" groups where R' and R" are the same or different and represent hydrogen or unsubstituted $C_{1-2}$ alkyl; and
the aryl, heteroaryl, carbocyclyl and heterocyclyl groups and moieties in $R^6$ and $R^7$ are unsubstituted or substituted by 1, 2, 3 or 4 unsubstituted substituents selected from halogen atoms, and cyano, nitro, $C_{1-4}$ alkyl, $C_{1-4}$ alkoxy, $C_{2-4}$ alkenyl, $C_{2-4}$ alkenyloxy, $C_{1-4}$ haloalkyl, $C_{2-4}$ haloalkenyl, $C_{1-4}$ haloalkoxy, $C_{2-4}$ haloalkenyloxy, hydroxyl, $C_{1-4}$ hydroxyalkyl, —SR' and —NR'R" groups wherein each R' and R" is the same or different and represents hydrogen or unsubstituted $C_{1-4}$ alkyl, or from substituents of formula —COON, —COOR$^A$, —COR$^A$, —SO$_2$R$^A$, —CONH$_2$, —SO$_2$NH$_2$, —CONHR$^A$, —SO$_2$NHR$^A$, —CONR$^A$R$^B$, —SO$_2$NR$^A$R$^B$, —OCONH$_2$, —OCONHR$^A$, —OCONR$^A$R$^B$, —NHCOR$^A$, —NR$^B$COR$^A$, —NHCOOR$^A$, —NR$^B$COOR$^A$, —NR$^B$COOH, —NHCOOH, —NHSO$_2$R$^A$, —NR$^B$SO$_2$R$^A$, —NHSO$_2$OR$^A$, —NR$^B$SO$_2$OH, —NHSO$_2$H, —NR$^B$SO$_2$OR$^A$, —NHCONH$_2$, —NR$^A$CONH$_2$, —NHCONHR$^B$, —NR$^A$CONHR$^B$, —NHCONR$^A$R$^{13}$ or —NR$^A$CONR$^A$R$^B$ wherein R$^A$ and R$^B$ are the same or different and represent unsubstituted $C_{1-6}$ alkyl, $C_{3-6}$ cycloalkyl, non-fused phenyl or a non-fused 5- to 6-membered heteroaryl, or R$^A$ and R$^B$ when attached to the same nitrogen atom form a non-fused 5- or 6-membered heterocyclyl group.

When R$^{12}$ and/or R$^{13}$ represent the α substituents or an α-substituted or α,α-disubstituted glycine or glycine ester compound, any functional groups in these R$^{12}$ and R$^{13}$ groups may be protected. It will be known to the person skilled in the art that the term "protected" when used in relation to a functional substituent in a side chain of an α-amino acid means a derivative of such a substituent which is substantially non-functional. Suitable protecting groups will be described later.

The compounds of the invention contain a motif which is hydrolysable by an intracellular carboxylesterase. Compounds of the invention can cross the cell membrane, and, if in the ester form, can be hydrolysed to the acid by the intracellular carboxylesterases. The polar hydrolysis product accumulates in the cell since it does not readily cross the cell membrane. Hence the HSP90 activity of the compound is prolonged and enhanced within the cell.

Preferably the compounds of the invention are phenylamide derivatives of formula (I) or tautomers thereof, or pharmaceutically acceptable salts thereof.

In another broad aspect the invention provides the use of a compound as defined above in the manufacture of a medicament for inhibiting the activity of HSP90. More preferably, the invention provides the use of a compound as defined above in the manufacture of a medicament for use in treating a disorder mediated by HSP90.

In a further aspect the invention provides a compound as defined above for use in treating the human or animal body, or for use in inhibiting the activity of HSP90. More preferably, the invention provides the use of a compound as defined above for use in treating or preventing disorders mediated by HSP90.

The invention also provides a pharmaceutical composition which comprises a compound as defined above and a pharmaceutically acceptable carrier or diluent.

The compounds with which the invention is concerned may be used for the inhibition of HSP90 activity ex vivo or in vivo.

The compounds of the invention are also particularly useful in the treatment of inflammation, for example in the treatment of rheumatoid arthritis.

The compounds of the invention are also particularly useful in the treatment of cancer, in particular breast cancer, ovarian cancer, pancreatic cancer and hepatocellular carcinoma.

In one aspect of the invention, the compounds of the invention may be used in the preparation of a composition for treatment of cancer (for example monocyte-derived cancers), inflammatory and immune disorders such as rheumatoid arthritis, psoriasis, Crohn's disease, ulcerative colitis, systemic lupus erythematosis, and disorders related to angiogenesis age related macular degeneration, diabetic retinopathy and endometriosis. The compounds may also be of use in the protection of normal cells against the action of cytotoxic agents or in the management of viral infection or Alzheimer's Disease.

As mentioned above, the compounds with which the invention is concerned are of use for inhibition of Hsp90 activity Inhibition of Hsp90 activity is a mechanism for treatment of a variety of diseases, including cell proliferative disease such as cancer (including malignancies of the monocytic cell lineage, e.g., juvenile myelomonocytic leukaemia) and psoriasis, polyglutamine disease such as Huntingdon's disease, neurogenerative disease such as Alzheimers disease, autoimmune disease such as rheumatoid arthritis (including systemic juvenile idiopathic arthritis), diabetes, haematological disease, inflammatory disease, cardiovascular disease, atherosclerosis, primary biliary cirrhosis, Wegener's granulomatosis, and the inflammatory sequela of infection. Particular examples of diseases treatable by inhibition of HSP90 activity are cell proliferative disease such as cancer (including malignancies of the monocytic cell lineage, e.g., juvenile myelomonocytic leukaemia) and psoriasis, polyglutamine disease such as Huntingdon's disease, neurogenerative disease such as Alzheimers disease, autoimmune disease such as rheumatoid arthritis (including systemic juvenile idiopathic arthritis), haematological disease, inflammatory disease, cardiovascular disease, atherosclerosis, primary biliary cirrhosis, Wegener's granulomatosis, and the inflammatory sequelia of infection.

Autoimmune disease often has an inflammatory component. Such conditions include acute disseminated alopecia universalise, ANCA positive diseases, Behcet's disease, Chagas' disease, chronic fatigue syndrome, dysautonomia, encephalomyelitis, ankylosing spondylitis, aplastic anemia, hidradenitis suppurativa, autoimmune hepatitis, autoimmune oophoritis, celiac disease, inflammatory bowel disease, Crohn's disease, diabetes mellitus type 1, Fanconi syndrome, giant cell arteritis, glomerulonephritis, Goodpasture's syndrome, Grave's disease, Guillain-Barre syndrome, Hashimoto's disease, Henoch-Schnlein purpura, Kawasaki's disease, systemic lupus erythematosus, microscopic colitis, microscopic polyarteritis, mixed connective tissue disease, multiple sclerosis, myasthenia gravis, opsocionus myoclonus syndrome, optic neuritis, Ord's thyroiditis, pemphigus, polyarteritis nodosa, polymyalgia, rheumatoid arthritis, Reiter's syndrome, Sjogren's syndrome, temporal arteritis, Wegener's granulomatosis, warm autoimmune haemolytic anemia, interstitial cystitis, lyme disease, morphea, psoriasis, sarcoidosis, scleroderma, ulcerative colitis, and vitiligo.

Other inflammatory conditions which may be treated with the compounds of the invention include, for example, appendicitis, dermatitis, dermatomyositis, endocarditis, fibrositis, gingivitis, glossitis, hepatitis, hidradenitis suppurativa, iritis, laryngitis, mastitis, myocarditis, nephritis, otitis, pancreatitis, parotitis, percarditis, peritonoitis, pharyngitis, pleuritis, pneumonitis, prostatistis, pyelonephritis, and stomatisi, transplant rejection (involving organs such as kidney, liver, heart, lung, pancreas (e.g., islet cells), bone marrow, cornea, small bowel, skin allografts, skin homografts, and heart valve xengrafts, sewrum sickness, and graft vs host disease), acute pancreatitis, chronic pancreatitis, acute respiratory distress syndrome, Sexary's syndrome, congenital adrenal hyperplasia, nonsuppurative thyroiditis, hypercalcemia associated with cancer, pemphigus, bullous dermatitis herpetiformis, severe erythema multiforme, exfoliative dermatitis, seborrheic dermatitis, seasonal or perennial allergic rhinitis, bronchial asthma, contact dermatitis, astopic dermatitis, drug hypersensistivity reactions, allergic conjunctivitis, keratitis, herpes zoster ophthalmicus, iritis and oiridocyclitis, chorioretinitis, optic neuritis, symptomatic sarcoidosis, fulminating or disseminated pulmonary tuberculosis chemotherapy, idiopathic thrombocytopenic purpura in adults, secondary thrombocytopenia in adults, acquired (autoimmune) haemolytic anemia, leukaemia and lymphomas in adults, acute leukaemia of childhood, regional enteritis, autoimmune vasculitis, multiple sclerosis, chronic obstructive pulmonary disease, solid organ transplant rejection, sepsis, primary biliary cirrhosis and primary sclerosing cholangitis.

Preferred treatments using compounds of the invention include treatment of transplant rejection, rheumatoid arthritis, psoriatic arthritis, Type 1 diabetes, asthma, inflammatory bowel disease, systemic lupus erythematosis, and inflammation accompanying infectious conditions (e.g., sepsis), psoriasis, Crohns disease, ulcerative colitis, chronic obstructive pulmonary disease, multiple sclerosis, atopic dermatitis, and graft versus host disease. For example, compounds of the invention may be used in the treatment of transplant rejection, rheumatoid arthritis, psoriatic arthritis, asthma, inflammatory bowel disease, systemic lupus erythematosis, and inflammation accompanying infectious conditions (e.g., sepsis), psoriasis, Crohns disease, ulcerative colitis, chronic obstructive pulmonary disease, multiple sclerosis, atopic dermatitis, and graft versus host disease.

Another preferred use of the compounds of the invention is in the treatment of cancers, in particular in the treatment of breast cancer, ovarian cancer, pancreatic cancer and hepatocellular carcinoma.

DETAILED DESCRIPTION OF THE INVENTION

Although the above definitions potentially include molecules of high molecular weight, it is preferable, in line with general principles of medicinal chemistry practice, that the compounds with which this invention is concerned should have molecular weights of no more than 900, more preferably no more than 600. The alkyl, alkenyl and alkynyl groups and moieties in $R^2$, $R^3$, $R^4$, $R^5$, $R^6$, $R^8$, $R^9$, $Alk^1$, $R^{12}$ and $R^{13}$ are unsubstituted or substituted with 1, 2 or 3 unsubstituted substituents which are the same or different and are selected from halogen atoms and $C_{1-4}$ alkyl, $C_{2-4}$ alkenyl, $C_{1-4}$ alkoxy, $C_{2-4}$ alkenyloxy, $C_{1-4}$ haloalkyl, $C_{2-4}$ haloalkenyl, $C_{1-4}$ haloalkoxy, $C_{2-4}$ haloalkenyloxy, hydroxyl, —SR', cyano, nitro, $C_{1-4}$ hydroxyalkyl and —NR'R" groups where R' and R" are the same or different and represent hydrogen or unsubstituted $C_{1-2}$ alkyl. Unless otherwise specified, the substituents described above are preferably themselves unsubstituted.

Preferred substituents include halogen atoms and $C_{1-4}$ alkyl, $C_{2-4}$ alkenyl, $C_{1-4}$ alkoxy, $C_{2-4}$ alkenyloxy, $C_{1-4}$ haloalkyl, $C_{2-4}$ haloalkenyl, $C_{1-4}$ haloalkoxy, $C_{2-4}$ haloalkenyloxy, hydroxyl, mercapto, cyano, nitro, $C_{1-4}$ hydroxyalkyl, $C_{2-4}$ hydroxyalkenyl, $C_{1-4}$ alkylthio, $C_{2-4}$ alkenylthio, and —NR'R" groups wherein each R' and R" is the same or different and represents hydrogen or $C_{1-4}$ alkyl.

More preferred substituents include halogen, $C_{1-4}$ alkyl, $C_{2-4}$ alkenyl, $C_{1-4}$ alkoxy, hydroxyl, $C_{1-4}$ haloalkyl, $C_{2-4}$ haloalkenyl, $C_{1-4}$ haloalkyloxy and —NR'R" wherein R' and R" are the same or different and represent hydrogen or $C_{1-2}$ alkyl. More preferred substituents are halogen, unsubstituted $C_{1-4}$ alkyl, $C_{1-4}$ alkoxy, hydroxyl and —NR'R" groups where R' and R" are the same or different and represent hydrogen or unsubstituted $C_{1-2}$ alkyl. For example, particularly preferred substituents include unsubstituted $C_{1-4}$ alkyl, $C_{1-4}$ alkoxy, hydroxyl and —NR'R" groups where R' and R" are the same or different and represent hydrogen or unsubstituted $C_{1-2}$ alkyl.

When the alkyl, alkenyl and alkynyl moieties are substituted by two or three substituents, it is preferred that not more than two substituents are selected from cyano and nitro. More preferably, not more than one substituent is selected from cyano and nitro.

As used herein, a $C_{1-6}$ alkyl group or moiety is a linear or branched alkyl group or moiety containing from 1 to 6 carbon atoms, for example a $C_{1-4}$ alkyl group or moiety containing from 1 to 4 carbon atoms. Examples of $C_{1-4}$ alkyl groups include methyl, ethyl, n-propyl, i-propyl, n-butyl, i-butyl and t-butyl. For the avoidance of doubt, where two alkyl moieties are present in a group, the alkyl moieties may be the same or different.

As used herein, a $C_{2-6}$ alkenyl group or moiety is a linear or branched alkenyl group or moiety one having at least one double bond of either E or Z stereochemistry where applicable and containing from 2 to 6 carbon atoms, for example a $C_{2-4}$ alkenyl group or moiety containing from 2 to 4 carbon atoms, such as —CH=CH$_2$ or —CH$_2$—CH=CH$_2$, —CH$_2$—CH$_2$—CH=CH$_2$, —CH$_2$—CH=CH—CH$_3$, —CH=C(CH$_3$)—CH$_3$ and —CH$_2$—C(CH$_3$)=CH$_2$. For the avoidance of doubt, where two alkenyl moieties are present in a group, they may be the same or different.

As used herein, a $C_{2-6}$ alkynyl group or moiety is a linear or branched alkynyl group or moiety containing from 2 to 6 carbon atoms, for example a $C_{2-4}$ alkynyl group or moiety containing from 2 to 4 carbon atoms. Exemplary alkynyl groups include —C≡CH or —CH$_2$—C≡CH, as well as 1- and 2-butynyl, 2-methyl-2-propynyl, 2-pentynyl, 3-pentynyl, 4-pentynyl, 2-hexynyl, 3-hexynyl, 4-hexynyl and 5-hexynyl. For the avoidance of doubt, where two alkynyl moieties are present in a group, they may be the same or different.

As used herein, a $C_{1-6}$ alkylene group or moiety is a linear or branched alkylene group or moiety, for example a $C_{1-4}$ alkylene group or moiety. Examples include methylene, n-ethylene, n-propylene and —C(CH$_3$)$_2$— groups and moieties.

As used herein, a $C_{2-6}$ alkenylene group or moiety is a linear or branched alkenylene group or moiety, for example a $C_{2-4}$ alkenylene group or moiety. Examples include —CH=CH—, —CH=CH—CH$_2$—, —CH$_2$—CH=CH— and —CH=CH—CH=CH—.

As used herein, a $C_{2-6}$ alkynylene group or moiety is a linear or branched alkynylene group or moiety, for example a $C_{2-4}$ alkynylene group or moiety. Examples include —C≡C—, —C≡C—CH$_2$— and —CH$_2$—C≡C—.

As used herein, a halogen atom is typically chlorine, fluorine, bromine or iodine.

As used herein, a $C_{1-6}$ alkoxy group or $C_{2-6}$ alkenyloxy group is typically a said $C_{1-6}$ alkyl (e.g. a $C_{1-4}$ alkyl) group or a said $C_{2-6}$ alkenyl (e.g. a $C_{2-4}$ alkenyl) group respectively which is attached to an oxygen atom.

A haloalkyl, haloalkenyl, haloalkoxy or haloalkenyloxy group is typically a said alkyl, alkenyl, alkoxy or alkenyloxy group respectively which is substituted by one or more said halogen atoms. Typically, it is substituted by 1, 2 or 3 said halogen atoms. Preferred haloalkyl and haloalkoxy groups include perhaloalkyl and perhaloalkoxy groups such as —CX$_3$ and —OCX$_3$ wherein X is a said halogen atom, for example chlorine and fluorine.

As used herein, a $C_{1-4}$ hydroxyalkyl group is a $C_{1-4}$ alkyl group substituted by one or more hydroxy groups. Typically, it is substituted by one, two or three hydroxy groups. Preferably, it is substituted by a single hydroxy group.

As used herein, a 5- or 6-membered heteroaryl group or moiety is a monocyclic 5- or 6-membered aromatic ring containing at least one heteroatom, for example 1, 2, 3 or 4 heteroatoms, selected from O, S and N. When the ring contains 4 heteroatoms these are preferably all nitrogen atoms. Examples include thienyl, furyl, pyrrolyl, imidazolyl, thiazolyl, isothiazolyl, pyrazolyl, oxazolyl, isoxazolyl, triazolyl, thiadiazolyl, oxadiazolyl, pyridinyl, pyridazinyl, pyrimidinyl, pyrazinyl, triazinyl and tetrazolyl groups. Thienyl, pyrrolyl, imidazolyl, thiazolyl, isothiazolyl, pyrazolyl, oxazolyl, isoxazolyl, triazolyl, pyridinyl, pyridazinyl, pyrimidinyl and pyrazinyl groups are preferred, e.g. pyrrolyl, imidazolyl, thiazolyl, isothiazolyl, pyrazolyl, oxazolyl, isoxazolyl, triazolyl, pyridinyl, pyridazinyl, pyrimidinyl and pyrazinyl groups. More preferred groups are thienyl, pyridinyl, pyridazinyl, pyrimidinyl, pyrazinyl, pyrrolyl and triazinyl, e.g. pyridinyl, pyridazinyl, pyrimidinyl, pyrazinyl, pyrrolyl and triazinyl.

As used herein, a 4- to 7-membered heterocyclyl group or moiety is a non-aromatic, saturated or unsaturated $C_{4-7}$ carbocyclic ring in which one or more, for example 1, 2, 3 or 4, of the carbon atoms are replaced with a moiety selected from N, O, S, S(O) and S(O)$_2$, and wherein one or more of the remaining carbon atoms is optionally replaced by a group —C(O)— or —C(S)—. When one or more of the remaining carbon atoms is replaced by a group —C(O)— or —C(S)—, preferably only one or two (more preferably two) such carbon atoms are replaced. Preferred heterocyclyl groups are 5- and 6-membered heterocyclyl groups.

Suitable heterocyclyl groups and moieties include azetidinyl, oxetanyl, thietanyl, pyrrolidinyl, imidazolidinyl, oxazolidinyl, isoxazolidinyl, thiazolidinyl, isothiazolidinyl, tetrahydrofuranyl, tetrahydrothienyl, tetrahydropyranyl, tetrahydrothiopyranyl, dithiolanyl, dioxolanyl, pyrazolidinyl, piperidinyl, piperazinyl, hexahydropyrimidinyl, methylenedioxyphenyl, ethylenedioxyphenyl, thiomorpholinyl, S-oxo-thiomorpholinyl, S,S-dioxo-thiomorpholinyl, morpholinyl, 1,2-dioxolanyl, 1,4-dioxolanyl, trioxolanyl, trithianyl, imidazolinyl, pyranyl, pyrazolinyl, thioxolanyl, thioxothiazolidinyl, 1H-pyrazol-5-(4H)-onyl, 1,3,4-thiadiazol-2(3H)-thionyl, oxopyrrolidinyl, oxothiazolidinyl, oxopyrazolidinyl, succinimido and maleimido groups and moieties. Preferred heterocyclyl groups are pyrrolidinyl, imidazolidinyl, oxazolidinyl, isoxazolidinyl, thiazolidinyl, isothiazolidinyl, tetrahydrofuranyl, tetrahydrothienyl, tetrahydropyranyl, tetrahydrothiopyranyl, dithiolanyl, dioxolanyl, pyrazolidinyl, piperidinyl, piperazinyl, hexahydropyrimidinyl, thiomorpholinyl and morpholinyl groups and moieties. More preferred heterocyclyl groups are pyrrolidinyl, imidazolidinyl, oxazolidinyl, isoxazolidinyl, thiazolidinyl, isothiazolidinyl, pyrazolidinyl, piperidinyl, piperazinyl, hexahydropyrimidinyl, thiomorpholinyl and morpholinyl groups and moieties, more preferably pyrrolidinyl, imidazolidinyl, pyrazolidinyl, piperidinyl, piperazinyl and hexahydropyrimidinyl groups and moieties. Particularly preferred groups include piperidinyl and pyrrolidinyl.

When a heterocyclyl group or moiety is fused to another group, it may be fused to a further phenyl, 5- to 6-membered heteroaryl or 5- to 6-membered heterocyclyl group. When a heterocyclyl group or moiety is fused to another group, it may be fused to a further phenyl or 5- to 6-membered heteroaryl group, more preferably to a phenyl group. Preferred fused heterocyclyl groups include indolinyl, isoindolinyl, 2,3-dihydro-1H-benzo[d]imidazolyl, 2,3-dihydro-1H-indazolyl, 2,3-dihydrobenzo[d]thiazolyl, 2,3-dihydrobenzo[d]isothiazolyl and 2,3-dihydrobenzo[d]oxazole 2,3-dihydrobenzo[d]isoxazolyl. More preferred fused heterocyclyl groups include indolinyl and isoindolinyl, most preferably isoindolinyl.

For the avoidance of doubt, although the above definitions of heteroaryl and heterocyclyl groups refer to an "N" moiety which can be present in the ring, as will be evident to a skilled chemist the N atom will be protonated (or will carry a substituent as defined below) if it is attached to each of the adjacent ring atoms via a single bond.

As used herein, a $C_{3-7}$ carbocyclic group or moiety is a non-aromatic saturated or unsaturated hydrocarbon ring having from 3 to 7 carbon atoms. Preferably it is a saturated or mono-unsaturated hydrocarbon ring (i.e. a cycloalkyl moiety or a cycloalkenyl moiety) having from 3 to 7 carbon atoms, more preferably having from 3 to 6 carbon atoms. Examples include cyclopropyl, cyclobutyl, cyclopentyl and cyclohexyl and their mono-unsaturated variants, more particularly cyclopentyl and cyclohexyl. A $C_{3-7}$ carbocyclyl group or moiety also includes $C_{3-7}$ carbocyclyl groups or moieties described above but wherein one or more ring carbon atoms are replaced by a group —C(O)—. More preferably one or two ring carbon atoms (most preferably two) are replaced by —C(O)—. A preferred such group is benzoquinone.

When a carbocyclyl group or moiety is fused to another group, it may be fused to a further phenyl, 5- to 6-membered heteroaryl or 5- to 6-membered heterocyclyl ring. For example it may be fused to a further phenyl ring. An exemplary fused carbocyclyl group is indanyl. More preferably carbocyclyl groups are monocyclic (i.e. non-fused).

Unless otherwise stated, the aryl, heteroaryl, carbocyclyl and heterocyclyl groups and moieties are unsubstituted or substituted by 1, 2, 3 or 4 unsubstituted substituents selected from halogen atoms, and cyano, nitro, $C_{1-4}$ alkyl, $C_{1-4}$ alkoxy, $C_{2-4}$ alkenyl, $C_{2-4}$ alkenyloxy, $C_{1-4}$ haloalkyl, $C_{2-4}$ haloalkenyl, $C_{1-4}$ haloalkoxy, $C_{2-4}$ haloalkenyloxy, hydroxyl, $C_{1-4}$ hydroxyalkyl, —SW and —NR'R" groups wherein each R' and R" is the same or different and represents hydrogen or unsubstituted $C_{1-4}$ alkyl, or from substituents of formula —COOH, —COOR$^A$, —COR$^A$, —SO$_2$R$^A$, —CONH$_2$, —SO$_2$NH$_2$, —CONHR$^A$, —SO$_2$NHR$^A$, —CONR$^A$R$^B$, —SO$_2$NR$^A$R$^B$, —OCONH$_2$, —OCONHR$^A$, —OCONR$^A$R$^B$, —NHCOR$^A$, —NR$^B$COR$^A$, —NHCOOR$^A$, —NR$^B$COOR$^A$, —NR$^B$COOH, —NHCOOH, —NHSO$_2$R$^A$, —NR$^B$SO$_2$R$^A$, —NHSO$_2$OR$^A$, —NR$^B$SO$_2$OH, —NHSO$_2$H, —NR$^B$SO$_2$OR$^A$, —NHCONH$_2$, —NR$^A$CONH$_2$, —NHCONHR$^B$, —NR$^A$CONHR$^B$, —NHCONR$^A$R$^B$ or —NR$^A$CONR$^A$R$^B$ wherein R$^A$ and R$^B$ are the same or different and represent unsubstituted $C_{1-6}$ alkyl, $C_{3-6}$ cycloalkyl, non-fused phenyl or a non-fused 5- to 6-membered heteroaryl, or R$^A$ and R$^B$ when attached to the same nitrogen atom form a non-fused 5- or 6-membered heterocyclyl group. Unless otherwise stated, the substituents are preferably themselves unsubstituted. In particular it is preferred that R$^A$ and R$^B$ are unsubstituted.

When the phenyl, heteroaryl, heterocyclyl and carbocyclyl moieties are substituted by two, three or four substituents, it is preferred that not more than two substituents are selected from cyano and nitro. More preferably, not more than one substituent is selected from cyano and nitro. Furthermore, when the phenyl, heteroaryl, heterocyclyl and carbocyclyl moieties are substituted by two or three substituents, it is preferred that not more than one substituent is selected from —COON, —COOR$^A$, —COR$^A$, —SO$_2$R$^A$, —CONH$_2$, —SO$_2$NH$_2$, —CONHR$^A$, —SO$_2$NHR$^A$, —CONR$^A$R$^B$, —SO$_2$NR$^A$R$^B$, —OCONH$_2$, —OCONHR$^A$, —OCONR$^A$R$^B$, —NHCOR$^A$, —NR$^B$COR$^A$, —NHCOOR$^A$, —NR$^B$COOR$^A$, —NR$^B$COOH, —NHCOOH, —NHSO$_2$R$^A$, —NR$^B$SO$_2$R$^A$, —NHSO$_2$OR$^A$, —NR$^B$SO$_2$OH, —NHSO$_2$H, —NR$^B$SO$_2$OR$^A$, —NHCONH$_2$, —NR$^A$CONH$_2$, —NHCONHR$^B$, —NR$^A$CONHR$^B$, —NHCONR$^A$R$^B$ or —NR$^A$CONR$^A$R$^B$.

Typically the phenyl, heteroaryl, heterocyclyl and carbocyclyl moieties in the aryl, heteroaryl, carbocyclyl and heterocyclyl groups and moieties are unsubstituted or substituted by 1, 2, 3 or 4 substituents, for example by 1, 2 or 3 substituents. Preferred substituents include halogen atoms and C$_{1-4}$ alkyl, C$_{2-4}$ alkenyl, C$_{1-4}$ alkoxy, C$_{2-4}$ alkenyloxy, C$_{1-4}$ haloalkyl, C$_{2-4}$ haloalkenyl, C$_{1-4}$ haloalkoxy, C$_{2-4}$ haloalkenyloxy, hydroxyl, mercapto, cyano, nitro, C$_{1-4}$ hydroxyalkyl, C$_{2-4}$ hydroxyalkenyl, C$_{1-4}$ alkylthio, C$_{2-4}$ alkenylthio and —NR'R" groups wherein each R' and R" is the same or different and represents hydrogen or C$_{1-4}$ alkyl. Preferably the substituents are themselves unsubstituted. More preferred substituents include halogen atoms and unsubstituted C$_{1-4}$ alkyl, C$_{1-4}$ alkoxy, hydroxyl, C$_{1-4}$ haloalkyl, C$_{1-4}$ haloalkoxy, C$_{1-4}$ hydroxyalkyl, cyano, nitro, —SR' and —NR'R" groups where R' and R" are the same or different and represent hydrogen or unsubstituted C$_{1-2}$ alkyl. More preferred substituents include halogen atoms and C$_{1-2}$ alkyl and C$_{1-2}$ alkoxy groups.

As used herein the term "salt" includes base addition, acid addition and quaternary salts. Compounds of the invention which are acidic can form salts, including pharmaceutically acceptable salts, with bases such as alkali metal hydroxides, e.g. sodium and potassium hydroxides; alkaline earth metal hydroxides e.g. calcium, barium and magnesium hydroxides; with organic bases e.g. N-methyl-D-glucamine, choline tris (hydroxymethyl)amino-methane, L-arginine, L-lysine, N-ethyl piperidine, dibenzylamine and the like. Those compounds (I) which are basic can form salts, including pharmaceutically acceptable salts with inorganic acids, e.g. with hydrohalic acids such as hydrochloric or hydrobromic acids, sulphuric acid, nitric acid or phosphoric acid and the like, and with organic acids e.g. with acetic, tartaric, succinic, fumaric, maleic, malic, salicylic, citric, methanesulphonic, p-toluenesulphonic, benzoic, benzenesulfonic, glutamic, lactic, and mandelic acids and the like.

Compounds of the invention which contain one or more actual or potential chiral centres, because of the presence of asymmetric carbon atoms, can exist as a number of diastereoisomers with R or S stereochemistry at each chiral centre. The invention includes all such diastereoisomers and mixtures thereof.

As used herein the term "prodrug" represents a derivative of a phenylamide compound of formula (I) which is administered in a less active form and which, once administered, is prodrug is metabolised in vivo into an active metabolite of formula (I). Various forms of prodrug are known in the art. For examples of such prodrugs see: Design of Prodrugs, edited by H. Bundgaard, (Elsevier, 1985) and Methods in Enzymology, Vol. 42, p. 309-396, edited by K. Widder, et al. (Academic Press, 1985); A Textbook of Drug Design and Development, edited by Krogsgaard-Larsen and H. Bundgaard, Chapter 5 "Design and Application of Prodrugs", by H. Bundgaard p. 113-191 (1991); H. Bundgaard, Advanced Drug Deliver Reviews, 8, 1-38 (1992); H. Bundgaard, et al., Journal of Pharmaceutical Sciences, 77, 285 (1988); and N. Kakeya, et al., Chem Pharm Bull, 32, 692 (1984).

Examples of prodrugs include cleavable esters of compounds of formula (I). An in vivo cleavable ester of a compound of the invention containing a carboxy group is, for example, a pharmaceutically-acceptable ester which is cleaved in the human or animal body to produce the parent acid. Suitable pharmaceutically-acceptable esters for carboxy include C$_{1-6}$ alkylesters, for example methyl or ethyl esters; C$_{1-6}$ alkoxymethyl esters, for example methoxymethyl ester; C$_{1-6}$ alkanoyloxymethyl esters; phthalidyl esters; C$_{3-8}$ cycloalkoxycarbonyloxyC$_{1-6}$alkyl esters, for example 1-cyclohexylcarbonyloxyethyl; 1,3-dioxolan2-ylmethyl esters, for example 5-methyl-1,3-dioxolan-2-ylmethyl; C$_{1-6}$ alkoxycarbonyloxyethyl esters, for example 1-methoxycarbonyloxyethyl; aminocarbonylmethyl esters and mono- or di-N—(C$_{1-6}$ alkyl) versions thereof, for example N,N-dimethylaminocarbonylmethyl esters and N-ethylaminocarbonylmethyl esters; and may be formed at any carboxy group in the compounds of the invention. An in vivo cleavable ester of a compound of the invention containing a hydroxy group is, for example, a pharmaceutically-acceptable ester which is cleaved in the human or animal body to produce the parent hydroxy group. Suitable pharmaceutically acceptable esters for hydroxy include C$_{1-6}$ alkanoyl esters, for example acetyl esters; and benzoyl esters wherein the phenyl group may be substituted with aminomethyl or N-substituted mono- or di-C$_{1-6}$ alkyl aminomethyl, for example 4-aminomethylbenzoyl esters and 4-N,N-dimethylaminomethylbenzoyl esters.

Further examples of such prodrugs include in vivo cleavable amides of a compound of formula (I). Examples of such in vivo cleavable amides include an N—C$_{1-6}$ alkylamide and an N,N-di-(C$_{1-6}$ alkyl)amide such as N-methyl, N-ethyl, N-propyl, N,N-dimethyl, N-ethyl-N-methyl or N,N-diethylamide.

Preferred prodrugs of the invention include carbamate, acetyloxy and carbonate derivatives. For example, a hydroxy group of a compound of formula (I) can be present in a prodrug as —O—CONR$^i$R$^{ii}$, —O—COR$^{iii}$ or —O—C(O)OR$^{iii}$ where R$^{iii}$ is unsubstituted or substituted C$_{1-4}$ alkyl, and R$^i$ and R$^{ii}$ are the same or different and represent C$_{1-4}$ alkyl or NR$^i$R$^{ii}$ forms a 4- to 7-membered heterocyclyl ring. Substituents on the alkyl and heterocyclyl groups are as defined earlier. Preferably the alkyl groups in R$^i$, R$^{ii}$ and R$^{iii}$ are unsubstituted. When NR$^i$R$^{ii}$ forms a 4- to 7-membered heterocyclyl ring, preferably it is a 5- or 6-membered heterocyclyl ring. Preferably the heterocyclyl ring is unsubstituted.

Other preferred prodrugs of the invention include amino acid derivatives. Suitable amino acids include α-amino acids linked to group A via their —OH group. Such prodrugs can cleave in vivo to produce compounds of formula (I) bearing a hydroxy group. Accordingly, such amino acid groups are preferably employed at positions of formula (I) where a hydroxy group is eventually required. Exemplary prodrugs of this embodiment of the invention are therefore compounds of formula (I) bearing a group of formula —OC(O)—CH(NH$_2$)R$^{iv}$ where R$^{iv}$ is an amino acid side chain. Preferred amino acids include glycine, alanine, valine and serine. The amino acid can also be functionalised, for example the amino group can be alkylated. A suitable functionalised amino acid is N,N-dimethylglycine.

R$^1$ represents either hydrogen or hydroxy. Preferably R$^1$ is a hydroxy group.

Preferably R$^2$ represents a hydrogen or halogen atom or a hydroxy, unsubstituted C$_{1-4}$ alkyl or unsubstituted C$_{1-4}$ alkoxy group. More preferably R$^2$ represents a hydrogen atom.

Preferably R$^3$ represents a hydrogen or halogen atom or a hydroxy, unsubstituted C$_{1-4}$ alkyl or unsubstituted C$_{1-4}$ alkoxy group. More preferably R$^3$ represents a hydroxy group.

Preferably R$^4$ represents a hydrogen or halogen atom or a hydroxy, unsubstituted C$_{1-4}$ alkyl or unsubstituted C$_{1-4}$ alkoxy group. More preferably $R^4$ represents an unsubstituted $C_{1-4}$ alkyl group, preferably an isopropyl group.

Preferably $R^5$ represents a hydrogen or halogen atom or a hydroxy, unsubstituted $C_{1-4}$ alkyl or unsubstituted $C_{1-4}$ alkoxy group. More preferably $R^5$ represents a hydrogen atom.

In a first embodiment, $R^6$ is selected from $C_{1-4}$ alkyl and $R^7$ represents —$CR^8R^9$-A wherein $R^8$ and $R^9$ are the same or different and represent a hydrogen or halogen atom or a $C_{1-4}$ alkyl, $C_{2-4}$ alkenyl, $C_{1-4}$ alkoxy, hydroxy or —NR'R" group where R' and R" are the same or different and represent hydrogen or unsubstituted $C_{1-4}$ alkyl, and A represents a phenyl ring or a 5- or 6-membered heteroaryl group and is substituted with a group W. Preferably $R^6$ is an unsubstituted $C_{1-2}$ alkyl group, more preferably $R^6$ is —$CH_3$.

When $R^6$ is $C_{1-4}$ alkyl, preferably $R^8$ and $R^9$, which are the same or different, represent a hydrogen or halogen atom or an unsubstituted $C_{1-4}$ alkyl or $C_{1-4}$ alkoxy group. More preferably $R^8$ and $R^9$, which are the same or different, represent hydrogen or an unsubstituted $C_{1-2}$ alkyl. Most preferably $R^8$ and $R^9$ are both hydrogen.

When $R^6$ is $C_{1-4}$ alkyl, preferably A represents a phenyl ring substituted with a group W. Preferably the phenyl ring bears no substituents other than the group W.

In accordance with this first embodiment, most preferably $R^6$ represents —$CH_3$ and $R^7$ represents —$CH_2$-phenyl wherein the phenyl ring is substituted with a single group W.

In a second embodiment, $R^6$ and $R^7$, together with the nitrogen atom to which they are bonded, form a 5- or 6-membered heterocyclyl group which is either (a) unfused, or (b) fused to a phenyl ring or a 5- to 6-membered heteroaryl group, and wherein either the heterocyclyl group or, when fused, the heterocyclyl group or the phenyl ring or heteroaryl group to which it is fused, is substituted with a group W.

In accordance with this second embodiment, preferably $R^6$ and $R^7$, together with the nitrogen atom to which they are bonded, form a pyrrolidinyl, piperidinyl or isoindolinyl group which is substituted with a group W and is optionally further substituted with 1 or 2 groups which are the same or different and are selected from halogen atoms and unsubstituted $C_{1-4}$ alkyl, $C_{1-4}$ alkoxy, hydroxyl, $C_{1-4}$ haloalkyl, $C_{1-4}$ haloalkoxy, $C_{1-4}$ hydroxyalkyl, cyano, nitro, —SR' and —NR'R" groups where R' and R" are the same or different and represent hydrogen or unsubstituted $C_{1-2}$ alkyl. More preferably $R^6$ and $R^7$, together with the nitrogen atom to which they are bonded, form a pyrrolidinyl, piperidinyl or isoindolinyl group which is substituted with a single group W.

Preferably $Alk^1$ represents a bond, an unsubstituted $C_{1-4}$ alkylene group, or an unsubstituted —($C_{1-2}$ alkylene)-NH—($C_{1-4}$ alkylene)- group. When $Alk^1$ is an unsubstituted $C_{1-4}$ alkylene group it is preferably a methylene, ethylene or propylene group. When $Alk^1$ is a propylene group preferably it is a straight chain group (i.e. —$CH_2$—$CH_2$—$CH_2$—). When $Alk^1$ is an unsubstituted —($C_{1-2}$ alkylene)-NH—($C_{1-4}$ alkylene)- group, preferably it is a —$CH_2$—NH—($C_{1-4}$ alkylene)- group, more preferably a —$CH_2$—NH—$CH_2CH_2$—$CH_2$— group.

R represents a group of formula (X) or (Y):

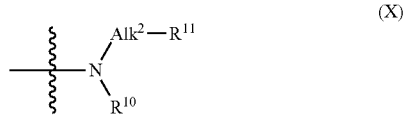

(X)

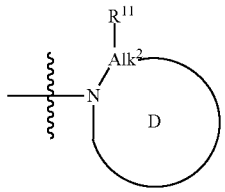

(Y)

Ring D is present when group R is of formula (Y). Preferred groups (Y) include those where Ring D is a non-fused 5- to 6-membered heteroaryl or heterocyclyl group where $R^{11}$ is linked to the group $Alk^2$, which provides the carbon atom adjacent the nitrogen atom shown in Ring D. More preferably Ring D is a non-fused 5- to 6-membered heterocyclyl group, for example a pyrrolidinyl, oxazolidinyl, isoxazolidinyl, imidazolidinyl, pyrazolidinyl, thiazolidinyl, isothiazolidinyl, piperidinyl, hexahydropyrimidinyl, piperazinyl, morpholinyl or thiomorpholinyl group. More preferably Ring D is a pyrrolidinyl, piperazinyl or piperidinyl group, more preferably a piperidyl or piperazinyl group.

When ring D is present, -$Alk^2$- is —$C(R^{12})$—. In particular, the carbon atom of $Alk^2$ forms part of the ring D, and (in addition to being bonded to two other ring atoms) bears group $R^{12}$ as well as bearing group $R^{11}$. Preferred examples of $R^{12}$ are discussed in more detail below.

Preferably Ring D, in addition to containing $Alk^2$ and bearing group $R^{11}$, is unsubstituted or substituted by 1 or 2 groups selected from halogen atoms and $C_{1-4}$ alkyl, $C_{1-4}$ alkoxy and hydroxyl groups. More preferably Ring D, apart from containing $Alk^2$ and bearing group $R^{11}$, is unsubstituted.

When R represents a group of formula (X), $R^{10}$ preferably represents a hydrogen atom or an unsubstituted $C_{1-2}$ alkyl. More preferably $R^{10}$ represents a hydrogen atom Preferably R represents a group of formula (X).

$Alk^2$ represents a methylene group substituted with an $R^{12}$ group and, when R represents a group of formula (X), an $R^{13}$ group. $R^{12}$ and $R^{13}$ are hydrogen or the α substituents of an α-substituted or α,α-disubstituted glycine or glycine ester. These substituents may therefore be independently selected from hydrogen and the side chains of a natural or non-natural alpha-amino acid. In such side chains any functional groups may be protected.

It will be known to the person skilled in the art that the term "protected" when used in relation to a functional substituent in a side chain of an α-amino acid means a derivative of such a substituent which is substantially non-functional. For example, carboxy groups may be esterified (for example as a $C_1$-$C_6$ alkyl ester), amino groups may be converted to amides (for example as a $NHCOC_1$-$C_6$ alkyl amide) or carbamates (for example as an $NHC(\!=\!O)OC_1$-$C_6$ alkyl or a $NHC(\!=\!O)OCH_2Ph$ carbamate), hydroxyl groups may be converted to ethers (for example an $OC_1$-$C_6$ alkyl or a $O(C_1$-$C_6$ alkyl) phenyl ether) or esters (for example a $OC(\!=\!O)C_1$-$C_6$ alkyl ester) and thiol groups may be converted to thioethers (for example a tert-butyl or benzyl thioether) or thioesters (for example a $SC(\!=\!O)C_1$-$C_6$ alkyl thioester).

Examples of $R^{12}$ and $R^{13}$ include hydrogen, phenyl and groups of formula —$CR^aR^bR^c$ in which:

(a) $R^a$, $R^b$ and $R^c$ are the same or different and represent a hydrogen atom or a $C_{1-6}$ alkyl, $C_{2-6}$ alkenyl, $C_{2-6}$ alkynyl, phenyl, 5- to 6-membered heteroaryl, phenyl($C_{1-6}$) alkyl or ($C_{3-8}$)carbocyclyl group, —OH, —SH, halogen, —CN, —$CO_2$H, ($C_{1-4}$)perfluoroalkyl, —$CH_2OH$, —$O(C_{1-6})$alkyl, —$O(C_{2-6})$alkenyl, —$S(C_{1-6})$alkyl, —SO($C_{1-6}$)alkyl, —SO$_2$($C_{1-6}$) alkyl, —S($C_{2-6}$)alkenyl, —SO($C_{2-6}$)alkenyl or —SO$_2$($C_{2-6}$)alkenyl group; or (b) two of $R^a$, $R^b$ and $R^c$ represent a group mentioned in (a) above and the other of $R^a$, $R^b$ and $R^c$ represents a group -Q-W wherein Q represents a bond or —O—, —S—, —SO— or —SO$_2$— and W represents a phenyl, phenyl ($C_{1-6}$)alkyl, $C_{3-8}$ carbocyclyl, $C_{3-8}$ carbocyclyl($C_{1-6}$) alkyl, $C_{4-8}$ cycloalkenyl, $C_{4-8}$ eycloalkenyl($C_{1-6}$)alkyl, 5- or 6-membered heteroaryl or 5- or 6-membered heteroaryl($C_{1-6}$)alkyl group, which group W is unsubstituted or substituted by one or more substituents which are the same or different and represent hydroxyl, halogen, —CN, —CONH$_2$, —CONH($C_{1-6}$)alkyl, —CONH ($C_{1-6}$alkyl)$_2$, —CHO, —CH$_2$OH, —($C_{1-4}$)perfluoroalkyl, —O($C_{1-6}$)alkyl, —S($C_{1-6}$)alkyl, —SO($C_{1-6}$) alkyl, —SO$_2$($C_{1-6}$)alkyl, —NO$_2$, —NH$_2$, —NH($C_{1-6}$) alkyl, —N(($C_{1-6}$)alkyl)$_2$, —NHCO($C_{1-6}$)alkyl, ($C_{1-6}$) alkyl, ($C_{2-6}$)alkenyl, ($C_{2-6}$)alkynyl, ($C_{3-8}$)carbocyclyl, ($C_{4-8}$)cycloalkenyl, phenyl or benzyl; or (c) one of $R^a$, $R^b$ and $R^c$ represents a group mentioned in (a) above and the other two of $R^a$, $R^b$ and $R^c$, together with the carbon atom to which they are attached, form a 3 to 8-membered carbocyclyl, 5- to 6-membered heteroaryl or 5- to 6-membered heterocyclyl ring, or $R^a$, $R^b$ and $R^c$, together with the carbon atom to which they are attached, form a tricyclic system.

For example, in one embodiment each of $R^a$, $R^b$ and $R^c$ is the same or different and represents a hydrogen atom or a $C_{1-6}$ alkyl, $C_{2-6}$ alkenyl, phenyl($C_{1-6}$)alkyl or ($C_{3-8}$)carbocyclyl group.

In another embodiment, $R^c$ is hydrogen and $R^a$ and $R^b$ are the same or different and represent phenyl or a 5- to 6-membered heteroaryl group. Particularly suitable heteroaryl groups include pyridyl.

In another embodiment $R^c$ represents a hydrogen atom or a $C_{1-6}$ alkyl, $C_{2-6}$ alkenyl, $C_{2-6}$ alkynyl, phenyl($C_{1-6}$)alkyl or ($C_{3-8}$)carbocyclyl group, and $R^a$ and $R^b$, together with the carbon atom to which they are attached, form a 3 to 8-membered carbocyclyl, 5- to 6-membered heteroaryl or 5- to 6-membered heterocyclyl ring.

In another embodiment $R^a$, $R^b$ and $R^c$, together with the carbon atom to which they are attached, form a tricyclic system. A particularly suitable tricyclic system is adamantyl.

In another embodiment $R^a$ and $R^b$ are the same or different and represent a $C_{1-6}$ alkyl, $C_{2-6}$ alkenyl, $C_{2-6}$ alkynyl or phenyl ($C_{1-6}$) alkyl group, or a group as defined for $R^c$ below other than hydrogen, or $R^a$ and $R^b$, together with the carbon atom to which they are attached, form a $C_{3-8}$ carbocyclyl or 5- or 6-membered heterocyclyl group, and $R^c$ represents a hydrogen atom or a group selected from —OH, —SH, halogen, —CN, —CO$_2$H, ($C_{1-4}$)perfluoroalkyl, —CH$_2$OH, —O($C_{1-6}$) alkyl, —O($C_{2-6}$)alkenyl, —S($C_{1-6}$)alkyl, —SO($C_{1-6}$)alkyl, —SO$_2$($C_{1-6}$) alkyl, —S($C_{2-6}$)alkenyl, —SO($C_{2-6}$)alkenyl and —SO$_2$($C_{2-6}$)alkenyl, or $R^c$ represents a group -Q-W wherein Q represents a bond or —O—, —S—, —SO— or —SO$_2$— and W represents a phenyl, phenyl($C_{1-6}$)alkyl, $C_{3-8}$ carbocyclyl, $C_{3-8}$ cycloalkyl($C_{1-6}$)alkyl, $C_{4-8}$ cycloalkenyl, $C_{4-8}$ cycloalkenyl($C_{1-6}$)alkyl, 5- or 6-membered heteroaryl or 5- or 6-membered heteroaryl($C_{1-6}$)alkyl group, which group W is unsubstituted or substituted by one or more substituents which are the same or different and represent hydroxyl, halogen, —CN, —CONH$_2$, —CONH($C_{1-6}$)alkyl, —CONH ($C_{1-6}$alkyl)$_2$, —CHO, —CH$_2$OH, —($C_{1-4}$)perfluoroalkyl, —O($C_{1-6}$)alkyl, —S($C_{1-6}$)alkyl, —SO($C_{1-6}$)alkyl, —SO$_2$ ($C_{1-6}$)alkyl, —NO$_2$, —NH$_2$, —NH($C_{1-6}$)alkyl, —N(($C_{1-6}$) alkyl)$_2$, —NHCO($C_{1-6}$)alkyl, ($C_{1-6}$)alkyl, ($C_{2-6}$)alkenyl, ($C_{2-6}$)alkynyl, ($C_{3-8}$)carbocyclyl, ($C_{4-8}$)cycloalkenyl, phenyl or benzyl.

In another embodiment, when R is a group of formula (X), the substituents $R^{12}$ and $R^{13}$, taken together with the carbon to which they are attached, form a 3- to 6-membered saturated carbocyclyl or heterocyclyl ring. Suitable carbocyclyl rings include cyclopropyl, cyclopentyl and cyclohexyl ring; suitable heterocyclyl rings include piperidin-4-yl rings.

In a preferred embodiment, either:
(i) $R^{12}$ and $R^{13}$ are the same or different and represent hydrogen, $C_{1-6}$ alkyl, $C_{3-7}$ carbocyclyl, $C_{6-10}$ aryl, —($C_{1-4}$ alkyl)-($C_{6-10}$ aryl), or —($C_{1-4}$ alkyl)-($C_{3-7}$ carbocyclyl); or
(ii) $R^{12}$ and $R^{13}$, together with the carbon atom to which they are bonded, form a $C_{3-7}$ carbocyclyl group;

wherein the alkyl groups and moieties are unsubstituted or substituted with 1 or 2 substituents selected from unsubstituted $C_{1-4}$ alkyl, $C_{1-4}$ alkoxy, hydroxy and —NR'R" groups where R' and R" are the same or different and represent hydrogen or unsubstituted $C_{1-2}$ alkyl, and wherein the aryl and carbocyclyl groups and moieties are unsubstituted or substituted with 1 or 2 substituents selected from halogen atoms and unsubstituted $C_{1-4}$ alkyl, $C_{1-4}$ alkoxy, hydroxyl, $C_{1-4}$ haloalkyl, $C_{1-4}$ haloalkoxy, $C_{1-4}$ hydroxyalkyl, cyano, nitro, —SR' and —NR'R" groups where R' and R" are the same or different and represent hydrogen or unsubstituted $C_{1-2}$ alkyl.

When $R^{12}$ and $R^{13}$ do not together form a carbocyclyl group, then preferably $R^{12}$ and $R^{13}$ are the same or different and represent a hydrogen atom or an unsubstituted group selected from $C_{1-4}$ alkyl, $C_{3-7}$ carbocyclyl, phenyl, -hydroxy-($C_{1-4}$alkyl, —($C_{1-4}$)alkoxy-($C_{1-4}$alkyl, —($C_{1-2}$)alkyl-phenyl or —($C_{1-2}$)alkyl-($C_{3-7}$)carbocyclyl.

When $R^{12}$ and $R^{13}$ do not together form a carbocyclyl group, then preferably one of $R^{12}$ and $R^{13}$ is other than hydrogen. Where one of $R^{12}$ and $R^{13}$ is methyl, then preferably the other group is hydrogen or methyl.

When $R^{12}$ and $R^{13}$ do not together form a carbocyclyl group, then preferably one of $R^{12}$ and $R^{13}$ is hydrogen or unsubstituted $C_{1-2}$ alkyl and the other of $R^{12}$ and $R^{13}$ is an unsubstituted group selected from $C_{1-4}$ alkyl, $C_{3-7}$ carbocyclyl, phenyl, -hydroxy-($C_{1-4}$)alkyl, —($C_{1-4}$)alkoxy-($C_{1-4}$) alkyl, —($C_{1-2}$)alkyl-phenyl or —($C_{1-2}$)alkyl-($C_{3-7}$)carbocyclyl.

When $R^{12}$ and $R^{13}$ form a carbocyclyl group, together with the carbon atom to which they are bonded, preferably the carbocyclyl group is an unsubstituted $C_{3-7}$ carbocyclyl group. A more preferred carbocyclyl group is a cyclopentyl group.

$R^{11}$ is either a carboxylic acid group —COOH or an ester group —COOR$^{20}$. The term "ester" or "esterified carboxyl group" in connection with substituent $R^{11}$ above means a group —COOR$^{20}$ in which R$^{20}$ is the group characterising the ester, notionally derived from the alcohol R$^{20}$—OH. In one embodiment, $R^{11}$ is preferably an ester group —COOR$^{20}$.

Where $R^{11}$ is an ester group, it must be one which in the compound of the invention is hydrolysable by one or more intracellular carboxylesterase enzymes to a carboxylic acid group. Intracellular carboxylesterase enzymes capable of hydrolysing the ester group of a compound of the invention to the corresponding acid include the three known human enzyme isotypes hCE-1, hCE-2 and hCE-3. Although these are considered to be the main enzymes other enzymes such as biphenylhydrolase (BPH) may also have a role in hydrolysing the conjugates. In general, if the carboxylesterase hydrolyses the free amino acid ester to the parent acid it will also hydrolyse the ester motif when covalently conjugated to the HSP90 inhibitor. Hence, the broken cell assay described later provides a straightforward, quick and simple first screen for esters which have the required hydrolysis profile. Ester motifs selected in that way may then be re-assayed in the same carboxylesterase assay when conjugated to the HSP90 inhibitor via the chosen conjugation chemistry, to confirm that it is still a carboxylesterase substrate in that background.

Macrophages are known to play a key role in inflammatory disorders through the release of cytokines in particular TNF-α and IL-1. In rheumatoid arthritis they are major contributors to the maintenance of joint inflammation and joint destruction. Macrophages are also involved in tumour growth and development. Hence agents that selectively target macrophage cell proliferation could be of value in the treatment of cancer and autoimmune disease. Targeting specific cell types would be expected to lead to reduced side-effects. The inventors have discovered a method of targeting HSP90 inhibitors to macrophages and other cells derived from the myelomonocytic lineage such as monocytes, osteoclasts and dendritic cells. This is based on the observation that the way in which the esterase motif is linked to the HSP90 inhibitor determines whether it is hydrolysed, and hence whether or not it accumulates in different cell types. Specifically it has been found that macrophages and other cells derived from the myelo-monocytic lineage contain the human carboxylesterase hCE-1 whereas other cell types do not. The compounds of formula (I), wherein in all cases the nitrogen of the esterase motif (X) or (Y) is not directly linked to a carbonyl (—C(=O)—), will only be hydrolysed by hCE-1 and hence the inhibitors will selectively accumulate in macrophage-related cells. Herein, unless "monocyte" or "monocytes" is specified, the term macrophage or macrophages will be used to denote macrophages (including tumour associated macrophages) and/or monocytes.

Subject to the requirement that they be hydrolysable by intracellular carboxylesterase enzymes, examples of particular ester groups —COOR$^{20}$ include those wherein R$^{20}$ is —CR$^{14}$R$^{15}$R$^{16}$ wherein:

(i) R$^{15}$ represents hydrogen or a group of formula —[C$_{1-4}$ alkylene]$_b$-(Z$^1$)$_a$—[C$_{1-4}$ alkyl] or —[C$_{1-4}$ alkylene]$_b$-(Z$^1$)$_a$—[C$_{2-4}$ alkenyl] wherein a and b are the same or different and represent 0 or 1, and Z$^1$ represents —O—, —S—, or —NR$^{17}$— wherein R$^{17}$ is hydrogen or C$_{1-4}$ alkyl, R$^{16}$ represents hydrogen or C$_{1-4}$ alkyl, and R$^{14}$ represents hydrogen or C$_{1-4}$ alkyl;

(ii) R$^{15}$ represents a phenyl or a 5- or 6-membered heteroaryl group optionally fused to a further phenyl, 5- or 6-membered heteroaryl, C$_{3-7}$ carbocyclyl or 5- or 6-membered heterocyclyl group, R$^{16}$ represents hydrogen or C$_{1-4}$ alkyl, and R$^{14}$ represents hydrogen;

(iii) R$^{15}$ represents a group of formula -(Alk$^4$)—NR$^{18}$R$^{19}$ wherein Alk$^4$ represents a C$_{1-4}$ alkylene group and either (a) R$^{18}$ and R$^{19}$ are the same or different and represent hydrogen or C$_{1-4}$ alkyl, or (b) R$^{18}$ and R$^{19}$, together with the nitrogen atom to which they are bonded, form a 5- or 6-membered heteroaryl or 5- or 6-membered heterocyclyl group optionally fused to a further phenyl, 5- or 6-membered heteroaryl, C$_{3-7}$ carbocyclyl or 5- or 6-membered heterocyclyl group; R$^{16}$ represents hydrogen or C$_{1-4}$ alkyl, and R$^{14}$ represents hydrogen; or (iv) R$^{15}$ and R$^{16}$, together with the carbon atom to which they are bonded, form a phenyl, 5- or 6-membered heteroaryl, C$_{3-7}$ carbocyclyl or 5- or 6-membered heterocyclyl group which is optionally fused to a further phenyl, 5- or 6-membered heteroaryl, C$_{3-7}$ carbocyclyl or 5- or 6-membered heterocyclyl group, and R$^{14}$ represents hydrogen.

Preferred substituents on the alkyl, alkylene and alkenyl groups in R$^{14}$, R$^{15}$, R$^{16}$, R$^{17}$, R$^{18}$, R$^{19}$ and Alk$^4$ groups include one or two substituents which are the same or different and are selected from halogen, C$_{1-4}$ alkyl, C$_{2-4}$ alkenyl, C$_{1-4}$ alkoxy, hydroxyl and —NR'R" wherein R' and R" are the same or different and represent hydrogen or C$_{1-2}$ alkyl. More preferred substituents are halogen, C$_{1-2}$ alkoxy, hydroxyl and —NR'R" wherein R' and R" are the same or different and represent hydrogen or C$_{1-2}$ alkyl. Most preferably the alkyl, alkylene and alkenyl groups in R$^{15}$, R$^{16}$ and Alk$^4$ are unsubstituted.

Preferred substituents on the phenyl, heteroaryl, carbocyclyl and heterocyclyl groups in or formed by R$^{15}$, R$^{16}$, R$^{18}$ and R$^{19}$ groups include one or two substituents which are the same or different and are selected from halogen atoms and C$_{1-4}$ alkyl, C$_{1-4}$ alkylene, C$_{1-4}$ alkoxy, C$_{1-4}$ haloalkyl, hydroxyl, cyano, nitro and —NR'R" groups wherein each R' and R" is the same or different and represents hydrogen or C$_{1-4}$ alkyl, more preferably halogen atoms and C$_{1-2}$ alkyl, C$_{1-2}$ alkylene, C$_{1-2}$ alkoxy and hydroxyl groups. More preferably the phenyl, heteroaryl, carbocyclyl and heterocyclyl groups in or formed by R$^{15}$, R$^{16}$, R$_{18}$ and R$^{19}$ are unsubstituted or substituted by a C$_{1-2}$ alkylene group, in particular a methylene group. Most preferably the phenyl, heteroaryl, carbocyclyl and heterocyclyl groups in or formed by R$^{15}$, R$^{16}$, R$^{18}$ and R$^{19}$ are unsubstituted.

When R$^{15}$ represents a group of formula —[C$_{1-4}$ allylene]$_b$-(Z$^1$)$_a$-[C$_{1-4}$ alkyl], preferably either a or b is zero, for example both a and b are zero. When [C$_{1-4}$ alkylene] is present, it is preferably a C$_{1-3}$ alkylene, more preferably a C$_{1-2}$ alkylene such as a group —CH$_2$—CH$_2$—.

When R$^{15}$ represents a group of formula —[C$_{1-4}$ allylene]$_b$-(Z$^1$)$_a$[C$_{1-4}$ alkyl], preferably C$_{1-4}$ alkyl is a C$_{1-3}$ alkyl group such as methyl, ethyl or n-propyl, most preferably methyl.

When R$^{15}$ represents a group of formula —[C$_{1-4}$ alkylene]$_b$-(Z$^1$)$_a$—[C$_{1-4}$ alkyl] and a is 1, Z$^1$ is preferably —O— or —NR$^{17}$— wherein R$^{17}$ is hydrogen or C$_{1-2}$ alkyl, more preferably Z$^1$ is —O—.

When R$^{15}$ represents a group of formula —[C$_{1-4}$ allylene]$_b$-(Z$^1$)$_a$—[C$_{2-4}$ alkenyl], preferably either a or b is zero, more preferably both a and b are zero. When [C$_{1-4}$ alkylene] is present, it is preferably a C$_{1-3}$ alkylene, more preferably a C$_{1-2}$ alkylene.

When R$^{15}$ represents a group of formula —[C$_{1-4}$ alkylene]$_b$-(Z$^1$)$_a$—[C$_{2-4}$ alkenyl], preferably C$_{2-4}$ alkenyl is a C$_{2-3}$ alkenyl group, in particular —CH=CH$_2$.

When R$^{15}$ represents a group of formula —[C$_{1-4}$ alkylene]$_b$-(Z$^1$)$_a$—[C$_{1-4}$ alkenyl] and a is 1, Z$^1$ is preferably —O— or —NR$^{17}$— wherein R$^{17}$ is hydrogen or C$_{1-2}$ alkyl, more preferably Z$^1$ is —O—. Most preferably Z$^1$ is absent (i.e. a is zero).

When R$^{15}$ represents hydrogen or a group of formula —[C$_{1-4}$ alkylene]$_b$-(Z$^1$)$_a$—[C$_{1-4}$ alkyl] or —[C$_{1-4}$ alkylene]$_b$-(Z$^1$)$_a$—[C$_{2-4}$ alkenyl], preferably R$^{15}$ represents hydrogen or a C$_{1-4}$ alkyl or C$_{2-4}$ alkenyl group, or a group —(C$_{1-4}$ alkyl)-O—(C$_{1-4}$ alkyl). More preferably R$^{15}$ represents hydrogen, methyl, ethyl, n-propyl, —CH=CH$_2$ or —CH$_2$—CH$_2$—O—CH$_3$, most preferably methyl.

When R$^{15}$ represents hydrogen or a group of formula —[C$_{1-4}$ alkylene]$_b$-(Z$^1$)$_a$—[C$_{1-4}$ alkyl] or —[C$_{1-4}$ alkylene]$_b$-(Z$^1$)$_a$—[C$_{2-4}$ alkenyl], preferably R$^{16}$ represents hydrogen or C$_{1-2}$ alkyl, more preferably hydrogen or methyl.

When R$^{15}$ represents hydrogen or a group of formula —[C$_{1-4}$ alkylene]$_b$-(Z$^1$)$_a$—[C$_{1-4}$ alkyl] or —[C$_{1-4}$ alkylene]$_b$—(Z$^1$)$_a$—[C$_{2-4}$ alkenyl], preferably R$^{14}$ represents hydrogen or C$_{1-2}$ alkyl, more preferably R$^{14}$ represents hydrogen or methyl.

When R$^{15}$ represents hydrogen or a group of formula —[C$_{1-4}$ alkylene]$_b$-(Z$^1$)$_a$—[C$_{1-4}$ alkyl] or —[C$_{1-4}$ alkylene]$_b$-(Z$^1$)$_a$—[C$_{2-4}$ alkenyl], preferably the alkyl, alkylene and alkenyl groups in both R$^{15}$ and R$^{16}$ are unsubstituted.

When R$^{15}$ represents a phenyl or a 5- or 6-membered heteroaryl group optionally fused to a further phenyl, 5- or 6-membered heteroaryl, C$_{3-7}$ carbocyclyl or 5- or 6-membered heterocyclyl group, preferably it represents a non-fused phenyl or a non-fused 5- to 6-membered heteroaryl group. Preferred heteroaryl groups include pyridyl, pyrrolyl, isothiazolyl, pyrazolyl and isoxazolyl, most preferably pyridyl.

When R$^{15}$ represents a phenyl or a 5- or 6-membered heteroaryl group optionally fused to a further phenyl, 5- or 6-membered heteroaryl, C$_{3-7}$ carbocyclyl or 5- or 6-membered heterocyclyl group, preferably the phenyl, heteroaryl, carbocyclyl and heterocyclyl groups in R$^{13}$ are unsubstituted.

When R$^{15}$ represents a phenyl or a 5- or 6-membered heteroaryl group optionally fused to a further phenyl, 5- or 6-membered heteroaryl, C$_{3-7}$ carbocyclyl or 5- or 6-membered heterocyclyl group, R$^{16}$ preferably represents hydrogen or C$_{1-4}$ alkyl, more preferably hydrogen or C$_{1-2}$ alkyl, most preferably hydrogen. Preferably the C$_{1-4}$ alkyl groups of R$^{16}$ are unsubstituted.

When R$^{15}$ represents a group of formula -(Alk$^4$)—NR$^{18}$R$^{19}$, Alle preferably represents a C$_{1-2}$ alkylene group, preferably either —CH$_2$— or —CH$_2$CH$_2$—.

When R$^{15}$ represents a group of formula -(Alk$^4$)—NR$^{18}$R$^{19}$ and R$^{18}$ and R$^{19}$ are the same or different and represent hydrogen or C$_{1-4}$ alkyl, preferably R$^{18}$ represents hydrogen or C$_{1-2}$ alkyl, more preferably R$^{18}$ represents a methyl group. When R$^{15}$ represents a group of formula -(Alk$^4$)—NR$^{18}$R$^{19}$ and R$^{18}$ and R$^{19}$ are the same or different and represent hydrogen or C$_{1-4}$ alkyl, preferably R$^{19}$ represents hydrogen or C$_{1-2}$ alkyl, more preferably R$^{19}$ represents a methyl group.

When R$^{15}$ represents a group of formula -(Alk$^4$)—NR$^{18}$R$^{19}$ and R$^{18}$ and R$^{19}$, together with the nitrogen atom to which they are bonded, form a 5- or 6-membered heteroaryl or 5- or 6-membered heterocyclyl group optionally fused to a further phenyl, 5- or 6-membered heteroaryl, C$_{3-7}$ carbocyclyl or 5- or 6-membered heterocyclyl group, preferably they form a non-fused 5- to 6-membered heteroaryl or non-fused 5- to 6-membered heterocyclyl group. More preferably they form a 5- to 6-membered heterocyclyl group. Preferred heterocyclyl groups include piperidinyl, piperazinyl, morpholinyl and pyrrolidinyl, most preferably morpholinyl.

When R$^{15}$ represents a group of formula -(Alk$^4$)—NR$^{18}$R$^{19}$, Alk$^4$ preferably represents a C$_{1-2}$ alkylene group, more preferably a group —CH$_2$CH$_2$—.

When R$^{15}$ represents a group of formula -(Alk$^4$)—NR$^{18}$R$^{19}$, R$^{16}$ preferably represents hydrogen or C$_{1-2}$ alkyl, most preferably hydrogen.

When R$^{15}$ represents a group of formula -(Alk$^4$)—NR$^{18}$R$^{19}$, preferably the alkyl and alkylene groups in Alk$^4$, R$^{18}$ and R$^{19}$ are unsubstituted. When R$^{15}$ represents a group of formula -(Alk$^4$)—NR$^{18}$R$^{19}$, preferably the phenyl, heteroaryl, carbocyclyl and heterocyclyl groups in R$^{18}$ and R$^{19}$ are unsubstituted.

When R$^{15}$ represents a group of formula -(Alk$^4$)—NR$^{18}$R$^{19}$, preferred groups include —CH$_2$—CH$_2$—NMe$_2$ and —CH$_2$—CH$_2$-morpholinyl.

When R$^{15}$ and R$^{16}$, together with the carbon atom to which they are bonded, form a phenyl, 5- or 6-membered heteroaryl, C$_{3-7}$ carbocyclyl or 5- or 6-membered heterocyclyl group which is optionally fused to a further phenyl, 5- or 6-membered heteroaryl, C$_{3-7}$ carbocyclyl or 5- or 6-membered heterocyclyl group, preferred groups include non-fused phenyl, non-fused 5- to 6-membered heteroaryl, non-fused 5- to 6-membered heterocyclyl, non-fused C$_{3-7}$ carbocyclyl and C$_{3-7}$ carbocyclyl fused to a phenyl ring, more preferably non-fused phenyl, non-fused 5- to 6-membered heterocyclyl, non-fused C$_{3-7}$ carbocyclyl and C$_{3-7}$ carbocyclyl fused to a phenyl ring.

When R$^{15}$ and R$^{16}$ form a cyclic group together with the carbon atom to which they are bonded, preferred non-fused 5- to 6-membered heterocyclyl groups include piperidinyl, tetrahydrofuranyl, piperazinyl, morpholinyl and pyrrolidinyl groups, more preferably piperidinyl and tetrahydrofuranyl groups. When R$^{15}$ and R$^{16}$ form a cyclic group together with the carbon atom to which they are bonded, preferred non-fused C$_{3-7}$ carbocyclyl groups include cyclopentyl and cyclohexyl, more preferably cyclopentyl. When R$^{15}$ and R$^{16}$ form a cyclic group together with the carbon atom to which they are bonded, preferred C$_{3-7}$ carbocyclyl groups fused to a phenyl ring include indanyl.

When R$^{15}$ and R$^{16}$ form a cyclic group together with the carbon atom to which they are bonded, preferably the phenyl, heteroaryl, carbocyclyl and heterocyclyl groups formed are unsubstituted or substituted by one or two substituents which are the same or different and are selected from halogen atoms and C$_{1-4}$ alkyl, C$_{1-4}$ alkylene, C$_{1-4}$ alkoxy, C$_{1-4}$ haloalkyl, hydroxyl, cyano, nitro and —NR'R'' groups wherein each R' and R'' is the same or different and represents hydrogen or C$_{1-4}$ alkyl, more preferably selected from halogen atoms or C$_{1-2}$ alkyl, C$_{1-2}$ alkylene, C$_{1-2}$ alkoxy and hydroxyl groups. Most preferably the phenyl, heteroaryl, carbocyclyl and heterocyclyl groups formed are unsubstituted or substituted by a C$_{1-2}$ alkyl group (such as a methyl group) or by a C$_{1-2}$ alkylene group (such as by a methylene group). Even more preferably the phenyl, heteroaryl, carbocyclyl and heterocyclyl groups so formed are unsubstituted.

Preferred R$^{11}$ groups are —COOH and —COOR$^{20}$ where R$^{20}$ represents C$_{1-4}$ alkyl groups (such as methyl, ethyl, n- or iso-propyl and n-, sec- and tert-butyl), C$_{3-7}$ carbocyclyl groups (such as cyclopentyl and cyclohexyl), C$_{2-4}$ alkenyl groups (such as allyl), and also phenyl, benzyl, 2-pyridylmethyl, 3-pyridylmethyl, 4-pyridylmethyl, N-methylpiperidin-4-yl, tetrahydrofuran-3-yl, methoxyethyl, indanyl, norbonyl, dimethylaminoethyl and morpholinoethyl groups. More preferably R$^{20}$ represents C$_{1-4}$ alkyl or C$_{3-7}$ carbocyclyl. When R$^{11}$ is —COOR$^{20}$ more preferably R$^{20}$ represents unsubstituted C$_{1-4}$ alkyl or C$_{3-7}$ carbocyclyl. Most preferred R$^{20}$ groups include cyclopentyl, t-butyl and iso-propyl.

In a preferred embodiment of the invention there is provided a compound which is (a) a phenylamide derivative of formula (IA) or a tautomer thereof, or (b) a pharmaceutically acceptable salt, N-oxide, hydrate, prodrug or solvate thereof:

(IA)

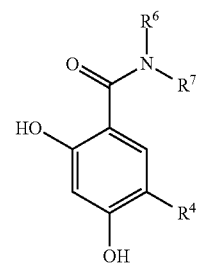

wherein:
R$^4$ represents an unsubstituted C$_{1-4}$ alkyl group;
either:
  R$^6$ represents —CH$_3$, R$^7$ represents —CR$^8$R$^9$-A wherein R$^8$ and R$^9$ are the same or different and represent a hydrogen or halogen atom or an unsubstituted C$_{1-4}$ alkyl or C$_{1-4}$ alkoxy group, and A represents a phenyl ring substituted with a group W; or
  R$^6$ and R$^7$, together with the nitrogen atom to which they are bonded, form a pyrrolidine, piperidine or isoindoline group which is substituted with a group W and which is optionally further substituted with 1 or 2 groups which are the same or different and are selected from halogen atoms and unsubstituted C$_{1-4}$ alkyl, C$_{1-4}$ alkoxy, hydroxyl, C$_{1-4}$ haloalkyl, C$_{1-4}$ haloalkoxy, C$_{1-4}$ hydroxyalkyl, cyano, nitro, —SR' and —NR'R" groups where R' and R" are the same or different and represent hydrogen or unsubstituted C$_{1-2}$ alkyl;
Alk$^1$ represents a bond, an unsubstituted C$_{1-4}$ alkylene group, or an unsubstituted —(C$_{1-2}$ alkylene)-NH—(C$_{1-4}$ alkylene)- group;
R represents a group of formula (X) wherein R$^{10}$ represents hydrogen;
Alk$^2$ represents a group of formula —C(R$^{12}$)(R$^{13}$)— wherein either:
  R$^{12}$ and R$^{13}$ are the same or different and represent hydrogen, C$_{1-6}$ alkyl, C$_{3-7}$ carbocyclyl, C$_{6-10}$ aryl, —(C$_{1-4}$ alkyl)-(C$_{6-10}$ aryl), or —(C$_{1-4}$ alkyl)-(C$_{3-7}$ carbocyclyl); or
  R$^{12}$ and R$^{13}$, together with the carbon atom to which they are bonded, form a C$_{3-7}$ carbocyclyl group,
wherein the alkyl groups and moieties in R$^{12}$ and R$^{13}$ are unsubstituted or substituted with 1 or 2 substituents selected from unsubstituted C$_{1-4}$ alkyl, C$_{1-4}$ alkoxy, hydroxy and —NR'R" groups where R' and R" are the same or different and represent hydrogen or unsubstituted C$_{1-2}$ alkyl, and wherein the aryl and carbocyclyl groups and moieties in R$^{12}$ and R$^{13}$ are unsubstituted or substituted with 1 or 2 substituents selected from halogen atoms and unsubstituted C$_{1-4}$ alkyl, C$_{1-4}$ alkoxy, hydroxyl, C$_{1-4}$ haloalkyl, C$_{1-4}$ haloalkoxy, C$_{1-4}$ hydroxyalkyl, cyano, nitro, —SW and —NR'R" groups where R' and R" are the same or different and represent hydrogen or unsubstituted C$_{1-2}$ alkyl; and
R$^{11}$ is selected from —COOH and —COOR$^{20}$ wherein R$^{20}$ represents unsubstituted C$_{1-4}$ alkyl or C$_{3-7}$ carbocyclyl.

In the case of a compound of formula (IA), preferably R$^4$ represents isopropyl. Furthermore, preferably either:
  R$^6$ represents —CH$_3$, and R$^7$ represents —CH$_2$-phenyl wherein the phenyl ring is substituted with a single group W; or
  R$^6$ and R$^7$, together with the nitrogen atom to which they are bonded, form a pyrrolidinyl, piperidinyl or isoindolinyl group which is substituted with a single group W.

In the case of a compound of formula (IA), preferably one of R$^{12}$ and R$^{13}$ is hydrogen or unsubstituted C$_{1-2}$ alkyl and the other of R$^{12}$ and R$^{13}$ is an unsubstituted group selected from C$_{1-4}$ alkyl, C$_{3-7}$ carbocyclyl, phenyl, -hydroxy-(C$_{1-4}$)alkyl, —(C$_{1-4}$)alkoxy-(C$_{1-4}$)alkyl, —(C$_{1-2}$)alkyl-phenyl or —(C$_{1-2}$)alkyl-(C$_{3-7}$)carbocyclyl.

Particularly preferred compounds of formula (I) are:
cyclopentyl N-(1-{[2,4-dihydroxy-5-(propan-2-yl)phenyl]carbonyl}piperidin-4-yl)-L-leucinate;
cyclopentyl N-(1-{[2,4-dihydroxy-5-(propan-2-yl)phenyl]carbonyl}piperidin-4-yl)-2-methylalaninate;
cyclopentyl N-(1-{[2,4-dihydroxy-5-(propan-2-yl)phenyl]carbonyl}piperidin-4-yl)-L-valinate;
cyclopentyl (2S)-[(1-{[2,4-dihydroxy-5-(propan-2-yl)phenyl]carbonyl}piperidin-4-yl)amino](phenyl)ethanoate;
cyclopentyl N-(1-{[2,4-dihydroxy-5-(propan-2-yl)phenyl]carbonyl}piperidin-4-yl)-L-alaninate;
tert-butyl N-(1-{[2,4-dihydroxy-5-(propan-2-yl)phenyl]carbonyl}piperidin-4-yl)-L-leucinate;
cyclopentyl N-(1-{[2,4-dihydroxy-5-(propan-2-yl)phenyl]carbonyl}piperidin-3-yl)-L-leucinate;
tert-butyl N-(1-{[2,4-dihydroxy-5-(propan-2-yl)phenyl]carbonyl}piperidin-4-yl)-L-alaninate;
cyclopentyl N-(1-{[2,4-dihydroxy-5-(propan-2-yl)phenyl]carbonyl}piperidin-4-yl)-L-phenylalaninate;
cyclopentyl N-(1-{[2,4-dihydroxy-5-(propan-2-yl)phenyl]carbonyl}piperidin-4-yl)-L-norleucinate;
tert-butyl O-tert-butyl-N-(1-{[2,4-dihydroxy-5-(propan-2-yl)phenyl]carbonyl}piperidin-4-yl)-L-serinate;
cyclopentyl N-(1-{[2,4-dihydroxy-5-(propan-2-yl)phenyl]carbonyl}piperidin-4-yl)-D-leucinate;
cyclopentyl 3-cyclohexyl-N-(1-{[2,4-dihydroxy-5-(propan-2-yl)phenyl]carbonyl}piperidin-4-yl)-L-alaninate;
cyclopentyl (2S)-cyclohexyl[(1-{[2,4-dihydroxy-5-(propan-2-yl)phenyl]carbonyl}piperidin-4-yl)amino]ethanoate;
tert-butyl (2S)-cyclohexyl[(1-{[2,4-dihydroxy-5-(propan-2-yl)phenyl]carbonyl}piperidin-4-yl)amino]ethanoate;
tert-butyl N-(1-{[2,4-dihydroxy-5-(propan-2-yl)phenyl]carbonyl}piperidin-4-yl)-L-phenylalaninate;
cyclopentyl O-tert-butyl-N-(1-{[2,4-dihydroxy-5-(propan-2-yl)phenyl]carbonyl}piperidin-4-yl)-L-serinate;
cyclopentyl N-(1-{[2,4-dihydroxy-5-(propan-2-yl)phenyl]carbonyl}piperidin-4-yl)-L-serinate;
tert-butyl N-(1-{[2,4-dihydroxy-5-(propan-2-yl)phenyl]carbonyl}piperidin-4-yl)-D-leucinate;
cyclopentyl N-(1-{[2,4-dihydroxy-5-(propan-2-yl)phenyl]carbonyl}pyrrolidin-3-yl)-L-leucinate;
cyclopentyl N-[(1-{[2,4-dihydroxy-5-(propan-2-yl)phenyl]carbonyl}piperidin-4-yl)methyl]-L-leucinate;
cyclopentyl N-[(1-{[2,4-dihydroxy-5-(propan-2-yl)phenyl]carbonyl}piperidin-4-yl)methyl]-L-alaninate;
cyclopentyl N-[(1-{[2,4-dihydroxy-5-(propan-2-yl)phenyl]carbonyl}piperidin-4-yl)methyl]-L-phenylalaninate;
tert-butyl N-[(1-{[2,4-dihydroxy-5-(propan-2-yl)phenyl]carbonyl}piperidin-4-yl)methyl]-L-leucinate;
tert-butyl N-[(1-{[2,4-dihydroxy-5-(propan-2-yl)phenyl]carbonyl}piperidin-4-yl)methyl]-phenylalaninate;
tert-butyl N-[(1-{[2,4-dihydroxy-5-(propan-2-yl)phenyl]carbonyl}piperidin-4-yl)methyl]-L-alaninate;
tert-butyl N-[(1-{[2,4-dihydroxy-5-(propan-2-yl)phenyl]carbonyl}piperidin-4-yl)methyl]-D-leucinate;
cyclopentyl N-[(1-{[2,4-dihydroxy-5-(propan-2-yl)phenyl]carbonyl}piperidin-4-yl)methyl]-D-leucinate;
cyclopentyl N-[(1-{[2,4-dihydroxy-5-(propan-2-yl)phenyl]carbonyl}piperidin-4-yl)methyl]-L-valinate;
cyclopentyl (2S)-cyclohexyl {[(1-{[2,4-dihydroxy-5-(propan-2-yl)phenyl]carbonyl}piperidin-4-yl)methyl]amino}ethanoate;
tert-butyl (2S)-cyclohexyl {[(1-{[2,4-dihydroxy-5-(propan-2-yl)phenyl]carbonyl}piperidin-4-yl)methyl]amino}ethanoate;
cyclopentyl N-[(1-{[2,4-dihydroxy-5-(propan-2-yl)phenyl]carbonyl}piperidin-4-yl)methyl]-2-methyl-L-alaninate;
cyclopentyl N-[(1-{[2,4-dihydroxy-5-(propan-2-yl)phenyl]carbonyl}piperidin-4-yl)methyl]-L-serinate;
cyclopentyl O-tert-butyl-N-[(1-{[2,4-dihydroxy-5-(propan-2-yl)phenyl]carbonyl}piperidin-4-yl)methyl]-L-serinate;

tert-butyl O-tert-butyl-N-[(1-{[2,4-dihydroxy-5-(propan-2-yl)phenyl]carbonyl}piperidin-4-yl)methyl]-L-serinate;
cyclopentyl (2S)-{[(1-{[2,4-dihydroxy-5-(propan-2-yl)phenyl]carbonyl}piperidin-4-yl)methyl]amino}(phenyl)ethanoate;
tert-butyl N-[(1-{[2,4-dihydroxy-5-(propan-2-yl)phenyl]carbonyl}piperidin-4-yl)methyl]-L-serinate;
cyclopentyl N-[2-(1-{[2,4-dihydroxy-5-(propan-2-yl)phenyl]carbonyl}piperidin-4-yl)ethyl]-L-leucinate;
cyclopentyl N-[2-(1-{[2,4-dihydroxy-5-(propan-2-yl)phenyl]carbonyl}piperidin-4-yl)ethyl]-L-alaninate;
cyclopentyl N-[2-(1-{[2,4-dihydroxy-5-(propan-2-yl)phenyl]carbonyl}piperidin-4-yl)ethyl]-phenylalaninate;
tert-butyl N-[2-(1-{[2,4-dihydroxy-5-(propan-2-yl)phenyl]carbonyl}piperidin-4-yl)ethyl]-L-phenylalaninate;
tert-butyl N-[2-(1-{[2,4-dihydroxy-5-(propan-2-yl)phenyl]carbonyl}piperidin-4-yl)ethyl]-L-leucinate;
tert-butyl N-[2-(1-{[2,4-dihydroxy-5-(propan-2-yl)phenyl]carbonyl}piperidin-4-yl)ethyl]-L-alaninate;
cyclopentyl N-[2-(1-{[2,4-dihydroxy-5-(propan-2-yl)phenyl]carbonyl}piperidin-4-yl)ethyl]-2-methylalaninate;
cyclopentyl O-tert-butyl-N-[2-(1-{[2,4-dihydroxy-5-(propan-2-yl)phenyl]carbonyl}piperidin-4-yl)ethyl]-L-serinate;
cyclopentyl N-[2-(1-{[2,4-dihydroxy-5-(propan-2-yl)phenyl]carbonyl}piperidin-4-yl)ethyl]-L-valinate;
cyclopentyl N-[2-(1-{[2,4-dihydroxy-5-(propan-2-yl)phenyl]carbonyl}piperidin-4-yl)ethyl]-L-serinate;
cyclopentyl (2S)-cyclohexyl {[2-(1-{[2,4-dihydroxy-5-(propan-2-yl)phenyl]carbonyl}piperidin-4-yl)ethyl]amino}ethanoate;
tert-butyl (2S)-cyclohexyl{[2-(1-{[2,4-dihydroxy-5-(propan-2-yl)phenyl]carbonyl}piperidin-4-yl)ethyl]amino}ethanoate;
tert-butyl (2S)-{[2-(1-{[2,4-dihydroxy-5-(propan-2-yl)phenyl]carbonyl}piperidin-4-yl)ethyl]amino}(phenyl)ethanoate;
cyclopentyl (2S)-{[2-(1-{[2,4-dihydroxy-5-(propan-2-yl)phenyl]carbonyl}piperidin-4-yl)ethyl]amino}(phenyl)ethanoate;
tert-butyl N-[2-(1-{[2,4-dihydroxy-5-(propan-2-yl)phenyl]carbonyl}piperidin-4-yl)ethyl]-L-serinate;
tert-butyl O-tert-butyl-N-[2-(1-{[2,4-dihydroxy-5-(propan-2-yl)phenyl]carbonyl}piperidin-4-yl)ethyl]-L-serinate;
cyclopentyl N-[(2-{[2,4-dihydroxy-5-(propan-2-yl)phenyl]carbonyl}-2,3-dihydro-1H-isoindol-5-yl)methyl]-L-leucinate;
cyclopentyl N-[(2-{[2,4-dihydroxy-5-(propan-2-yl)phenyl]carbonyl}-2,3-dihydro-1H-isoindol-5-yl)methyl]-2-methylalaninate;
tert-butyl N-[(2-{[2,4-dihydroxy-5-(propan-2-yl)phenyl]carbonyl}-2,3-dihydro-1H-isoindol-5-yl)methyl]-L-alaninate;
ethyl N-[(2-{[2,4-dihydroxy-5-(propan-2-yl)phenyl]carbonyl}-2,3-dihydro-1H-isoindol-5-yl)methyl]-L-alaninate;
propan-2-yl N-[(2-{[2,4-dihydroxy-5-(propan-2-yl)phenyl]carbonyl}-2,3-dihydro-1H-isoindol-5-yl)methyl]-L-alaninate;
cyclopentyl N-[(2-{[2,4-dihydroxy-5-(propan-2-yl)phenyl]carbonyl}-2,3-dihydro-1H-isoindol-5-yl)methyl]-L-alaninate;
cyclopentyl 1-{[(2-{[2,4-dihydroxy-5-(propan-2-yl)phenyl]carbonyl}-2,3-dihydro-1H-isoindol-5-yl)methyl]amino}cyclopentanecarboxylate;
cyclopentyl N-[2-(2-{[2,4-dihydroxy-5-(propan-2-yl)phenyl]carbonyl}-2,3-dihydro-1H-isoindol-5-yl)ethyl]-L-leucinate;
tert-butyl N-[2-(2-{[2,4-dihydroxy-5-(propan-2-yl)phenyl]carbonyl}-2,3-dihydro-1H-isoindol-5-yl)ethyl]-L-leucinate;
cyclopentyl 1-{[2-(2-{[2,4-dihydroxy-5-(propan-2-yl)phenyl]carbonyl}-2,3-dihydro-1H-isoindol-5-yl)ethyl]amino}cyclopentanecarboxylate;
cyclopentyl N-[3-(2-{[2,4-dihydroxy-5-(propan-2-yl)phenyl]carbonyl}-2,3-dihydro-1H-isoindol-5-yl)propyl]-L-leucinate;
cyclopentyl 1-{[3-(2-{[2,4-dihydroxy-5-(propan-2-yl)phenyl]carbonyl}-2,3-dihydro-1H-isoindol-5-yl)propyl]amino}cyclopentanecarboxylate;
cyclopentyl N-(3-[{{[2,4-dihydroxy-5-(propan-2-yl)phenyl]carbonyl}(methyl)amino]methyl}benzyl)-L-leucinate;
cyclopentyl N-(3-{[{[2,4-dihydroxy-5-(propan-2-yl)phenyl]carbonyl}(methyl)amino]methyl}benzyl)-2-methylalaninate;
cyclopentyl 1-[(3-{[{[2,4-dihydroxy-5-(propan-2-yl)phenyl]carbonyl}(methyl)amino]methyl}benzyl)amino]cyclopentanecarboxylate;
cyclopentyl (2S)-[(3-{[{[2,4-dihydroxy-5-(propan-2-yl)phenyl]carbonyl}(methyl)amino]methyl}benzyl)amino](phenyl)ethanoate;
cyclopentyl N-(4-{[{[2,4-dihydroxy-5-(propan-2-yl)phenyl]carbonyl}(methyl)amino]methyl}benzyl)-L-leucinate;
cyclopentyl (2S)-[(4-{[{[2,4-dihydroxy-5-(propan-2-yl)phenyl]carbonyl}(methyl)amino]methyl}benzyl)amino](phenyl)ethanoate;
cyclopentyl N-(4-{[{[2,4-dihydroxy-5-(propan-2-yl)phenyl]carbonyl}(methyl)amino]methyl}benzyl)-2-methylalaninate;
cyclopentyl N-[2-(4-{[{[2,4-dihydroxy-5-(propan-2-yl)phenyl]carbonyl}(methyl)amino]methyl}phenyl)ethyl]-2-methylalaninate;
cyclopentyl N-{[(2R)-1-{[2,4-dihydroxy-5-(propan-2-yl)phenyl]carbonyl}pyrrolidin-2-yl]methyl}-L-leucinate;
cyclopentyl N-{[(2S)-1-{[2,4-dihydroxy-5-(propan-2-yl)phenyl]carbonyl}pyrrolidin-2-yl]methyl}-L-leucinate;
cyclopentyl N-(1-{[2,4-dihydroxy-5-(propan-2-yl)phenyl]carbonyl}pyrrolidin-3-yl)-D-leucinate;
N-(4-{[{[2,4-dihydroxy-5-(propan-2-yl)phenyl]carbonyl}(methyl)amino]methyl}benzyl)-L-leucine;
N-[(2-{[2,4-dihydroxy-5-(propan-2-yl)phenyl]carbonyl}-2,3-dihydro-1H-isoindol-5-yl)methyl]-L-leucine;
N-[(2-{[2,4-dihydroxy-5-(propan-2-yl)phenyl]carbonyl}-2,3-dihydro-1H-isoindol-5-yl)methyl]-2-methylalanine;
N-[3-(2-{[2,4-dihydroxy-5-(propan-2-yl)phenyl]carbonyl}-2,3-dihydro-1H-isoindol-5-yl)propyl]-L-leucine;
N-[2-(2-{[2,4-dihydroxy-5-(propan-2-yl)phenyl]carbonyl}-2,3-dihydro-1H-isoindol-5-yl)ethyl]-L-leucine;
N-[(2-{[2,4-dihydroxy-5-(propan-2-yl)phenyl]carbonyl}-2,3-dihydro-1H-isoindol-5-yl)methyl]-L-alanine;
1-{[(2-{[2,4-dihydroxy-5-(propan-2-yl)phenyl]carbonyl}-2,3-dihydro-1H-isoindol-5-yl)methyl]amino}cyclopentanecarboxylic acid;
N-(3-{[{[2,4-dihydroxy-5-(propan-2-yl)phenyl]carbonyl}(methyl)amino]methyl}benzyl)-L-leucine;
(2S)-[(4-{[{[2,4-dihydroxy-5-(propan-2-yl)phenyl]carbonyl}(methyl)amino]methyl}benzyl)amino](phenyl)ethanoic acid;
N-(4-{[{[2,4-dihydroxy-5-(propan-2-yl)phenyl]carbonyl}(methyl)amino]methyl}benzyl)-2-methylalanine;
N-(3-{[{[2,4-dihydroxy-5-(propan-2-yl)phenyl]carbonyl}(methyl)amino]methyl}benzyl)-2-methylalanine;
1-[(3-{[{[2,4-dihydroxy-5-(propan-2-yl)phenyl]carbonyl}(methyl)amino]methyl}benzyl)amino]cyclopentanecarboxylic acid;

(2S)-[(3-{[{[[2,4-dihydroxy-5-(propan-2-yl)phenyl]carbonyl}(methyl)amino]methyl}benzyl)amino](phenyl)ethanoic acid;

1-{[3-(2-{[2,4-dihydroxy-5-(propan-2-yl)phenyl]carbonyl}-2,3-dihydro-1H-isoindol-5-yl)propyl]amino}cyclopentanecarboxylic acid;

N-[2-(4-{[{[2,4-dihydroxy-5-(propan-2-yl)phenyl]carbonyl}(methyl)amino]methyl}phenyl)ethyl]-2-methylalanine;

N-[2-(1-{[2,4-dihydroxy-5-(propan-2-yl)phenyl]carbonyl}piperidin-4-yl)ethyl]-L-alanine;

1-{[2-(2-{[2,4-dihydroxy-5-(propan-2-yl)phenyl]carbonyl}-2,3-dihydro-1H-isoindol-5-yl)ethyl]amino}cyclopentanecarboxylic acid;

N-{[(2S)-1-{[2,4-dihydroxy-5-(propan-2-yl)phenyl]carbonyl}pyrrolidin-2-yl]methyl}-L-leucine;

N-(1-{[2,4-dihydroxy-5-(propan-2-yl)phenyl]carbonyl}pyrrolidin-3-yl)-L-leucine;

N-(1-{[2,4-dihydroxy-5-(propan-2-yl)phenyl]carbonyl}piperidin-4-yl)-L-leucine;

N-(1-{[2,4-dihydroxy-5-(propan-2-yl)phenyl]carbonyl}piperidin-4-yl)-2-methylalanine;

N-(1-{[2,4-dihydroxy-5-(propan-2-yl)phenyl]carbonyl}piperidin-4-yl)-L-valine;

(2S)-[(1-{[2,4-dihydroxy-5-(propan-2-yl)phenyl]carbonyl}piperidin-4-yl)amino](phenyl)ethanoic acid;

N-(1-{[2,4-dihydroxy-5-(propan-2-yl)phenyl]carbonyl}piperidin-4-yl)-L-alanine;

N-(1-{[2,4-dihydroxy-5-(propan-2-yl)phenyl]carbonyl}piperidin-4-yl)-L-phenylalanine;

N-(1-{[2,4-dihydroxy-5-(propan-2-yl)phenyl]carbonyl}piperidin-3-yl)-L-leucine;

N-[(1-{[2,4-dihydroxy-5-(propan-2-yl)phenyl]carbonyl}piperidin-4-yl)methyl]-L-leucine;

N-[2-(1-{[2,4-dihydroxy-5-(propan-2-yl)phenyl]carbonyl}piperidin-4-yl)ethyl]-L-leucine;

N-(1-{[2,4-dihydroxy-5-(propan-2-yl)phenyl]carbonyl}piperidin-4-yl)-L-norleucine;

N-[(1-{[2,4-dihydroxy-5-(propan-2-yl)phenyl]carbonyl}piperidin-4-yl)methyl]-L-alanine;

N-[(1-{[2,4-dihydroxy-5-(propan-2-yl)phenyl]carbonyl}piperidin-4-yl)methyl]-L-phenylalanine;

N-[(1-{[2,4-dihydroxy-5-(propan-2-yl)phenyl]carbonyl}piperidin-4-yl)methyl]-D-leucine;

N-(1-{[2,4-dihydroxy-5-(propan-2-yl)phenyl]carbonyl}piperidin-4-yl)-D-leucine;

3-cyclohexyl-N-(1-{[2,4-dihydroxy-5-(propan-2-yl)phenyl]carbonyl}piperidin-4-yl)-L-alanine;

N-[2-(1-{[2,4-dihydroxy-5-(propan-2-yl)phenyl]carbonyl}piperidin-4-yl)ethyl]-L-phenylalanine;

N-[(1-{[2,4-dihydroxy-5-(propan-2-yl)phenyl]carbonyl}piperidin-4-yl)methyl]-L-valine;

(2S)-cyclohexyl[(1-{[2,4-dihydroxy-5-(propan-2-yl)phenyl]carbonyl}piperidin-4-yl)amino]ethanoic acid;

N-[2-(1-{[2,4-dihydroxy-5-(propan-2-yl)phenyl]carbonyl}piperidin-4-yl)ethyl]-2-methylalanine;

O-tert-butyl-N-[2-(1-{[2,4-dihydroxy-5-(propan-2-yl)phenyl]carbonyl}piperidin-4-yl)ethyl]-L-serine;

(2S)-cyclohexyl{[(1-{[2,4-dihydroxy-5-(propan-2-yl)phenyl]carbonyl}piperidin-4-yl)methyl]amino}ethanoic acid;

N-[(1-{[2,4-dihydroxy-5-(propan-2-yl)phenyl]carbonyl}piperidin-4-yl)methyl]-2-methylalanine;

N-[(1-{[2,4-dihydroxy-5-(propan-2-yl)phenyl]carbonyl}piperidin-4-yl)methyl]-L-serine;

O-tert-butyl-N-[(1-{[2,4-dihydroxy-5-(propan-2-yl)phenyl]carbonyl}piperidin-4-yl)methyl]-L-serine;

(2S)-{[(1-{[2,4-dihydroxy-5-(propan-2-yl)phenyl]carbonyl}piperidin-4-yl)methyl]amino}(phenyl)ethanoic acid;

N-[2-(1-{[2,4-dihydroxy-5-(propan-2-yl)phenyl]carbonyl}piperidin-4-yl)ethyl]-L-valine;

O-tert-butyl-N-(1-{[2,4-dihydroxy-5-(propan-2-yl)phenyl]carbonyl}piperidin-4-yl)-L-serine;

(2S)-cyclohexyl{[2-(1-{[2,4-dihydroxy-5-(propan-2-yl)phenyl]carbonyl}piperidin-4-yl)ethyl]amino}ethanoic acid;

(2S)-{[2-(1-{[2,4-dihydroxy-5-(propan-2-yl)phenyl]carbonyl}piperidin-4-yl)ethyl]amino}(phenyl)ethanoic acid;

N-(1-{[2,4-dihydroxy-5-(propan-2-yl)phenyl]carbonyl}piperidin-4-yl)-L-serine;

cyclopentyl N-{3-[(1-{[2,4-dihydroxy-5-(propan-2-yl)phenyl]carbonyl}piperidin-4-yl)amino]propyl}-L-leucinate; and N-{3-[(1-{[2,4-dihydroxy-5-(propan-2-yl)phenyl]carbonyl}piperidin-4-yl)amino]propyl}-L-leucine.

As mentioned above, the compounds with which the invention is concerned are inhibitors of HSP90 activity and are therefore of use for treatment of cancer, autoimmune and inflammatory diseases, including chronic obstructive pulmonary disease, asthma, rheumatoid arthritis, psoriasis, inflammatory bowel disease, Crohn's disease, ulcerative colitis, multiple sclerosis, diabetes, atopic dermatitis, graft versus host disease, systemic lupus erythematosis, viral infection, Alzheimer's disease and others. For example, the compounds may be used in the treatment of cancer, autoimmune and inflammatory diseases, including chronic obstructive pulmonary disease, asthma, rheumatoid arthritis, psoriasis, inflammatory bowel disease, Crohn's disease, ulcerative colitis, multiple sclerosis, atopic dermatitis, graft versus host disease, systemic lupus erythematosis, viral infection and Alzheimer's disease. A preferred utility of the compounds of the invention is for use in the treatment of cancer, in particular breast cancer, ovarian cancer, pancreatic cancer or hepatocellular carcinoma. Another preferred utility of the compounds of the invention is for use in the treatment of inflammation.

It will be understood that the specific dose level for any particular patient will depend upon a variety of factors including the activity of the specific compound employed, the age, body weight, general health, sex, diet, time of administration, route of administration, rate of excretion, drug combination and the severity of the particular disease undergoing treatment. Optimum dose levels and frequency of dosing will be determined by clinical trial, but an exemplary dosage would be 0.1-1000 mg per day.

The compounds with which the invention is concerned may be prepared for administration by any route consistent with their pharmacokinetic properties. The orally administrable compositions may be in the form of tablets, capsules, powders, granules, lozenges, liquid or gel preparations, such as oral, topical, or sterile parenteral solutions or suspensions. Tablets and capsules for oral administration may be in unit dose presentation form, and may contain conventional excipients such as binding agents, for example syrup, acacia, gelatin, sorbitol, tragacanth, or polyvinyl-pyrrolidone; fillers, for example lactose, sugar, maize-starch, calcium phosphate, sorbitol or glycine; tabletting lubricant, for example magnesium stearate, talc, polyethylene glycol or silica; disintegrants, for example potato starch, or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives such as suspending agents, for example sorbitol, syrup, methyl cellulose, glucose syrup, gelatin hydrogenated edible fats; emulsifying agents, for example lecithin, sorbitan monooleate, or acacia; non-aqueous vehicles (which may include edible oils), for example almond oil, fractionated coconut oil, oily esters such as glycerine, propylene glycol, or ethyl alcohol; preservatives, for example methyl or propyl p-hydroxybenzoate or sorbic acid, and if desired conventional flavouring or colouring agents.

For topical application to the skin, the drug may be made up into a cream, lotion or ointment. Cream or ointment formulations which may be used for the drug are conventional formulations well known in the art, for example as described in standard textbooks of pharmaceutics such as the British Pharmacopoeia.

For topical application by inhalation, the drug may be formulated for aerosol delivery for example, by pressure-driven jet atomizers or ultrasonic atomizers, or preferably by propellant-driven metered aerosols or propellant-free administration of micronized powders, for example, inhalation capsules or other "dry powder" delivery systems. Excipients, such as, for example, propellants (e.g. Frigen in the case of metered aerosols), surface-active substances, emulsifiers, stabilizers, preservatives, flavourings, and fillers (e.g. lactose in the case of powder inhalers) may be present in such inhaled formulations. For the purposes of inhalation, a large number of apparata are available with which aerosols of optimum particle size can be generated and administered, using an inhalation technique which is appropriate for the patient. In addition to the use of adaptors (spacers, expanders) and pear-shaped containers (e.g. Nebulator®, Volumatic®), and automatic devices emitting a puffer spray (Autohaler®), for metered aerosols, in particular in the case of powder inhalers, a number of technical solutions are available (e.g. Diskhaler®, Rotadisk®, Turbohaler® or the inhalers for example as described in European Patent Application EP 0 505 321).

For topical application to the eye, the drug may be made up into a solution or suspension in a suitable sterile aqueous or non aqueous vehicle. Additives, for instance buffers such as sodium metabisulphite or disodium edeate; preservatives including bactericidal and fungicidal agents such as phenyl mercuric acetate or nitrate, benzalkonium chloride or chlorhexidine, and thickening agents such as hypromellose may also be included.

The active ingredient may also be administered parenterally in a sterile medium. Depending on the vehicle and concentration used, the drug can either be suspended or dissolved in the vehicle. Advantageously, adjuvants such as a local anaesthetic, preservative and buffering agents can be dissolved in the vehicle.

The compounds of the invention may be used in conjunction with a number of known pharmaceutically active substances. For example, the compounds of the invention may be used with cytotoxics, HDAC inhibitors, kinase inhibitors, aminopeptidase inhibitors and monoclonal antibodies (for example those directed at growth factor receptors). Preferred cytotoxics include, for example, taxanes, platins, anti-metabolites such as 5-fluoracil, topoisomerase inhibitors and the like. The medicaments of the invention comprising amino acid derivatives of formula (I), tautomers thereof or pharmaceutically acceptable salts, N-oxides, hydrates, prodrugs or solvates thereof therefore typically further comprise a cytotoxic, an HDAC inhibitor, a kinase inhibitor, an aminopeptidase inhibitor and/or a monoclonal antibody.

Further, the present invention provides a pharmaceutical composition comprising:
(a) a phenylamide derivative of formula (I), a tautomer thereof or a pharmaceutically acceptable salt, N-oxide, hydrate, prodrug or solvate thereof;
(b) a cytotoxic agent, an HDAC inhibitor, a kinase inhibitor, an aminopeptidase inhibitor and/or a monoclonal antibody; and
(c) a pharmaceutically acceptable carrier or diluent.

Also provided is a product comprising:
(a) phenylamide derivative of formula (I), a tautomer thereof or a pharmaceutically acceptable salt, N-oxide, hydrate, prodrug or solvate thereof; and
(b) a cytotoxic agent, an HDAC inhibitor, a kinase inhibitor, an aminopeptidase inhibitor and/or a monoclonal antibody, for the separate, simultaneous or sequential use in the treatment of the human or animal body.

Synthesis

There are multiple synthetic strategies for the synthesis of the compounds of formula (I) with which the present invention is concerned, but all rely on known chemistry, known to the synthetic organic chemist. Thus, compounds according to formula (I) can be synthesised according to procedures described in the standard literature and are well-known to those skilled in the art. Typical literature sources are "Advanced organic chemistry", $4^{th}$ Edition (Wiley), J March, "Comprehensive Organic Transformation", $2^{nd}$ Edition (Wiley), R. C. Larock, "Handbook of Heterocyclic Chemistry", $2^{nd}$ Edition (Pergamon), A. R. Katritzky, review articles such as found in "Synthesis", "Acc. Chem. Res.", "Chem. Rev", or primary literature sources identified by standard literature searches online or from secondary sources such as "Chemical Abstracts" or "Beilstein". The compounds of the invention may be prepared by a number of processes generally described below and more specifically in the Examples hereinafter. In the reactions described below, it may be necessary to protect reactive functional groups, for example hydroxyl, amino and carboxy groups, where these are desired in the final product, to avoid their unwanted participation in the reactions [see for example Greene, T. W., "Protecting Groups in Organic Synthesis", John Wiley and Sons, 1999]. Conventional protecting groups may be used in conjunction with standard practice. In some instances deprotection may be the final step in the synthesis of a compound of general formula (I), and the processes according to the invention described herein after are understood to extend to such removal of protecting groups.

Scheme 1-Generic scheme for the preparation of the amino acid ester building blocks ($R^{12}$, $R^{13}$ and $R^{20}$ are as defined herein, P is a suitable protecting group):

Route 1:

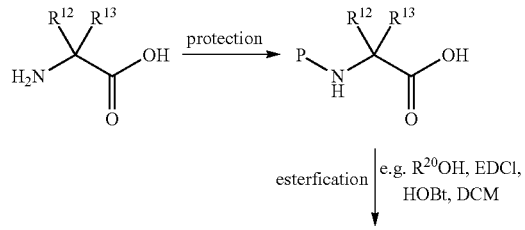

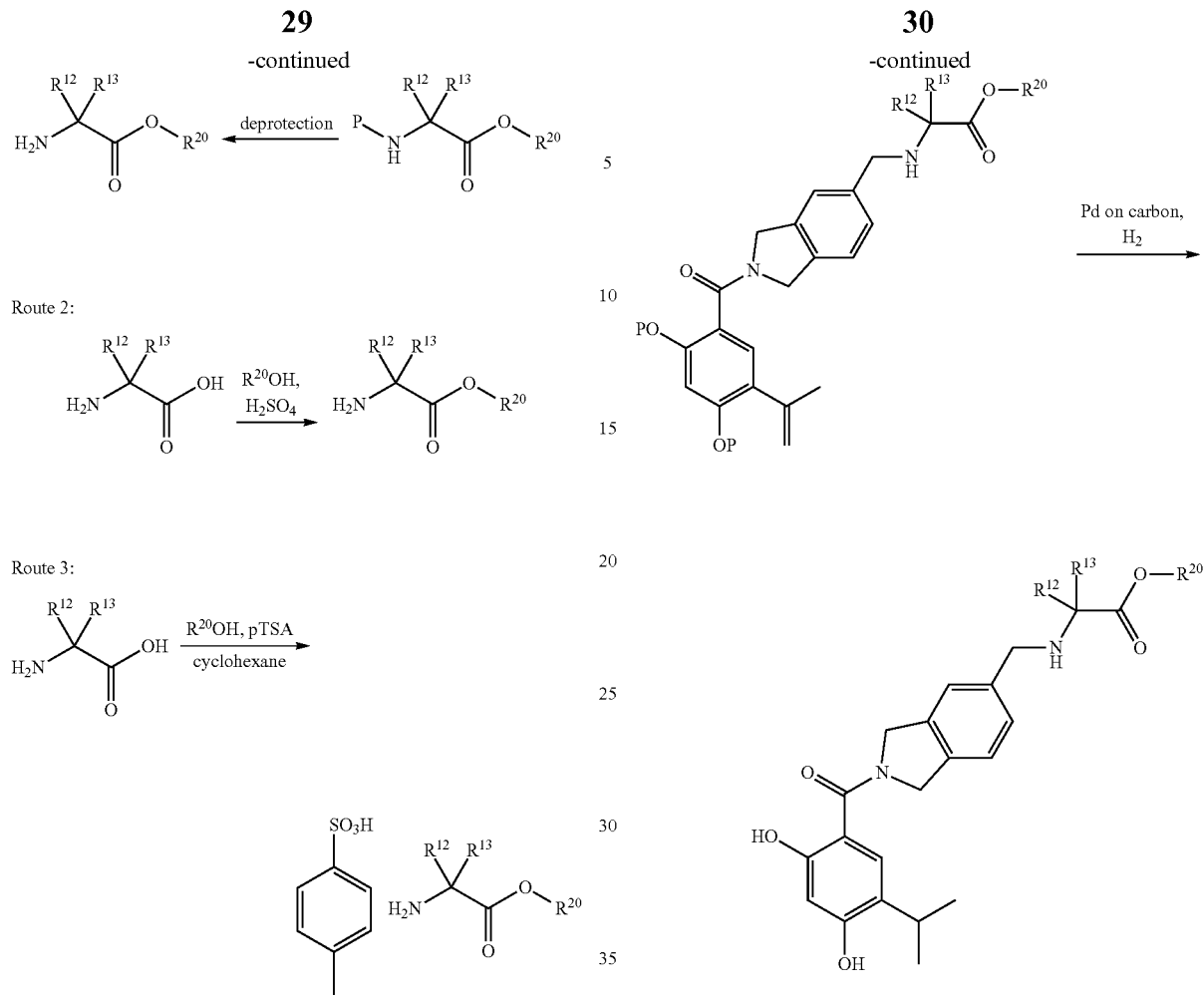

The amino acid ester building blocks can be prepared in a number of ways. Scheme 1 illustrates the main routes employed for their preparation for the purpose of this application. To the chemist skilled in the art it will be apparent that there are other methodologies that will also achieve the preparation of these intermediates. Examples of the preparation of such intermediates are described in WO2009/106848, WO2006/117567 and W2008/040934.

Scheme 2 - Generic scheme for the preparation of isoindoline based inhibitors of Hsp90 ($R^{12}$, $R^{13}$, and $R^{20}$ are as defines herein, P is a suitable protecting group, X is a suitable halogen):

Route 1:

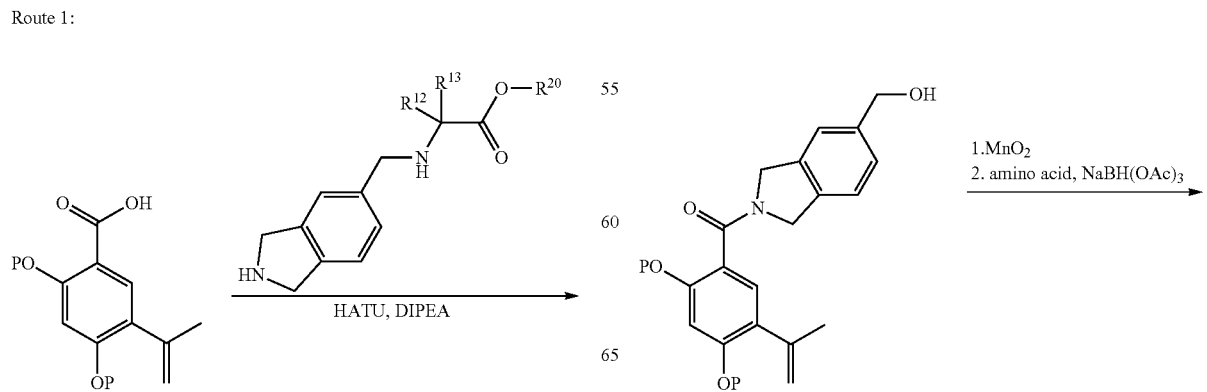

31
-continued
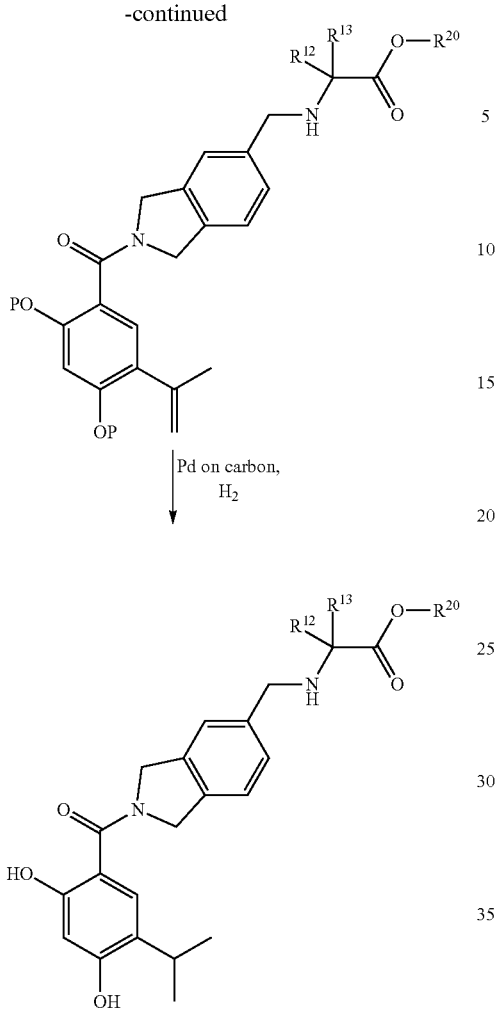
Route 3:
32
-continued
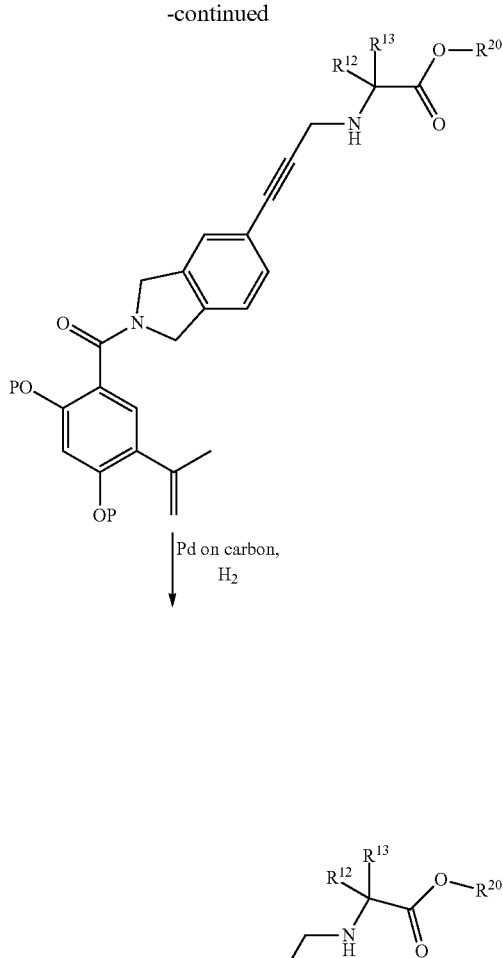
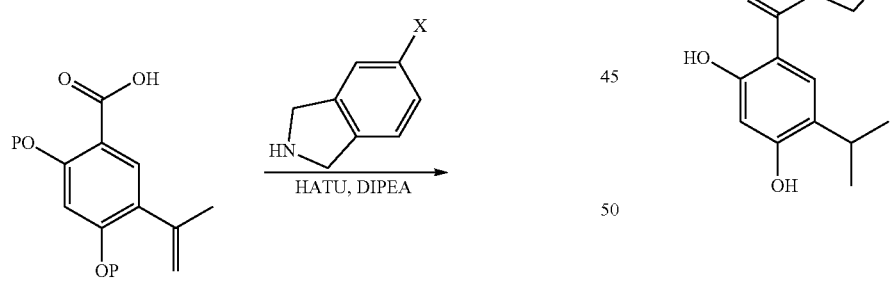
Route 4:
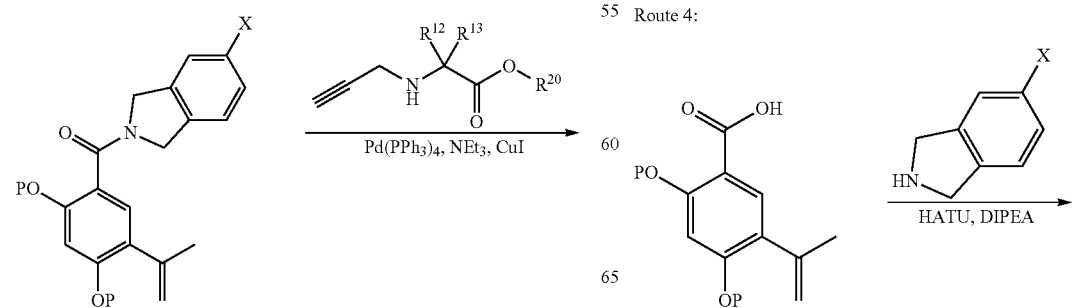

33
-continued

34
-continued

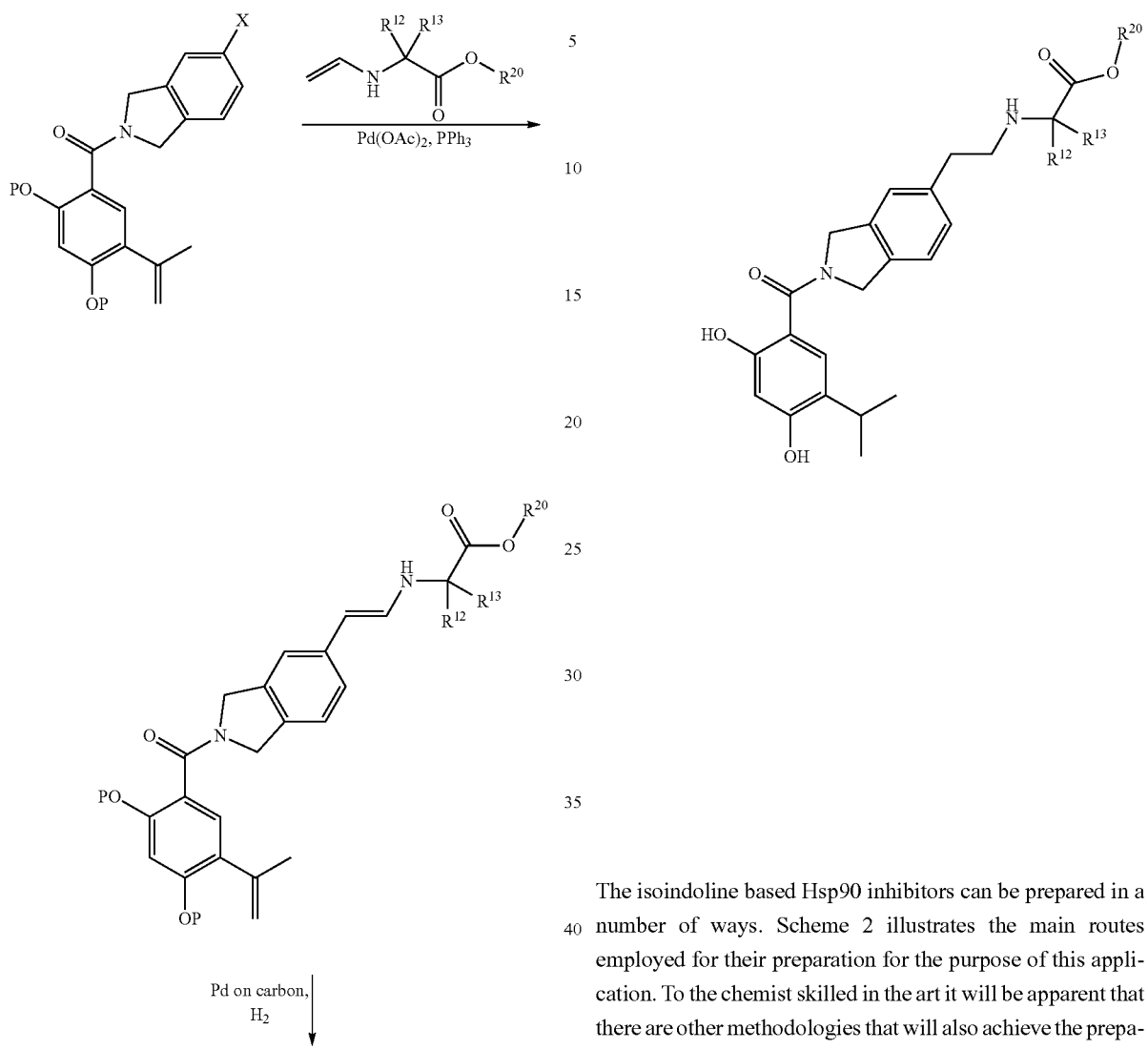

The isoindoline based Hsp90 inhibitors can be prepared in a number of ways. Scheme 2 illustrates the main routes employed for their preparation for the purpose of this application. To the chemist skilled in the art it will be apparent that there are other methodologies that will also achieve the preparation of these intermediates Scheme 3-Generic scheme for the preparation of piperidine based inhibitors of Hsp90 ($R^{12}$, $R^{13}$ and $R^{20}$ are as defined herein, P is a suitable protecting group)

Route 1:

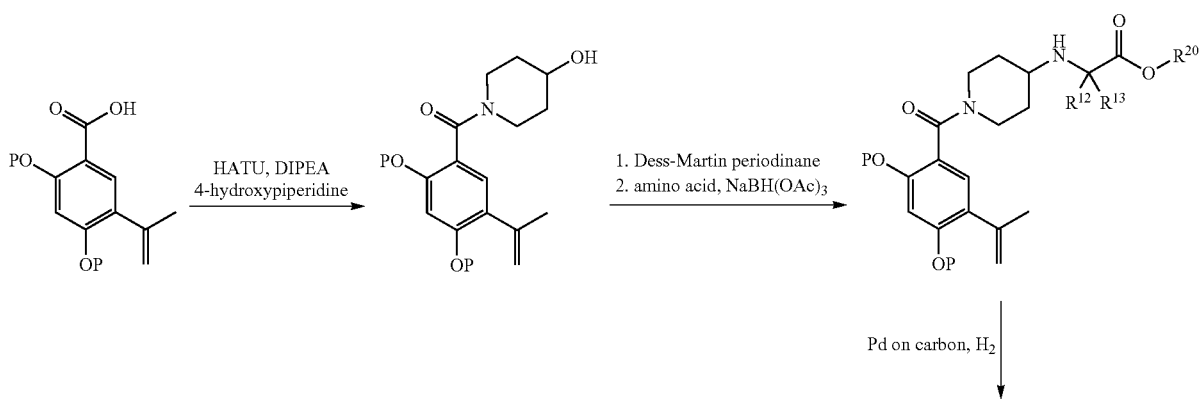

-continued
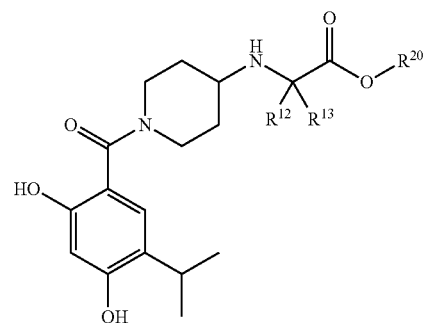
Route 2:
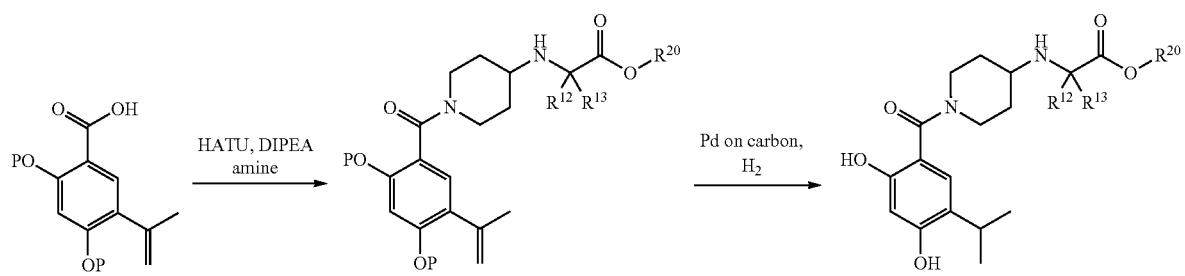
Route 3:
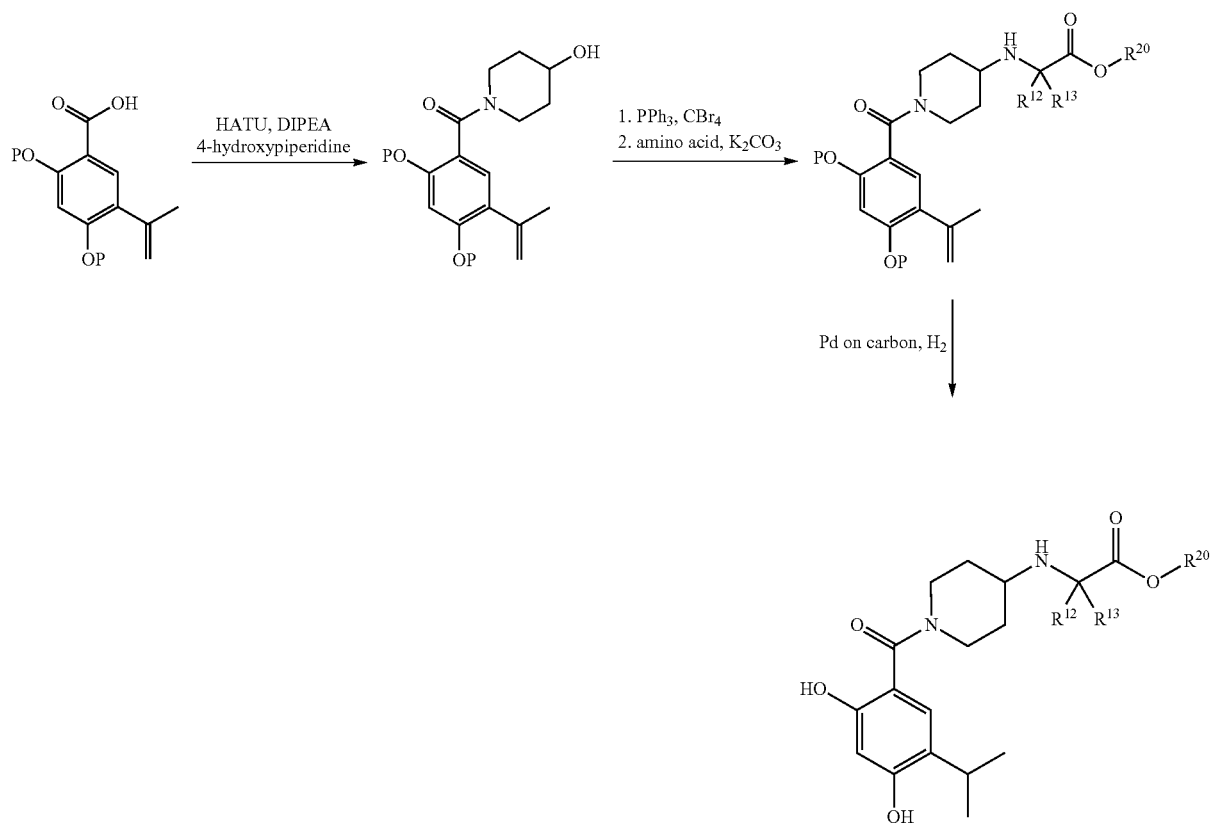

The piperidine based Hsp90 inhibitors can be prepared in a number of ways. Schemes 3, 4 and 5 illustrate the main routes employed for their preparation for the purpose of this application. To the chemist skilled in the art it will be apparent that there are other methodologies that will also achieve the preparation of these intermediates Scheme 4 - Generic scheme for the preparation of piperidino-methyl based inhibitors of Hsp90 ($R^{12}$, $R^{13}$ and $R^{20}$ are as defined herein, P is a suitable protecting group):

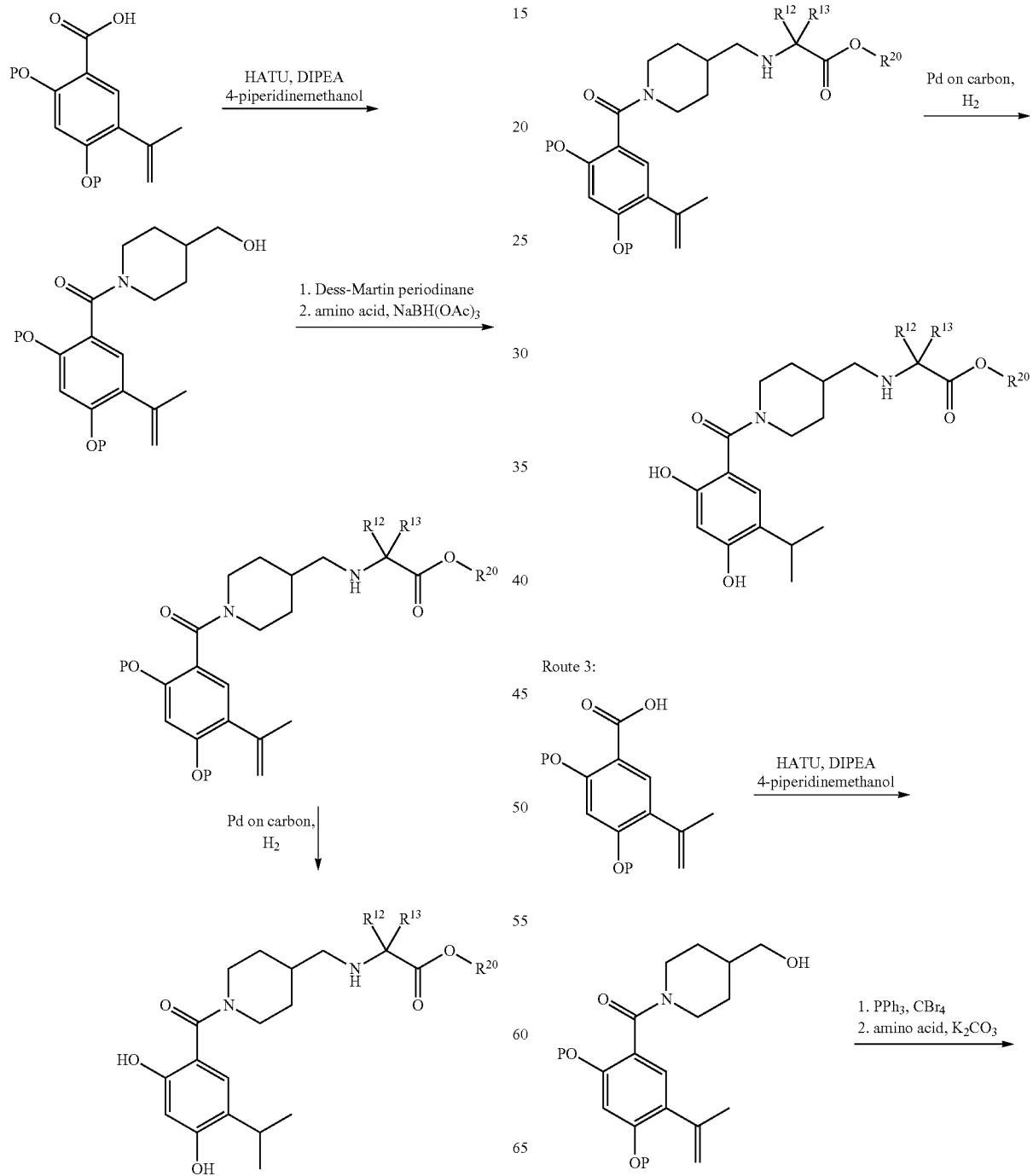

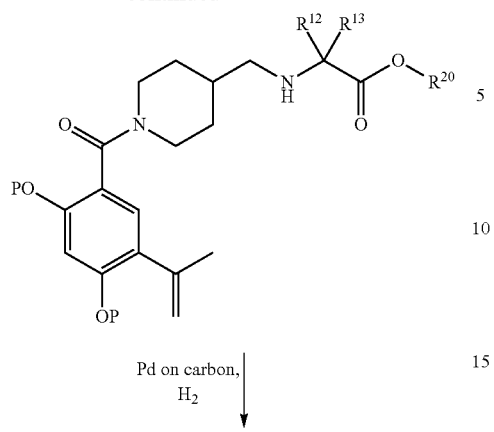
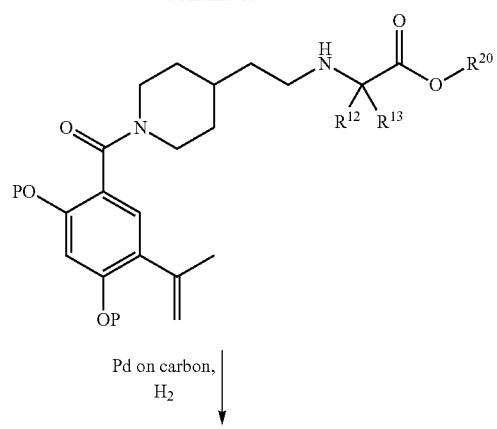
Scheme 5 - Generic scheme for the preparation of piperidino-ethyl based inhibitors of Hsp90 ($R^{12}$, $R^{13}$ and $R^{20}$ are as defined herein, P is a suitable protecting group):
Route 1:
Route 2:
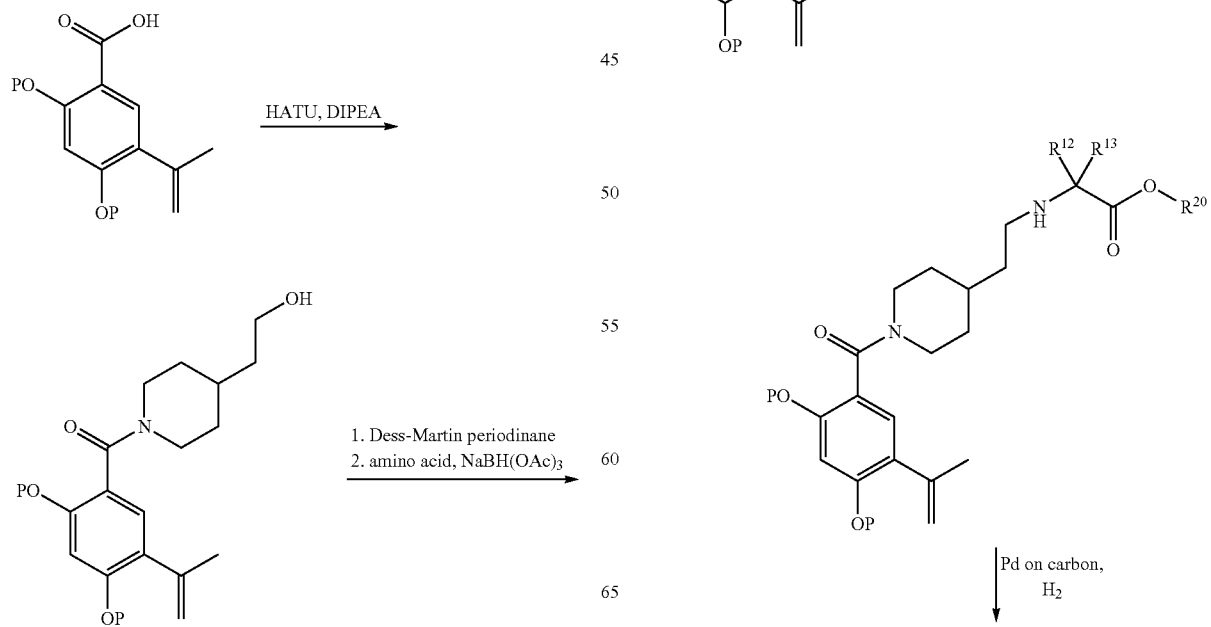

41
-continued
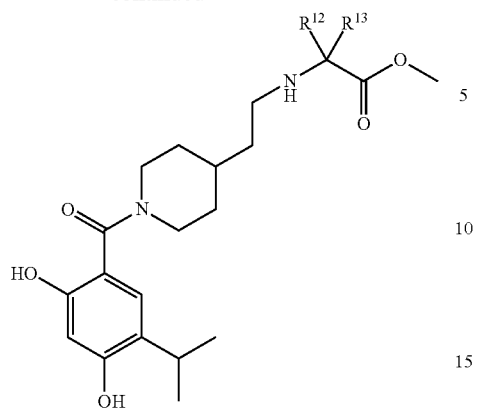
Route 3:
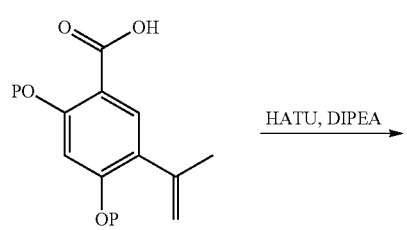
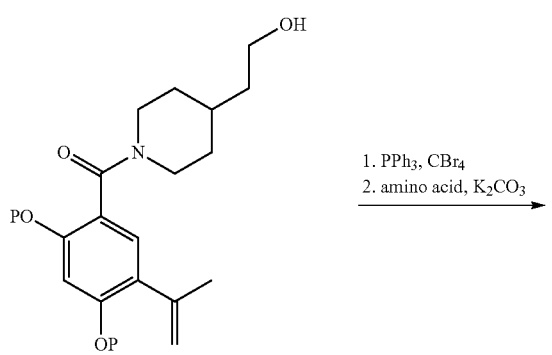
Pd on carbon, H₂ ↓
42
-continued
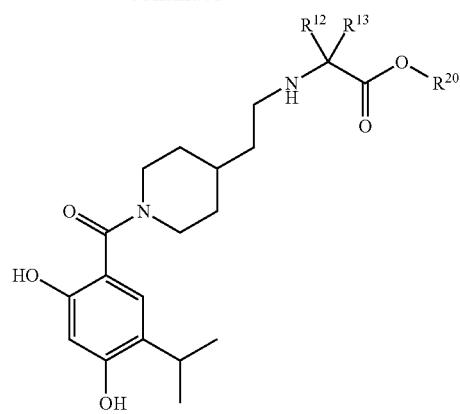
Scheme 6 - Generic scheme for the preparation of pyrrolidine based inhibitors of Hsp90 (R¹², R¹³ and R²⁰ are as defined herein, P is a suitable protecting group):
Route 1:
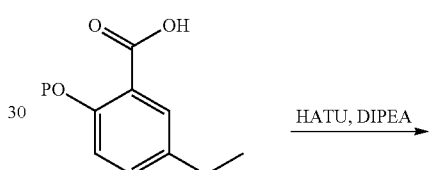
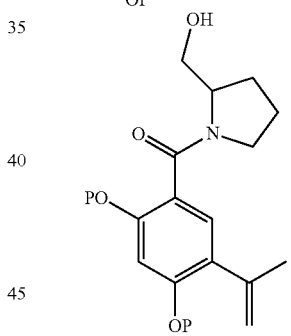
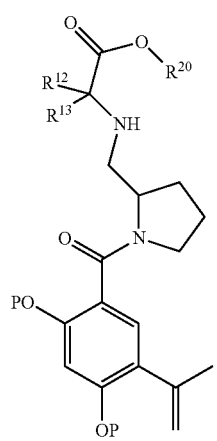
Pd on carbon, H₂ ↓

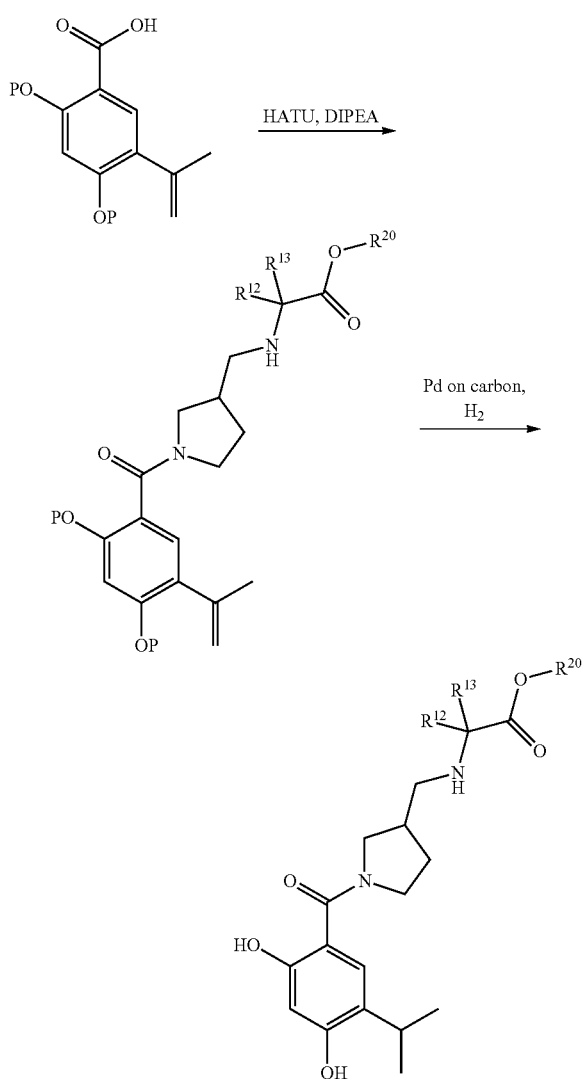

Route 2:

The pyrrolidine based Hsp90 inhibitors can be prepared in a number of ways. Scheme 6 illustrates the main routes employed for their preparation for the purpose of this application. To the chemist skilled in the art it will be apparent that there are other methodologies that will also achieve the preparation of these intermediates The following examples illustrate the preparation and properties of some specific compounds of the invention. The following abbreviations are used:

ACN=acetonitrile
Boc=tert-butoxycarbonyl
$CO_2$=carbon dioxide
DCE=dichloroethane
DCM=dichloromethane
Dess-Martin periodinane=1,1,1-Triacetoxy-1,1-dihydro-1,2-benziodoxol-3(1H)-one
DIPEA=diisopropylethylamine
DMAP=4-dimethylaminopyridine
DMF=dimethylformamide
DMP=Dess-Martin periodinane
DMSO=dimethyl sulfoxide
EDCI=N-(3-Dimethylaminopropyl)-N'-ethylcarbodiimide hydrochloride
$Et_2O$=diethyl ether
EtOAc=ethyl acetate
EtOH=ethanol
$Et_3N$ or TEA=triethylamine
ELS=Evaporative Light Scattering
g=gram(s)
HATU=2-(1H-7-Azabenzotriazol-1-yl)-1,1,3,3-tetramethyl uronium hexafluorophosphate
HCl=hydrochloric acid
HOBt=1-hydroxybenzotriazole
LC/MS=high performance liquid chromatography/mass spectrometry
$LiAlH_4$=lithium aluminium hydride
LiOH=lithium hydroxide
MeOH=methanol
$MgSO_4$=magnesium sulfate
mg=milligram(s)
mol=moles
mmol=millimole(s)
mL=milliliter
$N_2$=nitrogen
$Na_2CO_3$=sodium carbonate
$NaHCO_3$=sodium hydrogen carbonate
$Na_2SO_4$=sodium sulphate
NaH=sodium hydride
NaOH=sodium hydroxide
$NH_3$=ammonia
$NH_4Cl$=ammonium chloride
NMR=nuclear magnetic resonance
Pd/C=palladium on carbon
RT=room temperature
sat.=saturated aqueous solution
STAB=Sodium triacetoxyborohydride
TBAF=Tetrabutylammonium fluoride
TFA=trifluoroacetic acid
THF=tetrahydrofuran
TLC=thin layer chromatography Commercially available reagents and solvents (HPLC grade) were used without further purification. Solvents were removed using a Buchi rotary evaporator or a VirTis Benchtop SLC Freeze-dryer. Microwave irradiation was carried out using a Biotage Initiator™ Eight microwave synthesizer. Purification of compounds by flash chromatography column was performed using silica gel, particle size 40-63 µm (230-400 mesh) obtained from Fluorochem. Purification of compounds by preparative HPLC was performed on Gilson systems using reverse phase Axia™ prep Luna C18 columns (10 µm, 100×21.2 mm), gradient 0-100% B (A=water+0.05% TFA, B=acetonitrile) over 10 min, flow=25 mL/min, UV detection at 254 nm.

$^1$H NMR spectra were recorded on a Bruker 300 MHz AV spectrometer in deuterated solvents. Chemical shifts δ are in parts per million. Thin-layer chromatography (TLC) analysis was performed with Kieselgel 60 $F_{254}$ (Merck) plates and visualized using UV light.

Analytical HPLC/MS was performed on an Agilent HP 1100 LC system using reverse phase Luna C18 columns (3 μm, 50×4.6 mm), gradient 5-95% B (A=water+0.1% Formic acid, B=acetonitrile+0.1% Formic acid) over 2.25 min, flow=2.25 mL/min. UV spectra were recorded at 220 and 254 nm using a G1315B DAD detector. Mass spectra were obtained over the range m/z 150 to 800 on a LC/MSD SL G1956B detector. Data were integrated and reported using ChemStation and ChemStation Data Browser softwares.

Intermediates

Preparation of 2,4-bis(benzyloxy)-5-(prop-1-en-2-yl) benzoic acid (Intermediate A)

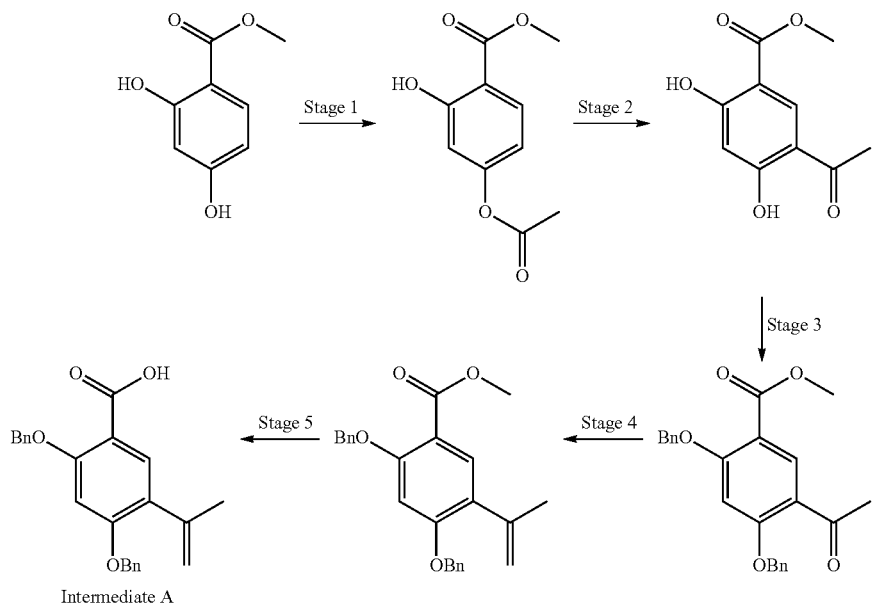

Intermediate A

Stage 1-methyl 4-(acetyloxy)-2-hydroxybenzoate

To a solution of methyl 2,4-dihydroxybenzoate (100.00 g, 595 mmol) in toluene (400 mL) was added 4-dimethylaminopyridine (0.45 g, 4.5 mmol) and acetic anhydride (60 mL, 635 mmol). The mixture was heated at 55° C. for 1 hour, then concentrated under vacuum. The product crystallized on standing overnight, and was used without further purification. LC/MS: m/z 211 [M-F-1-1]$^+$

Stage 2-methyl 5-acetyl-2,4-dihydroxybenzoate

The solid obtained in Stage 1 was broken into small chunks, and dissolved in toluene (500 mL). The solution was cooled (ice bath), then trifluoromethanesulfonic acid (52 mL, 588 mmol) was added slowly via a dropping funnel. After addition was complete the mixture was stirred for 30 minutes, warmed to room temperature and stirred for a further 2 hours. Acetyl chloride (4 ml, 56 mmol) was added and the solution stirred for a further 18 hours. The mixture was then poured into a 3 liter separating funnel and quenched by addition of sodium acetate solution (48.00 g in 400 mL water). Ethyl acetate was added (1000 mL) and the organic layer was washed with water (2 times 400 mL). The organic fraction was dried (MgSO$_4$), concentrated and purified by recrystallisation (10% isopropanol-heptane, approx. 1000 mL the hot solution was decanted from the recrystallisation flask to separate out a black, oiled-out residue) to yield the desired product (67.47 g, 321 mmol, 54% yield over 2 steps). The filtrate could be concentrated and recrystallised (EtOH) to yield a second crop of product. LC/MS: m/z 211 [M+H]$^+$

Stage 3-methyl 5-acetyl-2,4-bis(benzyloxy)benzoate

To a solution of product obtained in Stage 2 (67.47 g, 321 mmol) in acetonitrile (500 mL) was added potassium carbonate (97.26 g, 703 mmol) and benzyl bromide (77 ml, 643 mmol). The mixture was stirred at 75° C. for 18 hours. Additional benzyl bromide (2 ml, 16.7 mmol) was added and the mixture stirred for a further 24 hours. The solution was then poured into water (3000 ml) and the reaction flask washed out with further water (1000 ml). The product suspension was stirred thoroughly, product was collected by filtration and washed with water (500 mL) and dried under vacuum. The product was purified by recrystallisation (ethanol, approx 1100 mL) to yield the desired product (116.50 g, 89% yield). The filtrate could be concentrated and recrystallised (EtOH, approx 50 mL) to yield a second crop of product (6.60 g, 5% yield). LC/MS: m/z 391.25 [M+H]$^+$

Stage 4-methyl 2,4-bis(benzyloxy)-5-(prop-1-en-2-yl)benzoate

To a rapidly stirred suspension of methyltriphenylphosphonium bromide (34.00 g, 95.2 mmol) in dry THF (100 mL) was added potassium tert-butoxide (8.66 g, 77.2 mmol). The mixture was stirred vigorously for 30 minutes. The product of Stage 3 was added via a funnel (25.01 g, 64.1 mmol), and the mixture stirred for 30 minutes then quenched by addition of methanol (20 mL). The reaction mixture was concentrated under vacuum and the residue obtained purified by recrystallisation (methanol, approximately 400 mL) to yield the desired product (17.63 g, 71% yield). LC/MS: m/z 389.25 [M+H]$^+$

Stage 5—2,4-bis(benzyloxy)-5-(prop-1-en-2-yl)benzoic acid (Intermediate A)

To the product obtained in Stage 4 (38.33 g, 98.7 mmol) in methanol (500 mL) was added potassium hydroxide (12.70 g, 226 mmol). The mixture was heated at 75° C. for 20 hours, then cool to room temperature and poured into 2M HCl (2000 mL) and diluted with further water (1000 mL). After standing at room temperature for 30 minutes, the product was collected by filtration and purified by recrystallisation (ethanol) to yield the desired product (29.53 g, 80% yield). $^1$H NMR (300 MHz, d6-DMSO) 12.32 (1H, br s), 7.60 (1H, s), 7.52 (2H, d, J=7.0 Hz), 7.27-7.49 (8H, m), 6.94 (1H, s), 5.22 (4H, d, J=10.2 Hz), 5.06 (2H, d, J=7.2 Hz), 2.03 (3H, s). LC/MS: m/z 375.25 [M+H]$^+$ Preparation of Intermediates B1-B8 (Method 1)

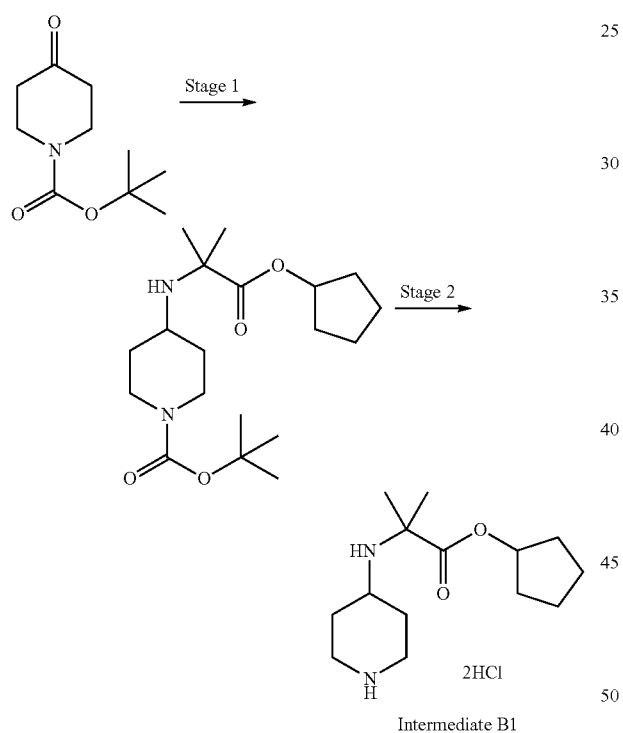

Intermediate B1

Stage 1-tert-butyl 4-{[1-(cyclopentyloxy)-2-methyl-1-oxopropan-2-yl]amino}piperidine-1-carboxylate To a solution of N-Boc-piperidinone (2.00 g, 10.0 mmol) in dichloroethane (25 mL) was added α,α-dimethylglycine cyclopentyl ester tosylate (3.97 g, 11.6 mmol) and sodium triacetoxyborohydride (4.248 g, 20.0 mmol). The mixture was stirred at room temperature for 22 hours then poured into ethyl acetate (300 mL). The organic layer was washed with water (3 times 100 mL), dried (MgSO$_4$) and concentrated to yield the desired product (3.556 g, 84% yield) which was carried forward without further purification. LC/MS: m/z 355.25 [M+H]$^+$

Stage 2—cyclopentyl 2-methyl-N-piperidin-4-ylalaninate dihydrochloride (Intermediate B1)

To the product obtained in stage 1 (3.540 g, 10.0 mmol) in dioxane (20 mL) was added HCl (20 mL, 4M solution in dioxane, 80 mmol). The solution was stirred at room temperature for 1 hour then concentrated under vacuum to yield the desired product (3.270 g, 100% yield, dihydrochloride salt) which was used without further purification. LC/MS: m/z 255.25 [M+H]$^+$ The Following Compounds were Prepared in a Simiar Fashion to Intermediate B1:

Intermediate B2—cyclopentyl N-piperidin-4-yl-L-leucinate dihydrochloride

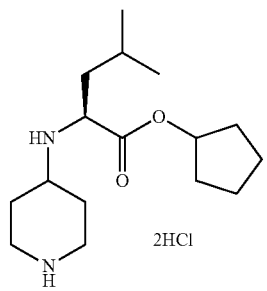 [SMILES: CC(C)C[C@H](NC1CCNCC1)C(=O)OC1CCCC1]

LC/MS: m/z 283.25 [M+H]$^+$

Intermediate B3—cyclonentyl N-piperidin-4-yl-L-norleucinate dihydrochloride

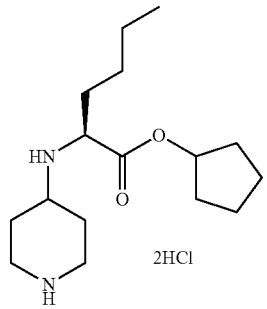 [SMILES: CCCC[C@H](NC1CCNCC1)C(=O)OC1CCCC1]

LC/MS: m/z 283 [M+H]$^+$

Intermediate B4—cyclopentyl N-piperidin-4-yl-L-phenylalaninate dihydrochloride

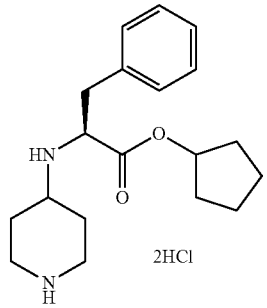 [SMILES: O=C(OC1CCCC1)[C@H](Cc1ccccc1)NC1CCNCC1]

LC/MS: m/z 317 [M41]$^+$

Intermediate B5—cyclopentyl N-piperidin-4-yl-L-alaninate dihydrochloride

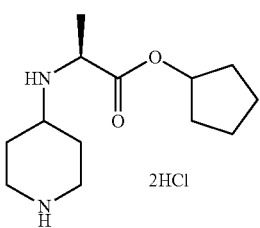 [SMILES: C[C@H](NC1CCNCC1)C(=O)OC1CCCC1]

LC/MS: m/z 283.25 [M+H]+

Intermediate B6—cyclopentyl (2S)-phenyl(piperidin-4-ylamino)ethanoate dihydrochloride

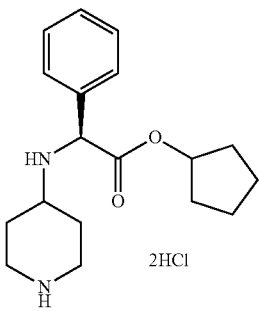 [SMILES: O=C(OC1CCCC1)[C@@H](NC1CCNCC1)c1ccccc1]

LC/MS: m/z 241 [M+H]+

Intermediate B7—cyclopentyl dihydrochloride

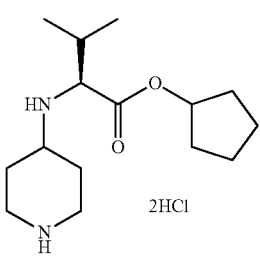 [SMILES: CC(C)[C@H](NC1CCNCC1)C(=O)OC1CCCC1]

LC/MS: m/z 255 [M+H]+

Intermediate B8—tert-butyl N-piperidin-4-yl-L-leucinate

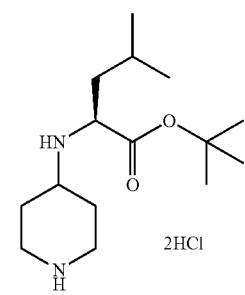 [SMILES: CC(C)C[C@H](NC1CCNCC1)C(=O)OC(C)(C)C]

LC/MS: m/z 271.25 [M+H]+

Preparation of intermediate B9—tert-butyl N-piperidin-4-yl-L-alaninate (Method 2)

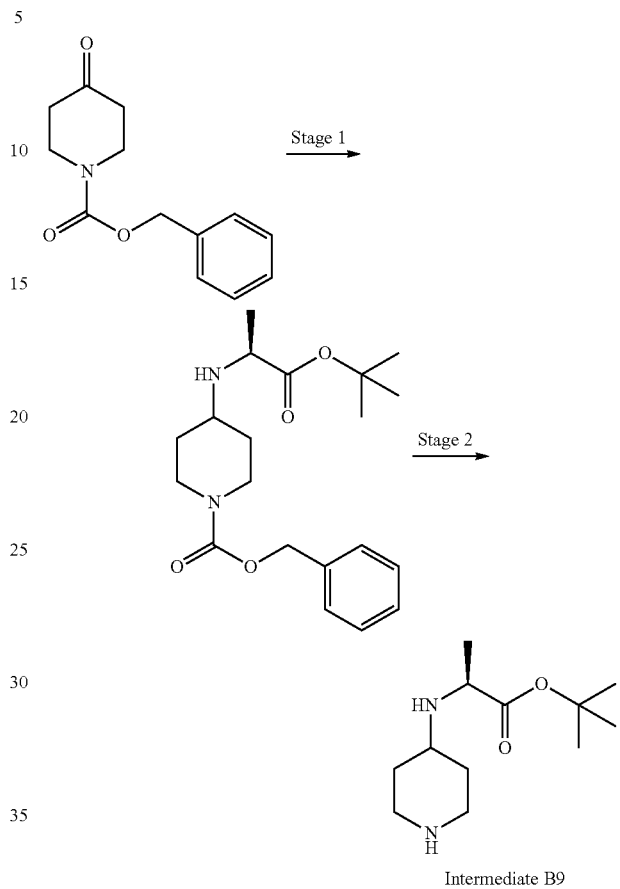

Stage 1—benzyl 4-{[(2S)-1-tert-butoxy-1-oxopropan-2-yl]amino}piperidine-1-carboxylate To a solution of N-Cbz-4-piperidinone (3.497 g, 15.0 mmol) in dichloroethane (100 mL) was added L-alanine tert-butyl ester hydrochloride (2.731 g, 15.03 mmol) and sodium triacetoxyborohydride (6.47 g, 30.5 mmol). The mixture was stirred for 20 hours at room temperature, then quenched by the addition of saturated ammonium chloride (100 mL). The mixture was poured into ethyl acetate (500 mL), washed with water (2 times 100 mL), dried (MgSO$_4$) and concentrated to yield the desired product (5.30 g, 97% yield). LC/MS: m/z 325.25 [M+H]+

Stage 2-tert-butyl N-piperidin-4-yl-L-alaninate (Intermediate B9)

To a solution of the product from Stage 1 (5.304 g, 14.6 mmol) in ethyl acetate (200 mL) was added palladium on carbon (1.77 g, 10%, 1.67 mmol, 11 mol %). The reaction vessel was evacuated and filled with hydrogen twice, then stirred for 3 h. The flask was purged with nitrogen, Celite was added, and the mixture filtered through a pad of Celite to yield the desired product (3.044 g, 72% yield). LC/MS: m/z 229.25 [M+H]+

Preparation of Intermediate B10—cyclopentyl N-piperidin-3-yl-L-leucinate dihydrochloride

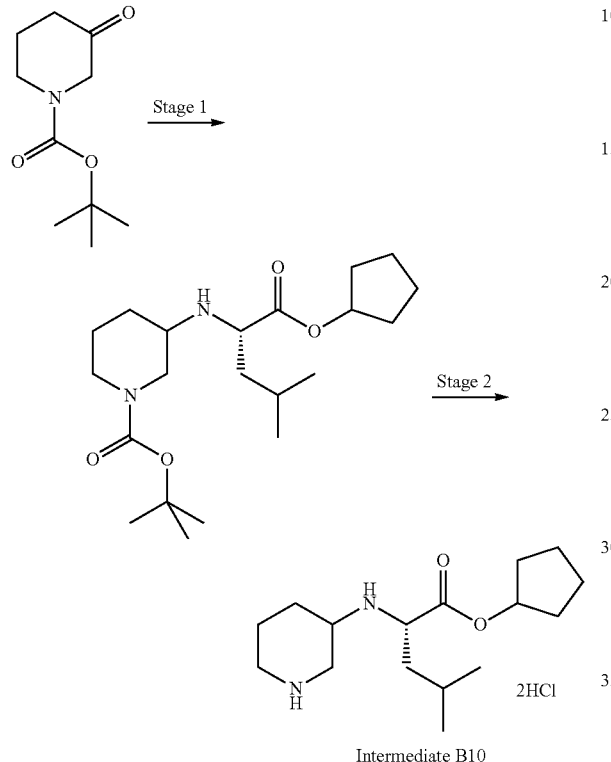

Intermediate B10

Preparation of Intermediate B11—cyclopentyl N-pyrrolidin-3-yl-L-leucinate

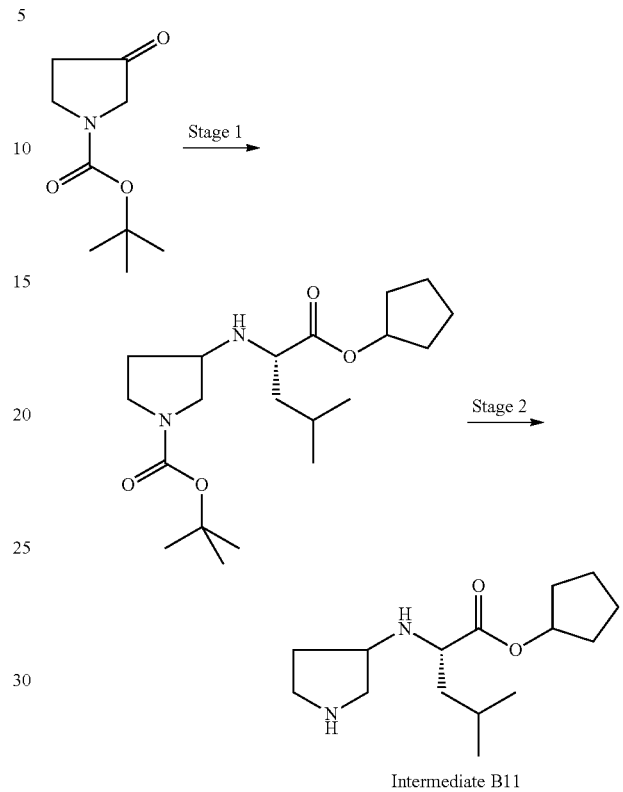

Intermediate B11

Stage 1—cyclopentyl N-[1-(tert-butoxycarbonyl) piperidin-3-yl]-L-leucinate

To a solution of 3-oxo-piperidine-1-carboxylic acid tert-butyl ester (0.458 g, 2.3 mmol) in dichloroethane (18 mL) was added the tosic acid salt of (S)-2-amino-4-methyl-pentanoic acid cyclopentyl ester (0.496 g, 2.53 mmol) and sodium triacetoxyborohydride (0.975 g, 4.6 mmol). The solution was stirred at room temperature for 18 hours. An aqueous solution of sodium hydrogen carbonate (20 mL) was added and the mixture stirred for 20 minutes. The desired product was extracted into ethyl acetate (3 times 15 mL). The organic layers were combined, dried (MgSO4) and concentrated to give the desired product (0.840 g, 95% yield) which was used without further purification. LC/MS: m/z 383 [M+H]+

Stage 2—cyclopentyl N-piperidin-3-yl-L-leucinate dihydrochloride

To a solution of 3-((S)-1-cyclopentyloxycarbonyl-3-methyl-butylamino)-piperidine-1-carboxylic acid tert-butyl ester (0.840 g, 2.20 mmol) in dichloromethane (5 mL) was added 4M hydrogen chloride in dioxane (10 mL). The reaction was stirred at room temperature for 90 minutes and then concentrated to give the product (184 mg, 24% yield). LC/MS: m/z 283 [M+H]+

Stage 1—cyclopentyl N-[1-(tert-butoxycarbonyl) pyrrolidin-3-yl]-L-leucinate

To a solution of N-tert-butoxycarbonyl-3-pyrrolidinone (0.382 g, 4.76 mmol) in dichloroethane (20 mL) was added L-leucine cyclopentyl ester tosylate (1.96 g, 5.3 mmol) and sodium triacetoxyborohydride (2.65 g, 12.5 mmol). The mixture was stirred at room temperature for 3 hours, then poured into ethyl acetate (150 mL) and quenched with saturated ammonium chloride solution (50 mL) and washed with saturated sodium hydrogen carbonate solution (3 times 30 mL). The organic extracts were dried (MgSO4), concentrated and purified by flash column chromatography (7:3 ethyl acetate: heptane) to yield the desired product. LC/MS: m/z 369.25 [M+H]+

Stage 2—cyclopentyl N-pyrrolidin-3-yl-L-leucinate

To a solution of the product of Stage 1 in dichloromethane (5 mL) was added HCl (2 times 10 mL, 4M solution in dioxane, 80 mmol). The mixture was stirred at room temperature for 1 hour, diethyl ether (100 mL) was added and the product collected by filtration. The solid was washed with diethyl ether (50 mL) then dried under vacuum to give the desired product (0.855 g, 53% yield over two steps). LC/MS: m/z 269.25 [M+H]+

53

Preparation of 1-{[2,4-bis(benzyloxy)-5-(prop-1-en-2-yl)phenyl]carbonyl}piperidine-4-carbaldehyde (Intermediate C)

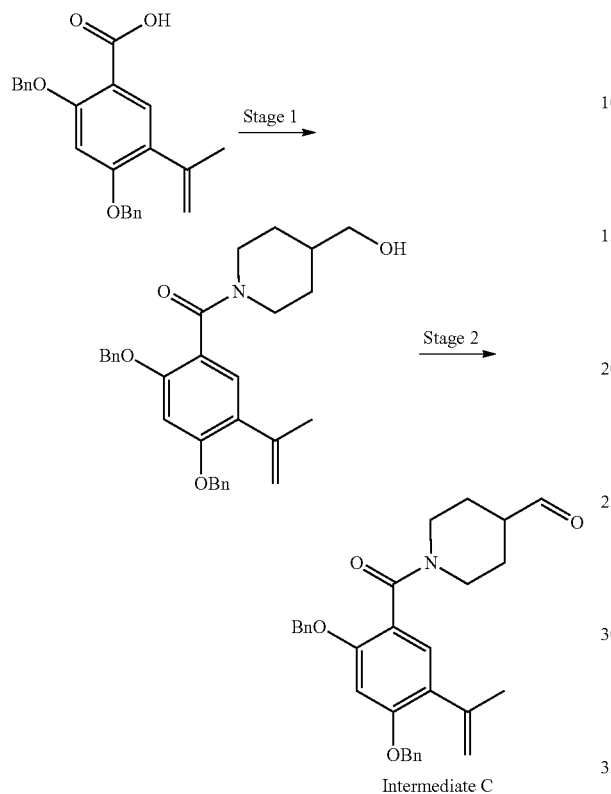

Intermediate C

54

Preparation of (1-{[2,4-bis(benzyloxy)-5-(prop-1-en-2-yl)phenyl]carbonyl}piperidin-4-yl)acetaldehyde (Intermediate D)

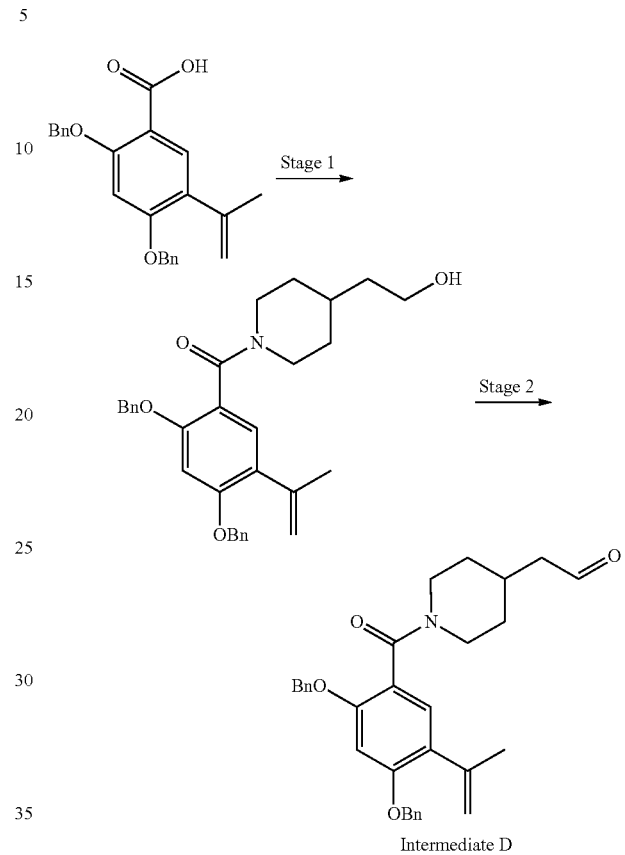

Intermediate D

Stage 1—[2,4-bis(benzyloxy)-5-(prop-1-en-2-yl)phenyl][4-(hydroxymethyl)piperidin-1-yl]methanone To a solution of Intermediate A (2.156 g, 5.76 mmol), in dichloromethane (50 mL) was added 4-piperidinemethanol (1.186 g, 10.3 mmol), triethylamine (5 mL, 35 mmol) and EDCI (3.39 g, 17.7 mmol). The mixture was stirred at room temperature for 36 hours, poured into ethyl acetate (250 mL), and washed with 1M HCl (200 mL). The organic extract was dried (MgSO$_4$), concentrated and purified by flash column chromatography to yield the desired product (1.456 g, 54% yield). LC/MS: m/z 472.25 [M+H]$^+$ Stage 2—1-{[2,4-bis(benzyloxy)-5-(prop-1-en-2-yl)phenyl]carbonyl}piperidine-4-carbaldehyde (Intermediate C)

To a solution of the product of Stage 1 (0.250 g, 0.53 mmol) in dichloromethane (20 mL) was added 4 Å molecular sieves (1.68 g), N-methylmorpholine-N-oxide (0.323 g, 2.75 mmol) and tetrapropylammonium perruthenate (0.011 g, 0.031 mmol, 6 mol %). The mixture was stirred at room temperature for 90 minutes, then filtered through a pad of silica gel (35 mm across×50 mm deep), washing with ethyl acetate (100 mL). The filtrate was concentrated under vacuum to yield the desired product (0.194 g, 78% yield), which was used without further purification.

Stage 1—[2,4-bis(benzyloxy)-5-(prop-1-en-2-yl)phenyl][4-(2-hydroxyethyl)piperidin-1-yl]methanone To 4-piperidine ethanol (1.026 g, 7.9 mmol) in dichloromethane (10 mL) was added Intermediate A (1.84 g, 4.92 mmol), N,N-diisopropylethylamine (2 mL, 11.5 mmol) and EDCI (3.87 g, 20 mmol). The mixture was stirred for 7 hours, then loaded directly onto a silica gel column and eluted with ethyl acetate to give the desired product (1.808 g, 76% yield). LC/MS: m/z 486.25 [M+H]$^+$ Stage 2—(1-{[2,4-bis(benzyloxy)-5-(prop-1-en-2-yl)phenyl]carbonyl}piperidin-4-yl)acetaldehyde (Intermediate D)

To a solution of the product of Stage 1 (0.245 g, 0.50 mmol) in dichloromethane (8 mL) was added Dess-Martin periodinane (0.275 g, 0.64 mmol). After 2 hours, a second portion of Dess-Martin periodinane (0.105 g, 0.24 mmol) was added and the mixture stirred for a further 30 minutes. The reaction was quenched by addition of 1:1 saturated sodium hydrogen carbonate:sodium thiosulfate (10 mL). After stirring for 5 minutes, the mixture was poured into ethyl acetate (100 mL) and washed with water (3 times 20 mL). The organic extract was dried and concentrated and carried forward without any further purification.

Preparation of Intermediate E—2-{[2,4-bis(benzyloxy)-5-(prop-1-en-2-yl)phenyl]carbonyl}-2,3-dihydro-1H-isoindole-5-carbaldehyde

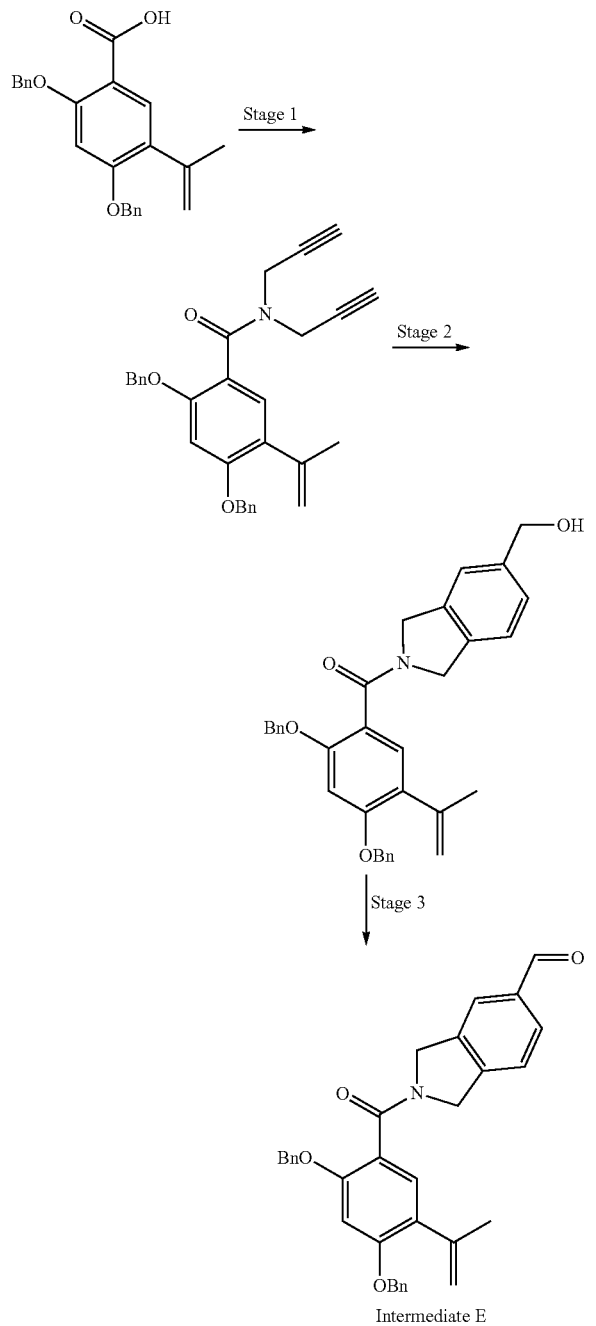

Stage 1—2,4-bis(benzyloxy)-5-(prop-1-en-2-yl)-N,N-di(prop-2-yl)-1-yl)benzamide To a solution of N,N-dipropargylamine hydrochloride (3.36 g, 25.9 mmol) in dichloromethane (100 mL) was added N,N-diisopropylethylamine (10 mL, 57 mmol), Intermediate A (3.48 g, 10.1 mmol), 4-dimethylaminopyridine (0.245 g, 2 mmol) and EDCI (5.69 g, 29.7 mmol). The mixture was stirred at room temperature for 100 hours, then poured into diethyl ether (400 mL) and washed with 1M HCl solution (4 times 50 mL). The organic fraction was dried (MgSO$_4$), filtered through a plug of Celite (washing with ether), then concentrated under vacuum to yield the desired product (3.208 g, 71% yield). LC/MS: m/z 450 [M+H]$^+$

Stage 2—[2,4-bis(benzyloxy)-5-(prop-1-en-2-yl)phenyl][5-(hydroxymethyl)-1,3-dihydro-2H-isoindol-2-yl]methanone To a solution of the product of Stage 1 (3.208 g, 7.13 mmol) in toluene (20 mL) was added propargyl alcohol (1 mL, 17.2 mmol). The solution was heated to 65° C., then RhCl(PPh$_3$)$_3$ (0.033 g, 0.020 g, 0.06 mmol) was added in two portions five minutes apart. The mixture was heated for two hours, cooled and the product mixture concentrated onto silica gel. Purification by flash column chromatography (SiO$_2$, 7:3 ethyl acetate:heptane) yielded the desired product (2.483 g, 69% yield). LC/MS: m/z 506.25 [M+H]$^+$

Stage 3—2-{[2,4-bis(benzyloxy)-5-(prop-1-en-2-yl)phenyl]carbonyl}-2,3-dihydro-1H-isoindole-5-carbaldehyde (Intermediate E)

To a solution of the product of Stage 2 (0.915 g, 1.8 mmol) in dichloromethane (100 mL) was added manganese dioxide (4.310 g, 50 mmol). The suspension was stirred for 30 minutes then filtered through Celite. The filtrate was concentrated to yield the desired product that was used without further purification (0.805 g, 89% yield).

Preparation of Intermediate F—(2-{[2,4-bis(benzyloxy)-5-(prop-1-en-2-yl)phenyl]carbonyl}-2,3-dihydro-1H-isoindol-5-yl)acetaldehyde

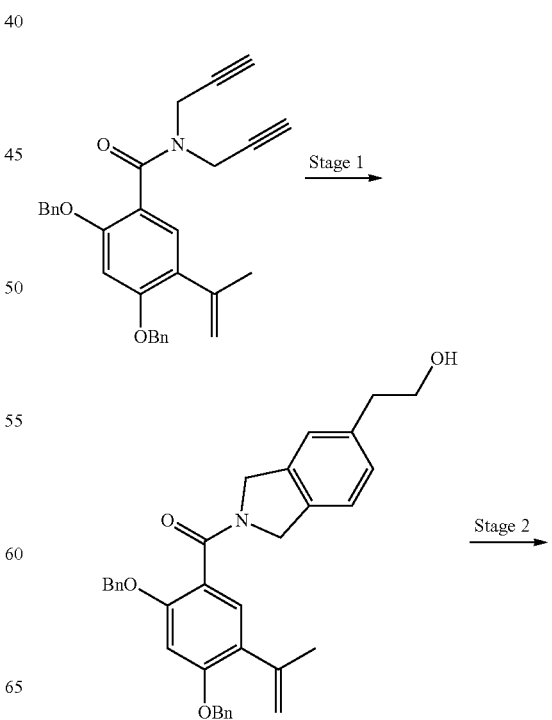

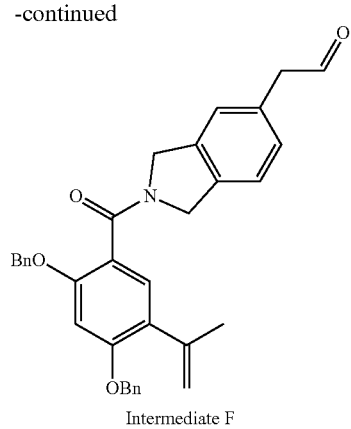

Intermediate F

Stage 1—[2,4-bis(benzyloxy)-5-(prop-1-en-2-yl)phenyl][5-(2-hydroxyethyl)-1,3-dihydro-2H-isoindol-2-yl]methanone To a solution of 2,4-bis-benzyloxy-5-isopropenyl-N,N-diprop-2-ynyl-benzamide (0.940 g, 2.1 mmol) in ethyl acetate (2 mL) was added 3-butyn-1-ol (0.30 mL, 4.0 mmol) and RhCl(PPh$_3$)$_3$ (0.162 g, 0.17 mmol). The mixture was stirred at room temperature for 24 hours, then loaded directly onto a silica gel column, eluting with 7:3 ethyl acetate:heptane to give the desired product (0.444 g, 38% yield). LC/MS: m/z 520.25 [M+H]$^+$

Stage 2—(2-{[2,4-bis(benzyloxy)-5-(prop-1-en-2-yl)phenyl]carbonyl}-2,3-dihydro-1H-isoindol-5-yl)acetaldehyde (Intermediate F)

To a solution of the product of Stage 1 (0.169 g, 0.32 mmol) in dichloromethane (5 mL) was added Dess-Martin periodinane (0.295 g, 0.69 mmol). The solution was stirred for 90 minutes then quenched by addition of 1:1 saturated sodium hydrogen carbonate:saturated sodium thiosulfate (20 mL). After two minutes, the mixture was poured into dichloromethane (100 mL), and product extracted with dichloromethane (100 mL). The combined organic extracts were dried (MgSO$_4$) and concentrated to yield the desired product which was used without further purification.

Preparation of Intermediate G—3-(2-{[2,4-bis(benzyloxy)-5-(prop-1-en-2-yl)phenyl]carbonyl}-2,3-dihydro-1H-isoindol-5-yl)propanal

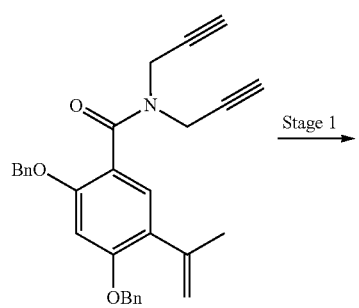

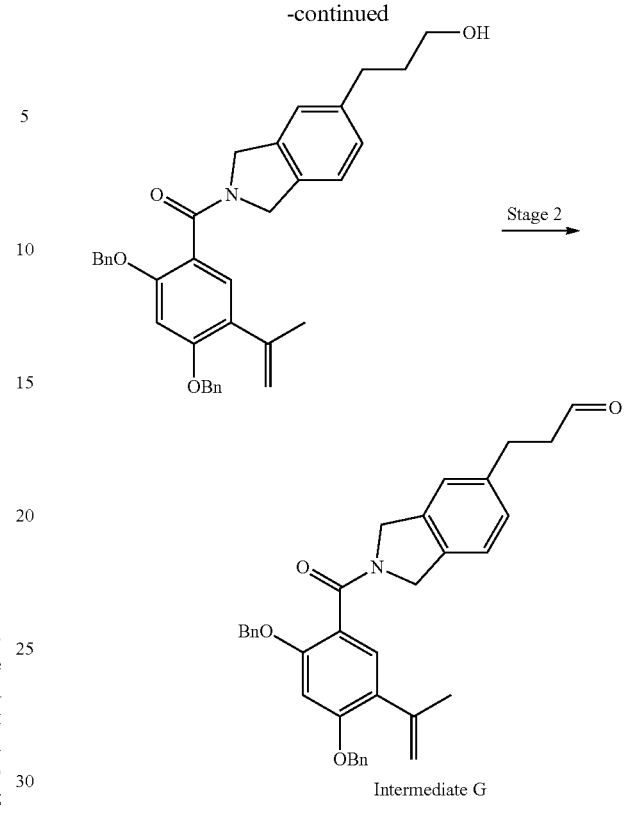

Intermediate G

Stage 1—[2,4-bis(benzyloxy)-5-(prop-1-en-2-yl)phenyl][5-(3-hydroxypropyl)-1,3-dihydro-2H-isoindol-2-yl]methanone To a solution of 2,4-bis-benzyloxy-5-isopropenyl-N,N-diprop-2-ynyl-benzamide (0.545 g, 1.21 mmol) in ethyl acetate (10 mL) was added 4-pentyn-1-ol (0.30 mL, 3.2 mmol) and RhCl(PPh$_3$)$_3$ (0.161 g, 0.17 mmol). Solvent was removed under vacuum, and the mixture stirred at room temperature overnight. Additional 4-pentyn-1-ol (2.5 mL, 26 mmol) and RhCl(PPh$_3$)$_3$ (0.155 g, 0.17 mmol) were added and the mixture stirred for 48 hours. The mixture was loaded onto a silica gel column and eluted with 7:3 ethyl acetate:heptane to yield the desired product (0.254 g, 39% yield). LC/MS: m/z 534.25 [M+H]$^+$

Stage 2—3-(2-{[2,4-bis(benzyloxy)-5-(prop-1-en-2-yl)phenyl]carbonyl}-2,3-dihydro-1H-isoindol-5-yl)propanal (Intermediate G)

To a solution of the product of Stage 1 (0.160 g, 0.30 mmol) in dichloromethane (5 mL) was added Dess-Martin periodinane (0.290 g, 0.68 mmol). The solution was stirred for 90 minutes then quenched by addition of 1:1 saturated sodium hydrogen carbonate:saturated sodium thiosulfate (20 mL). After two minutes, the mixture was poured into dichloromethane (100 mL), and product extracted with dichloromethane (100 mL). The combined organic extracts were dried (MgSO$_4$) and concentrated to yield the desired product which was used without further purification.

Preparation of Intermediate H—2,4-bis(benzyloxy)-N-(3-formylbenzyl)-N-methyl-5-(prop-1-en-2-yl)benzamide

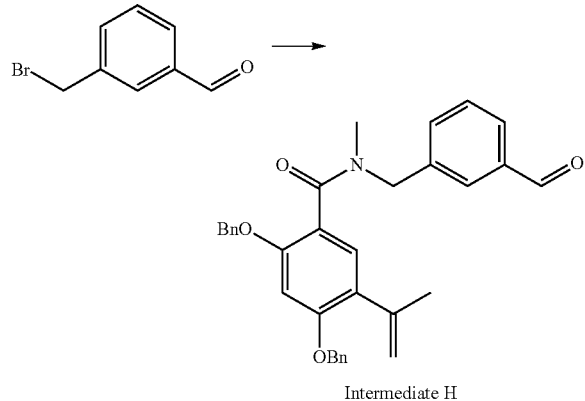

Intermediate H

To 3-(bromomethyl)benzaldehyde (0.734 g, 3.69 mmol) was added methylamine (8M in methanol). The mixture was stirred for 1 hour and then concentrated under vacuum. The residue obtained was dissolved in dichloromethane (10 mL) and N,N-diisopropylethylamine (5 mL, 28.6 mmol), Intermediate A (1.29 g, 3.45 mmol) and HATU (3.17 g, 8.28 mmol) were added. The mixture was stirred at room temperature for 18 hours, then loaded directly onto a silica gel column and eluted with heptane:ethyl acetate to yield the desired product (0.128 g, 14% yield). LC/MS: m/z 506.25 [M+H]$^+$

Preparation of Intermediate I—2,4-bis(benzyloxy)-N-(4-formylbenzyl)-N-methyl-5-(prop-1-en-2-yl)benzamide

Stage 1—4-{[(tert-butoxycarbonyl)amino]methyl}benzoic acid

To a solution of 4-aminomethyl benzoic acid (19.22 g, 126 mmol) in THF (200 mL) was added saturated sodium hydrogen carbonate solution (300 mL) and di-tert-butyl dicarbonate (42.72 g, 195.7 mmol). The mixture was stirred at room temperature for 48 hours, then poured into ethyl acetate (250 mL). The aqueous layer was washed with ethyl acetate (250 mL), then acidified with 2M HCl solution. The precipitate was collected by filtration and dried under high vacuum to yield the desired product (24.6 g, 78% yield). LC/MS: m/z 274 [M+Na]$^+$

Stage 2—{4-[(methylamino)methyl]phenyl}methanol

To a cooled (ice bath) suspension of lithium aluminium hydride (5.03 g, 132 mmol) in tetrahydrofuran (100 mL) was added slowly a solution of the product of Stage 1 (5.34 g, 21 mmol) in tetrahydrofuran (20 mL). After addition was complete, the mixture was warmed to room temperature then heated at reflux for 96 hours. The mixture was then cooled to room temperature and excess lithium aluminium hydride quenched by careful addition of ethyl acetate (20 mL over 15 minutes) followed by slow addition of 2M HCl (100 mL). The mixture was extracted with ethyl acetate (2 times 100 mL). The aqueous layer was then basified by addition of sodium hydroxide and di-tert-butyl dicarbonate (9.0 g, 27 mmol) was added. The mixture was stirred at room temperature for 3 hours, then product was extracted with ethyl acetate (3 times 250 mL), the combined organic extracts were dried (MgSO$_4$) and concentrated.

To the residue obtained (1.278 g, 16% yield) was added HCl (10 mL, 4M solution in dioxane). The solution was stirred at room temperature for 1 hour, then concentrated under vacuum. The solid obtained was washed with diethyl ether (2 times 50 mL), and dried to yield the desired product (0.890 g, 23% yield). LC/MS: m/z 152 [M+H]$^+$

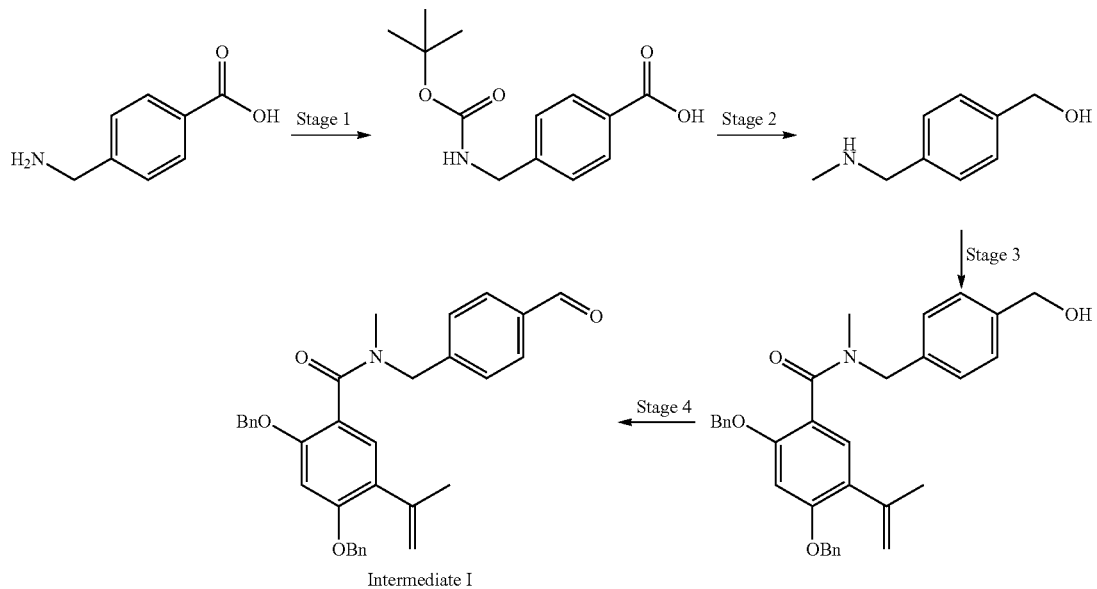

Intermediate I

Stage 3—2,4-bis(benzyloxy)-N-[4-(hydroxymethyl)benzyl]-N-methyl-5-(prop-1-en-2-yl)benzamide To a suspension of the product of Stage 2 (0.890 g, 4.6 mmol) in dichloromethane (20 mL) was added Intermediate A (1.278 g, 3.42 mmol), N,N-diisopropylethylamine (7 mL, 40 mmol) and EDCI (3.05 g, 15.9 mmol), The mixture was stirred for 16 hours then poured into ethyl acetate and washed with 0.5M HCl (2 times 50 mL) and brine (100 mL). The organic fraction was dried (MgSO$_4$), concentrated and purified by flash column chromatography (SiO$_2$, 1:1 ethyl acetate:heptane) to yield the desired product (0.646 g, 37% yield). LC/MS: m/z 508.25 [M+H]$^+$ Stage 4—2,4-bis(benzyloxy)-N-(4-formylbenzyl)-N-methyl-5-(prop-1-en-2-yl)benzamide (Intermediate I)

To a solution of the product of Stage 3 (630 mg, 1.24 mmol) in dichloromethane (100 mL) was added manganese dioxide (4.60 g, 52.8 mmol). The mixture was stirred for 10 minutes then filtered through Celite and concentrated to yield the desired product (0.506 g, 81% yield) which was used without further purification.

Preparation of Intermediate J—1-{[2,4-bis(benzyloxy)-5-(prop-1-en-2-yl)phenyl]carbonyl}piperidin-4-one

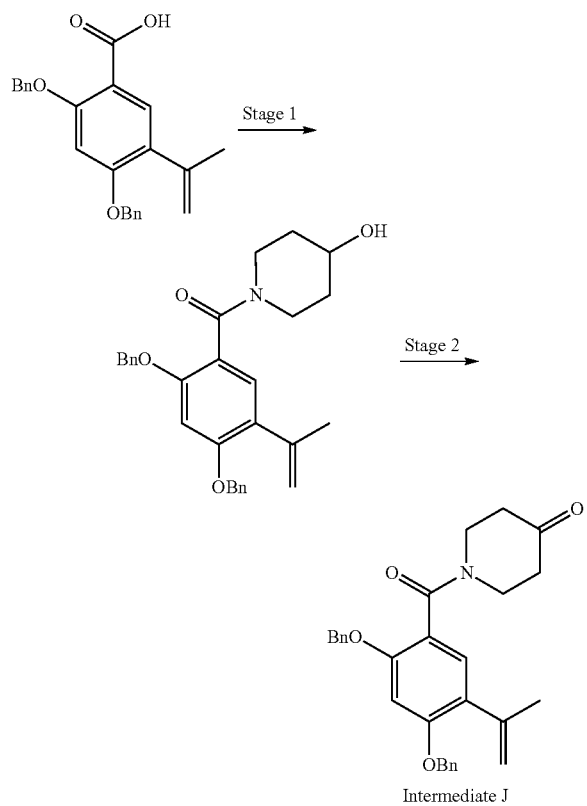

Stage 1—[2,4-bis(benzyloxy)-5-(prop-1-en-2-yl)phenyl](4-hydroxypiperidin-1-yl)methanone To a solution of intermediate A (2.313 g, 6.2 mmol) in DCM (20 mL) was added 4-hydroxypiperidine (1.11 g, 10.97 mmol), DIPEA (3 mL) and EDC (2.62 g, 13.7 mmol). The solution was stirred at room temperature for 23 hours, then purified directly by dry flash chromatography (ethyl acetate) to yield the desired product (1.764 g, 62% yield). LC/MS: m/z 458.25 [M+H]$^+$ Stage 2—1-{[2,4-bis(benzyloxy)-5-(prop-1-en-2-yl)phenyl]carbonyl}piperidin-4-one (Intermediate J)

To a solution of the product of Stage 1 (0.850 g, 1.85 mmol) in DCM (30 mL) was added Dess-Martin periodinane (1.42 g, 3.34 mmol). The reaction was stirred at room temperature until consumption of the starting material was complete. The reaction was quenched by addition of 1:1 saturated sodium hydrogen carbonate:sodium thiosulfate (30 mL), then extracted with ethyl acetate (20 mL, 10 mL). The combined organic extracts were dried (MgSO$_4$) and concentrated to yield the desired product which was used without further purification (containing some excess oxidant). LC/MS: m/z 456 [M+H]$^+$

EXAMPLES

Preparation of Example 1 cyclopentyl N-(1-{[2,4-dihydroxy-5-(propan-2-yl)phenyl]carbonyl}piperidin-4-yl)-L-leucinate

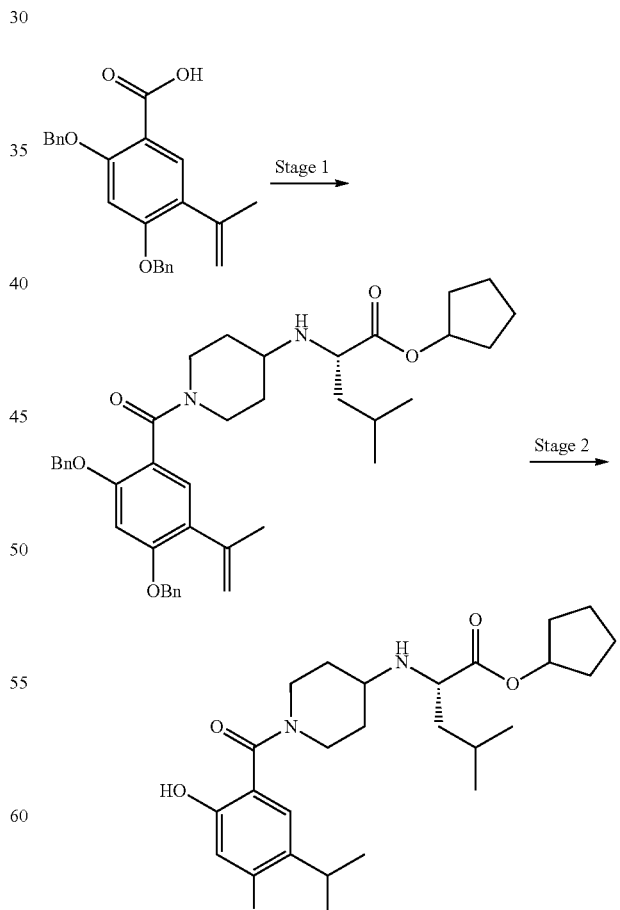

Stage 1—cyclopentyl N-(1-{[2,4-bis(benzyloxy)-5-(prop-1-en-2-yl)phenyl]carbonyl}piperidin-4-yl)-L-leucinate To a solution of Intermediate A (0.883 g, 2.37 mmol) in dichloromethane (10 mL) was added triethylamine (2 mL, 14.3 mmol), Intermediate B2 (1.043 g, 2.9 mmol), 4-dimethylaminopyridine (0.094 g, 0.77 mmol) and EDCI (1.47 g, 7.7 mmol). The mixture was stirred at room temperature for 18 hours, then poured into ethyl acetate (150 mL). The organic extract was washed with water (3 times 50 mL), dried ($MgSO_4$), concentrated and purified by flash column chromatography ($SiO_2$, 7:3 EtOAc:heptane) to yield the desired product (0.908 g, 60% yield). LC/MS: m/z 639.25 $[M+H]^+$ Stage 2—cyclopentyl N-(1-{[2,4-dihydroxy-5-(propan-2-yl)phenyl]carbonyl}piperidin-4-yl)-L-leucinate (Example 1)

To a solution of the product of Stage 1 (0.908 g, 1.92 mmol) in ethyl acetate (30 mL) was added palladium on carbon (0.857 g, 10%, 0.8 mmol, 56%). The reaction vessel was evacuated and filled with hydrogen twice. The mixture was stirred for 1 hour then purged with nitrogen. Celite was added, and the mixture filtered through Celite, washing with additional ethyl acetate (100 ml). The filtrate was then concentrated to yield the desired product (0.596 g, 91% yield). $^1$H NMR (300 MHz, d6-DMSO) 9.46 (1H, s), 9.41 (1H, s), 6.79 (1H, s), 6.32 (1H, s), 5.09 (1H, t, J=6.0 Hz), 3.69-3.93 (2H, m), 3.17-3.29 (1H, m), 3.05 (1H, sep, J=6.8 Hz), 2.91 (2H, q, J=10.5 Hz), 2.45-2.63 (1H, m), 1.50-1.97 (12H, m), 1.33 (2H, t, J=7.0 Hz), 1.14-1.26 (1H, m), 1.09 (6H, d, J=6.9 Hz), 0.87 (3H, d, J=6.7 Hz), 0.84 (3H, d, J=6.6 Hz). LC/MS: purity >98%, m/z 461.25 $[M+H]^+$ The Following Compounds were Prepared in a Simiar Fashion to Example 1:

Example 2 cyclopentyl N-(1-{[2,4-dihydroxy-5-(propan-2-yl)phenyl]carbonyl}piperidin-4-yl)-2-methylalaninate Prepared from Intermediate A and Intermediate B1. $^1$H NMR (300 MHz, d6-DMSO) 9.47 (1H, s), 9.42 (1H, s), 6.79 (1H, s), 6.33 (1H, s), 5.04 (1H, t, J=5.8 Hz), 3.75-3.95 (2H, m), 3.05 (1H, sep, J=6.8 Hz), 2.86 (2H, t, J=12.2 Hz), 2.54-2.61 (1H, obs m), 1.47-1.98 (12H, m), 1.17 (6H, s), 1.09 (6H, d, J=6.8 Hz)
LC/MS: purity 98%, m/z 433.25 $[M+H]^+$ Example 3 cyclopentyl N-(1-{[2,4-dihydroxy-5-(propan-2-yl)phenyl]carbonyl}piperidin-4-yl)-L-valinate Prepared from Intermediate A and Intermediate B7. $^1$H NMR ($CDCl_3$) 10.01 (1H, br s), 7.07 (1H, s), 6.40 (1H, s), 5.26 (1H, t, J=5.8 Hz), 4.29-4.03 (2H, m), 3.32-3.01 (4H, m), 1H, br s), 2.72 (1H, br s), 2.01-1.35 (15H, m), 1.22 (6H, d, J=7.0 Hz), 0.96 (6H, m)
LC/MS: purity 100%, m/z 477 $[M+H]^+$ Example 4 cyclopentyl (2S)-[(1-{[2,4-dihydroxy-5-(propan-2-yl)phenyl]carbonyl}piperidin-4-yl)amino](phenyl)ethanoate Prepared from Intermediate A and Intermediate B6. $^1$H NMR ($CDCl_3$) 7.51-7.29 (5H, m), 7.02 (1H, s), 6.37 (1H, s), 5.20 (1H, m), 4.52 (1H, s), 4.32-4.04 (2H, m), 3.13-2.95 (2H, m), 2.87-2.61 (1H, m), 2.16-1.38 (12H, m), 1.17 (6H, d, J=6.8 Hz)
LC/MS: purity 100%, m/z 481 $[M+H]^+$ Example 5 cyclopentyl N-(1-{[2,4-dihydroxy-5-(propan-2-yl)phenyl]carbonyl}piperidin-4-yl)-L-alaninate Prepared from Intermediate A and Intermediate B5. $^1$H NMR (300 MHz, d6-DMSO) 9.45 (1H, s), 9.41 (1H, s), 6.80 (1H, s), 6.33 (1H, s), 5.76 (1H, s), 5.09 (1H, m), 4.09 (1H, q, J=5.4 Hz), 3.84 (2H, br s), 3.05 (1H, m), 2.89 (2H, q, J=10.8 Hz), 2.66-2.55 (1H, m), 1.67-1.50 (12H, m), 1.21-1.16 (3H, d, J=7.2 Hz), 1.10 (6H, d, J=7.0 Hz). LC/MS: purity 100%, m/z 419 $[M+H]^+$ Example 6 tert-butyl N-(1-{[2,4-dihydroxy-5-(propan-2-yl)phenyl]carbonyl}piperidin-4-yl)-L-leucinate Prepared from Intermediate A and Intermediate B8. $^1$H NMR (300 MHz, d3-MeOD) 6.84 (1H, s), 6.21 (1H, s), 3.92-4.09 (2H, m), 3.25 (1H, obs m), 3.06 (1H, sep, J=6.9 Hz), 3.00-3.04 (2H, m), 2.54-2.67 (1H, m), 1.48-1.90 (4H, m), 1.39, (9H, s), 1.11-1.45 (3H, m), 1.07 (6H, d, J=6.9 Hz), 0.85 (3H, d, J=6.6 Hz), 0.82 (3H, d, J=6.6 Hz)
LC/MS: purity 98%, m/z 449.25 $[M+H]^+$ Example 7 cyclopentyl N-(1-{[2,4-dihydroxy-5-(propan-2-yl)phenyl]carbonyl}piperidin-3-yl)-L-leucinate Prepared from Intermediate A and Intermediate B10. $^1$H NMR (300 MHz, d3-MeOD) 7.0 (1H, s), 6.37 (1H, s), 5.36 (1H, br s), 4.42 (1H, br s), 4.10 (2H, br s), 3.27-2.84 (3H, m), 2.36-1.57 (16H, m), 1.19 (6H, d, J=7.0 Hz), 1.06-0.96 (6H, m). LC/MS: purity >98%, m/z 461 $[M+H]^+$ Example 8 tert-butyl N-(1-{[2,4-dihydroxy-5-(propan-2-yl)phenyl]carbonyl}piperidin-4-yl)-L-alaninate Prepared from Intermediate A and Intermediate B9. $^1$H NMR (300 MHz, d6-DMSO) 9.46 (1H, s), 9.41 (1H, s), 6.80 (1H, s), 6.33 (1H, s), 4.01-4.13 (1H, m), 3.73-3.95 (2H, m), 3.21-3.25 (1H, q, J=6.9 Hz), 3.00-3.12 (1H, m), 2.80-2.97 (2H, m), 2.55-2.69 (1H, m), 1.56-1.79 (2H, m), 1.41 (9H, s), 1.22 (3H, d, J=7.2 Hz), 1.12-1.22 (2H, m), 1.11 (6H, t, J=6.9 Hz). LC/MS: purity 98%, m/z 407.25 $[M+H]^+$ Example 9 cyclopentyl N-(1-{[2,4-dihydroxy-5-(propan-2-yl)phenyl]carbonyl}piperidin-4-yl)-L-phenylalaninate Prepared from Intermediate A and Intermediate B4. $^1$H NMR (300 MHz, d3-MeOD) 7.35-7.12 (5H, m), 6.95 (1H, s), 6.33 (1H, s), 5.12-5.02 (1H, m), 4.04 (1H, br s), 3.66 (1H, dd, J=6.0, 8.7 Hz), 3.18 (1H, dt, J=6.9, 13.8 Hz), 3.08-2.91 (2H, m), 2.90-2.78 (1H, m), 2.73 (1H, t, J=9.9 Hz), 1.96-1.22 (14H, m), 1.19 (6H, d, J=6.8 Hz). LC/MS: purity 100%, m/z 495 $[M+H]^+$

Example 10 cyclopentyl N-(1-{[2,4-dihydroxy-5-(propan-2-yl)phenyl]carbonyl}piperidin-4-yl)-L-norleucinate Prepared from Intermediate A and Intermediate B3. $^1$H NMR (300 MHz, d3-MeOD) 7.01 (1H, d, J=3.8 Hz), 6.37 (1H, d, J=1.3 Hz), 5.36 (2H, br s), 4.81 (2H, s), 4.46 (1H, br s), 4.17 (2H, br s), 3.16 (6H, m), 2.35 (2H, m), 2.17-1.54 (8H, m), 1.42 (3H, m), 1.19 (6H, d, J=6.8 Hz), 1.03-0.87 (3H, m). LC/MS: purity 96%, m/z 461 [M+H]$^+$

Example 11 tert-butyl O-tert-butyl-N-(1-{[2,4-dihydroxy-5-(propan-2-yl)phenyl]carbonyl}piperidin-4-yl)-L-serinate

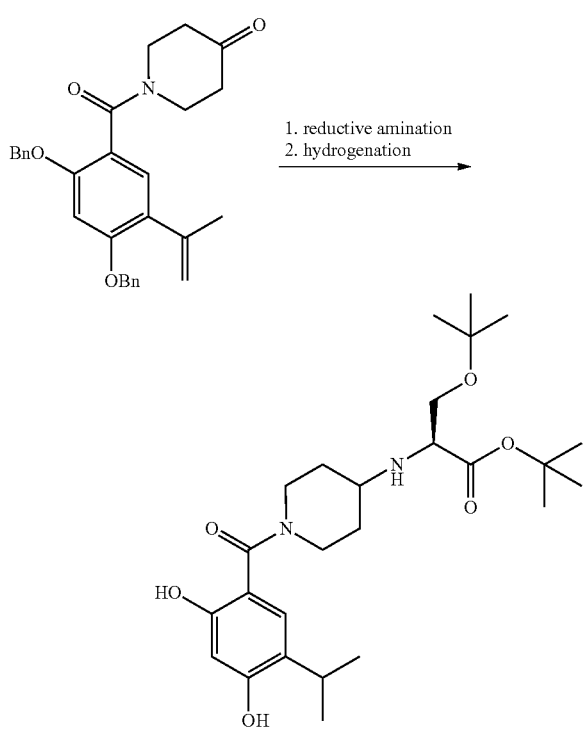

Example 11

Step 1: To a solution of Intermediate J (0.150 g, 0.3 mmol) in dichloroethane (10 mL) was added (S)-2-amino-3-tert-butoxy-propionic acid tert-butyl ester (0.069 g, 0.3 mmol) and sodium triacetoxyborohydride (0.127 g, 0.6 mmol). The solution was stirred at room temperature for 2 hours. An aqueous solution of sodium hydrogen bicarbonate (10 mL) was added and the desired product extracted into ethyl acetate (3 times 10 mL). The organic layers were combined, dried (MgSO$_4$) and concentrated. The residue was purified by flash chromatography (SiO$_2$, gradient elution from 100% heptane to 100% ethyl acetate), to give the product as a clear oil (0.090 g, 45% yield). $^1$H NMR (300 MHz, d3-MeOD) 7.43-7.29 (12H, m), 7.07 (1H, d, J=20 Hz), 6.77 (1H, d, J=5.3 Hz), 5.25-5.08 (5H, m), 5.04 (2H, d, J=5.5 Hz), 4.51 (1H, d, J=13.8 Hz); 3.58 (5H, m), 3.11-2.63 (4H, m), 1.96-1.57 (9H, m), 1.31 (2H, m), 1.16 (9H, s)

LC/MS: purity 100%; m/z 669 [M+H]$^+$.

Step 2: The hydrogenation of the product obtained to give Example 11 was performed as described for Example 1. $^1$H NMR (300 MHz, d3-MeOD) 6.98 (1H, s), 6.35 (1H, s), 4.34 (3H, m), 4.02-3.76 (2H, m), 3.55-3.38 (1H, m), 3.26-3.11 (1H, m), 3.09-2.90 (2H, m), 2.27-2.10 (2H, m), 1.81-1.60 (2H, m), 1.56 (9H, s), 1.26 (9H, s), 1.19 (6H, d, J=7.0 Hz). LC/MS: purity 98%, m/z 479 [M+H]$^+$ The Following Compounds were Prepared in a Simiar Fashion to Example 11

Example 12 cyclopentyl N-(1-{[2,4-dihydroxy-5-(propan-2-yl)phenyl]carbonyl}piperidin-4-yl)-D-leucinate Prepared from Intermediate J and D-leucine cyclopentyl ester tosylate. $^1$H NMR (300 MHz, d3-MeOD) 6.95 (1H, s), 6.32 (1H, s), 5.22 (1H, t, J=5.7 Hz), 4.11 (2H, d, J=11.9 Hz), 3.41 (1H, t, J=7.3 Hz), 3.28-2.93 (3H, m), 2.77-2.58 (1H, m), 2.03-1.28 (16H, m), 1.18 (6H, d, J=7.0 Hz), 0.94 (6H, dd, J=6.7, 8.9 Hz). LC/MS: purity 100%, m/z 461 [M+H]$^+$

Example 13 cyclopentyl 3-cyclohexyl-N-(1-{[2,4-dihydroxy-5-(propan-2-yl)phenyl]carbonyl}piperidin-4-yl)-L-alaninate Prepared from Intermediate J and L-cyclohexylalanine cyclopentyl ester tosylate. $^1$H NMR (300 MHz, d3-MeOD) 6.97 (1H, s), 6.36 (1H, s), 5.37 (1H, t, J=5.6 Hz), 4.31 (2H, br s), 4.15 (1H, m), 3.45 (1H, m), 3.18 (1H, dt, J=13.8, 6.9 Hz), 3.09-2.86 (2H, m), 2.13 (2H, t, J=16.1 Hz), 1.93 (3H, d, J=11.5 Hz), 1.87-1.62 (15H, m), 1.45 (1H, br s), 1.39-1.21 (3H, m), 1.19 (6H, d, J=7.0 Hz), 1.16-0.91 (2H, m). LC/MS: purity 98%, m/z 501 [M+H]$^+$

Example 14 cyclopentyl (2S)-cyclohexyl[(1-{[2,4-dihydroxy-5-(propan-2-yl)phenyl]carbonyl}piperidin-4-yl)amino]ethanoate Prepared from Intermediate J and L-cyclohexylglycine cyclopentyl ester tosylate. $^1$H NMR (300 MHz, d3-MeOD) 6.98 (1H, s), 6.35 (1H, s), 5.42-5.27 (1H, m), 4.32 (2H, br s), 4.06 (1H, d, J=3.6 Hz), 3.49-3.37 (1H, m), 3.18 (1H, dt, J=13.8, 6.9 Hz), 3.08-2.82 (2H, m), 2.26-1.64 (18H, m), 1.96 (3H, br s), 1.35 (2H, t, J=9.7 Hz), 1.19 (6H, d, J=7.0 Hz). LC/MS: purity 100%, m/z 387 [M+H]$^+$

Example 15 tert-butyl (2S)-cyclohexyl[(1-{[2,4-dihydroxy-5-(propan-2-yl)phenyl]carbonyl}piperidin-4-yl)amino]ethanoate Prepared from Intermediate J and L-cyclohexylglycine tert-butyl ester hydrochloride. $^1$H NMR (300 MHz, d3-MeOD) 6.98 (1H, s), 6.36 (1H, s), 4.32 (2H, br s), 3.97 (2H, br s), 2.26-1.63 (15H, m), 1.57 (9H, s), 1.37 (3H, t, J=10.9 Hz), 1.19 (6H, d, J=6.8 Hz)

LC/MS: purity 100%, m/z 475 [M+H]$^+$

Preparation of Example 16 tert-butyl N-(1-{[2,4-dihydroxy-5-(propan-2-yl)phenyl]carbonyl}piperidin-4-yl)-L-phenylalaninate Prepared from Intermediate J and L-phenylalanine tert-butyl ester hydrochloride. $^1$H NMR (300 MHz, d3-MeOD) 7.34-7.17 (5H, m), 6.95 (1H, s), 6.32 (1H, s), 4.06 (2H, br s), 3.58 (1H, dd, J=8.5, 6.2 Hz), 3.18 (6H, m), 2.88-2.66 (2H, m), 1.96-1.73 (2H, m), 1.32 (9H, s), 1.18 (6H, d, J=7.0 Hz). LC/MS: purity 99%, m/z 483 [M+H]$^+$

Example 17 cyclopentyl O-tert-butyl-N-(1-{[2,4-dihydroxy-5-(propan-2-yl)phenyl]carbonyl}piperidin-4-yl)-L-serinate Prepared from Intermediate J and L-O-tert-butyl serine cyclopentyl ester. $^1$H NMR (300 MHz, d6-DMSO) 9.45 (1H, s), 9.40 (1H, s), 6.80 (1H, s), 6.33 (1H, s), 5.10 (1H, t, J=5.6 Hz), 3.75-3.94 (2H, m), 3.30-3.51 (3H, m), 3.06 (1H, sep, J=7.0 Hz), 2.80-2.99 (2H, m), 2.57-2.67 (1H, m), 1.44-1.98 (12H, m), 1.10 (6H, d, J=9.1 Hz), 1.08 (9H, s)

LC/MS: purity 100%, m/z 491 [M+H]$^+$

Example 18 cyclopentyl N-(1-{[2,4-dihydroxy-5-(propan-2-yl)phenyl]carbonyl}piperidin-4-yl)-L-serinate Prepared from Intermediate J and L-O-benzyl-serine cyclopentyl ester. $^1$H NMR (300 MHz, d3-MeOD) 6.98 (1H, s), 6.35 (1H, s), 5.42-5.29 (1H, m), 4.34 (1H, br s), 4.29 (2H, t, J=3.3 Hz), 4.08-4.01 (2H, m), 3.61-3.46 (1H, m), 3.18 (1H, dt, J=6.8, 13.8 Hz), 3.01 (2H, t, J=13.0 Hz), 2.18 (2H, br s), 2.04-1.93 (2H, m), 1.93-1.60 (8H, m), 1.19 (6H, d, J=7.0 Hz). LC/MS: purity 100%, m/z 435 [M+H]$^+$

Example 19 tert-butyl N-(1-{[2,4-dihydroxy-5-(propan-2-yl)phenyl]carbonyl}piperidin-4-yl)-D-leucinate Prepared from Intermediate J and D-leucine tert-butyl ester hydrochloride. $^1$H NMR (300 MHz, d3-MeOD) 6.96 (1H, s), 6.33 (1H, s), 4.19-3.96 (2H, m), 3.27-2.91 (4H, m), 2.79-2.64 (1H, m), 1.99-1.66 (4H, m), 1.50 (8H, s), 1.46-1.21 (5H, m), 1.19 (6H, d, J=7.0 Hz), 0.95 (6H, dd, J=6.6, 9.6 Hz). LC/MS: purity 95%, m/z 449 [M+H]$^+$

Example 20 cyclopentyl N-(1-{[2,4-dihydroxy-5-(propan-2-yl)phenyl]carbonyl}pyrrolidin-3-yl)-L-leucinate Prepared from Intermediate A and Intermediate B11. $^1$H NMR (300 MHz, d6-DMSO) 10.74 (0.5H, s), 10.63 (0.5H, s), 9.70 (1H, s), 7.05 (1H, s), 6.31 (1H, s), 4.96-5.14 (1H, m), 2.97-3.66 (8H, m), 2.05-2.35 (1H, m), 1.27-1.98 (11H, m), 1.12 (3H, d, J=6.9 Hz), 1.12 (3H, d, J=6.9 Hz), 0.85 (6H, t, J=6.7 Hz). LC/MS: purity >98%, m/z 447.25 [M+H]$^+$

Preparation of Example 21 cyclopentyl N-[(1-{[2,4-dihydroxy-5-(propan-2-yl)phenyl]carbonyl}piperidin-4-yl)methyl]-L-leucinate

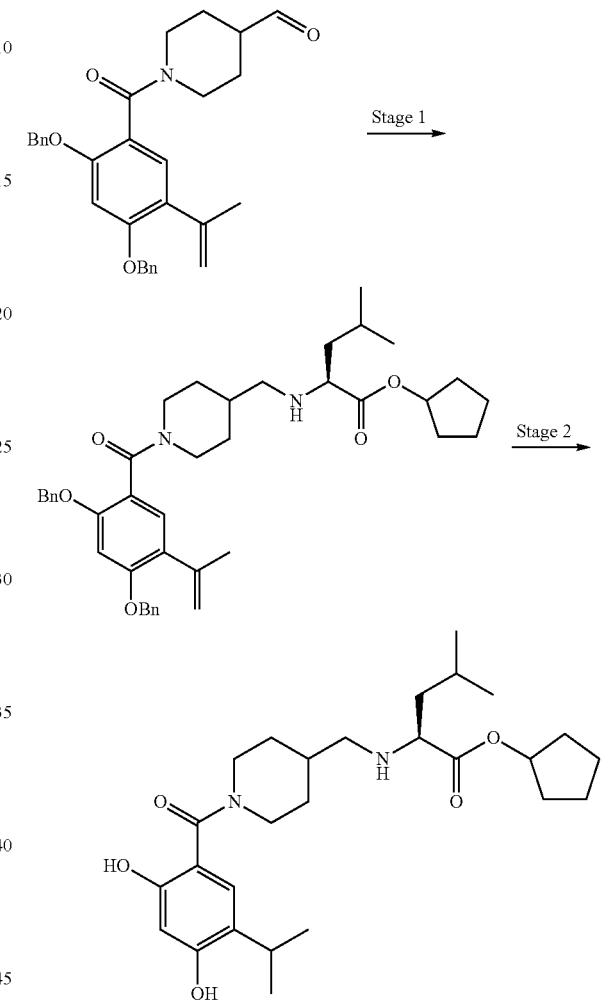

Example 21

Stage 1—cyclopentyl N-[(1-{[2,4-bis(benzyloxy)-5-(prop-1-en-2-yl)phenyl]carbonyl}piperidin-4-yl)methyl]-L-leucinate To a solution of Intermediate C (0.194 g, 0.41 mmol) in dichloroethane (10 mL) was added L-leucine cyclopentyl ester tosylate (0.240 g, 0.61 mmol) then sodium triacetoxyborohydride (0.240 g, 1.13 mmol). The mixture was stirred for 1 hour then quenched by addition of saturated ammonium chloride (20 mL). The mixture was poured into ethyl acetate (200 mL) and washed with saturated sodium hydrogen carbonate (2 times 25 mL). The organic fraction was dried (MgSO$_4$), concentrated and then purified by flash column chromatography (SiO$_2$, 7:3 ethyl acetate:heptane) to yield the desired product (0.211 g, 79% yield). LC/MS: m/z 653.25 [M+H]$^+$

Stage 2—cyclopentyl N-[(1-{[2,4-dihydroxy-5-(propan-2-yl)phenyl]carbonyl}piperidin-4-yl)methyl]-L-leucinate (Example 21)

To a solution of the product of Stage 2 (0.211 g, 0.32 mmol) in ethyl acetate (10 mL) was added palladium on carbon (0.194 g, 10%, 0.18 mmol, 57%). The reaction vessel was evacuated and filled with hydrogen twice, then stirred for 90 minutes. The flask was purged with nitrogen, Celite was added, then the mixture was filtered through a pad of Celite, washing with further ethyl acetate (100 mL, 50 mL). The filtrate was concentrated to yield the desired product (0.151 mg, 99% yield). $^1$H NMR (300 MHz, d6-DMSO) 9.26 (1H, s), 9.41 (1H, s), 6.80 (1H, s), 6.32 (1H, s), 5.09 (1H, t, J=6.0 Hz), 3.85-4.05 (2H, m), 3.00-3.10 (2H, m), 2.77 (2H, t, J=12.0 Hz), 2.38 (1H, dd, J=6.9, 11.4 Hz), 2.23 (1H, dd, J=6.6, 11.4 Hz), 1.50-1.91 (12H, m), 1.32 (2H, t, J=6.9 Hz), 1.09 (6H, d, J=6.9 Hz), 0.98-1.04 (3H, m), 0.86 (3H, d, J=6.6 Hz), 0.83 (3H, d, J=6.6 Hz)

LC/MS: purity >98%, m/z 475.25 [M+H]$^+$

The Following Compounds were Prepared in a Simiar Fashion to Example 21:

Example 22 cyclopentyl N-[(1-{[2,4-dihydroxy-5-(propan-2-yl)phenyl]carbonyl}piperidin-4-yl)methyl]-L-alaninate Prepared from Intermediate C and L-alanine cyclopentyl ester tosylate. $^1$H NMR (300 MHz, d3-MeOD) 6.92 (1H, s), 6.33 (1H, s), 5.21 (1H, m), 4.12 (2H, m), 3.31 (2H, m), 3.18 (1H, pentet, J=6.9 Hz), 2.95 (2H, t, J=12.6 Hz), 2.46 (2H, m), 1.75 (12H, m), 1.28 (3H, d, J=6.9 Hz), 1.19 (6H, d, J=6.9 Hz). LC/MS: purity 95%, m/z 433 [M+H]$^+$

Example 23 cyclopentyl N-[(1-{[2,4-dihydroxy-5-(propan-2-yl)phenyl]carbonyl}piperidin-4-yl)methyl]-L-phenylalaninate Prepared from Intermediate C and L-phenylalanine cyclopentyl ester tosylate. $^1$H NMR (300 MHz; d3-MeOD) 7.24 (5H, m), 6.95 (1H, s), 6.33 (1H, s), 5.06 (1H, m), 4.15 (2H, m), 3.46 (1H, t, J=6.3 Hz), 3.18 (1H, pentet, J=6.9 Hz), 2.96 (4H, m), 2.45 (2H, m), 1.70 (13H, m), 1.18 (6H, d, J=6.9 Hz). LC/MS: purity 98%, m/z 509 [M+H]$^+$

Example 24 tert-butyl N-[(1-{[2,4-dihydroxy-5-(propan-2-yl)phenyl]carbonyl}piperidin-4-yl)methyl]-L-leucinate Prepared from Intermediate C and L-leucine tert-butyl ester. $^1$H NMR (300 MHz, d3-MeOD) 6.96 (1H, s), 6.33 (1H, s), 4.18 (2H, m), 3.33 (1H, m), 3.15 (2H, m), 2.95 (2H, t, J=12.3 Hz), 2.44 (2H, m), 1.75 (4H, m), 1.49 (9H, s), 1.30 (3H, m), 1.18 (6H, d, J=6.6 Hz), 0.94 (6H, m). LC/MS: purity 98%, m/z 463 [M+H]$^+$

Example 25 tert-butyl N-[(1-{[2,4-dihydroxy-5-(propan-2-yl)phenyl]carbonyl}piperidin-4-yl)methyl]-L-phenylalaninate Prepared from Intermediate C and L-phenylalanine tert-butyl ester. $^1$H NMR (300 MHz, d3-MeOD) 7.26 (5H, m), 6.95 (1H, s), 6.34 (1H, s), 4.16 (2H, m), 3.40 (1H, m), 3.33 (1H, m), 3.18 (1H, pentent, J=6.9 Hz), 2.92 (4H, m), 2.46 (2H, m), 1.74 (3H, m), 1.36 (9H, s), 1.31 (1H, m), 1.18 (6H, d, J=6.9 Hz). LC/MS: purity 95%, m/z 497 [M+H]$^+$

Example 26 tert-butyl N-[(1-{[2,4-dihydroxy-5-(propan-2-yl)phenyl]carbonyl}piperidin-4-yl)methyl]-L-alaninate Prepared from Intermediate C and L-alanine tert-butyl ester. $^1$H NMR (300 MHz, d3-MeOD) 6.96 (1H, s), 6.33 (1H, s), 4.19 (2H, m), 3.33 (2H, m), 3.20 (2H, m), 2.96 (2H, t, J=12.6 Hz), 2.46 (2H, m), 1.80 (3H, m), 1.49 (9H, s), 1.27 (3H, d, J=7.2 Hz), 1.18 (6H, d, J=6.9 Hz). LC/MS: purity 95%, m/z 421 [M+H]$^+$

Example 27 tert-butyl N-[(1-{[2,4-dihydroxy-5-(propan-2-yl)phenyl]carbonyl}piperidin-4-yl)methyl]-D-leucinate Prepared from Intermediate C and D-leucine tert-butyl ester. $^1$H NMR (300 MHz, d3-MeOD) 6.96 (1H, s), 6.33 (1H, s), 4.18 (2H, m), 3.33 (1H, m), 3.16 (2H, m), 2.95 (2H, t, J=12.0 Hz), 2.46 (2H, m), 1.72 (4H, m), 1.50 (9H, s), 1.35 (3H, m), 1.18 (6H, d, J=6.9 Hz), 0.93 (6H, m). LC/MS: purity 98%, m/z 463 [M+H]$^+$

Example 28 cyclopentyl N-[(1-{[2,4-dihydroxy-5-(propan-2-yl)phenyl]carbonyl}piperidin-4-yl)methyl]-D-leucinate Prepared from Intermediate C and D-leucine cyclopentyl ester tosylate. $^1$H NMR (300 MHz, d3-MeOD) 6.95 (1H, s), 6.33 (1H, s), 5.21 (1H, m), 4.18 (1H, m), 3.33 (1H, m), 3.20 (2H, m), 2.95 (2H, t, J=12.6 Hz), 2.42 (2H, m), 1.72 (13H, m), 1.50 (2H, m), 1.32 (1H, m), 1.21 (6H, d, J=6.9 Hz), 0.91 (6H, m). LC/MS: purity 98%, m/z 475 [M+H]$^+$

Example 29 cyclopentyl N-[(1-{[2,4-dihydroxy-5-(propan-2-yl)phenyl]carbonyl}piperidin-4-yl)methyl]-L-valinate Prepared from Intermediate C and L-valine cyclopentyl ester tosylate. $^1$H NMR (300 MHz, d3-MeOD) 6.96 (1H, s), 6.34 (1H, s), 4.21 (2H, m), 3.92 (1H, m), 3.18 (1H, pentet, J=6.6 Hz), 3.01 (4H, m), 2.37 (1H, m), 1.90 (3H, m), 1.35 (2H, m), 1.19 (9H, m), 1.08 (3H, d, J=6.9 Hz). LC/MS: purity 95%, m/z 393 [M+H]$^+$

Example 30 cyclopentyl (2S)-cyclohexyl{[(1-{[2,4-dihydroxy-5-(propan-2-yl)phenyl]carbonyl}piperidin-4-yl)methyl]amino}ethanoate Prepared from Intermediate C and L-cyclohexylglycine cyclopentyl ester tosylate. $^1$H NMR (300 MHz, d3-MeOD) 6.96 (1H, s), 6.35 (1H, s), 5.36 (1H, m), 4.22 (2H, m), 1.88

(1H, s, d, J=3.9 Hz), 3.18 (1H, pentet, J=6.9 Hz), 2.98 (4H, m), 2.10-1.70 (18H, m), 1.36 (4H, m), 1.18 (6H, d, J=6.9 Hz), 1.02 (2H, m). LC/MS: purity 98%, m/z 501 [M+H]⁺

Example 31 tert-butyl (2S)-cyclohexyl{[(1-{[2,4-dihydroxy-5-(propan-2-yl)phenyl]carbonyl}piperidin-4-yl)methyl]amino}ethanoate Prepared from Intermediate C and L-cyclohexylglycine tert-butyl ester. ¹H NMR (300 MHz, d3-MeOD) 6.95 (1H, s), 6.33 (1H, s), 4.18 (2H, m), 3.18 (1H, pentet, J=6.9 Hz), 3.95 (3H, m), 2.49 (1H, m), 2.38 (1H, m), 1.72 (9H, m), 1.50 (9H, s), 1.30 (4H, m), 1.22 (6H, d, J=7.0 Hz), 0.90 (2H, m). LC/MS: purity 98%, m/z 489 [M+H]⁺

Example 32 cyclopentyl N-[(1-{[2,4-dihydroxy-5-(propan-2-yl)phenyl]carbonyl}piperidin-4-yl)methyl]-2-methyl-L-alaninate Prepared from Intermediate C and α,α-dimethylglycine cyclopentyl ester tosylate. ¹H NMR (300 MHz, d3-MeOD) 9.50 (1H, s), 9.45 (1H, m), 8.91 (1H, m), 6.82 (1H, s), 6.35 (1H, s), 5.21 (1H, m), 3.23 (1H, m), 3.07 (2H, m), 2.85 (4H, m), 1.75 (8H, m), 1.48 (6H, s), 1.17 (2H, m), 1.11 (6H, d, J=6.9 Hz). LC/MS: purity 90%, m/z 447 [M+H]⁺

Example 33 cyclopentyl N-[(1-{[2,4-dihydroxy-5-(propan-2-yl)phenyl]carbonyl}piperidin-4-yl)methyl]-L-serinate Prepared from Intermediate C and L-O-benzyl-serine cyclopentyl ester tosylate. ¹H NMR (300 MHz, d3-MeOD) 6.97 (1H, s), 6.34 (1H, s), 5.34 (1H, m), 4.25 (2H, m), 4.14 (1H, m), 4.08 (2H, m), 3.18 (1H, pentet, J=6.9 Hz), 3.03 (4H, m), 2.09 (1H, m), 1.80 (10H, m), 1.43 (2H, m), 1.18 (6H, d, J=6.9 Hz). LC/MS: purity 95%, m/z 447 [M+H]⁺

Example 34 cyclopentyl O-tert-butyl-N-[(1-{[2,4-dihydroxy-5-(propan-2-yl)phenyl]carbonyl}piperidin-4-yl)methyl]-L-serinate Prepared from Intermediate C and L-O-tert-butyl serine cyclopentyl ester tosylate. ¹H NMR (300 MHz, d3-MeOD) 6.96 (1H, s), 6.33 (1H, s), 5.22 (1H, m), 4.18 (2H, m), 3.64 (2H, m), 3.37 (1H, m), 3.32 (2H, m), 3.18 (1H, pentet, J=6.9 Hz), 2.96 (2H, m), 2.51 (2H, m), 1.77 (9H, m), 1.25 (2H, m), 1.18 (15H, m). LC/MS: purity 98%, m/z 505 [M+H]⁺

Example 35 tert-butyl O-tert-butyl-N-[(1-{[2,4-dihydroxy-5-(propan-2-yl)phenyl]carbonyl}piperidin-4-yl)methyl]-L-serinate Prepared from Intermediate C and L-O-tert-butyl serine tert-butyl ester. ¹H NMR (300 MHz, d3-MeOD) 6.96 (1H, s), 6.33 (1H, s), 4.19 (2H, m), 3.60 (2H, m), 3.18 (1H, pentet, J=6.9 Hz), 2.95 (3H, m), 2.51 (2H, m), 1.81 (3H, m), 1.50 (9H, s), 1.27 (2H, m), 1.19 (15H, m). LC/MS: purity 98%, m/z 493 [M+H]⁺

Example 36 cyclopentyl (2S)-{[(1-{[2,4-dihydroxy-5-(propan-2-yl)phenyl]carbonyl}piperidin-4-yl)methyl]amino}(phenyl)ethanoate Prepared from Intermediate C and L-phenylglycine cyclopentyl ester tosylate. NMR (300 MHz, d3-MeOD) 7.36 (5H, m), 6.95 (1H, s), 6.33 (1H, s), 5.17 (1H, m), 4.33 (1H, s), 4.15 (2H, m), 3.18 (1H, pentet, J=6.9 Hz), 2.94 (2H, t, J=11.1 Hz), 2.40 (2H, m), 1.88-1.40 (11H, m), 1.17 (6H, d, J=6.9 Hz), 0.91 (2H, m). LC/MS: purity 98%, m/z 495 [M+H]⁺

Example 37 tert-butyl N-[(1-{[2,4-dihydroxy-5-(propan-2-yl)phenyl]carbonyl}piperidin-4-yl)methyl]-L-serinate Prepared from Intermediate C and L-O-tert-butyl serine cyclopentyl ester tosylate. ¹H NMR (300 MHz, d3-MeOD) 6.96 (1H, s), 6.33 (1H, s), 4.29 (2H, m), 3.74 (3H, m), 3.25 (1H, t, J=5.1 Hz), 3.20 (1H, pentet, J=6.6 Hz), 2.96 (2H, t, J=12.6 Hz), 2.55 (1H, m), 2.49 (1H, m), 1.89 (4H, m), 1.50 (9H, s), 1.18 (6H, d, J=6.6 Hz). LC/MS: purity 98%, m/z 437 [M+H]⁺

Preparation of Example 38 cyclopentyl N-[2-(1-{[2,4-dihydroxy-5-(propan-2-yl)phenyl]carbonyl}piperidin-4-yl)ethyl]-L-leucinate

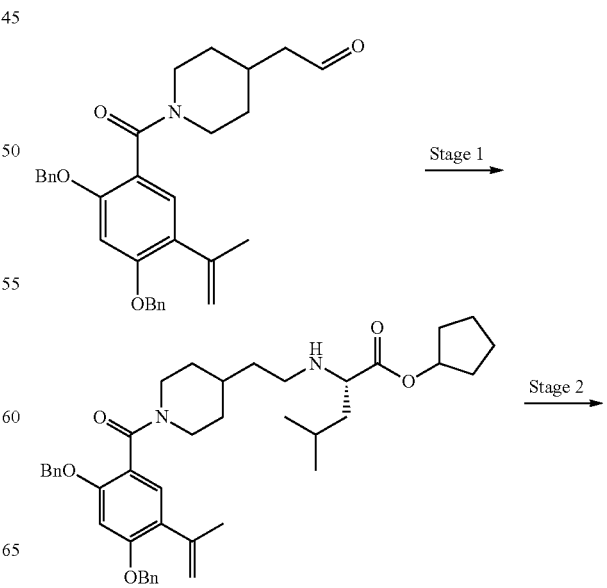

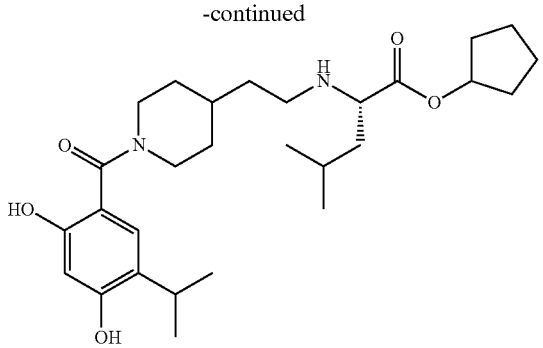

Example 38

Stage 1—cyclopentyl N-[2-(1-{[2,4-bis(benzyloxy)-5-(prop-1-en-2-yl)phenyl]carbonyl}piperidin-4-yl)ethyl]-L-leucinate To a solution of Intermediate D (0.245 g, 0.5 mmol) in dichloroethane (10 mL) was added L-leucine cyclopentyl ester tosylate (0.398 g, 1.07 mmol) and sodium triacetoxyborohydride (0.417 g, 1.97 mmol). The mixture was stirred for one hour then loaded directly onto a silica gel column and eluted with 7:3 ethyl acetate:heptane to yield the desired product (0.250 g, 75% yield). LC/MS: m/z 667.25 [M+H]$^+$ Stage 2—cyclopentyl N-[2-(1-{([2,4-dihydroxy-5-(propan-2-yl)phenyl]carbonyl}piperidin-4-yl)ethyl]-L-leucinate (Example 38)

To a solution of the product of Stage 1 (0.250 g, 0.37 mmol) in ethyl acetate (10 mL) was added palladium on carbon (0.238 g, 10%, 0.22 mmol, 60%). The reaction vessel was evacuated and filled with hydrogen twice. The mixture was stirred for 1 hour, then purged with nitrogen. Celite was added, and the mixture filtered through Celite, washing with additional ethyl acetate (100 mL). The filtrate was concentrated to yield the desired product (77.1 mg, 42% yield). $^1$H NMR (300 MHz, CDCl$_3$) 7.03 (1H, s), 6.42 (1H, s), 5.25 (1H, t, J=5.8 Hz), 4.30 (2H, d, J=13.3 Hz), 3.31 (1H, t, J=7.3 Hz), 3.16 (1H, sep, 6.9 Hz), 2.92 (2H, t, J=12.8 Hz), 2.53-2.74 (2H, m), 1.43-1.97 (17H, m), 1.20 (6H, d, J=6.9 Hz), 0.94 (3H, d, J=6.5 Hz), 0.92 (3H, d, J=6.5 Hz)

LC/MS: purity 98%, m/z 489.25 [M+H]$^+$

The Following Compounds were Prepared in a Simiar Fashion to Example 38

Example 39 cyclopentyl N-[2-(1-{[2,4-dihydroxy-5-(propan-2-yl)phenyl]carbonyl}piperidin-4-yl)ethyl]-L-alaninate Prepared from Intermediate D and L-alanine cyclopentyl ester tosylate. $^1$H NMR (300 MHz, d3-MeOD) 6.96 (1H, s), 6.34 (1H, s), 5.34 (1H, m), 4.17 (2H, m), 4.07 (1H, m), 3.19 (3H, m), 2.98 (2H, t, J=12 Hz), 1.96 (2H, m), 1.93 (11H, m), 1.56 (3H, d, J=7.2 Hz), 1.29 (2H, m), 1.18 (6H, d, J=6.9 Hz). LC/MS: purity >98%, m/z 447.25 [M+H]$^+$ Example 40 cyclopentyl N-[2-(1-{[2,4-dihydroxy-5-(propan-2-yl)phenyl]carbonyl}piperidin-4-yl)ethyl]-L-phenylalaninate Prepared from Intermediate D and L-phenylalanine cyclopentyl ester tosylate. $^1$H NMR (300 MHz, d3-MeOD) 7.44-7.17 (5H, m), 6.95 (1H, s), 6.34 (1H, s), 5.17, (1H, m), 4.35-4.12 (4H, m), 3.46-3.35 (1H, m), 3.27-2.85 (6H, m), 1.93-1.21, (13H, m), 1.19 (6H, d, J=7.0 Hz). LC/MS: purity 98.4%, m/z 523 [M+H]$^+$ Example 41 tert-butyl N-[2-(1-{[2,4-dihydroxy-5-(propan-2-yl)phenyl]carbonyl}piperidin-4-yl)ethyl]-L-phenylalaninate Prepared from Intermediate D and L-phenylalanine tert-butyl ester. $^1$H NMR (300 MHz, d3-MeOD) 7.46-7.21 (5H, m), 6.95 (1H, s), 6.34 (1H, s), 4.32-4.09 (3H, m), 3.27-2.88 (6H, m), 1.84-1.63 (5H, m), 1.34 (9H, s), 1.19 (6H, d, J=7.0 Hz). LC/MS: purity 97.5%, m/z 511 [M+H]$^+$ Example 42 tert-butyl N-[2-(1-{[2,4-dihydroxy-5-(propan-2-yl)phenyl]carbonyl}piperidin-4-yl)ethyl]-L-leucinate Prepared from Intermediate D and L-leucine tert-butyl ester. $^1$H NMR (300 MHz, d3-MeOD) 6.95 (1H, s), 6.33 (1H, s), 4.17 (2H, m), 3.33 (1H, m), 3.28 (1H, m), 2.95 (2H, t, J=12.6 Hz), 2.65 (2H, m), 1.74 (4H, m), 1.57 (11H, m), 1.44 (4H, m), 1.20 (6H, d, J=9.0 Hz), 0.97 (6H, m). LC/MS: purity 96%, m/z 477 [M+H]$^+$ Example 43 tert-butyl N-[2-(1-{[2,4-dihydroxy-5-(propan-2-yl)phenyl]carbonyl}piperidin-4-yl)ethyl]-L-alaninate Prepared from Intermediate D and L-alanine tert-butyl ester. $^1$H NMR (300 MHz, d3-MeOD) 6.96 (1H, s), 6.33 (1H, s), 4.17 (2H, m), 3.19 (3H, m), 2.95 (2H, t, J=12.0 Hz), 2.60 (2H, m), 1.78 (4H, m), 1.50 (9H, m), 1.27 (3H, d, J=6.9 Hz), 1.23 (2H, m), 1.18 (6H, d, J=6.9 Hz). LC/MS: purity 98%, m/z 435 [M+H]$^+$ Example 44 cyclopentyl N-[2-(1-{[2,4-dihydroxy-5-(propan-2-yl)phenyl]carbonyl}piperidin-4-yl)ethyl]-2-methylalaninate Prepared from Intermediate D and α,α-dimethylglycine cyclopentyl ester. $^1$H NMR (300 MHz, d3-MeOD) 6.96 (1H, s), 6.34 (1H, s), 5.26-5.39 (1H, m), 4.29 (2H, br. s.), 3.28 (1H, br. s.), 3.18 (1H, dt, J=13.6, 6.8 Hz), 3.03-3.12 (2H, m), 2.98 (2H, t, J=12.4 Hz), 1.64-2.01 (11H, m), 1.59 (6H, s), 1.24-1.38 (3H, m), 1.19 (6H, d, J=7.0 Hz) LC/MS: purity 97%, m/z 461 [M+H]$^+$ Example 45 cyclopentyl O-tert-butyl-N-[2-(1-{[2,4-dihydroxy-5-(propan-2-yl)phenyl]carbonyl}piperidin-4-yl)ethyl]-L-serinate Prepared from Intermediate D and L-O-tert-butylserine cyclopentyl ester tosylate. $^1$H NMR (300 MHz, CDCl$_3$) 7.04 (1H, d, J=14.3 Hz), 6.45 (1H, d, J=11 Hz), 5.28 (1H, t, J=5.64 Hz), 4.41-4.21 (2H, m), 3.84-3.56 (2H, m), 3.16 (1H, septet, J=6.78 Hz), 3.03-2.73 (4H, m), 2.07 (1H, d, J=9.1 Hz), 1.95-

1.52 (12H, m), 1.40-1.21 (6H, m), 1.17 (9H, s). LC/MS: purity 98%, m/z 519.25 [M+H]⁺

Example 46 cyclopentyl N-[2-(1-{[2,4-dihydroxy-5-(propan-2-yl)phenyl]carbonyl}piperidin-4-yl)ethyl]-L-valinate Prepared from Intermediate D and L-valine cyclopentyl ester tosylate. ¹H NMR (300 MHz, d3-MeOD) 6.95 (1H, s), 6.34 (1H, s), 5.31-5.44 (1H, m), 4.08-4.35 (2H, m), 3.94 (1H, d, J=3.8 Hz), 3.05-3.25 (3H, m), 2.96 (2H, t, J=12.5 Hz), 2.26-2.42 (1H, m), 1.89-2.08 (3H, m), 1.61-1.88 (8H, m), 1.13-1.24 (12H, m) and 1.05 (6H, d, J=6.8 Hz) LC/MS: purity 85%, m/z 475 [M+H]⁺

Example 47 cyclopentyl N-[2-(1-{[2,4-dihydroxy-5-(propan-2-yl)phenyl]carbonyl}piperidin-4-yl)ethyl]-L-serinate Prepared from Intermediate D and L-O-benzyl-serine cyclopentyl ester tosylate. ¹H NMR (300 MHz, d3-MeOD): 6.96 (1H, s), 6.35 (1H, s), 5.33-5.24 (1H, m), 4.63-4.46 (1H, m), 4.27-4.13 (1H, m), 3.94-3.88 (1H, m), 3.83-3.77 (1H, m), 3.73 (1H, t, J=4.1 Hz), 3.18 (1H, septet, J=6.9 Hz), 3.05-2.82 (4H, m), 1.85-1.52 (15H, m), 1.19 (6H, d, J=6.9 Hz). LC/MS: purity 96%, m/z 463.25 [M+H]⁺

Example 48 cyclopentyl (2S)-cyclohexyl{[2-(1-{[2,4-dihydroxy-5-(propan-2-yl)phenyl]carbonyl}piperidin-4-yl)ethyl]amino}ethanoate Prepared from Intermediate D and L-cyclohexylglycine cyclopentyl ester tosylate. ¹H NMR: (300 MHz, d3-MeOD) 6.89 (1H, s), 6.28 (1H, s), 5.31 (1H, t, J=5.7 Hz), 4.14 (2H, d, J=12.3 Hz), 3.83 (1H, d, J=3.8 Hz), 3.27 (2H, quin, J=1.5 Hz), 3.13 (1H, quin, J=6.8 Hz), 2.97-3.08 (2H, m), 2.90 (2H, t, J=12.3 Hz), 1.84-2.00 (3H, m), 1.56-1.84 (15H, m), 1.16-1.39 (5H, m), 1.14 (6H, d, J=7.0 Hz), 0.9-1.07 (1H, m). LC/MS: purity 95%, m/z 515.25 [M+H]⁺

Example 49 tert-butyl (2S)-cyclohexyl{[2-(1-{[2,4-dihydroxy-5-(propan-2-yl)phenyl]carbonyl}piperidin-4-yl)ethyl]amino}ethanoate Prepared from Intermediate D and L-cyclohexylglycine tert-butyl ester. ¹H NMR: (300 MHz, d3-MeOD) 6.88 (1H, s), 6.35 (1H, s), 3.94-4.18 (2H, m), 3.58-3.72 (2H, m), 2.80-3.16 (5H, m), 1.54-1.96 (11H, m), 1.46 (9H, s), 1.13-1.32 (4H, m), 1.09 (6H, d, J=6.8 Hz), 0.87-1.04 (2H, m). LC/MS: purity 95%, m/z 503 [M+H]⁺

Example 50 tert-butyl (2S)-{[2-(1-{[2,4-dihydroxy-5-(propan-2-yl)phenyl]carbonyl}piperidin-4-yl)ethyl]amino}(phenyl)ethanoate Prepared from Intermediate D and L-phenylglycine tert-butyl ester. 1H NMR (300 MHz, d3-MeOD): (4:7 mixture of rotamers) 7.43-7.28 (5H, m), 6.94 (1H, s), 6.32 (1H, s), 4.34 (1H, br s), 3.18 (1H, septet, J=6.9 Hz), 2.93 (2H, t, J=13.1 Hz), 2.69-2.54 (2H, m), 1.79-1.46 (9H, m), 1.41 (Rotamer A, 9H, s), 1.40 (Rotamer B, 9H, s), 1.18 (6H, d, J=6.9 Hz). LC/MS: purity 100%, m/z 497.25 [M+H]⁺

Example 51 cyclopentyl (2S)-{[2-(1-{[2,4-dihydroxy-5-(propan-2-yl)phenyl]carbonyl}piperidin-4-yl)ethyl]amino}(phenyl)ethanoate Prepared from Intermediate D and L-phenylglycine cyclopentyl ester tosylate. ¹H NMR (300 MHz, d3-MeOD), 7.45-7.25 (5H, m), 6.94 (1H, s), 6.32 (1H, s), 5.24-5.11 (2H, m), 4.42 (1H, s), 4.23-409 (1H, m), 3.18 (1H, septet, J=6.9 Hz), 3.01-2.88 (2H, m), 2.71-2.53 (2H, m), 1.81-1.53 (15H, m), 1.18 (6H, d, J=7.0 Hz). LC/MS: purity 100%, m/z 509.25 [M+H]⁺

Example 52 tert-butyl N-[2-(1-{[2,4-dihydroxy-5-(propan-2-yl)phenyl]carbonyl}piperidin-4-yl)ethyl]-L-serinate Prepared from Intermediate D and L-O-benzylserine tert-butyl ester. ¹H NMR (300 MHz, d3-MeOD) 6.98 (1H, s); 6.35 (1H, s); 4.53-4.47 (1H, m); 4.32-4.15 (2H, m); 3.18 (1H, septet, J=6.9 Hz); 3.10-2.88 (2H, m); 2.40-2.24 (2H, m); 1.94-1.76 (2H, m); 1.61-1.55 (2H, m); 1.50 (9H, s); 1.47-1.30 (5H, m); 1.18 (6H, d, J=6.9 Hz)
LC/MS: purity 99%, m/z 541.25 [M+H]⁺

Example 53 tert-butyl O-tert-butyl-N-[2-(1-{[2,4-dihydroxy-5-(propan-2-yl)phenyl]carbonyl}piperidin-4-yl)ethyl]-L-serinate Prepared from Intermediate D and L-tert-butyl serine tert-butyl ester. ¹H NMR (300 MHz, d3-MeOD): 6.96 (1H, s); 6.34 (1H, s); 4.56-4.40 (1H, m); 4.28-4.13 (2H, m); 3.69-3.60 (1H, m); 3.18 (1H, septet, J=6.9 Hz); 2.95 (2H, t, J=11.7 Hz); 2.81-2.61 (1H, m); 1.81-1.72 (2H, m); 1.50 (9H, s); 1.32-1.23 (8H, m); 1.20 (9H, s); 1.18 (6H, d, J=6.9 Hz). LC/MS: purity 97%, m/z 507.25 [M+H]⁺

Preparation of Example 54 cyclopentyl N-[(2-{[2,4-dihydroxy-5-(propan-2-yl)phenyl]carbonyl}-2,3-dihydro-1H-isoindol-5-yl)methyl]-L-leucinate -continued

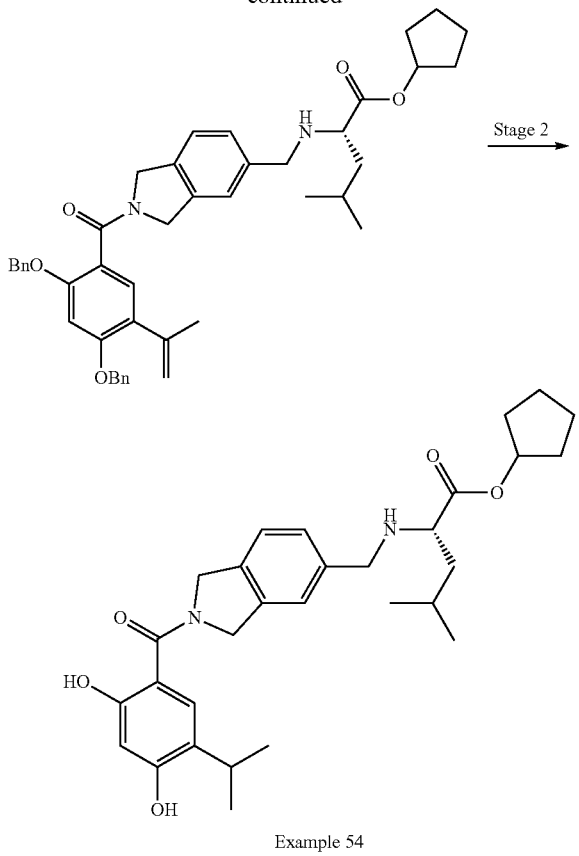

Example 54

Stage 1—cyclopentyl N-[(2-{[2,4-bis(benzyloxy)-5-(prop-1-en-2-yl)phenyl]carbonyl}-2,3-dihydro-1H-isoindol-5-yl)methyl]-L-leucinate

To a solution of Intermediate E (0.120 g, 0.24 mmol) in dichloroethane (3 mL) was added L-leucine cyclopentyl ester tosylate (0.120 g, 0.32 mmol) and sodium triacetoxyborohydride (0.152 g, 0.71 mmol). The mixture was stirred at room temperature for 90 minutes then poured into a mixture of dichloromethane (50 mL)/saturated ammonium chloride (25 mL). The product was extracted with dichloromethane (2 times 50 mL), and the combined extracts were dried (MgSO$_4$), concentrated and purified by flash column chromatography (SiO$_2$, 96:4 dichloromethane:methanol) to yield the desired product (0.082 g, 50% yield). LC/MS: m/z 506.25 [M+H]$^+$

Stage 2—cyclopentyl N-[(2-{[2,4-dihydroxy-5-(propan-2-yl)phenyl]carbonyl}-2,3-dihydro-1H-isoindol-5-yl)methyl]-L-leucinate (Example 54)

To a solution of the product of Stage 1 (0.082 g, 0.12 mmol) in ethyl acetate (5 mL) was added potassium carbonate (0.302 g, 2.18 mmol) and palladium on carbon (0.108 g, 0.10 mmol). The reaction vessel was evacuated and filled with hydrogen twice and then stirred for 2 hours. The reaction vessel was then flushed with nitrogen, filtered through Celite, washed with further ethyl acetate (50 mL). The organic fractions were concentrated to yield the desired product (0.055 g, 91% yield). $^1$H NMR (300 MHz, CDCl$_3$) 7.29-7.42 (2H, m), 7.11-7.23 (3H, m), 5.13-5.21 (1H, m), 4.88-5.04 (4H, m), 3.73 (1H, d, J=12.6 Hz), 3.55 (1H, d, J=12.7 Hz), 3.08-3.22 (2H, m), 1.44-1.89 (10H, m), 1.35-1.44 (2H, m), 1.18 (6H, d, J=6.8 Hz), 0.84 (3H, dd, J=1.1, 6.6 Hz), 0.78 (3H, dd, J=1.6, 6.5 Hz). LC/MS: purity >98%, m/z 509.25 [M+H]$^+$ The Following Compounds were Prepared in a Simiar Fashion to Example 54

Example 55 cyclopentyl N-[(2-{[2,4-dihydroxy-5-(propan-2-yl)phenyl]carbonyl}-2,3-dihydro-1H-isoindol-5-yl)methyl]-2-methylalaninate

Prepared from Intermediate E and α,α-dimethylglycine cyclopentyl ester. $^1$H NMR (300 MHz, CDCl$_3$) 7.43 (1H, s), 7.31 (1H, s), 5.23-5.31 (1H, m), 4.97-5.11 (6H, m), 3.66 (2H, br s), 3.51 (1H, s), 3.15-3.26 (1H, m), 1.50-2.07 (9H, m), 1.39 (6H, s), 1.30 (3H, s), 1.27 (3H, s). LC/MS: purity >98%, m/z 481.25 [M+H]$^+$

Example 56 tert-butyl N-[(2-{[2,4-dihydroxy-5-(propan-2-yl)phenyl]carbonyl}-2,3-dihydro-1H-isoindol-5-yl)methyl]-L-alaninate

Prepared from Intermediate E and L-alanine tert-butyl ester. $^1$H NMR (300 MHz, d6-DMSO) 8.44 (1H, br s), 4.99 (2H, quin, J=6.4 Hz), 4.02 (2H, m), 1.39 (6H, d, J=8.7 Hz), 1.21-1.27 (12H, m). LC/MS: purity >98%, m/z 455.25 [M+H]$^+$

Example 57 ethyl N-[(2-{[2,4-dihydroxy-5-(propan-2-yl)phenyl]carbonyl}-2,3-dihydro-1H-isoindol-5-yl)methyl]-L-alaninate

Prepared from Intermediate E and L-alanine ethyl ester. $^1$H NMR (300 MHz, CDCl$_3$) 7.31 (1H, s), 7.11-7.22 (3H, m), 6.02 (1H, s), 4.78-5.03 (4H, m), 4.16 (2H, q, J=7.1 Hz), 3.67 (2H, ABq, J=12.4 Hz), 3.37 (1H, q, J=7.0 Hz), 3.12 (1H, sep, J=6.9 Hz), 1.28 (3H, d, J=7.0 Hz), 1.23 (3H, t, J=8.0 Hz), 1.18 (3H, d, J=6.9 Hz), 1.17 (3H, d, J=7.5 Hz). LC/MS: purity >98%, m/z 427.25 [M+H]$^+$

Example 58 propan-2-yl N-[(2-{[2,4-dihydroxy-5-(propan-2-yl)phenyl]carbonyl}-2,3-dihydro-1H-isoindol-5-yl)methyl]-L-alaninate

Prepared from Intermediate E and L-alanine isopropyl ester. $^1$H NMR (300 MHz, CDCl$_3$) 11.49 (1H, s), 7.46 (1H, s), 7.15-7.30 (3H, m), 6.30 (1H, s), 4.99-5.16 (4H, m), 3.76 (2H, ABq, J=12.6 Hz), 3.36 (1H, q, J=7.1 Hz), 3.20 (1H, sep, J=6.9 Hz), 1.34 (3H, d, J=7.1 Hz), 1.25-1.33 (9H, m). LC/MS: purity >98%, m/z 441.25 [M+H]$^+$

Example 59 cyclopentyl N-[(2-{[2,4-dihydroxy-5-(propan-2-yl)phenyl]carbonyl}-2,3-dihydro-1H-isoindol-5-yl)methyl]-L-alaninate Prepared from Intermediate E and L-alanine cyclopentyl ester. $^1$H NMR (300 MHz, CDCl$_3$) 7.20-7.35 (4H, m), 6.20 (1H, s), 5.35 (1H, t, J=5.5 Hz), 4.70-5.00 (4H, m), 4.15 (2H, ABq, J=13.3 Hz), 3.71-3.80 (1H, m), 3.75 (1H, q, J=7.0 Hz), 3.18 (1H, sep, J=6.1 Hz), 1.57-2.03 (8H, m), 1.26 (3H, d, J=7.0 Hz), 1.25 (3H, d, J=7.0 Hz). LC/MS: purity >98%, m/z 467.25 [M+H]$^+$

Example 60 cyclopentyl 1-{[(2-{[2,4-dihydroxy-5-(propan-2-yl)phenyl]carbonyl}-2,3-dihydro-1H-isoindol-5-yl)methyl]amino}cyclopentanecarboxylate Prepared from Intermediate E and cycloleucine cyclopentyl ester. $^1$H NMR (300 MHz, d6-DMSO) 10.08 (1H, br s), 9.66 (1H, br s), 9.38-9.54 (2H, m), 7.32-7.55 (3H, m), 7.05 (1H, s), 6.41 (1H, s), 5.20-5.29 (1H, m), 4.82 (4H, m), 4.14 (2H, m), 3.10 (1H, sep, J=6.8 Hz), 1.55-2.29 (16H, m), 1.14 (6H, d, J=6.9 Hz). LC/MS: purity >98%, m/z 507.25 [M+H]$^+$

Preparation of Example 61 cyclopentyl N-[2-(2-{[2,4-dihydroxy-5-(propan-2-yl)phenyl]carbonyl}-2,3-dihydro-1H-isoindol-5-yl)ethyl]-L-leucinate

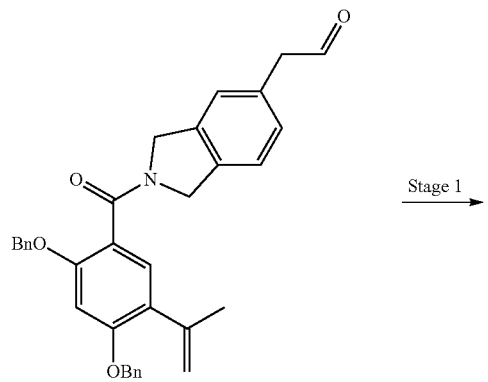

Stage 1 →

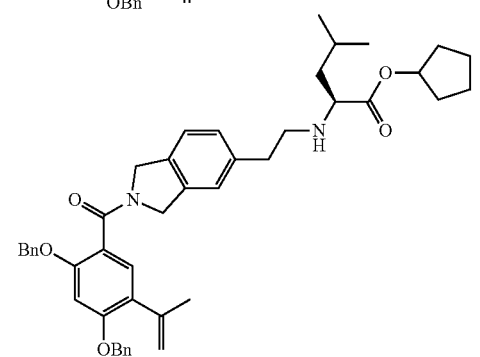

Stage 2 →

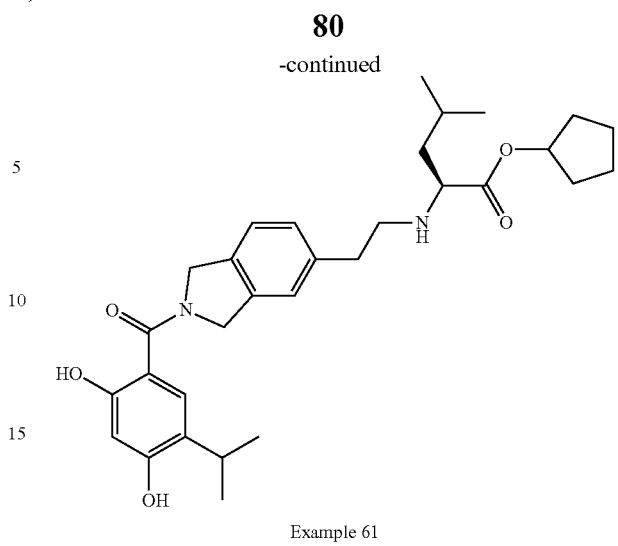

Example 61

Stage 1—cyclopentyl N-[2-(2-{[2,4-bis(benzyloxy)-5-(prop-1-en-2-yl)phenyl]carbonyl}-2,3-dihydro-1H-isoindol-5-yl)ethyl]-L-leucinate To a solution of Intermediate F (0.165 g, 0.32 mmol) in dichloroethane (10 mL) was added L-leucine cyclopentyl ester tosylate (0.197 g, 0.52 mmol) and sodium triacetoxyborohydride (0.151 g, 0.71 mmol). The mixture was stirred for 90 minutes, then quenched by addition of saturated ammonium chloride (20 mL). The product was extracted with dichloromethane (3 times 100 mL) and the combined organic extracts were dried (MgSO$_4$), concentrated and purified by flash column chromatography (SiO$_2$, ethyl acetate) to yield the desired product (0.089 g, 53% yield). LC/MS: m/z 701.25 [M+H]$^+$

Stage 2—cyclopentyl N-[2-(2-{[2,4-dihydroxy-5-(propan-2-yl)phenyl]carbonyl}-2,3-dihydro-1H-isoindol-5-yl)ethyl]-L-leucinate (Example 61)

To a solution of the product of Stage 1 (0.089 g, 0.16 mmol) in ethyl acetate (2 mL) was added potassium carbonate (0.215 g, 1.55 mmol) and palladium on carbon (0.079 g, 10%, 0.07 mmol, 46%). The reaction vessel was evacuated and filled with hydrogen twice. The mixture was stirred for 18 hours then flushed with nitrogen and filtered through Celite, washed with ethyl acetate and concentrated to yield the desired product (0.035 g, 41% yield). $^1$H NMR (300 MHz, d6-DMSO) 7.43 (1H, s), 7.05-7.20 (3H, m), 6.33 (1H, s), 5.23 (1H, t, J=5.4 Hz), 4.95-5.11 (4H, m), 3.21-3.28 (2H, m), 2.45-2.81 (3H, m), 1.56-1.94 (11H, m), 1.48 (2H, t, J=6.1 Hz), 1.27 (6H, d, J=6.8 Hz), 0.91 (6H, t, J=7.2 Hz). LC/MS: purity >98%, m/z 523.25 [M+H]$^+$ The Following Compounds were Prepared in a Simiar Fashion to Example 61

Example 62 tert-butyl N-[2-(2-{[2,4-dihydroxy-5-(propan-2-yl)phenyl]carbonyl}-2,3-dihydro-1H-isoindol-5-yl)ethyl]-L-leucinate Prepared from Intermediate F and L-leucine tert-butyl ester. $^1$H NMR (300 MHz, d3-MeOD) 7.31-7.12 (4H, m), 6.38 (1H, s), 3.24-3.04 (2H, m), 2.90-2.69 (4H, m), 1.76-1.56 (1H, m), 1.45 (9H, s), 1.23 (6H, d, J=7.0 Hz), 0.93 (6H, dd, J=10.9, 6.6 Hz). LC/MS: purity >98%, m/z 511 [M+H]$^+$

Example 63 cyclopentyl 1-{[2-(2-{[2,4-dihydroxy-5-(propan-2-yl)phenyl]carbonyl}-2,3-dihydro-1H-isoindol-5-yl)ethyl]amino}cyclopentanecarboxylate Prepared from Intermediate F and cycloleucine cyclopentyl ester. $^1$H NMR (300 MHz, d3-MeOD) 6.99-7.20 (4H, m), 6.26 (1H, s) 5.01 (1H, t, J=5.7 Hz), 3.38-3.67 (3H, m), 3.09 (1H, sep, J=6.8 Hz), 2.57-2.75 (4H, m), 1.37-2.15 (16H, m), 1.10 (6H, d, J=6.9 Hz) LC/MS: purity >98%, m/z 521.25 [M+H]+

Preparation of Example 64 cyclopentyl N-[3-(2-{[2,4-dihydroxy-5-(propan-2-yl)phenyl]carbonyl}-2,3-dihydro-1H-isoindol-5-yl)propyl]-L-leucinate

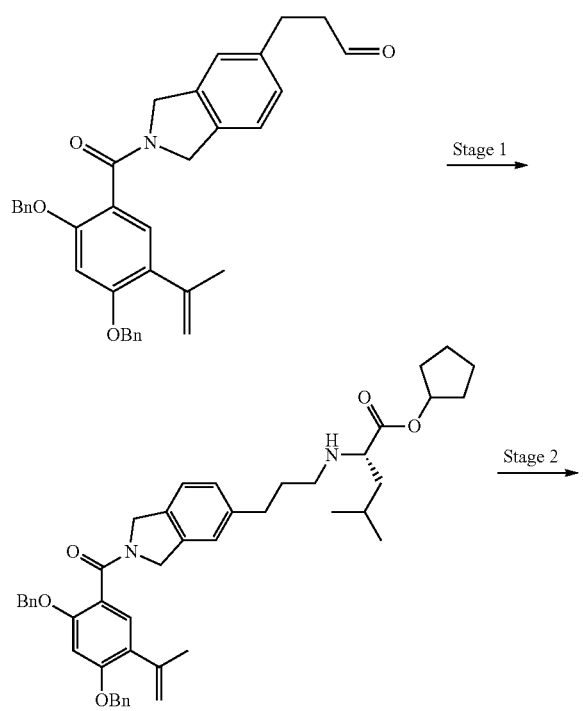

Example 64

Stage 1—cyclopentyl N-[3-(2-{[2,4-bis(benzyloxy)-5-(prop-1-en-2-yl)phenyl]carbonyl}-2,3-dihydro-1H-isoindol-5-yl)propyl]-L-leucinate To a solution of Intermediate G (0.160 g, 0.3 mmol) in dichloroethane (5 mL) was added L-leucine cyclopentyl ester tosylate (0.163 g, 0.44 mmol) and sodium triacetoxyborohydride (0.187 g, 0.88 mmol). The mixture was stirred for 90 minutes, then quenched by addition of saturated ammonium chloride (20 mL). The product was extracted with dichloromethane (3 times 100 mL) and the combined organic extracts were dried (MgSO4), concentrated and purified by flash column chromatography (SiO2, ethyl acetate) to yield the desired product (0.077 g, 48% yield). LC/MS: m/z 715.25 [M+H]+

Stage 2—cyclopentyl N-[3-(2-{[2,4-dihydroxy-5-(propan-2-yl)phenyl]carbonyl}-2,3-dihydro-1H-isoindol-5-yl)propyl]-L-leucinate (Example 64)

To a solution of the product of Stage 1 (0.070 g, 0.14 mmol) in ethyl acetate (2 mL) was added potassium carbonate (0.208 g, 1.53 mmol) and palladium on carbon (0.069 g, 10%, 0.07 mmol, 50%). The reaction vessel was evacuated and filled with hydrogen twice. The mixture was stirred for 18 hours then flushed with nitrogen and filtered through Celite, washed with ethyl acetate and concentrated to yield the desired product (0.054 g, 71% yield). $^1$H NMR (300 MHz, d6-DMSO) 7.42 (1H, s), 7.10-7.28 (3H, m), 6.27 (1H, s), 5.22 (1H, t, J=5.7 Hz), 4.94-5.12 (4H, m), 3.20-3.35 (1H, m), 2.74-2.93 (4H, m), 1.43-1.96 (11H, m), 1.26 (6H, d, J=6.8 Hz), 0.91 (3H, d, J=6.5 Hz), 0.88 (3H, d, J=6.5 Hz). LC/MS: purity >98%, m/z 537.25 [M+H]+

The Following Compounds were Prepared in a Similar Fashion to Example 64

Example 65 cyclopentyl 1-{[3-(2-{[2,4-dihydroxy-5-(propan-2-yl)phenyl]carbonyl}-2,3-dihydro-1H-isoindol-5-yl)propyl]amino}cyclopentanecarboxylate Prepared from Intermediate G and cycloleucine cyclopentyl ester. $^1$H NMR (300 MHz, d3-MeOD) 7.35-7.14 (5H, m), 5.35-5.22 (1H, m), 3.25-3.15, (1H, m), 3.00 (2H, t), 2.78 (2H, t), 2.37-2.20 (2H, m), 2.11-1.80 (10H, m), 1.69 (6H, br. s.), 1.22 (6H, d, J=6.8 Hz) LC/MS: purity >98%, m/z 535 [M+H]+

Preparation of Example 66 cyclopentyl N-(3-{[{[2,4-dihydroxy-5-(propan-2-yl)phenyl]carbonyl}(methyl)amino]methyl}benzyl)-L-leucinate

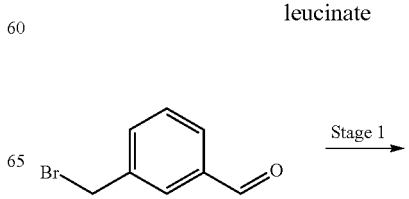

Stage 1

-continued

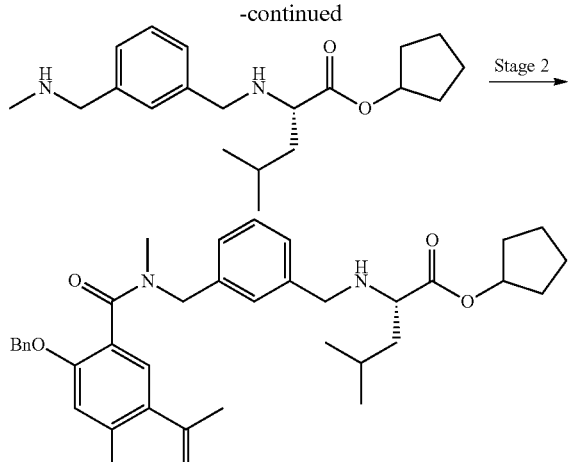

Stage 3

Example 66

Stage 1—cyclopentyl N-{3-[(methylamino)methyl]benzyl}-L-leucinate

To a solution of 3-(bromomethyl)-benzaldehyde (0.513 g, 2.57 mmol) in dichloroethane (10 mL) was added L-leucine cyclopentyl ester tosylate (1.29 g, 3.46 mmol) and sodium triacetoxyborohydride (1.37 g, 6.46 mmol). The mixture was stirred for 30 minutes at room temperature then poured into ethyl acetate (200 mL). The organic extracts were washed with saturated ammonium chloride (2 times 50 mL) and water (50 mL). The organic extracts were then dried (MgSO$_4$) and concentrated. The residue was dissolved in ethanol (30 mL) and methylamine hydrochloride (4.17 g, 61.7 mmol) was added followed by sodium hydrogen carbonate (4.32 g, 51 mmol). The mixture was stirred at room temperature for 18 hours then concentrated under vacuum, loaded directly onto a silica gel column and eluted with 95:5 dichloromethane:methanol to yield the desired product (0.130 g, 15% yield). LC/MS: m/z 333.25 [M+H]$^+$ Stage 2—cyclopentyl N-(3-{[{[2,4-bis(benzyloxy)-5-(prop-1-en-2-yl)phenyl]carbonyl}(methyl)amino]methyl}benzyl)-L-leucinate To a solution of the product of Stage 1 (0.130 g, 0.39 mmol) in dichloromethane (5 mL) was added triethylamine (0.20 mL, 1.43 mmol), Intermediate A (0.100 g, 0.26 mmol) and HATU (0.190 g, 0.50 mmol). The solution was stirred for 1 hour at room temperature then loaded directly onto a silica gel column and eluted with dichloromethane:methanol to yield the desired product (0.094 g, 33% yield). LC/MS: m/z 689.25 [M+H]$^+$ Stage 3—cyclopentyl N-(3-{[{[2,4-dihydroxy-5-(propan-2-yl)phenyl]carbonyl}(methyl)amino]methyl}benzyl)-L-leucinate (Example 66)

To a solution of the product of Stage 2 (0.094 g, 0.14 mmol) was added potassium carbonate (0.268 g, 1.94 mmol) and palladium on carbon (0.095 g, 10% on carbon, 0.09 mmol). The reaction vessel was evacuated and filled with hydrogen twice. The mixture was stirred at room temperature overnight, then the flask was flushed with nitrogen and Celite added. The mixture was filtered through a plug of Celite and the concentrated filtrate purified by reverse phase HPLC to yield the desired product (0.001 g, 3% yield). $^1$H NMR (300 MHz, d6-DMSO) 9.62 (1H, s), 9.50 (2H, br s), 7.27-7.50 (4H, m), 6.90 (1H, s), 6.37 (1H, s), 5.20 (1H, t, J=5.25 Hz), 4.57 (2H, s), 4.05-4.27 (2H, m), 3.88-4.03 (1H, m), 3.05 (1H, sep, J=6.9 Hz), 2.82 (3H, s), 1.54-1.92 (11H, m), 1.07 (6H, d, J=7.0 Hz), 0.90 (6H, d, J=6.0 Hz). LC/MS: purity >98%, m/z 511.25 [M+H]$^+$ Example 67 cyclopentyl N-(3-{[{[2,4-dihydroxy-5-(propan-2-yl)phenyl]carbonyl}(methyl)amino]methyl}benzyl)-2-methylalaninate

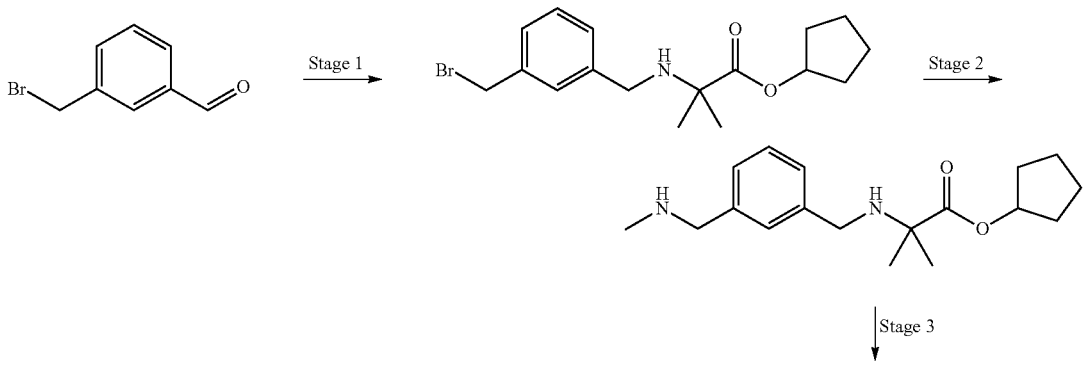

Stage 3

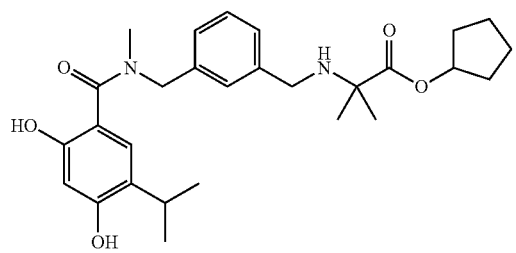

Example 67

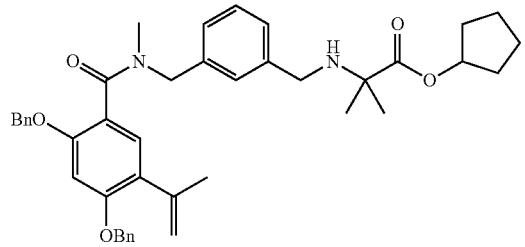

Stage 1—cyclopentyl N-[3-(bromomethyl)benzyl]-2-methylalaninate

To a solution of 3-(bromomethyl)-benzaldehyde (0.503 g, 2.52 mmol) in dichloroethane (20 mL) was added α,α-dimethylglycine cyclopentyl ester (0.893 g, 5.2 mmol) and sodium triacetoxyborohydride (1.47 g, 6.9 mmol). The mixture was stirred at room temperature for 3 hours, then poured into ethyl acetate (200 mL) and washed with saturated ammonium chloride solution (3 times 50 mL). The organic fraction was dried (MgSO$_4$), concentrated and purified by flash column chromatography (SiO$_2$, 7:3 heptane:ethyl acetate) to yield the desired product (0.350 g, 39% yield). LC/MS: m/z 354/356 [M+H]$^+$

Stage 2—cyclopentyl 2-methyl-N-{3-[(methylamino)methyl]benzyl}alaninate

To the product of Stage 1 (0.350 g, 1.01 mmol) was added methylamine in methanol (25 mL, 8M solution, 200 mmol). The solution was stirred at room temperature for 24 hours, then poured into ethyl acetate (350 mL) and washed with water (4 times 50 mL). The organic fraction was dried (MgSO$_4$), concentrated and purified by flash column chromatography (SiO$_2$, 9:1 dichloromethane:methanol then 4:1 dichloromethane:methanol) to yield the desired product (0.096 g, 31% yield). LC/MS: m/z 305.25 [M+H]$^+$

Stage 3—cyclopentyl N-(3-{[{[2,4-bis(benzyloxy)-5-(prop-1-en-2-yl)phenyl]carbonyl}(methyl)amino]methyl}benzyl)-2-methylalaninate To a solution of the product of Stage 2 (0.096 g, 0.31 mmol) in dichloromethane (5 mL) was added N,N-diisopropylethylamine (1 mL, 5.7 mmol), Intermediate A (0.118 g, 0.31 mmol) and HATU (0.180 g, 0.47 mmol). The solution was stirred at room temperature for 1 hour, then loaded directly onto a silica gel column and eluted with 1:1 heptane:ethyl acetate to yield the desired product (0.167 g, 81% yield). LC/MS: m/z 661.25 [M+H]$^+$

Stage 4—cyclopentyl N-(3-{[{[2,4-dihydroxy-5-(propan-2-yl)phenyl]carbonyl}(methyl)amino]methyl}benzyl)-2-methylalaninate (Example 67)

To a solution of the product of Stage 3 (0.096 g, 0.14 mmol) in ethyl acetate (10 mL) was added potassium carbonate (0.195 g, 1.4 mmol) and palladium on carbon (0.202 g, 10%, 0.19 mmol). The reaction vessel was evacuated and filled with hydrogen twice. The mixture was stirred at room temperature for 24 hours, then flushed with nitrogen. Celite was added and the mixture filtered through a plug of Celite. The filtrate was concentrated and purified by flash column chromatography (SiO$_2$, 7:3 ethyl acetate:heptane) to yield the desired product (0.009 g, 14% yield). $^1$H NMR (300 MHz, d3-MeOD) 7.19-7.40 (4H, m), 7.02 (1H, s), 6.35 (1H, s), 5.20 (1H, m), 4.66 (2H, m), 3.63 (2H, s), 3.16 (1H, sep, J=6.9 Hz), 2.96 (3H, s), 1.56-1.98 (8H, m), 1.35 (6H, s), 1.12 (6H, d, J=6.9 Hz). LC/MS: purity >98%, m/z 483.25 [M+H]$^+$

Example 68 cyclopentyl 1-[(3-{[{[2,4-dihydroxy-5-(propan-2-yl)phenyl]carbonyl}(methyl)amino]methyl}benzyl)amino]cyclopentanecarboxylate

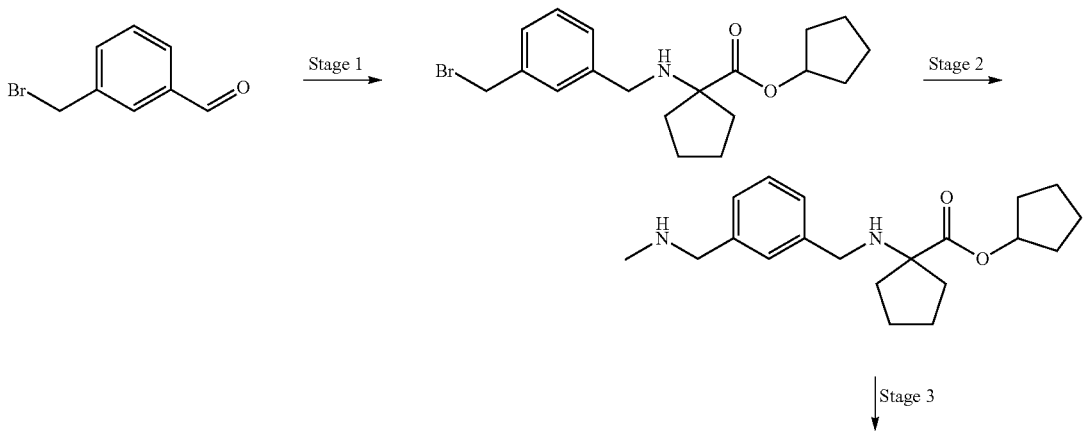

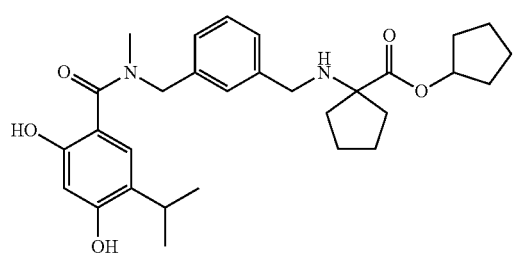

Example 68

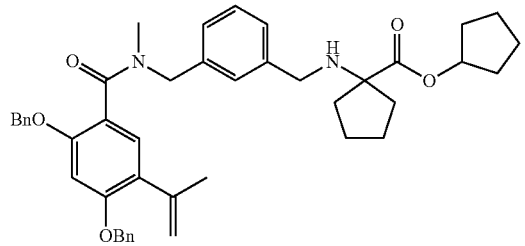

Stage 1—cyclopentyl 1-{[3-(bromomethyl)benzyl]amino}cyclopentanecarboxylate

To a solution of 3-(bromomethyl)-benzaldehyde (0.467 g, 2.44 mmol) in dichloroethane (20 mL) was added cycloleucine cyclopentyl ester (0.802 g, 4.06 mmol) and sodium triacetoxyborohydride (1.18 g, 5.56 mmol). The mixture was stirred at room temperature for 3 hours, then poured into ethyl acetate (200 mL) and washed with saturated ammonium chloride solution (3 times 50 mL). The organic fraction was dried (MgSO$_4$), concentrated and purified by flash column chromatography (SiO$_2$, 7:3 heptane:ethyl acetate) to yield the desired product (0.568 g, 61% yield). LC/MS: m/z 380/382 [M+H]$^+$

Stage 2—cyclopentyl 1-({3-[(methylamino)methyl]benzyl}amino)cyclopentane carboxylate To the product of Stage 1 (0.568 g, 1.49 mmol) was added methylamine in methanol (25 mL, 8M solution, 200 mmol). The solution was stirred at room temperature for 24 hours, then poured into ethyl acetate (350 mL) and washed with water (4 times 50 mL). The organic fraction was dried (MgSO$_4$), concentrated and purified by flash column chromatography (SiO$_2$, 9:1 dichloromethane:methanol then 4:1 dichloromethane:methanol) to yield the desired product (0.173 g, 17% yield). LC/MS: m/z 331.25 [M+H]$^+$

Stage 3—cyclopentyl 1-[(3-{[{[2,4-bis(benzyloxy)-5-(prop-1-en-2-yl)phenyl]carbonyl}(methyl)amino]methyl}benzyl)amino]cyclopentanecarboxylate To a solution of the product of Stage 2 (0.173 g, 0.45 mmol) in dichloromethane (5 mL) was added N,N-diisopropylethylamine (1 mL, 5.7 mmol), Intermediate A (0.142 g, 0.38 mmol) and HATU (0.206 g, 0.54 mmol). The solution was stirred at room temperature for 1 hour, then loaded directly onto a silica gel column and eluted with 1:1 heptane:ethyl acetate to yield the desired product (0.243 g, 78% yield). LC/MS: m/z 687.25 [M+H]$^+$

Stage 4—cyclopentyl 1-[(3-{[{[2,4-dihydroxy-5-(propan-2-yl)phenyl]carbonyl}(methyl)amino]methyl}benzyl)amino]cyclopentanecarboxylate (Example 68)

To a solution of the product of Stage 3 (0.243 g, 0.35 mmol) in ethyl acetate (10 mL) was added potassium carbonate (0.353 g, 2.55 mmol) and palladium on carbon (0.213 g, 10%, 0.2 mmol). The reaction vessel was evacuated and filled with hydrogen twice. The mixture was stirred at room temperature for 24 hours, then flushed with nitrogen. Celite was added and the mixture filtered through a plug of Celite. The filtrate was concentrated and purified by flash column chromatography (SiO$_2$, 7:3 ethyl acetate:heptane) to yield the desired product (0.016 g, 9% yield). $^1$H NMR (300 MHz, d3-MeOD) 7.19-7.36 (4H, m), 7.02 (1H, s), 6.35 (1H, s), 5.21 (1H, m), 4.66 (2H, s), 1.87 (2H, s), 3.16 (1H, sep, J=6.9 Hz), 2.03-2.15 (2H, m), 1.58-1.98 (14H, m), 1.12 (6H, d, J=6.9 Hz). LC/MS: purity >98%, m/z 509.25 [M+H]$^+$

Example 69 cyclopentyl (2S)-[(3-{[{[2,4-dihydroxy-5-(propan-2-yl)phenyl]carbonyl}(methyl)amino]methyl}benzyl)amino](phenyl)ethanoate

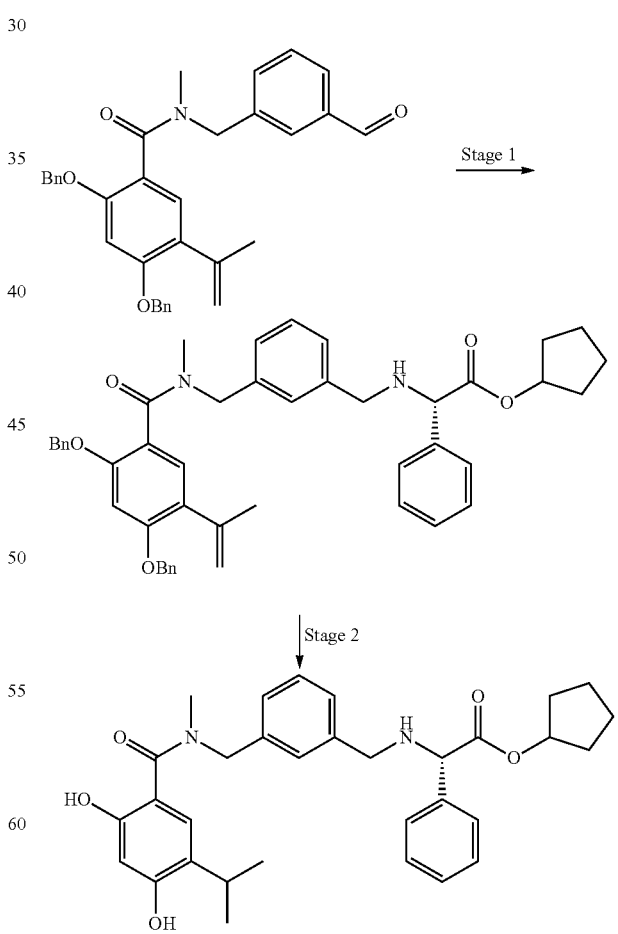

Example 69

Stage 1—cyclopentyl (2S)-[(3-{[{[2,4-bis(benzyloxy)-5-(prop-1-en-2-yl)phenyl]carbonyl}(methyl)amino]methyl}benzyl)amino](phenyl)ethanoate To a solution of Intermediate H (0.128 g, 0.25 mmol) in dichloroethane (10 mL) was added L-phenylglycine cyclopentyl ester tosylate (0.199 g, 0.51 mmol) and sodium triacetoxyborohydride. The solution was stirred at room temperature for 90 minutes then loaded directly onto a silica gel column and eluted with 7:3 ethyl acetate:heptane to yield the desired product (0.154 g, 86% yield). LC/MS: m/z 709.25 [M+H]$^+$ Stage 2—cyclopentyl (2S)-[(3-{[{[2,4-dihydroxy-5-(propan-2-yl)phenyl]carbonyl}(methyl)amino]methyl}benzyl)amino](phenyl)ethanoate (Example 69)

To a solution of the product of Stage 1 (0.154 g, 0.22 mmol) in ethyl acetate (10 mL) was added potassium carbonate (0.125 g, 0.90 mmol) and palladium on carbon (0.118 g, 10%, 0.11 mmol). The reaction vessel was evacuated and filled with hydrogen twice, and stirred for 3 hours. The mixture was purged with nitrogen, Celite was added and the mixture filtered through Celite, and washed with additional ethyl acetate (50 mL). The filtrate was concentrated to yield the desired product (0.056 g, 47% yield). $^1$H NMR (300 MHz, d6-DMSO) 9.62 (1H, br s), 9.47 (1H, br s), 7.07-7.38 (9H, m), 6.85 (1H, s), 6.36 (1H, s), 5.00-5.08 (1H, m), 4.52 (2H, s), 4.24 (1H, d, J=8.8 Hz), 3.62 (2H, d, J=5.3 Hz), 2.91-3.09 (2H, m), 2.81 (3H, s), 1.28-1.83 (8H, m), 1.03 (6H, d, J=6.6 Hz) LC/MS: purity >98%, m/z 531.25 [M+H]$^+$ Preparation of Example 70 cyclopentyl N-(4-{[{[2,4-dihydroxy-5-(propan-2-yl)phenyl]carbonyl}(methyl)amino]methyl}benzyl)-L-leucinate

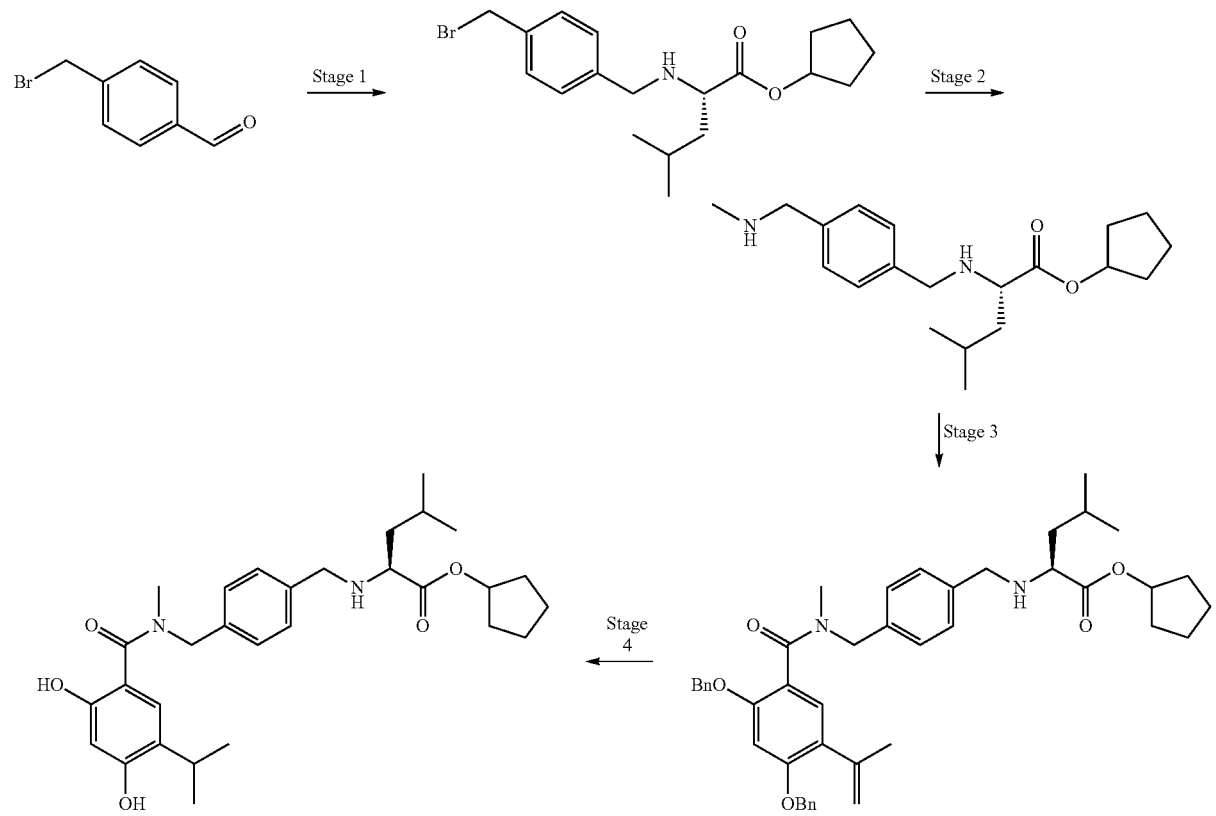

Example 70

Stage 1—cyclopentyl N-[4-(bromomethyl)benzyl]-L-leucinate

To a solution of 4-(bromomethyl)-benzaldehyde (0.940 g, 4.72 mmol) in dichloroethane (20 mL) was added L-leucine cyclopentyl ester tosylate (2.40 g, 6.4 mmol) and sodium triacetoxyborohydride (2.53 g, 11.9 mmol). The reaction mixture was stirred for 1 hour then poured into ethyl acetate (300 mL). The organic fraction was washed with saturated sodium hydrogen carbonate (100 mL, 3 times 50 mL) then dried (MgSO$_4$), concentrated and purified by flash column chromatography (SiO$_2$, gradient 0-3% methanol-dichloromethane) to yield the desired product (1.504 g, 83% yield). LC/MS: m/z 382/384 [M+H]$^+$ Stage 2—cyclopentyl N-{4-[(methylamino)methyl]benzyl}-L-leucinate To a solution of the product of Stage 1 (1.504 g, 3.9 mmol) in ethanol (30 mL) was added methylamine hydrochloride (1.98 g, 29 mmol) and sodium hydrogen carbonate (1.69 g, 20.1 mmol). The mixture was stirred at room temperature overnight, concentrated under vacuum and loaded directly onto a silica gel column, eluting with 1:9 methanol:dichloromethane to yield the desired product (0.120 g, 9.2% yield). LC/MS: m/z 333.25 [M+H]$^+$

Stage 3—cyclopentyl N-(4-{[{[2,4-bis(benzyloxy)-5-(prop-1-en-2-yl)phenyl]carbonyl}(methyl)amino]methyl}benzyl)-L-leucinate To a solution of Intermediate A (0.138 g, 0.37 mmol) in dichloromethane (10 mL) was added the product of Stage 2 (0.120 g, 0.36 mmol), N,N-diisopropylethylamine (1 mL, 5 mmol), HOBt (0.010 g, 0.074 mmol) and EDCI (0.094 g, 0.49 mmol). The solution was stirred at room temperature overnight, then loaded directly onto a silica gel column and eluted with 2:98 methanol:dichloromethane to yield the desired product (0.164 g, 64% yield). LC/MS: m/z 689.25 [M+H]$^+$

Stage 4—cyclopentyl N-(4-{[{[2,4-dihydroxy-5-(propan-2-yl)phenyl]carbonyl}(methyl)amino]methyl}benzyl)-L-leucinate (Example 70)

To a solution of the product of Stage 3 (0.081 g, 0.12 mmol) in ethyl acetate (5 mL) was added potassium carbonate (0.057 g, 0.41 mmol) and palladium on carbon (0.046 g, 0.04 mmol). The reaction vessel was evacuated and filled with hydrogen twice and stirred for 90 minutes. The reaction was flushed with nitrogen, filtered through Celite and washed with ethyl acetate. The filtrate was concentrated to yield the desired product (0.040 g, 66% yield). $^1$H NMR (300 MHz, CDCl$_3$) 7.36 (2H, d, J=8.1 Hz), 7.24 (2H, d, J=8.1 Hz), 7.09 (1H, s), 6.36 (1H, s), 5.23-5.30 (1H, m), 3.84 (1H, d, J=12.8 Hz), 3.67 (1H, d, J=12.8 Hz), 3.30 (1H, t, J=7.3 Hz), 3.30-3.20 (4H, m), 1.57-1.99 (9H, m), 1.50 (2H, t, J=7.1 Hz), 0.97 (6H, d, J=6.9 Hz), 0.92 (3H, d, J=6.6 Hz), 0.86 (3H, d, J=6.6 Hz). LC/MS: purity >98%, m/z 511.25 [M+H]$^+$

Preparation of Example 71 cyclopentyl (2S)-[(4-{[{[2,4-dihydroxy-5-(propan-2-yl)phenyl]carbonyl}(methyl)amino]methyl}benzyl)amino](phenyl)ethanoate

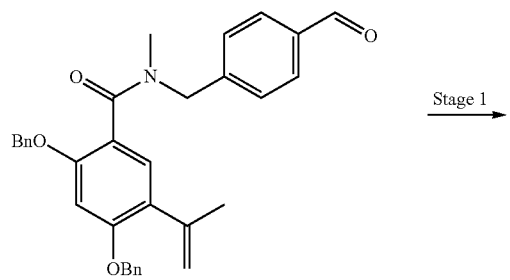

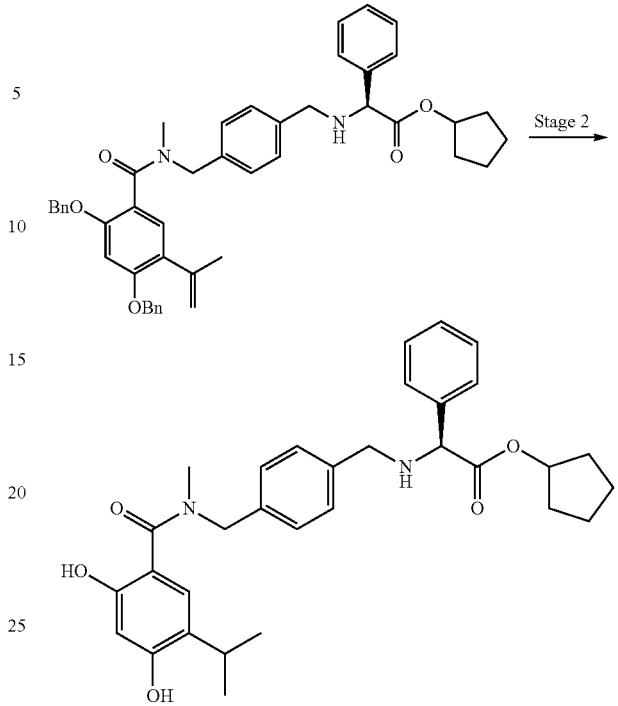

Example 71

Stage 1—cyclopentyl (2S)-[(4-{[{[2,4-bis(benzyloxy)-5-(prop-1-en-2-yl)phenyl]carbonyl}(methyl)amino]methyl}benzyl)amino](phenyl)ethanoate To a solution of Intermediate I (0.108 g, 0.21 mmol) in dichloroethane (10 mL) was added L-phenylglycine cyclopentyl ester tosylate (0.138 g, 0.35 mmol) and sodium triacetoxyborohydride (0.183 g, 0.86 mmol). The mixture was stirred at room temperature until all of Intermediate I was consumed, then poured into ethyl acetate and washed with saturated ammonium chloride (3 times 50 mL). The organic fraction was dried (MgSO$_4$), concentrated and purified by flash column chromatography (SiO$_2$, 7:3 heptane:ethyl acetate to 1:1 heptane:ethyl acetate) to yield the desire product (0.221 g, 100% yield). LC/MS: m/z 709.25 [M+H]$^+$

Stage 2—cyclopentyl (2S)-[(4-{[{[2,4-dihydroxy-5-(propan-2-yl)phenyl]carbonyl}(methyl)amino]methyl}benzyl)amino](phenyl)ethanoate (Example 71)

To a solution of the product of Stage 1 (0.221 g, 0.31 mmol) in ethyl acetate (10 mL) was added potassium carbonate (0.140 g, 1.01 mmol) and palladium on carbon (0.140 g, 10%, 0.13 mmol). The reaction vessel was evacuated and filled with hydrogen, then stirred at room temperature overnight. The reaction was flushed with nitrogen, Celite was added and the mixture filtered through a plug of Celite. The filtrate was concentrated to yield the desired product (0.035 g, 21% yield). $^1$H NMR (300 MHz, CDCl$_3$) 7.23-7.43 (10H, m), 7.09 (1H, s), 6.34 (1H, s), 5.21 (1H, m), 4.72 (2H, s), 4.36 (1H, s), 3.77 (2H, s), 3.08 (3H, s), 3.06 (1H, sep, J=6.9 Hz), 1.43-1.92 (9H, m), 0.98 (6H, d, J=6.9 Hz). LC/MS: m/z 531.25 [M-4-1]$^+$ The Following Compounds were Prepared in a Simiar Fashion to Example 71

Example 72 cyclopentyl N-(4-{[{[2,4-dihydroxy-5-(propan-2-yl)phenyl]carbonyl}(methyl)amino]methyl}benzyl)-2-methylalaninate Prepared from Intermediate I and α,α-dimethylglycine cyclopentyl ester tosylate $^1$H NMR (300 MHz, CDCl$_3$) 7.20-7.42 (4H, m), 7.06-7.12 (1H, m), 6.28 (1H, s), 5.28 (1H, m), 4.70 (2H, m), 3.66, (1H, m), 3.03-3.08 (4H, m), 1.59-2.02 (8H, m), 1.35 (6H, s), 0.97 (6H, d, J=6.9 Hz). LC/MS: purity >98%, m/z 482.35 [M+H]$^+$

Preparation of Example 73 cyclopentyl N-[2-(4-{[{[2,4-dihydroxy-5-(propan-2-yl)phenyl]carbonyl}(methyl)amino]methyl}phenyl)ethyl]-2-methylalaninate

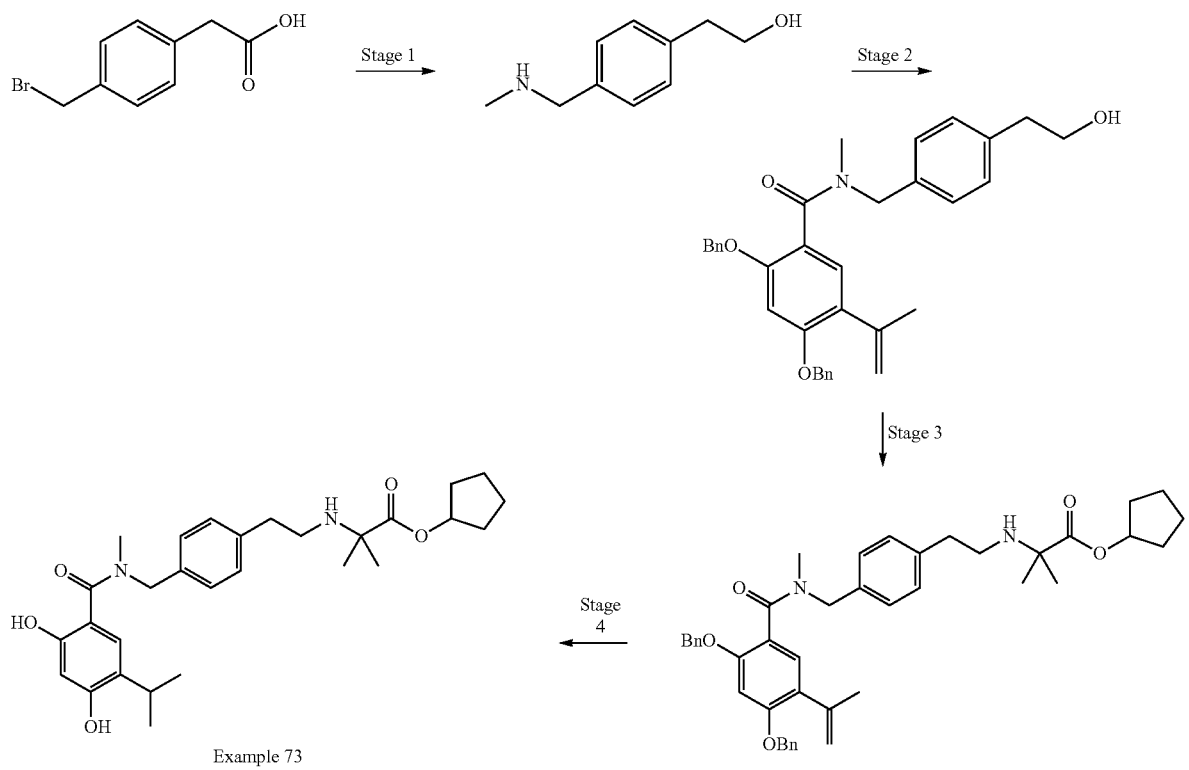

Example 73

Stage 1—2-{4-[(methylamino)methyl]phenyl}ethanol

To a solution of 4-(bromomethyl)-phenylacetic acid (0.586 g, 2.36 mmol) in toluene/tetrahydrofuran (10 mL/8 mL) was added borane-dimethylsulfide (4.5 mL, 45 mmol borane). The mixture was stirred at room temperature for 1 hour, then quenched by careful addition of water (50 mL). The mixture was poured into ethyl acetate (250 mL) and washed with water (50 mL) and saturated brine (50 mL). The organic fraction was dried (MgSO$_4$) and concentrated. To the residue obtained was added methylamine in methanol (20 mL, 8M solution, 160 mmol). The solution was stirred at room temperature for 15 minutes, then concentrated under vacuum and used without further purification. LC/MS: m/z 166 [M+H]$^+$

Stage 2—2,4-bis(benzyloxy)-N-[4-(2-hydroxyethyl)benzyl]-N-methyl-5-(prop-1-en-2-yl)benzamide To the product obtained in Stage 1 (~2 mmol) in dichloromethane (40 mL) was added N,N-diisopropylethylamine (5 mL, 28.7 mmol), Intermediate A (1.01 g, 2.7 mmol) and HATU (1.08 g, 2.84 mmol). The mixture was stirred at room temperature for 18 hours, then poured into ethyl acetate (300 mL). The organic extract was washed with 2M HCl solution (3 times 50 mL), and 1M sodium hydroxide solution (50 mL). The organic fraction was dried (MgSO$_4$), concentrated and purified by flash column chromatography (SiO$_2$, 1:1 heptane:ethyl acetate) to yield the desired product (0.712 g, 58% yield (2 steps). LC/MS: m/z 522.25 [M+H]$^+$

Stage 3—cyclopentyl N-[2-(4-{[{[2,4-bis(benzyloxy)-5-(prop-1-en-2-yl)phenyl]carbonyl}(methyl)amino]methyl}phenyl)ethyl]-2-methylalaninate To the product of Stage 2 (0.163 g, 0.31 mmol) in dichloromethane (10 mL) was added Dess-Martin periodinane (0.196 g, 0.46 mmol). The solution was stirred for 30 minutes then quenched by addition of 1:1 saturated sodium hydrogen carbonate:saturated sodium thiosulfate (10 mL). After stirring for 5 minutes the mixture was extracted with dichloromethane (2 times 100 mL), and the combined extracts were dried (MgSO$_4$) and concentrated. To the residue obtained (crude aldehyde) in dichloroethane (10 mL) was added α,α-dimethylglycine cyclopentyl ester (0.260 g, 0.66 mmol) and sodium triacetoxyborohydride (0.215 g, 1.01 mmol). The mixture was stirred for 1 hour, then quenched with saturated ammonium chloride (50 mL). Product was extracted with ethyl acetate (2 times 100 mL) and the combined extracts were dried (MgSO$_4$), concentrated and purified by flash column chromatography (SiO$_2$, 3:1 ethyl acetate:heptane) to yield the desired product (0.077 g, 37% yield). LC/MS: m/z 675.25 [M+H]$^+$ Stage 4—cyclopentyl N-[2-(4-{[{[2,4-dihydroxy-5-(propan-2-yl)phenyl]carbonyl}(methyl)amino]methyl}phenyl)ethyl]-2-methylalaninate (Example 73)

To a solution of the product of Stage 3 (0.077 g, 0.11 mmol) in ethyl acetate (10 mL) was added potassium carbonate (0.201 g, 1.45 mmol) and palladium on carbon (0.023 g, 10%, 0.02 mmol). The reaction vessel was evacuated and filled with hydrogen twice, then stirred overnight. After purging with nitrogen, a second portion of palladium on carbon (0.075 g, 0.06 mmol) was added, and the flask evacuated and filled with hydrogen. After 1 hour the reaction vessel was purged with nitrogen and the mixture filtered through Celite. The filtrate was concentrated to give the desired product (0.051 g, 94% yield). $^1$H NMR (300 MHz, CDCl$_3$) 7.20-7.35 (4H, m), 7.09-7.14 (1H, m), 6.40-6.47 (1H, m), 5.17-5.25 (1H, m), 4.67-4.75 (1H, m), 2.75-3.13 (7H, m), 1.23-1.94 (17H, m), 0.93-1.05 (6H, m). LC/MS: purity >98%, m/z 497.25 [M+H]$^+$ Preparation of Example 74 cyclopentyl N-{[(2R)-1-{[2,4-dihydroxy-5-(propan-2-yl)phenyl]carbonyl}pyrrolidin-2-yl]methyl}-L-leucinate

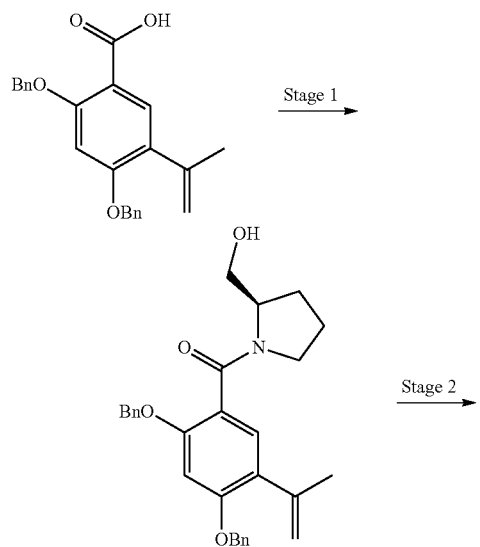

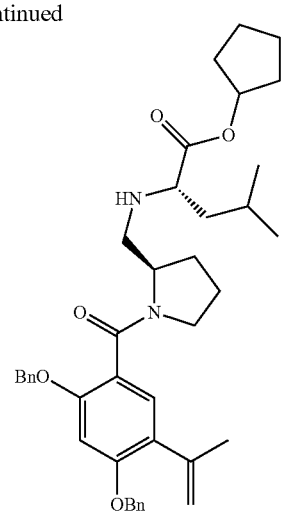

Stage 3

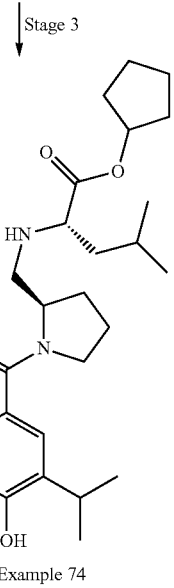

Example 74

Stage 1—[2,4-bis(benzyloxy)-5-(prop-1-en-2-yl)phenyl][(2R)-2-(hydroxymethyl)pyrrolidin-1-yl]methanone To a solution of Intermediate A (0.342 g, 0.91 mmol) in dichloromethane (10 mL) was added a solution of (R)-1-pyrrolidin-2-yl-methanol (1.00 g, 10 mmol) in dichloromethane (3 mL), then triethylamine (1 mL, 7.1 mmol) and EDCI (0.660 g, 3.43 mmol). The mixture was stirred at room temperature for 24 hours, then poured into ethyl acetate (200 mL). The organic layer was washed with 1M HCl solution (4 times 50 mL) then dried (MgSO$_4$), concentrated and used without further purification (0.344 g, 83% yield). LC/MS: m/z 458.25 [M+H]$^+$ Stage 2—cyclopentyl N-{[(2R)-1-{[2,4-bis(benzyloxy)-5-(prop-1-en-2-yl)phenyl]carbonyl}pyrrolidin-2-yl]methyl}-L-leucinate To a solution of the product of Stage 1 (0.277 g, 0.61 mmol) in dichloromethane (10 mL) was added Dess-Martin periodinane (0.370 g, 0.87 mmol). The solution was stirred at room temperature for 30 minutes, then quenched by addition of 1:1 saturated sodium hydrogen carbonate:sodium thiosulfate (20 mL). The mixture was stirred for 10 minutes then poured into ethyl acetate (100 mL) and washed with water (2 times 50 mL). The organic fraction was dried (MgSO$_4$) and concentrated. To a solution of the residue obtained (crude aldehyde) in dichloroethane (10 mL) was added L-leucine cyclopentyl ester tosylate (0.465 g, 1.25 mmol) and sodium triacetoxyborohydride (0.568 g, 2.7 mmol). The mixture was stirred for 1 hour then poured into 1:1 saturated ammonium chloride solution:dichloromethane. Product was extracted with dichloromethane (100 mL) and the combined organic extracts dried (MgSO$_4$), concentrated and purified by flash column chromatography (SiO$_2$, 7:3 ethyl acetate:heptane) to yield the desired product (0.047 g, 12% yield). LC/MS: m/z 639.25 [M+H]$^+$ Stage 3—cyclopentyl N-{[(2R)-1-{[2,4-dihydroxy-5-(propan-2-yl)phenyl]carbonyl}pyrrolidin-2-yl]methyl}-L-leucinate (Example 74)

To a solution of the product of Stage 2 (0.047 g, 0.07 mmol) in ethyl acetate (5 mL) was added palladium on carbon (0.023 g, 10% on carbon, 0.03 mmol). The reaction vessel was evacuated and filled with hydrogen twice. The reaction mixture was stirred for 30 minutes, then further palladium on carbon (0.075 g, 0.06 mmol) was added. The mixture was stirred for 30 minutes, the reaction was flushed with nitrogen, Celite was added and the reaction mixture filtered through a Celite pad, washing with ethyl acetate (100 mL). The filtrate was concentrated to yield the desired product (0.006 g, 17% yield) to which water was added followed by freeze drying overnight. $^1$H NMR (300 MHz, d6-DMSO) 10.76 (1H, br s), 9.95 (1H, br s), 7.29 (1H, s), 6.62 (1H, s), 5.37 (1H, s), 4.30-4.44 (1H, m), 3.59-3.83 (5H, m), 3.30-3.47 (2H, m), 1.50-2.30 (1H, m), 1.32-1.50 (6H, m), 1.06-1.22 (6H, m). LC/MS: purity >98%, m/z 461.25 [M+H]$^+$ Preparation of Example 75 cyclopentyl N-{[(2S)-1-{[2,4-dihydroxy-5-(propan-2-yl)phenyl]carbonyl}pyrrolidin-2-yl]methyl}-L-leucinate Example 75 was prepared in a simiar fashion to Example 74 starting with (S)-1-pyrrolidin-2-yl-methanol and Intermediate A.
$^1$H NMR (300 MHz, d6-DMSO) 10.04 (1H, br s), 9.75 (1H, br s), 9.39 (1H, br s), 7.00 (1H, s), 6.37 (1H, s), 5.23 (1H, t, J=5.64 Hz), 4.34 (1H, br s), 4.08 (1H, br s), 3.37-3.53 (2H, m), 3.05-3.11 (2H, m), 1.52-2.19 (15H, m), 1.12 (3H, d, J=6.9 Hz), 1.11 (3H, d, J=6.9 Hz), 0.92 (6H, d, J=5.2 Hz). LC/MS: purity >98%, m/z 461.25 [M+H]$^+$ Preparation of Example 76 cyclopentyl N-(1-{[2,4-dihydroxy-5-(propan-2-yl)phenyl]carbonyl}pyrrolidin-3-yl)-D-leucinate

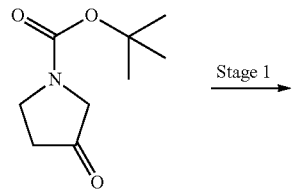

Stage 1

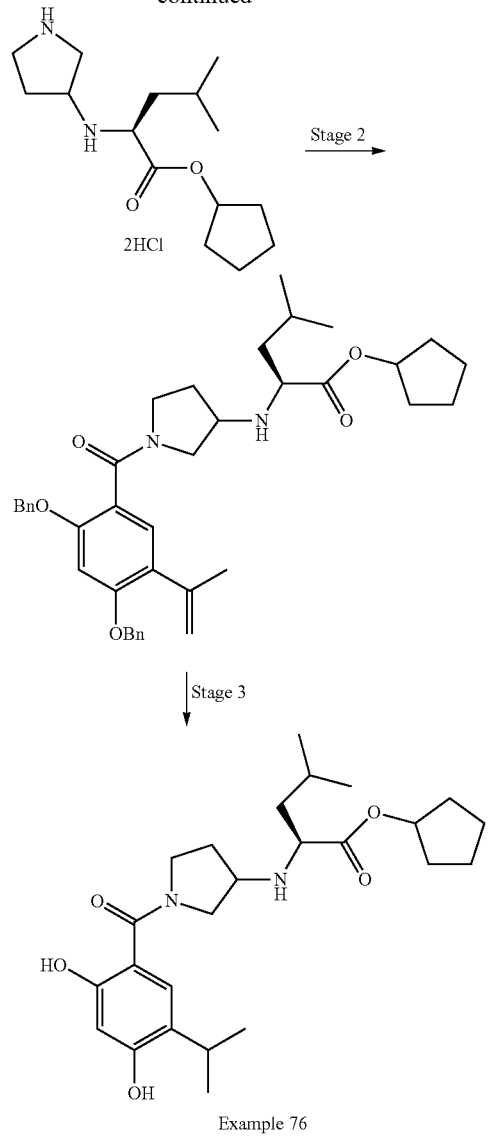

Example 76

Stage 1—cyclopentyl N-pyrrolidin-3-yl-D-leucinate dihydrochloride

To a solution of N-Boc-3-pyrrolidinone (0.382 g, 4.76 mmol) in dichloroethane (20 mL) was added L-leucine cyclopentyl ester tosylate (1.96 g, 5.3 mmol) and sodium triacetoxyborohydride (2.65 g, 12.5 mmol). The mixture was stirred at room temperature for 3 hours then poured into ethyl acetate (150 mL) and quenched with saturated ammonium chloride (50 mL). The organic layer was washed with saturated sodium hydrogen carbonate (3 times 30 mL), then dried (MgSO$_4$), concentrated and purified by flash column chromatography (SiO$_2$, 7:3 ethyl acetate:heptane) to yield the N-Boc protected product. This material was dissolved in dichloromethane (5 mL) then HCl (20 mL, 4M solution in dioxane, 80 mmol) was added (2 times 10 mL batches five minutes apart). The mixture was stirred at room temperature for 1 hour then diethyl ether (100 mL) was added. The precipitate was collected by filtration, washed with further diethyl ether (50 mL) then dried under vacuum to yield the desired product as the bis-HCl salt (0.855 g, 52% yield). LC/MS: m/z 269.25 [M+H]$^+$

Stage 2—cyclopentyl N-(1-{[2,4-bis(benzyloxy)-5-(prop-1-en-2-yl)phenyl]carbonyl}pyrrolidin-3-yl)-D-leucinate To a solution of Intermediate A (0.823 g, 2.2 mmol) in dichloromethane (12 mL) was added triethylamine (2 mL, 19.7 mmol), the product of Stage 1 (0.816 g, 2.39 mmol) and EDCI (3.11 g, 15.8 mmol). The mixture was stirred for 16 hours, poured into ethyl acetate (150 mL) and washed with water (4 times 50 mL). The organic fraction was dried (MgSO$_4$), concentrated and purified by flash column chromatography (SiO$_2$, 7:3 ethyl acetate:heptane) to yield the desired product (0.755 g, 55% yield). LC/MS: m/z 625.25 [M+H]$^+$

Stage 3—cyclopentyl N-(1-{[2,4-dihydroxy-5-(propan-2-yl)phenyl]carbonyl}pyrrolidin-3-yl)-D-leucinate (Example 76)

To a solution of the product of Stage 2 (0.755 g, 1.2 mmol) in ethyl acetate (25 mL) was added palladium on carbon (0.180 g, 10%, 0.17 mmol). The reaction vessel was evacuated and filled with hydrogen twice. The mixture was stirred for 3 hours, the reaction vessel was purged with nitrogen and a second portion of palladium on carbon (0.212 g, 10%, 0.2 mmol) was added. The mixture was stirred for a further 1 hour then the reaction vessel was purged with nitrogen and the reaction mixture filtered through a plug of Celite, washing with ethyl acetate (150 mL). The filtrate was concentrated to yield the desired product (0.493 g, 92% yield). $^1$H NMR (300 MHz, d6-DMSO) 10.74 (0.5H, s), 10.63 (0.5H, s), 9.70 (1H, s), 7.05 (1H, s), 6.31 (1H, s), 4.96-5.14 (1H, m), 2.97-3.66 (8H, m), 2.05-2.35 (1H, m), 1.27-1.98 (11H, m), 1.12 (3H, d, J=6.9 Hz), 1.12 (3H, d, J=6.9 Hz), 0.85 (6H, t, J=6.7 Hz). LC/MS: purity >98%, m/z 447.25 [M+H]$^+$ General Methods for the Preparation of Carboxylic Acids from the Corresponding Alkyl Ester Method A To a solution of cyclopentyl ester in ethanol was added 50% sodium hydroxide solution. The mixture was stirred at room temperature until all starting material had been consumed. The mixture was neutralised with HCl (1M solution) and extracted with ethyl acetate to yield the desired product which was purified by reverse phase HPLC.

Method B

To a solution of cyclopentyl ester in methanol was added 2M sodium hydroxide solution. The mixture was stirred at room temperature until all starting material had been consumed. The mixture was neutralised with HCl (1M solution) and extracted with ethyl acetate to yield the desired product which was purified by reverse phase HPLC.

Method C

To a solution of cyclopentyl ester in THF was added potassium trimethylsilanolate. The mixture was stirred for 2 hours. The mixture was concentrated and purified by reverse phase HPLC to yield the desired product.

Method D

To a solution of cyclopentyl ester in methanol was added 1M sodium hydroxide solution. The mixture was stirred at room temperature until all starting material had been consumed. The mixture was neutralised with HCl (1M solution), extracted with ethyl acetate and purified by reverse phase HPLC to yield the desired product.

Method E

To a solution of tert-butyl ester in DCM was added HCl (4M solution in dioxane). The mixture was stirred at 35° C. for 48 hours, then concentrated under vacuum and purified by reverse phase HPLC to yield the desired product.

Example 77

N-(4-{[{[2,4-dihydroxy-5-(propan-2-yl)phenyl]carbonyl}(methyl)amino]methyl}benzyl)-L-leucine Method A—Prepared from Example 70

$^1$H NMR (300 MHz, d6-DMSO) 9.65 (1H, br s), 9.54 (1H, br s), 7.49 (2H, d, J=7.8 Hz), 7.33 (2H, d, J=7.6 Hz), 6.87 (1H, s), 6.42 (1H, s), 4.57 (2H, br s), 4.12 (2H, q, J=7.4 Hz), 3.67-3.78 (1H, m), 2.99-3.12 (1H, m), 2.79 (3H, s), 1.62-1.82 (3H, m), 1.08 (6H, d, J=6.9 Hz), 0.88 (6H, app t, J=4.5 Hz). LC/MS: purity >98%, m/z 433.25 [M+H]$^+$

Example 78

N-[(2-{[2,4-dihydroxy-5-(propan-2-yl)phenyl]carbonyl}-2,3-dihydro-1H-isoindol-5-yl)methyl]-L-leucine Method A—Prepared from Example 54

$^1$H NMR (300 MHz, d6-DMSO) 10.07 (1H, br s), 9.65 (1H, br s), 7.31-7.51 (4H, m), 7.04 (1H, s), 4.79 (4H, m), 3.99-4.11 (2H, m), 1.46-1.57 (2H, m), 1.13 (6H, d, J=6.9 Hz), 0.87 (6H, app t, J=7.0 Hz). LC/MS: purity >98%, m/z 441.25 [M+H]$^+$

Example 79

N-[(2-{[2,4-dihydroxy-5-(propan-2-yl)phenyl]carbonyl}-2,3-dihydro-1H-isoindol-5-yl)methyl]-2-methylalanine Method A—Prepared from Example 55

$^1$H NMR (300 MHz, d3-MeOD) 7.35 (3H, br s), 7.05 (1H, s), 6.27 (1H, s), 4.08-4.87 (4H, m), 4.12 (2H, s), 3.10 (1H, sep, J=6.8 Hz), 1.58 (6H, s), 1.10 (6H, d, J=7.0 Hz) LC/MS: purity >98%, m/z 413.25 [M+H]$^+$

Example 80

N-[3-(2-{[2,4-dihydroxy-5-(propan-2-yl)phenyl]carbonyl}-2,3-dihydro-1H-isoindol-5-yl)propyl]-L-leucine Method A—Prepared from Example 64

$^1$H NMR (300 MHz, d6-DMSO) 7.07-7.34 (4H, m), 6.39 (1H, s), 4.66-4.79 (4H, m), 3.06-3.11 (2H, m), 2.55-2.89 (3H, m), 1.70-1.88 (2H, m), 1.31-1.59 (3H, m), 1.13 (6H, d, J=6.9 Hz), 0.86 (6H, t, J=7.2 Hz). LC/MS: purity >98%, m/z 469.25 [M+H]$^+$

Example 81

N-[2-(2-{[2,4-dihydroxy-5-(propan-2-yl)phenyl]carbonyl}-2,3-dihydro-1H-isoindol-5-yl)ethyl]-L-leucine Method A—Prepared from Example 61

$^1$H NMR (300 MHz, d6-DMSO) 7.07-7.31 (4H, m), 6.41 (1H, s), 4.64-4.80 (4H, m), 3.00-3.13 (2H, m), 2.70-2.92 (3H, m), 1.68-1.82 (1H, m), 1.28-1.51 (3H, m), 1.12 (6H, d, J=6.9 Hz), 0.85 (6H, t, J=6.6 Hz). LC/MS: purity >98%, m/z 455.25 [M+H]$^+$

Example 82

N-[(2-{[2,4-dihydroxy-5-(propan-2-yl)phenyl]carbonyl}-2,3-dihydro-4H-isoindol-5-yl)methyl]-L-alanine Method A—Prepared from Example 56

$^1$H NMR (300 MHz, d3-MeOD) 7.37-7.60 (3H, m), 7.17 (1H, s), 6.39 (1H, s), 4.94 (4H, s), 4.28 (2H, ABq, J=12.8 Hz), 4.08 (1H, q, J=9.5 Hz), 3.21 (1H, sep, J=6.8 Hz), 1.63 (3H, d, J=7.1 Hz). LC/MS: purity >98%, m/z 399.25 [M+H]$^+$

Example 83

1-{[(2-{[2,4-dihydroxy-5-(propan-2-yl)phenyl]carbonyl}-2,3-dihydro-1H-isoindol-5-yl)methyl]amino}cyclopentanecarboxylic acid Method A—Prepared from Example 60

$^1$H NMR (300 MHz, d6-DMSO) 7.02-7.52 (4H, m), 6.44 (1H, s), 5.00-5.10 (2H, m), 4.75 (4H, s), 3.09 (1H, sep, J=6.6 Hz), 1.40-1.80 (8H, m), 1.13 (6H, d, J=6.9 Hz) LC/MS: purity >98%, m/z 439.25 [M+H]$^+$

Example 84

N-(3-{[{[2,4-dihydroxy-5-(propan-2-yl)phenyl]carbonyl}(methyl)amino]methyl}benzyl)-L-leucine Method A—Prepared from Example 66

$^1$H NMR (300 MHz, d6-DMSO) 7.46 (1H, br s), 7.06-7.30 (4H, m), 6.83 (1H, s), 6.39 (1H, s), 4.33 (1H, d, J=13.4 Hz), 3.72 (1H, d, J=12.5 Hz), 3.39 (2H, d, J=12.4 Hz), 3.05 (1H, sep. J=6.5 Hz), 2.75 (3H, s), 1.82 (3H, s), 1.09 (6H, d, J=6.9 Hz), 0.76 (6H, d, J=5.5 Hz). LC/MS: purity >98%, m/z 443.25 [M+H]$^+$

Example 85

(2S)-[(4-{[{[2,4-dihydroxy-5-(propan-2-yl)phenyl]carbonyl}(methyl)amino]methyl}benzyl)amino](phenyl)ethanoic acid Method A—Prepared from Example 71

$^1$H NMR (300 MHz, d6-DMSO) 9.63 (1H, s), 9.52 (1H, s), 7.24-7.54 (9H, m), 6.87 (1H, s), 6.37 (1H, s), 4.74 (1H, s), 4.55 (2H, s), 4.94 (2H, ABq, J=13.3 Hz), 3.05 (1H, sep, J=6.8 Hz), 2.79 (3H, s), 1.07 (6H, d, J=6.9 Hz). LC/MS: purity >98%, m/z 463.25 [M+H]$^+$

Example 86

N-(4-{[{[2,4-dihydroxy-5-(propan-2-yl)phenyl]carbonyl}(methyl)amino]methyl}benzyl)-2-methylalanine Method A—Prepared from Example 72

$^1$H NMR (300 MHz, d6-DMSO) 9.61 (1H, s), 9.50 (1H, s), 9.18 (1H, br s), 7.46 (2H, d, J=8.2 Hz), 7.36 (2H, d, J=7.6 Hz), 6.88 (1H, s), 6.38 (1H, s), 4.57 (2H, s), 4.11 (2H, s), 3.06 (1H, sep, J=6.9 Hz), 2.80 (3H, s), 1.55 (6H, s), 1.09 (6H, d, J=6.9 Hz)

LC/MS: purity >98%, m/z 415.25 [M+H]$^+$

Example 87

N-(3-{[{[2,4-dihydroxy-5-(propan-2-yl)phenyl]carbonyl}(methyl)amino]methyl}benzyl)-2-methylalanine Method B—Prepared from Example 67

$^1$H NMR (300 MHz, d3-MeOD) 7.43-7.52 (4H, m), 7.01 (1H, s), 6.37 (1H, s), 4.72 (2H, s), 4.10 (2H, s), 3.17 (1H, sep, J=6.9 Hz), 3.04 (3H, s), 1.57 (6H, s), 1.14 (6H, d, J=6.9 Hz). LC/MS: purity >98%, m/z 415.25 [M+H]$^+$

Example 88

1-[(3-{[{[2,4-dihydroxy-5-(propan-2-yl)phenyl]carbonyl}(methyl)amino]methyl}benzyl)amino]cyclopentanecarboxylic acid Method B—Prepared from Example 68

$^1$H NMR (300 MHz, d3-MeOD) 7.41-7.52 (4H, m), 7.01 (1H, s), 6.37 (1H, s), 4.72 (2H, s), 4.14 (2H, s), 3.19 (1H, sep, J=6.9 Hz), 2.98 (3H, s), 1.75-1.94 (8H, m), 1.15 (6H, d,J=6.9 Hz). LC/MS: purity >98%, m/z 441.25 [M+H]$^+$

Example 89

(2S)-[(3-{[{[2,4-dihydroxy-5-(propan-2-yl)phenyl]carbonyl}(methyl)amino]methyl}benzyl)amino](phenyl)ethanoic acid Method B—Prepared from Example 69

$^1$H NMR (300 MHz, d3-MeOD) 7.33-7.54 (9H, m), 7.00 (1H, s), 6.36 (1H, s), 4.70 (2H, br s), 4.53 (1H, s), 4.14 (2H, ABq, J=15.8 Hz), 3.17 (1H, sep, J=6.9 Hz), 1.15 (6H, d,J=6.9 Hz). LC/MS: purity >98%, m/z 463.25 [M+H]$^+$

Example 90

1-{[3-(2-{[2,4-dihydroxy-5-(propan-2-yl)phenyl]carbonyl}-2,3-dihydro-1H-isoindol-5-yl)propyl]amino}cyclopentanecarboxylic acid Method A—Prepared from Example 65

$^1$H NMR (300 MHz, d6-DMSO) 10.07 (1H, br s), 9.61 (1H, br s), 7.11-7.33 (3H, m), 7.04 (1H, s), 6.39 (1H, s), 4.74 (4H, br s), 3.19-3.44 (4H, m), 3.09 (1H, sep, J=6.9 Hz), 2.59-2.76 (2H, m), 1.78-2.06 (4H, m), 1.64 (4H, m), 1.13 (6H, d, J=6.9 Hz)

LC/MS: purity >98%, m/z 467.25 [M+H]$^+$

Example 91

N-[2-(4-{[{[2,4-dihydroxy-5-(propan-2-yl)phenyl]carbonyl}(methyl)amino]methyl}phenyl)ethyl]-2-methylalanine Method A—Prepared from Example 73

$^1$H NMR (300 MHz, d6-DMSO) 7.10-7.23 (3H, m), m6.84 (1H, s), 6.36 (1H, s), 4.45-4.56 (2H, m), 3.04 (1H, sep, J=6.7 Hz), 2.77-2.85 (2H, m), 2.79 (3H, s), 1.78-1.83 (2H, m), 1.22-1.24 (6H, m), 1.06 (6H, d, J=6.9 Hz). LC/MS: purity >98%, m/z 429.25 [M+H]$^+$

Example 92

N-[2-(1-{[2,4-dihydroxy-5-(propan-2-yl)phenyl]carbonyl}piperidin-4-yl)ethyl]-L-alanine Method C—Prepared from Example 39

$^1$H NMR (300 MHz, d3-MeOD) ppm, 6.95 (1H, s), 6.34 (1H, s), 4.35 (2H, m), 3.19 (1H, m), 3.05 (1H, m), 2.97 (4H, m), 2.00 (5H, m), 1.49 (3H, d, J=7.2 Hz), 1.34 (2H, m), 1.26 (6H, d, J=4.8 Hz). LC/MS: purity >98%, m/z 379 [M+H]+

Example 93

1-{[2-(2-{[2,4-dihydroxy-5-(propan-2-yl)phenyl]carbonyl}-2,3-dihydro-1H-isoindol-5-yl)ethyl]amino}cyclopentanecarboxylic acid Method B—Prepared from Example 63
$^1$H NMR (300 MHz, d3-MeOD) 7.45-7.12 (4H, m), 6.38 (1H, s), 3.11-2.98 (2H, m), 2.43-2.25 (2H, m), 2.08-1.80 (8H, m), 1.22 (6H, d, J=7.0 Hz)
LC/MS: purity >98%, m/z 453 [M+H]+

Example 94

N-{[(2S)-1-{[2,4-dihydroxy-5-(propan-2-yl)phenyl]carbonyl}pyrrolidin-2-yl]methyl}-L-leucine Method B—Prepared from Example 75
$^1$H NMR (300 MHz, d6-DMSO) 9.70 (1H, br s), 6.99 (1H, s), 6.37 (1H, s), 5.23 (1H, t, J=5.6 Hz), 4.33 (1H, m), 4.01 (1H, m), 3.21-3.56 (4H, m), 3.10 (1H, sep, J=6.9 Hz), 1.62-2.20 (8H, m), 1.12 (3H, d, J=6.9 Hz), 1.11 (3H, d, J=6.9 Hz), 0.93 (6H, d, J=6.3 Hz). LC/MS: purity >98%, m/z 393.25 [M+H]+

Example 95

N-(1-{[2,4-dihydroxy-5-(propan-2-yl)phenyl]carbonyl}pyrrolidin-3-yl)-L-leucine

Method B—Prepared from Example 76
$^1$H NMR (300 MHz, d6-DMSO) 10.35 (1H, br s), 9.75 (1H, s), 9.24 (1H, br s), 7.02 (1H, s), 6.36 (1H, s), 3.45-4.0 (6H, m), 3.09 (1H, sep, J=6.9 Hz), 1.93-2.34 (2H, m), 1.59-1.80 (3H, m), 1.12 (6H, d, J=6.9 Hz), 0.92 (6H, d, J=5.6 Hz). LC/MS: purity >98%, m/z 379 [M+H]+

Example 96

N-(1-{[2,4-dihydroxy-5-(propan-2-yl)phenyl]carbonyl}piperidin-4-yl)-L-leucine

Method B—Prepared from Example 1
$^1$H NMR (300 MHz, d6-DMSO) 9.55 (1H, br s), 9.49 (1H, br s), 6.81 (1H, s), 6.36 (1H, s), 3.86-4.14 (2H, m), 3.59-3.76 (1H, m), 3.14-3.23 (1H, m), 3.06 (1H, sep, J=6.9 Hz), 2.83 (2H, q, J=11.1 Hz), 1.86-2.09 (2H, m), 1.35-1.83 (5H, m), 1.10 (6H, d, J=6.9 Hz), 0.91 (3H, d, J=6.3 Hz), 0.90 (3H, d, J=6.4 Hz). LC/MS: purity >98%, m/z 393.25 [M+H]+

Example 97

N-(1-{[2,4-dihydroxy-5-(propan-2-yl)phenyl]carbonyl}piperidin-4-yl)-2-methylalanine Method B—Prepared from Example 2
$^1$H NMR (300 MHz, d6-DMSO) 9.54 (1H, br s), 9.50 (1H, brr s), 8.80 (2H, br s), 6.82 (1H, s), 6.36 (1H, br s), 3.89-4.11 (1H, m), 3.24-3.54 (2H, m), 3.06 (1H, sep, J=6.8 Hz), 2.81-3.01 (2H, m), 1.91-2.03 (2H, m), 1.47-1.65 (2H, m), 1.51 (6H, s), 1.10 (6H, d, J=6.8 Hz). LC/MS: purity >98%, m/z 365.25 [M+H]+

Example 98

N-(1-{[2,4-dihydroxy-5-(propan-2-yl)phenyl]carbonyl}piperidin-4-yl)-L-valine

Method D—Prepared from Example 3
$^1$H NMR (300 MHz, d3-MeOD) 6.98 (1H, s), 6.36 (1H, s), 4.33 (1H, s), 4.02 (1H, d, J=3.6 Hz), 3.37 (1H, m), 3.18 (1H, dt, J=13.8, 6.9 Hz), 3.00 (2H, t, J=12.8 Hz), 2.42-2.29 (1H, m), 2.18 (2H, t, J=14.0 Hz), 1.71 (2H, m), 1.26 (1H, t, J=7.1 Hz), 1.22-1.15 (9H, m), 1.09 (3H, d, J=7.0 Hz). LC/MS: purity 100%, m/z 379 [M+H]+

Example 99

(2S)-[(1-{[2,4-dihydroxy-5-(propan-2-yl)phenyl]carbonyl}piperidin-4-yl)amino](phenyl)ethanoic acid Method D—Prepared from Example 4
$^1$H NMR (300 MHz, d3-MeOD) 7.61-7.47 (5H, m), 6.97 (1H, s), 6.34 (1H, s), 4.30 (1H, br s), 3.97-3.88 (1H, m), 3.42-3.36 (2H, m), 3.18 (1H, m), 2.95 (2H, m), 2.25 (2H, m), 1.7 (2H, m), 1.26 (2H, t, J=7.1 Hz), 1.18 (6H, d, J=7.0 Hz). LC/MS: purity 100%, m/z 413 [M+H]+

Example 100

N-(1-{[2,4-dihydroxy-5-(propan-2-yl)phenyl]carbonyl}piperidin-4-yl)-L-alanine

Method D—Prepared from Example 5
$^1$H NMR (300 MHz, d3-MeOD) 6.98 (1H, s), 6.36 (1H, s), 4.33 (1H, br s), 4.22 (1H, q, J=7.2 Hz), 3.53 (1H, m), 3.18 (1H, dt, J=6.8, 13.8 Hz), 3.02 (3H, t, J=13.5 Hz), 2.16 (2H, d, J=12.6 Hz), 1.67 (2H, m), 1.61 (3H, d, J=7.2 Hz), 1.19 (6H, d, J=6.8 Hz). LC/MS: purity >98%, m/z 351 [M+H]+

Example 101

N-(1-{[2,4-dihydroxy-5-(propan-2-yl)phenyl]carbonyl}piperidin-4-yl)-L-phenylalanine Method D—Prepared from Example 9
$^1$H NMR (300 MHz, d3-MeOD) 7.35 (5H, m), 6.96 (1H, s), 6.34 (1H, s), 4.30 (3H, m), 3.11-3.24 (4H, m), 2.95 (2H, br s), 2.13 (2H, t, J=12.0 Hz), 1.75-1.47 (2H, m), 1.18 (6H, d, J=7.0 Hz). LC/MS: purity 100%, m/z 427 [M+H]+

Example 102

N-(1-{[2,4-dihydroxy-5-(propan-2-yl)phenyl]carbonyl}piperidin-3-yl)-L-leucine

Method D—Prepared from Example 7
$^1$H NMR (300 MHz, d3-MeOD) 7.03 (1H, s), 6.37 (1H, s), 5.19-5.07 (1H, m), 4.48-4.29 (1H, m), 4.02 (2H, br s), 3.39 (1H, br s), 3.23-3.13 (2H, m), 2.37-2.18 (2H, m), 1.76-1.584 (5H, m), 1.19 (6H, d, J=6.8 Hz), 1.06-0.94 (6H, m). LC/MS: purity 95%, m/z 393 [M+H]+

Example 103

N-[(1-{[2,4-dihydroxy-5-(propan-2-yl)phenyl]carbonyl}piperidin-4-yl)methyl]-L-leucine Method D—Prepared from Example 21
$^1$H NMR (300 MHz, d6-DMSO) 9.52 (1H, br s), 9.46 (1H, br s), 8.82 (1H, br s), 6.82 (1H, s), 6.35 (1H, s), 3.91-4.14 (2H, m), 3.87 (1H, t, J=7.6 Hz), 3.07 (1H, sep, J=7.0 Hz), 2.69-3.00 (4H, m), 1.59-1.99 (6H, m), 1.09-1.23 (2H, m), 1.10 (6H, d, J=7.0 Hz), 0.93 (3H, d, J=6.1 Hz), 0.92 (3H, d, J=6.3 Hz). LC/MS: purity 98%, m/z 407.25 [M+H]$^+$ Example 104

N-[2-(1-{[2,4-dihydroxy-5-(propan-2-yl)phenyl]carbonyl}piperidin-4-yl)ethyl]-L-leucine Method D—Prepared from Example 38
$^1$H NMR (300 MHz, d6-DMSO) 9.50 (1H, br s), 9.44 (1H, br s), 8.87 (1H, br s), 6.81 (1H, s), 6.34 (1H, s), 3.91-4.10 (2H, m), 3.88 (1H, t, J=6.5 Hz), 3.06 (1H, sep, J=6.9 Hz), 2.73-3.10 (4H, m), 1.49-1.80 (8H, m), 1.10 (6H, d, J=6.9 Hz), 0.92 (3H, d, J=6.1 Hz), 0.92 (3H, d, J=6.3 Hz). LC/MS: purity 98%, m/z 421.25 [M+H]$^+$ Example 105

N-(1-{[2,4-dihydroxy-5-(propan-2-yl)phenyl]carbonyl}piperidin-4-yl)-L-norleucine Method D—Prepared from Example 10
$^1$H NMR (300 MHz, d3-MeOD) 7.00 (1H, d, J=3.8 Hz), 6.38 (1H, d, J=1.3 Hz), 3.99 (2H, br s), 3.28-2.90 (3H, m), 2.40-2.19 (1H, m), 2.07-1.55 (6H, m), 1.54-1.32 (4H, m), 1.19 (6H, d, J=7.0 Hz), 1.00-0.87 (3H, m). LC/MS: purity 96%, m/z 393 [M+H]$^+$ Example 106

N-[(1-{[2,4-dihydroxy-5-(propan-2-yl)phenyl]carbonyl}piperidin-4-yl)methyl]-L-alanine Method D—Prepared from Example 22
$^1$H NMR (300 MHz, d3-MeOD) 6.96 (1H, s), 6.33 (1H, s), 4.19 (2H, m), 3.24 (1H, m), 3.18 (1H, pentet, J=6.9 Hz), 2.97 (2H, t, J=12.0 Hz), 2.67 (2H, m), 1.91 (4H, m), 1.36 (3H, d, J=6.9 Hz), 1.28 (1H, m), 1.18 (6H, d, J=6.9 Hz). LC/MS: purity 98%, m/z 365 [M+H]$^+$ Example 107

N-[(1-{[2,4-dihydroxy-5-(propan-2-yl)phenyl]carbonyl}piperidin-4-yl)methyl]-L-phenylalanine Method D—Prepared from Example 23
$^1$H NMR (300 MHz, d3-MeOD) 7.21 (5H, m), 6.91 (1H, s), 6.26 (1H, s), 4.14 (4H, m), 3.23 (2H, m), 2.95 (4H, m), 2.50 (1H, m), 2.35 (1H, m), 1.69 (5H, m), 1.17 (6H, d, J=6.6 Hz). LC/MS: purity 98%, m/z 441 [M+H]$^+$ Example 108

N-[(1-{[2,4-dihydroxy-5-(propan-2-yl)phenyl]carbonyl}piperidin-4-yl)methyl]-D-leucine Method D—Prepared from Example 28
$^1$H NMR (300 MHz, d6-DMSO) 6.76 (1H, s), 6.34 (1H, s), 3.97 (2H, m), 3.34 (4H, m), 3.05 (1H, pentet, J=6.9 Hz), 2.70 (3H, m), 2.39 (1H, m), 2.14 (1H, m), 1.65 (5H, bcm), 1.27 (1H, m), 1.09 (6H, d, J=6.9 Hz), 1.02 (2H, m), 0.81 (6H, m). LC/MS: purity 98%, m/z 407 [M+H]$^+$ Example 109

N-(1-{[2,4-dihydroxy-5-(propan-2-yl)phenyl]carbonyl}piperidin-4-yl)-D-leucine

Method D—Prepared from Example 12
$^1$H NMR (300 MHz, d3-MeOD) 6.97 (1H, s), 6.35 (1H, s), 3.93 (1H, t, J=6.4 Hz), 3.61 (1H, t, J=7.0 Hz), 3.18 (2H, m), 3.00 (3H, br s), 2.29-2.03 (4H, m), 2.19-1.56 (4H, m), 1.18 (6H, d, J=7.0 Hz), 1.01 (6H, m). LC/MS: purity 100%, m/z 393 [M+H]$^+$ Example 110

3-cyclohexyl-N-(1-{[2,4-dihydroxy-5-(propan-2-yl)phenyl]carbonyl}piperidin-4-yl)-L-alanine Method D—Prepared from Example 13
$^1$H NMR (300 MHz, d3-MeOD) 6.98 (1H, s), 6.35 (1H, s), 4.32 (2H, br s), 4.05 (1H, br s), 3.57-3.38, (1H, m), 3.24-3.10 (1H, m), 3.10-2.92 (2H, m), 2.28-2.08 (2H, m), 1.94 (1H, d, J=11.9 Hz), 1.85-1.62 (8H, m), 1.27 (3H, br s), 1.19 (6H, d, J=7.0 Hz), 1.10-0.90, (2H, m). LC/MS: purity 97%, m/z 433 [M+H]$^+$ Example 111

N-[2-(1-{[2,4-dihydroxy-5-(propan-2-yl)phenyl]carbonyl}piperidin-4-yl)ethyl]-L-phenylalanine Method D—Prepared from Example 40
$^1$H NMR (300 MHz, d3-MeOD) 7.42-7.21 (5H, m), 6.94 (1H, s), 6.33 (1H, s), 4.15 (1H, s), 4.00-3.81 (1H, m), 3.27-2.79 (12H, m), 1.78-1.50 (4H, m), 1.19 (6H, d, J=6.8 Hz) LC/MS: purity 100%, m/z 455 [M+H]$^+$ Example 112

N-[(1-{[2,4-dihydroxy-5-(propan-2-yl)phenyl]carbonyl}piperidin-4-yl)methyl]-L-valine Method D—Prepared from Example 29
$^1$H NMR (300 MHz, d3-MeOD) 6.96 (1H, s), 6.34 (1H, s), 4.21 (2H, m), 3.92 (1H, m), 3.18 (1H, pentet, J=6.6 Hz), 3.01 (4H, m), 2.37 (1H, m), 1.90 (3H, m), 1.35 (2H, m), 1.19 (9H, m), 1.08 (3H, d, J=6.9 Hz). LC/MS: purity 95%, m/z 393 [M+H]$^+$ Example 113

(2S)-cyclohexyl[(1-{[2,4-dihydroxy-5-(propan-2-yl)phenyl]carbonyl}piperidin-4-yl-amino]ethanoic acid Method D—Prepared from Example 14
$^1$H NMR (300 MHz, d3-MeOD) 6.98 (1H, s), 6.35 (1H, s), 4.32 (2H, br s), 4.00-3.87 (2H, m), 3.18 (1H, dt, 13.8 Hz), 3.00 (2H, t, J=12.4 Hz), 2.17 (2H, t, J=14.0 Hz), 2.02 (2H, d, J=6.6 Hz), 1.92-1.56 (9H, m), 1.47-1.30 (3H, m), 1.26 (2H, t, J=7.2 Hz), 1.19 (6H, d, J=7.0 Hz). LC/MS: purity 97%, m/z 419 [M+H]$^+$ Example 114

N-[2-(1-{[2,4-dihydroxy-5-(propan-2-yl)phenyl]carbonyl}piperidin-4-yl)ethyl]-2-methylalanine Method E—Prepared from tert-butyl N-[2-(1-{[2,4-dihydroxy-5-(propan-2-yl)phenyl]carbonyl}piperidin-4-yl)ethyl]-2-methylalaninate ¹H NMR (300 MHz, d3-MeOD) 6.94 (1H, s), 6.33 (1H, s), 4.19 (2H, s), 2.78-3.24 (6H, m), 1.78 (3H, d, J=13.0 Hz), 1.63-1.70 (3H, m), 1.59 (6H, s) and 1.17 (6H, d, J=5.7 Hz) LC/MS: purity 97%, m/z 351 [M+H]$^+$ Example 115

O-tert-butyl-N-[2-(1-{[2,4-dihydroxy-5-(propan-2-yl)phenyl]carbonyl}piperidin-4-yl)ethyl]-L-serine Method B—Prepared from Example 45
¹H NMR: (300 MHz, d6-DMSO) 9.45 (1H, s), 9.41 (1H, s), 6.80 (1H, s), 6.33 (1H, s), 5.10 (1H, t, J=6.0 Hz), 3.48-3.36 (2H, m), 3.23, (1H, q, J=4.3 Hz), 3.11-3.01 (1H, septet, J=6.9 Hz), 2.84-2.71 (2H, m), 1.87-1.72 (1H, m), 1.69-1.49 (8H, m), 1.39-1.27 (2H, m), 1.10 (6H, d, J=6.8 Hz), 1.08 (9H, s). LC/MS: purity 97% m/z 451.25 [M+H]$^+$ Example 116

(2S)-cyclohexyl{[(1-{[2,4-dihydroxy-5-(propan-2-yl)phenyl]carbonyl}piperidin-4-yl)methyl]amino}ethanoic acid Method D—Prepared from Example 30
¹H NMR (300 MHz, d3-MeOD) 6.96 (1H, s), 6.35 (1H, s), 4.22 (2H, m), 3.92 (2H, m), 3.60 (1H, d, J=3.6 Hz), 3.18 (1H, pentet, J=6.9 Hz), 3.98 (4H, m), 2.10-1.70 (10H, m), 1.30 (4H, m), 1.18 (6H, d, J=6.9 Hz). LC/MS: purity 98%, m/z 433 [M+H]$^+$ Example 117

N-[(1-{[2,4-dihydroxy-5-(propan-2-yl)phenyl]carbonyl}piperidin-4-yl)methyl]-2-methylalanine Method D—Prepared from Example 32
¹H NMR (300 MHz, d3-MeOD) 6.97 (1H, s), 6.35 (1H, s), 4.24 (2H, m), 3.18 (1H, pentet, J=6.9 Hz), 3.01 (4H, m), 2.06 (1H, m), 1.89 (2H, m), 1.62 (6H, s), 1.36 (2H, m), 1.18 (6H, d, J=6.9 Hz). LC/MS: purity 98%, m/z 379 [M+M]$^+$ Example 118

N-[(1-{[2,4-dihydroxy-5-(propan-2-yl)phenyl]carbonyl}piperidin-4-yl)methyl]-L-serine Method D—Prepared from Example 33
¹H NMR (300 MHz, d3-MeOD) 6.97 (1H, s), 6.35 (1H, s), 4.25 (2H, m), 4.08 (3H, m), 3.21 (1H, pentet, J=6.9 Hz), 3.04 (4H, m), 2.08 (1H, m), 1.89 (2H, m), 1.33 (2H, m), 1.18 (6H, d, J=6.9 Hz). LC/MS: purity 95%, m/z 381 [M+H]$^+$ Example 119

O-tert-butyl-N-[(1-{([2,4-dihydroxy-5-(propan-2-yl)phenyl]carbonyl}piperidin-4-yl)methyl]-L-serine Method D—Prepared from Example 34
¹H NMR (300 MHz, d3-MeOD) 6.97 (1H, s), 6.35 (1H, s), 4.19 (3H, m), 3.93 (2H, m), 3.18 (1H, pentet, 6.9 Hz), 3.02 (4H, m), 2.08 (1H, m), 1.88 (2H, m), 1.35 (2H, m), 1.25 (9H, s), 1.18 (6H, d, J=6.9 Hz). LC/MS: purity 98%, m/z 437 [M+H]$^+$ Example 120

(2S)-{[(1-{[2,4-dihydroxy-5-(propan-2-yl)phenyl]carbonyl}piperidin-4-yl)methyl]amino}(phenyl)ethanoic acid Method D—Prepared from Example 36
¹H NMR (300 MHz, d3-MeOD) 7.53 (5H, m), 6.96 (1H, s), 6.33 (1H, s), 5.07 (1H, s), 4.20 (2H, m), 3.17 (1H, pentet, J=6.9 Hz), 3.01-2.81 (4H, m), 2.05 (1H, m), 1.82 (2H, m), 1.32 (2H, m), 1.17 (6H, d, J=6.9 Hz). LC/MS: purity 98%, m/z 427 [M+H]$^+$ Example 121

N-[2-(1-{[2,4-dihydroxy-5-(propan-2-yl)phenyl]carbonyl}piperidin-4-yl)ethyl]-L-valine Method D—Prepared from Example 46
¹H NMR (300 MHz, d3-MeOD) 6.84 (1H, s), 6.22 (1H, s), 4.89 (1H, s), 3.54 (1H, d, J=11.3 Hz), 3.42-3.46 (1H, m), 2.92-3.12 (2H, m), 2.85 (3H, t, J=12.5 Hz), 2.17 (2H, br. s), 1.53-1.73 (2H, m), 1.24 (6H, s), 1.05 (4H, m), 0.94 (6H, d, J=6.8 Hz)
LC/MS: purity 100%, m/z 407.25 [M+H]$^+$ Example 122

O-tert-butyl-N-(1-{[2,4-dihydroxy-5-(propan-2-yl)phenyl]carbonyl}piperidin-4-yl)-L-serine Method D—Prepared from Example 17
¹H NMR (300 MHz, d3-MeOD) 6.98 (1H, s), 6.34 (1H, s), 4.60 (1H, br s), 4.28 (2H, br s), 3.88-3.63 (2H, m), 3.56 3.25-2.84 (3H, m), 2.11 (2H, m), 1.64 (3H, m), 1.24 (9H, s), 1.19 (6H, d, J=7.0 Hz).
LC/MS: purity 100%, m/z 423 [M+H]$^+$ Example 123

(2S)-cyclohexyl{[2-(1-{[2,4-dihydroxy-5-(propan-2-yl)phenyl]carbonyl}piperidin-4-yl)ethyl]amino}ethanoic acid Method E—Prepared from Example 49
¹H NMR (300 MHz, d3-MeOD) 6.90 (1H, s), 6.28 (1H, s), 4.08-4.22 (2H, m), 3.67 (1H, br.s.), 3.12 (1H, quin, J=7.3 Hz), 2.99-3.07 (1H, m), 2.91 (1H, t, J=12.4 Hz), 1.54-1.94 (12H, m), 1.16-1.39 (7H, m), 1.13 (6H, d, J=7.0 Hz), 1.02-1.09 (1H, m). LC/MS: purity 92.60%, m/z 447.25 [M+H]$^+$ Example 124

(2S)-{[2-(1-{[2,4-dihydroxy-5-(propan-2-yl)phenyl]carbonyl}piperidin-4-yl)ethyl]amino}(phenyl)ethanoic acid Method E—Prepared from Example 50
¹H NMR (300 MHz, d3-MeOD) 7.63-7.46 (5H, m), 6.94 (1H, s), 6.33 (1H, s), 4.23-4.18 (1H, m), 3.18 (1H, septet, J=6.8 Hz), 3.11-3.03 (1H, m), 2.93 (2H, m), 1.77-1.61 (4H, m), 1.34-1.2 (2H, m), 1.18 (6H, d, J=6.9 Hz). LC/MS: purity 99%, m/z 441.25 [M+H]$^+$ Example 125

N-(1-{[2,4-dihydroxy-5-(propan-2-yl)phenyl]carbonyl}piperidin-4-yl)-L-serine

Method D—Prepared from Example 18
¹H NMR (300 MHz, d3-MeOD) 6.98 (1H, s), 6.35 (1H, s), 4.33 (1H, d, J=9.8 Hz), 4.27-4.21 (1H, m), 4.16-3.97 (3H, m), 3.63-3.47 (1H, m), 3.18 (1H, m), 3.01 (2H, t, J=12.7 Hz), 2.19 (2H, d, J=11.7 Hz), 1.81-1.58 (2H, m), 1.19 (6H, d, J=7.0 Hz). LC/MS: purity 100%, m/z 367 [M+H]+

Preparation of Example 126 cyclopentyl N-{3-[(1-{[2,4-dihydroxy-5-(propan-2-yl)phenyl]carbonyl}piperidin-4-yl)amino]propyl}-L-leucinate

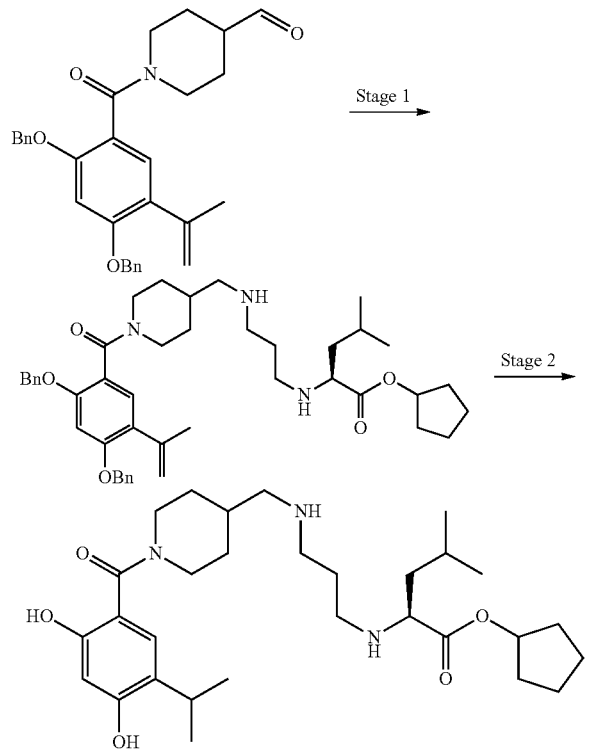

Stage 1—N-{3-[(1-{[2,4-bis(benzyloxy)-5-(prop-1-en-2-yl)phenyl]carbonyl}piperidin-4-yl)amino]propyl}-L-leucine To a stirred solution of Intermediate C (0.200 g, 0.43 mmol) was added sodium triacetoxyborohydride (0.136 g, 0.64 mmol) and cyclopentyl N-(3-aminopropyl)-L-leucinate (0.110 g, 0.43 mmol) under a nitrogen atmosphere. The reaction was stirred for 2 hours and then partitioned between water and DCM (100 ml/100 ml). The organic layer was separated and the aqueous extracted with DCM (100 ml). The combined organic layers were dried over $Na_2SO_4$ and solvent removed in vacuo to give the product as a yellow oil which was used in the next step without further purification. LC/MS: m/z 710 [M+H]+

Stage 2—cyclopentyl N-{3-[(1-{[2,4-dihydroxy-5-(propan-2-yl)phenyl]carbonyl}piperidin-4-yl)amino] propyl}-L-leucinate (Example 126)

The hydrogenation of the product obtained in Stage 1 to give Example 126 was performed as described for Example 1.
$^1$H NMR (300 MHz, d3-MeOD) 6.96 (1H, s), 6.34 (1H, s), 5.35 (1H, m), 4.22 (2H, m), 4.01 (1H, m), 3.92 (1H, t, J=6.6 Hz), 3.18 (5H, m), 2.99 (4H, m), 2.18 (2H, m), 2.05-1.60 (13H, m), 1.37 (2H, m), 1.18 (6H, d, J=6.9 Hz), 1.02 (6H, t, J=5.7 Hz)
LC/MS: purity 95%, m/z 532 [M+H]+

Example 127

N-{3-[(1-{[2,4-dihydroxy-5-(propan-2-yl)phenyl]carbonyl}piperidin-4-yl)amino]propyl}-L-leucine Method D—Prepared from Example 126
$^1$H NMR (300 MHz, d3-MeOD) 6.96 (1H, s), 6.34 (1H, s), 4.25 (2H, m), 3.93 (2H, m), 3.18 (5H, m), 2.99 (4H, m), 2.18 (2H, m), 1.99 (3H, m), 1.34 (2H, m), 1.19 (6H, d, J=6.8 Hz), 1.02 (6H, t, J=5.7 Hz), 0.95 (2H, m). LC/MS: purity 95%, m/z 464 [M+H]+

Biological Assays
HSP90 Enzyme Assay

An HTRF (homogeneous time resolved fluorescence) assay is used to measure the interaction of the compounds with HSP90. The assay measures binding of biotinylated Geldanamycin (bio-GM; Biomol, #EI-341, lot: A9199a) to human recombinant his-tagged HSP90α (HSP90; Prospec Technogene, #HSP9001, lot: 260HSP9001). A signal is generated by fluorescence resonance energy transfer from an Europium-cryptate labeled anti-his antibody (anti-his-K; Cisbio International, #61HISKLA, lot: 33V) via the HSP90-GM-biotin complex to a fluorescence acceptor (allophycocyanin) linked to streptavidin (SA-XL; Cisbio International, #610SAXLB, lot: 089).

Unlabeled GM or compounds compete with the bio-GM for binding to HSP90 resulting in reduced fluorescence energy transfer/assay signal.

A preformed (1 hour incubation) complex of HSP90 with the anti-his-K is added to the compound solution in a 384 well microplate (Corning, #3710) and incubated for 15 minutes. A preformed (1 hour incubation) complex of bio-GM with the SA-XL is added to the wells and incubated for 20 hours. All incubations are performed at room temperature. The final assay volume is 50 μl/well. The final concentrations in the assay are: 50 mM Hepes pH 7.3, 50 mM NaCl, 100 mM KF, 1 mM EDTA, 1 mM DTT, 0.1% Triton-X-100, 1 nM 40 nM HSP90, 40 nM SA-XL, 40 nM bio-GM. Test compounds are dissolved in DMSO, prediluted in assay buffer and tested at a final concentration between 5000 nM and 0.3 nM. The resulting DMSO concentration is 0.5% and included in all controls. High controls are without test compounds, low controls without test compounds, without HSP90 and without bio-GM. As a reference inhibitor unlabeled GM is used in the same concentrations as the test compounds.

Inhibition is calculated compared to the assay controls using an Excel spreadsheet (Microsoft). $IC_{50}$ values are calculated by non-linear least squares fitting to the standard dose-response model using GraphPad Prism (GraphPad Software Inc).

Proliferation Assay

Cells are seeded in 96 well tissue culture plates (1 well=30 mm$^2$) at an appropriate density (2000 cells per well for U937 cells, 2250 cells per well for HUT-78 and MINO cells) in 50 μl of culture medium (see below for details). 24 Hours later 50 μl of the compound prepared in the same medium is added as 3 fold dilutions to give final concentrations in the range 5-10, 000 nM (n=6 for each concentration). The plates are then incubated at 37° C., 5% $CO_2$ for 72 hours. Cell proliferation is assessed using WST-1 (a metabolic indicator dye, Roche Cat no. 11644807001) according to the manufacturer's instructions. The results are calculated as a percentage of vehicle response and plotted as a dose-response curve. $IC_{50}$ values represent the concentration of compound that inhibits the vehicle response by 50%.

Culture medium for U937 and RUT-78 cells is RPMI1640 (Sigma R0883) with 10% heat inactivated fetal calf serum (Hyclone SH30071, Perbio), plus 2 mM glutamine (Sigma G7513) and 50 U/ml penicillin and streptomycin sulphate (Sigma P0781). MINO cell culture medium is as for U937 and HUT-78 but supplemented with sodium pyruvate (Sigma S8636) to a final concentration of 1 mM.

LPS-Stimulation of THP-1 Cells

THP-1 cells are plated in 100 μl at a density of $4×10^4$ cells/well in V-bottomed 96 well tissue culture treated plates and incubated at 37° C. in 5% $CO_2$ for 16 hours. 2 Hours after the addition of the inhibitor in 100 μl of tissue culture media, the cells are stimulated with LPS (*E. Coli* strain 005:B5, Sigma) at a final concentration of 1 μg/ml and incubated at 37° C. in 5% $CO_2$ for 6 hours. TNF-α levels are measured from cell-free supernatants by sandwich ELISA (R&D Systems #QTA00B).

LPS-Stimulation of Human Whole Blood

Whole blood is taken by venous puncture using heparinised vacutainers (Becton Dickinson) and diluted in an equal volume of RPMI1640 tissue culture media (Sigma). 100 μl is then plated in V-bottomed 96 well tissue culture treated plates. 2 Hours after the addition of the inhibitor in 100 μl of RPMI1640 media, the blood is stimulated with LPS (*E. Coli* strain 005:B5, Sigma) at a final concentration of 100 ng/ml and incubated at 37° C. in 5% $CO_2$ for 6 hours. TNF-α levels are measured from cell-free supernatants by sandwich ELISA (R&D Systems #QTA00B).

Results:

$IC_{50}$ values are allocated to one of three ranges as follows:
Range A: $IC_{50}<100$ nM
Range B: $100$ nM$<IC_{50}<1000$ nM
Range C: $IC_{50}>1000$ nM
NT=not tested

TABLE 1

| Example | Enzyme Assay | THP-1 Assay | Whole Blood Assay |
|---|---|---|---|
| 1 | A | A | B |
| 2 | A | B | B |
| 3 | A | C | C |
| 4 | A | C | C |
| 5 | A | B | B |
| 6 | A | C | NT |
| 7 | B | C | NT |
| 8 | A | C | NT |
| 9 | A | B | B |
| 10 | A | B | C |
| 11 | A | C | NT |
| 12 | A | C | NT |
| 13 | A | B | A |
| 14 | B | C | NT |
| 15 | B | NT | NT |
| 16 | A | C | NT |
| 17 | A | A | B |
| 18 | A | B | NT |
| 19 | A | C | NT |
| 20 | A | C | C |
| 21 | A | A | B |
| 22 | A | A | A |
| 23 | A | B | B |
| 24 | A | C | NT |
| 25 | A | C | NT |
| 26 | A | C | NT |
| 27 | A | C | NT |
| 28 | A | B | B |
| 29 | A | C | NT |
| 30 | B | C | NT |
| 31 | B | NT | NT |
| 32 | A | B | B |
| 33 | A | B | B |
| 34 | A | B | B |
| 35 | A | C | NT |
| 36 | A | B | B |
| 37 | A | B | NT |
| 38 | A | B | B |
| 39 | A | A | NT |
| 40 | C | B | C |
| 41 | A | NT | NT |
| 42 | A | B | NT |
| 43 | A | NT | NT |
| 44 | A | A | B |
| 45 | A | B | B |
| 46 | A | C | NT |
| 47 | A | B | NT |
| 48 | B | C | NT |
| 49 | A | NT | NT |
| 50 | A | NT | NT |
| 51 | A | B | NT |
| 52 | A | NT | NT |
| 53 | A | NT | NT |
| 54 | A | B | B |
| 55 | A | B | B |
| 56 | B | C | C |
| 57 | A | NT | NT |
| 58 | A | NT | NT |
| 59 | A | A | B |
| 60 | A | A | B |
| 61 | A | B | B |
| 62 | A | B | C |
| 63 | A | B | B |
| 64 | A | A | B |
| 65 | A | B | B |
| 66 | A | B | C |
| 67 | A | B | B |
| 68 | A | B | C |
| 69 | B | C | C |
| 70 | A | B | B |
| 71 | B | B | B |
| 72 | A | B | B |
| 73 | A | B | B |
| 74 | B | C | C |
| 75 | C | C | C |
| 76 | A | C | C |
| 77 | A | NT | NT |
| 78 | A | NT | NT |
| 79 | A | NT | NT |
| 80 | A | NT | NT |
| 81 | A | NT | NT |
| 82 | A | NT | NT |
| 83 | A | NT | NT |
| 84 | A | NT | NT |
| 85 | A | NT | NT |
| 86 | A | NT | NT |
| 87 | A | NT | NT |
| 88 | A | NT | NT |
| 89 | A | NT | NT |
| 90 | A | NT | NT |
| 91 | A | NT | NT |
| 92 | A | NT | NT |
| 93 | A | NT | NT |
| 94 | B | NT | NT |
| 95 | A | NT | NT |
| 96 | A | NT | NT |
| 97 | A | NT | NT |
| 98 | A | NT | NT |
| 99 | A | NT | NT |
| 100 | A | NT | NT |
| 101 | A | NT | NT |
| 102 | B | NT | NT |
| 103 | A | NT | NT |
| 104 | A | NT | NT |
| 105 | A | NT | NT |
| 106 | A | NT | NT |
| 107 | A | NT | NT |
| 108 | A | NT | NT |

TABLE 1-continued

| Example | Enzyme Assay | THP-1 Assay | Whole Blood Assay |
|---------|--------------|-------------|-------------------|
| 109 | C | NT | NT |
| 110 | A | NT | NT |
| 111 | A | NT | NT |
| 112 | A | NT | NT |
| 113 | A | NT | NT |
| 114 | A | NT | NT |
| 115 | A | NT | NT |
| 116 | A | NT | NT |
| 117 | A | NT | NT |
| 118 | A | NT | NT |
| 119 | A | NT | NT |
| 120 | A | NT | NT |
| 121 | A | NT | NT |
| 122 | A | NT | NT |
| 123 | A | NT | NT |
| 124 | A | NT | NT |
| 125 | A | NT | NT |
| 126 | A | C | NT |
| 127 | A | NT | NT | resulting carboxylic acid accumulates selectively in these cell types. This accumulation of carboxylic acid as a consequence of hCE-1 hydrolysis results in the compound of Example 17 being significantly more potent than the parent non-ester compound CHR-7310 in U937 and THP-1 cells despite the ester Example 17 being weaker as an Hsp90 inhibitor than CHR-7310. It can also be seen that the compound of Example 17 is significantly weaker in Hut78 cells which do not contain hCE-1 and hence cannot hydrolyse Example 17 to its carboxylic acid. These data highlight the potency and selectivity benefits that can be achieved by the attachment of the amino acid (ester) motif in compounds such as Example 17.

Carboxylic Acid Accumulation in Intact hCE-1 Expressing (U937 & THP-1) and Non-Expressing (Hut78) Cells The assessment of the accumulation of ester-derived acid in intact human tumour cells can be measured using the following method:

U937, THP-1 or Hut 78 cells ($4 \times 10^4$/ml) were incubated at 37° C. in culture medium containing 6 µM compound. Incubations were terminated by centrifugation (300 g; 5 min; 4° C.). Supernatants were added to 4 volumes of HPLC-grade acetonitrile. After decanting the supernatant, the residual cell pellet ($1 \times 10^6$ cells) was extracted into 1 ml of acetonitrile. Samples were analyzed for the ester and acid metabolite at room temperature by LC/MS/MS (Sciex API3000). Chromatography was based on an AceCN (75*21 mm) column with a 5-95% (v/v) acetonitrile, 0.1% (v/v) formic acid mobile phase. Results are shown in Table 3:

TABLE 2

| Compound | Enzyme assay: Inhibition of Hsp90 ($IC_{50}$ nM) | Proliferation assay: | | Ratio of IC50's of Hut78 to U937 cells | THP-1 assay: Inhibition of TNFα release from LPS stimulated THP-1 (hCE-1 $^{+ve}$) cells ($IC_{50}$ nM) |
|---|---|---|---|---|---|
| | | Inhibition of U937 (hCE-1 $^{+ve}$) cell proliferation $IC_{50}$ (nM) | Inhibition of Hut78 (hCE-1 $^{-ve}$) cell proliferation $IC_{50}$ (nM) | | |
| CHR-7310 | 8 | 200 | 145 | ~1 | 476 |
| Example 17 | 42 (ester) 7 (acid) | 27 | 760 | 28 | 45 |

Table 2 shows that the acid of Example 17 has a similar $IC_{50}$ in the Hsp90 binding assay to the non-ester parent molecule CHR-7310 (i.e. the same chemical structure but in which the amino acid (ester) motif is absent), indicating that binding to the enzyme has not been disrupted by the attachment of the amino acid (ester) motif Esters such as Example 17 are hydrolysed by hCE-1 in monocytic hCE-1$^{+ve}$ cell lines such as U937 and THP-1 cells and as a consequence the

TABLE 3

| Compound | Acid accumulation by intact U937 cells (ng/10⁶ cells @ 6 h) | Acid accumulation by intact THP-1 cells (ng/10⁶ cells @ 6 h) | Acid accumulation by intact Hut78 cells (ng/10⁶ cells @ 6 h) |
|---|---|---|---|
| Example 1 | 1433 | 2393 | 7 |

Table 3 shows the selective accumulation of the acid derived intracellular hydrolysis from the compound of Example 1 in U937 and THP-1 monocytic cells which contain hCE-1 compared to Hut78 cells which do not contain hCE-1 and consequently cannot hydrolyse Example 1 to its corresponding acid. It can be seen that U937 and THP-1 cells accumulate significant amounts of carboxylic acid but negligible acid is detected in Hut78 cells.

Broken Cell Assay

In order to determine whether a compound containing a particular group $R^{20}$ is hydrolysable by one or more intracellular carboxylesterase enzymes to a —COOH group, the compound may be tested in the following assay:

Preparation of Cell Extract

U937 or HUT78 tumour cells (~109) are washed in 4 volumes of Dulbeccos PBS (~1 litre) and pelleted at 525 g for 10 minutes at 4° C. This is repeated twice and the final cell pellet is re-suspended in 35 ml of cold homogenising buffer (Trizma 10 mM, NaCl 130 mM, $CaCl_2$ 0.5 mM pH 7.0 at 25° C.). Homogenates are prepared by nitrogen cavitation (700 psi for 50 minutes at 4° C.). The homogenate is kept on ice and supplemented with a cocktail of inhibitors at final concentrations of Leupeptin 1 µM, Aprotinin 0.1 µM, E64 8 µM, Pepstatin Bestatin 162 µM, Chymostatin 33 mM.

After clarification of the cell homogenate by centrifugation at 525 g for 10 minutes, the resulting supernatant is used as a source of esterase activity and is stored at −80° C. until required.

Measurement of Ester Cleavage

Hydrolysis of esters to the corresponding carboxylic acids can be measured using the cell extract, prepared as above. To this effect cell extract (~30 µg/total assay volume of 0.5 ml) is incubated at 37° C. in a Tris-HCl 25 mM, 125 mM NaCl buffer, pH 7.5 at 25° C. At zero time the ester (substrate) is then added at a final concentration of 2.5 mM and the samples were incubated at 37° C. for the appropriate time (usually 0 or 80 minutes). Reactions are stopped by the addition of 2× volumes of acetonitrile. For zero time samples the acetonitrile is added prior to the ester compound. After centrifugation at 12000 g for 5 minutes, samples are analysed for the ester and its corresponding carboxylic acid at room temperature by LC/MS (Sciex API 3000, HP1100 binary pump, CTC PAL). Chromatography was based on an AceCN (75*2.1 mm) column and a mobile phase of 5-95% acetonitrile in water/0.1% formic acid.

The invention claimed is:

1. A compound which is (a) a phenylamide of formula (I) or a tautomer thereof, or (b) a pharmaceutically acceptable salt, N-oxide or hydrate thereof:

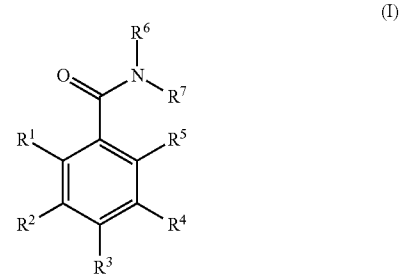

(I)

wherein:

$R^1$ and $R^3$ are hydroxy;

$R^2$, $R^4$ and $R^5$ are the same or different and represent hydrogen, halogen, $C_{1-6}$ alkyl, $C_{2-6}$ alkenyl, $C_{2-6}$ alkynyl, $C_{1-6}$ alkoxy, hydroxy, cyano, nitro or —NR'R" wherein R' and R" are the same or different and represent hydrogen or unsubstituted $C_{1-4}$ alkyl, and with the proviso that no more than two of $R^2$, $R^4$ and $R^5$ are cyano or nitro;

either:

(i) $R^6$ represents —$CH_3$, $R^7$ represents —$CR^8R^9$-A wherein $R^8$ and $R^9$ are the same or different and represent a hydrogen, halogen, an unsubstituted $C_{1-4}$ alkyl or $C_{1-4}$ alkoxy group, and A represents a phenyl ring substituted with a group W; or (ii) $R^6$ and $R^7$, together with the nitrogen atom to which they are bonded, form a pyrrolidinyl, piperidinyl or isoindolinyl group which is substituted with a group W and is optionally further substituted with 1 or 2 groups which are the same or different and are selected from halogen, unsubstituted $C_{1-4}$ alkyl, $C_{1-4}$ alkoxy, hydroxyl, $C_{1-4}$ haloalkyl, $C_{1-4}$ haloalkoxy, $C_{1-4}$ hydroxyalkyl, cyano, nitro, —SR' and —NR'R" where R' and R" are the same or different and represent hydrogen or unsubstituted $C_{1-2}$ alkyl;

W represents a group -Alk$^1$—R;

Alk$^1$ represents a bond, a $C_{1-4}$ alkylene group or a group —($C_{1-4}$alkylene)—NR'—($C_{1-4}$ alkylene)- wherein R' represents hydrogen or $C_{1-4}$alkyl;

R represents a group of formula (X)

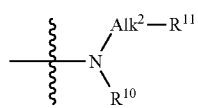

(X)

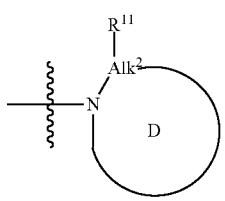

(Y)

$R^{10}$ represents a hydrogen atom or a $C_{1-4}$ alkyl group;

Alk$^2$ represents a group of formula —C($R^{12}$)($R^{13}$)— wherein one of $R^{12}$ and $R^{13}$ is hydrogen or unsubstituted $C_{1-2}$ alkyl and the other of $R^{12}$ and $R^{13}$ is an unsubstituted group selected from $C_{1-4}$ alkyl, $C_{3-7}$ carbocyclyl, phenyl, -hydroxy—($C_{1-4}$)alkyl, —($C_{1-4}$)alkoxy—($C_{1-4}$) alkyl, —($C_{1-2}$)alkyl-phenyl or —($C_{1-2}$)alkyl—($C_{3-7}$) carbocyclyl;

and $R^{11}$ is an ester group —COOR$^{20}$ wherein $R^{20}$ represents unsubstituted $C_{1-4}$ alkyl or $C_{3-7}$ carbocyclyl;

and wherein, unless otherwise stated:

the alkyl, alkenyl and alkynyl groups and moieties in $R^2$, $R^4$, $R^5$ and Alk$^1$, are unsubstituted or substituted with 1, 2 or 3 unsubstituted substituents which are the same or different and are selected from halogen, $C_{1-4}$ alkyl, $C_{2-4}$ alkenyl, $C_{1-4}$ alkoxy, $C_{2-4}$ alkenyloxy, $C_{1-4}$ haloalkyl, $C_{2-4}$ haloalkenyl, $C_{1-4}$ haloalkoxy, $C_{2-4}$ haloalkenyloxy, hydroxyl, —SR', cyano, nitro, $C_{1-4}$ hydroxyalkyl and —NR'R" where R' and R" are the same or different and represent hydrogen or unsubstituted $C_{1-2}$ alkyl.

2. A compound as claimed in claim 1 wherein $R^2$, $R^4$ and $R^5$ are the same or different and represent hydrogen, halogen, hydroxy, unsubstituted $C_{1-4}$ alkyl or unsubstituted $C_{1-4}$ alkoxy groups.

3. A compound as claimed in claim 1 wherein Alk$^1$ represents a bond, an unsubstituted $C_{1-4}$ alkylene group, or an unsubstituted —($C_{1-2}$ alkylene)—NH—($C_{1-4}$ alkylene)— group.

4. A compound as claimed in claim 1 wherein $R^{10}$ represents a hydrogen atom.

5. A compound as claimed in claim 1 which is (a) a phenylamide of formula (IA) or a tautomer thereof, or (b) a pharmaceutically acceptable salt, N-oxide or hydrate thereof:

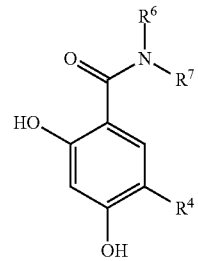

(IA)

wherein:

$R^4$ represents an unsubstituted $C_{1-4}$ alkyl group;

either:

$R^6$ represents —CH$_3$, $R^7$ represents —CR$^8$R$^9$-A wherein $R^8$ and $R^9$ are the same or different and represent a hydrogen or halogen or an unsubstituted $C_{1-4}$ alkyl or $C_{1-4}$ alkoxy group, and A represents a phenyl ring substituted with a group W; or $R^6$ and $R^7$, together with the nitrogen atom to which they are bonded, form a pyrrolidine, piperidine or isoindoline group which is substituted with a group W and which is optionally further substituted with 1 or 2 groups which are the same or different and are selected from halogen, unsubstituted $C_{1-4}$ alkyl, $C_{1-4}$ alkoxy, hydroxyl, $C_{1-4}$ haloalkyl, $C_{1-4}$ haloalkoxy, $C_{1-4}$ hydroxyalkyl, cyano, nitro, —SR' and —NR'R" where R' and R" are the same or different and represent hydrogen or unsubstituted $C_{1-2}$ alkyl;

Alk$^1$ represents a bond, an unsubstituted $C_{1-4}$ alkylene group, or an unsubstituted —($C_{1-2}$ alkylene)—NH—($C_{1-4}$ alkylene)—group;

$R^{10}$ represents hydrogen;

Alk$^2$ represents a group of formula —C($R^{12}$)($R^{13}$)— wherein one of $R^{12}$ and $R^{13}$ is hydrogen or unsubstituted $C_{1-2}$ alkyl and the other of $R^{12}$ and $R^{13}$ is an unsubstituted group selected from $C_{1-4}$ alkyl, $C_{3-7}$ carbocyclyl, phenyl, -hydroxy—($C_{1-4}$)alkyl, —($C_{1-4}$)alkoxy—($C_{1-4}$) alkyl, —($C_{1-2}$)alkyl-phenyl or —($C_{1-2}$)alkyl—($C_{3-7}$) carbocyclyl; and $R^{11}$ is —COOR$^{20}$ wherein $R^{20}$ represents unsubstituted $C_{1-4}$ alkyl or $C_{3-7}$ carbocyclyl.

6. A compound as claimed in claim 5 wherein $R^4$ represents isopropyl.

7. A compound as claimed in claim 5 wherein either:

$R^6$ represents —CH$_3$, $R^7$ represents —CH$_2$-phenyl wherein the phenyl ring is substituted with a single group W; or $R^6$ and $R^7$, together with the nitrogen atom to which they are bonded, form a pyrrolidinyl, piperidinyl or isoindolinyl group which is substituted with a single group W.

8. A compound as claimed in claim 1 which is selected from:

cyclopentyl N-(1-{[2,4-dihydroxy-5-(propan-2-yl)phenyl]carbonyl}piperidin-4-yl)-L-leucinate;

cyclopentyl N-(1-{[2,4-dihydroxy-5-(propan-2-yl)phenyl]carbonyl}piperidin-4-yl)-2-methylalaninate;

cyclopentyl N-(1-{[2,4-dihydroxy-5-(propan-2-yl)phenyl]carbonyl}piperidin-4-yl)-L-valinate;

cyclopentyl (2S)-[(1-{[2,4-dihydroxy-5-(propan-2-yl) phenyl]carbonyl}piperidin-4-yl)amino](phenyl)ethanoate;

cyclopentyl N-(1-{[2,4-dihydroxy-5-(propan-2-yl)phenyl]carbonyl}piperidin-4-yl)-L-alaninate;

tert-butyl N-(1-{[2,4-dihydroxy-5-(propan-2-yl)phenyl]carbonyl}piperidin-4-yl)-L-leucinate;
cyclopentyl N-(1-{[2,4-dihydroxy-5-(propan-2-yl)phenyl]carbonyl}piperidin-3-yl)-L-leucinate;
tert-butyl N-(1-{[2,4-dihydroxy-5-(propan-2-yl)phenyl]carbonyl}piperidin-4-yl)-L-alaninate;
cyclopentyl N-(1-{[2,4-dihydroxy-5-(propan-2-yl)phenyl]carbonyl}piperidin-4-yl)-L-phenylalaninate;
cyclopentyl N-(1-{[2,4-dihydroxy-5-(propan-2-yl)phenyl]carbonyl}piperidin-4-yl)-L-norleucinate;
tert-butyl O-tert-butyl-N-(1-{[2,4-dihydroxy-5-(propan-2-yl)phenyl] carbonyl}piperidin-4-yl)-L-serinate;
cyclopentyl N-(1-{[2,4-dihydroxy-5-(propan-2-yl)phenyl]carbonyl}piperidin-4-yl)-D-leucinate;
cyclopentyl 3-cyclohexyl-N-(1-{[2,4-dihydroxy-5-(propan-2-yl)phenyl]carbonyl}piperidin-4-yl)-L-alaninate;
cyclopentyl (2S)-cyclohexyl[(1-{[2,4-dihydroxy-5-(propan-2-yl)phenyl]carbonyl}piperidin-4-yl)aminoethanoate;
tert-butyl (2S)-cyclohexyl[(1-{[2,4-dihydroxy-5-(propan-2-yl)phenyl]carbonyl}piperidin-4-yl)aminoethanoate;
tert-butyl N-(1-{[2,4-dihydroxy-5-(propan-2-yl)phenyl]carbonyl}piperidin-4-yl)-L-phenylalaninate;
cyclopentyl O-tert-butyl-N-(1-{[2,4-dihydroxy-5-(propan-2-yl)phenyl]carbonyl}piperidin-4-yl)-L-serinate;
cyclopentyl N-(1-{[2,4-dihydroxy-5-(propan-2-yl)phenyl]carbonyl}piperidin-4-yl)-L-serinate;
tert-butyl N-(1-{[2,4-dihydroxy-5-(propan-2-yl)phenyl]carbonyl}piperidin-4-yl)-D-leucinate;
cyclopentyl N-(1-{[2,4-dihydroxy-5-(propan-2-yl)phenyl]carbonyl}pyrrolidin-3-yl)-L-leucinate;
cyclopentyl N-[(1-{[2,4-dihydroxy-5-(propan-2-yl)phenyl]carbonyl}piperidin-4-y1)methyl]-L-leucinate;
cyclopentyl N-[(1-{[2,4-dihydroxy-5-(propan-2-yl)phenyl]carbonyl}piperidin-4-y1)methyl]-L-alaninate;
cyclopentyl N-[(1-{[2,4-dihydroxy-5-(propan-2-yl)phenyl]carbonyl}piperidin-4-y1)methyl]-L-phenylalaninate;
tert-butyl N-[(1-{[2,4-dihydroxy-5-(propan-2-yl)phenyl]carbonyl}piperidin-4-y1)methyl]-L-leucinate;
tert-butyl N-[(1-{[2,4-dihydroxy-5-(propan-2-yl)phenyl]carbonyl}piperidin-4-y1)methyl]-L-phenylalaninate;
tert-butyl N-[(1-{[2,4-dihydroxy-5-(propan-2-yl)phenyl]carbonyl}piperidin-4-y1)methyl]-L-alaninate;
tert-butyl N-[(1-{[2,4-dihydroxy-5-(propan-2-yl)phenyl]carbonyl}piperidin-4-y1)methyl]-D-leucinate;
cyclopentyl N-[(1-{[2,4-dihydroxy-5-(propan-2-yl)phenyl]carbonyl}piperidin-4-y1)methyl]-D-leucinate;
cyclopentyl N-[(1-{[2,4-dihydroxy-5-(propan-2-yl)phenyl]carbonyl}piperidin-4-yl)methyl]-L-valinate;
cyclopentyl (2S)-cyclohexyl{[(1-{[2,4-dihydroxy-5-(propan-2-yl)phenyl]carbonyl}piperidin-4-yl)methyl]amino}ethanoate;
tert-butyl (2S)-cyclohexyl{[(1-{[2,4-dihydroxy-5-(propan-2-yl)phenyl]carbonyl}piperidin-4-yl)methyl]amino} ethanoate;
cyclopentyl N-[(1-{[2,4-dihydroxy-5-(propan-2-yl)phenyl]carbonyl}piperidin-4-yl)methyl]-2-methyl-L-alaninate;
cyclopentyl N-[(1-{[2,4-dihydroxy-5-(propan-2-yl)phenyl]carbonyl}piperidin-4-yl)methyl]-L-serinate;
cyclopentyl O-tert-butyl-N-[(1-{[2,4-dihydroxy-5-(propan-2-yl)phenyl]carbonyl}piperidin-4-yl)methyl]-L-serinate;
tert-butyl O-tert-butyl-N-[(1-{[2,4-dihydroxy-5-(propan-2-yl)phenyl]carbonyl}piperidin-4-yl)methyl]-L-serinate;
cyclopentyl (2S)-{[(1-{[2,4-dihydroxy-5-(propan-2-yl)phenyl]carbonyl}piperidin-4-yl)methyl]amino}(phenyl)ethanoate;
tert-butyl N-[(1-{[2,4-dihydroxy-5-(propan-2-yl)phenyl]carbonyl}piperidin-4-yl)methyl]-L-serinate;
cyclopentyl N-[2-(1-{[2,4-dihydroxy-5-(propan-2-yl)phenyl]carbonyl}piperidin-4-yl)ethyl]-L-leucinate;
cyclopentyl N-[2-(1-{[2,4-dihydroxy-5-(propan-2-yl)phenyl]carbonyl}piperidin-4-yl)ethyl]-L-alaninate;
cyclopentyl N-[2-(1-{[2,4-dihydroxy-5-(propan-2-yl)phenyl]carbonyl}piperidin-4-yl)ethyl]-L-phenylalaninate;
tert-butyl N-[2-(1-{[2,4-dihydroxy-5-(propan-2-yl)phenyl]carbonyl}piperidin-4-yl)ethyl]-L-phenylalaninate;
tert-butyl N-[2-(1-{[2,4-dihydroxy-5-(propan-2-yl)phenyl]carbonyl}piperidin-4-yl)ethyl]-L-leucinate;
tert-butyl N-[2-(1-{[2,4-dihydroxy-5-(propan-2-yl)phenyl]carbonyl}piperidin-4-yl)ethyl]-L-alaninate;
cyclopentyl N-[2-(1-{[2,4-dihydroxy-5-(propan-2-yl)phenyl]carbonyl}piperidin-4-yl)ethyl]-2-methylalaninate;
cyclopentyl O-tert-butyl-N-[2-(1-{[2,4-dihydroxy-5-(propan-2-yl)phenyl]carbonyl}piperidin-4-yl)ethyl]-L-serinate;
cyclopentyl N-[2-(1-{[2,4-dihydroxy-5-(propan-2-yl)phenyl]carbonyl}piperidin-4-yl)ethyl]-L-valinate;
cyclopentyl N-[2-(1-{[2,4-dihydroxy-5-(propan-2-yl)phenyl]carbonyl}piperidin-4-yl)ethyl]-L-serinate;
cyclopentyl (2S)-cyclohexyl{[2-(1-{[2,4-dihydroxy-5-(propan-2-yl)phenyl]carbonyl}piperidin-4-yl)ethyl]amino}ethanoate;
tert-butyl (2S)-cyclohexyl{[2-(1-{[2,4-dihydroxy-5-(propan-2-yl)phenyl]carbonyl}piperidin-4-yl)ethyl]amino}ethanoate;
tert-butyl (2S)-{[2-(1-{[2,4-dihydroxy-5-(propan-2-yl)phenyl]carbonyl}piperidin-4-yl)ethyl]amino}(phenyl)ethanoate;
cyclopentyl (2S)-{[2-(1-{[2,4-dihydroxy-5-(propan-2-yl)phenyl]carbonyl}piperidin-4-yl)ethyl]amino}(phenyl)ethanoate;
tert-butyl N-[2-(1-{[2,4-dihydroxy-5-(propan-2-yl)phenyl]carbonyl}piperidin-4-yl)ethyl]-L-serinate;
tert-butyl O-tert-butyl-N-[2-(1-{[2,4-dihydroxy-5-(propan-2-yl)phenyl]carbonyl}piperidin-4-yl)ethyl]-L-serinate;
cyclopentyl N-[(2-{[2,4-dihydroxy-5-(propan-2-yl)phenyl]carbonyl}-2,3-dihydro-1H-isoindol-5-yl)methyl]-L-leucinate;
cyclopentyl N-[(2-{[2,4-dihydroxy-5-(propan-2-yl)phenyl]carbonyl}-2,3-dihydro-1H-isoindol-5-yl)methyl]-2-methylalaninate;
tert-butyl N-[(2-{[2,4-dihydroxy-5-(propan-2-yl)phenyl]carbonyl}-2,3-dihydro-1H-isoindol-5-yl)methyl]-L-alaninate;
ethyl N-[(2-{[2,4-dihydroxy-5-(propan-2-yl)phenyl]carbonyl}-2,3-dihydro-1H-isoindol-5-yl)methyl]-L-alaninate;
propan-2-yl N-[(2-{[2,4-dihydroxy-5-(propan-2-yl)phenyl]carbonyl}-2,3-dihydro-1H-isoindol-5-yl)methyl]-L-alaninate;
cyclopentyl N-[(2-{[2,4-dihydroxy-5-(propan-2-yl)phenyl]carbonyl}-2,3-dihydro-1H-isoindol-5-yl)methyl]-L-alaninate;
cyclopentyl 1-{[(2-{[2,4-dihydroxy-5-(propan-2-yl)phenyl]carbonyl}-2,3-dihydro-1H-isoindol-5-yl)methyl]amino}cyclopentanecarboxylate;

cyclopentyl N-[2-(2-{[2,4-dihydroxy-5-(propan-2-yl)phenyl]carbonyl}-2,3-dihydro-1H-isoindol-5-yl)ethyl]-L-leucinate;
tert-butyl N-[2-(2-{[2,4-dihydroxy-5-(propan-2-yl)phenyl]carbonyl}-2,3-dihydro-1H-isoindol-5-yl)ethyl]-L-leucinate;
cyclopentyl 1-{[2-(2-{[2,4-dihydroxy-5-(propan-2-yl)phenyl]carbonyl}-2,3-dihydro-1H-isoindol-5-yl)ethyl]amino}cyclopentanecarboxylate;
cyclopentyl N-[3-(2-{[2,4-dihydroxy-5-(propan-2-yl)phenyl]carbonyl}-2,3-dihydro-1H-isoindol-5-yl)propyl]-L-leucinate;
cyclopentyl 1-{[3-(2-{[2,4-dihydroxy-5-(propan-2-yl)phenyl]carbonyl}-2,3-dihydro-1H-isoindol-5-yl)propyl]amino}cyclopentanecarboxylate;
cyclopentyl N-(3-{[{[2,4-dihydroxy-5-(propan-2-yl)phenyl]carbonyl}(methyl)amino]methyl}benzyl)-L-leucinate;
cyclopentyl N-(3-{[{[2,4-dihydroxy-5-(propan-2-yl)phenyl]carbonyl}(methyl)amino]methyl}benzyl)-2-methylalaninate;
cyclopentyl 1-[(3{[{[2,4-dihydroxy-5-(propan-2-yl)phenyl]carbonyl}(methyl)amino]methyl}benzyl)amino]cyclopentanecarboxylate;
cyclopentyl (2S)-[(3-{[{[2,4-dihydroxy-5-(propan-2-yl)phenyl]carbonyl}(methyl)amino]methyl}benzyl)amino](phenyl)ethanoate;
cyclopentyl N-(4-{[{[2,4-dihydroxy-5-(propan-2-yl)phenyl]carbonyl}(methyl)amino]methyl}benzyl)-L-leucinate;
cyclopentyl (2S)-[(4-{[{[2,4-dihydroxy-5-(propan-2-yl)phenyl]carbonyl}(methyl)amino]methyl}benzyl)amino](phenyl)ethanoate;
cyclopentyl N-(4-{[{[2,4-dihydroxy-5-(propan-2-yl)phenyl]carbonyl}(methyl)amino]methyl}benzyl)-2-methylalaninate;
cyclopentyl N-[2-(4-{[{[2,4-dihydroxy-5-(propan-2-yl)phenyl]carbonyl}(methyl)amino]methyl}phenyl)ethyl]-2-methylalaninate;
cyclopentyl N-{[(2R)-1-{[2,4-dihydroxy-5-(propan-2-yl)phenyl]carbonyl}pyrrolidin-2-yl]methyl}-L-leucinate;
cyclopentyl N-{[(2S)-1-{[2,4-dihydroxy-5-(propan-2-yl)phenyl]carbonyl}pyrrolidin-2-yl]methyl}-L-leucinate;
cyclopentyl N-(1-{[2,4-dihydroxy-5-(propan-2-yl)phenyl]carbonyl}pyrrolidin-3-yl)-D-leucinate;
N-(4-{[{[2,4-dihydroxy-5-(propan-2-yl)phenyl]carbonyl}(methyl)amino]methyl}benzyl)-L-leucine;
N-[(2-{[2,4-dihydroxy-5-(propan-2-yl)phenyl]carbonyl}-2,3-dihydro-1H-isoindol-5-yl)methyl]-L-leucine;
N-[(2-{[2,4-dihydroxy-5-(propan-2-yl)phenyl]carbonyl}-2,3-dihydro-1H-isoindol-5-yl)methyl]-2-methylalanine;
N-[3-(2-{[2,4-dihydroxy-5-(propan-2-yl)phenyl]carbonyl}-2,3-dihydro-1H-isoindol-5-yl)propyl]-L-leucine;
N-[2-(2-{[2,4-dihydroxy-5-(propan-2-yl)phenyl]carbonyl}-2,3-dihydro-1H-isoindol-5-yl)ethyl]-L-leucine;
N-[(2-{[2,4-dihydroxy-5-(propan-2-yl)phenyl]carbonyl}-2,3-dihydro-1H-isoindol-5-yl)methyl]-L-alanine;
1-{[(2-{[2,4-dihydroxy-5-(propan-2-yl)phenyl]carbonyl}-2,3-dihydro-1H-isoindol-5-yl)methyl]amino}cyclopentanecarboxylic acid;
N-(3-{[{[2,4-dihydroxy-5-(propan-2-yl)phenyl]carbonyl}(methyl)amino]methyl}benzyl)-L-leucine;
(2S)-[(4-{[{[2,4-dihydroxy-5-(propan-2-yl)phenyl]carbonyl}(methyl)amino]methyl}benzyl)amino](phenyl)ethanoic acid;
N-(4-{[{[2,4-dihydroxy-5-(propan-2-yl)phenyl]carbonyl}(methyl)amino]methyl}benzyl)-2-methylalanine;
N-(3-{[{[2,4-dihydroxy-5-(propan-2-yl)phenyl]carbonyl}(methyl)amino]methyl}benzyl)-2-methylalanine;
1-[(3-{[{[2,4-dihydroxy-5-(propan-2-yl)phenyl]carbonyl}(methyl)amino]methyl}benzyl)amino]cyclopentanecarboxylic acid;
(2S)-[(3-{[{[2,4-dihydroxy-5-(propan-2-yl)phenyl]carbonyl}(methyl)amino]methyl}benzyl)amino](phenyl)ethanoic acid;
1-{[3-(2-{[2,4-dihydroxy-5-(propan-2-yl)phenyl]carbonyl}-2,3-dihydro-1H-isoindol-5-yl)propyl]amino}cyclopentanecarboxylic acid;
N-[2-(4-{[{[2,4-dihydroxy-5-(propan-2-yl)phenyl]carbonyl}(methyl)amino]methyl}phenyl)ethyl]-2-methylalanine;
N-[2-(1-{[2,4-dihydroxy-5-(propan-2-yl)phenyl]carbonyl}piperidin-4-yl)ethyl]-L-alanine;
1-{[2-(2-{[2,4-dihydroxy-5-(propan-2-yl)phenyl]carbonyl}-2,3-dihydro-1H-isoindol-5-yl)ethyl]amino}cyclopentanecarboxylic acid;
N-{[(2S)-1-{[2,4-dihydroxy-5-(propan-2-yl)phenyl]carbonyl}pyrrolidin-2-yl]methyl}-L-leucine;
N-(1-{[2,4-dihydroxy-5-(propan-2-yl)phenyl]carbonyl}pyrrolidin-3-yl)-L-leucine;
N-(1-{[2,4-dihydroxy-5-(propan-2-yl)phenyl]carbonyl}piperidin-4-yl)-L-leucine;
N-(1-{[2,4-dihydroxy-5-(propan-2-yl)phenyl]carbonyl}piperidin-4-yl)-2-methylalanine;
N-(1-{[2,4-dihydroxy-5-(propan-2-yl)phenyl]carbonyl}piperidin-4-yl)-L-valine;
(2S)-[(1-{[2,4-dihydroxy-5-(propan-2-yl)phenyl]carbonyl}piperidin-4-yl)amino](phenyl)ethanoic acid;
N-(1-{[2,4-dihydroxy-5-(propan-2-yl)phenyl]carbonyl}piperidin-4-yl)-L-alanine;
N-(1-{[2,4-dihydroxy-5-(propan-2-yl)phenyl]carbonyl}piperidin-4-yl)-L-phenylalanine;
N-(1-{[2,4-dihydroxy-5-(propan-2-yl)phenyl]carbonyl}piperidin-3-yl)-L-leucine;
N-[(1-{[2,4-dihydroxy-5-(propan-2-yl)phenyl]carbonyl}piperidin-4-yl)methyl]-L-leucine;
N-[2-(1-{[2,4-dihydroxy-5-(propan-2-yl)phenyl]carbonyl}piperidin-4-yl)ethyl]-L-leucine;
N-(1-{[2,4-dihydroxy-5-(propan-2-yl)phenyl]carbonyl}piperidin-4-yl)-L-norleucine;
N-[(1-{[2,4-dihydroxy-5-(propan-2-yl)phenyl]carbonyl}piperidin-4-yl)methyl]-L-alanine;
N-[(1-{[2,4-dihydroxy-5-(propan-2-yl)phenyl]carbonyl}piperidin-4-yl)methyl]-L-phenylalanine;
N-[(1-{[2,4-dihydroxy-5-(propan-2-yl)phenyl]carbonyl}piperidin-4-yl)methyl]-D-leucine;
N-(1-{[2,4-dihydroxy-5-(propan-2-yl)phenyl]carbonyl}piperidin-4-yl)-D-leucine;
3-cyclohexyl-N-(1-{[2,4-dihydroxy-5-(propan-2-yl)phenyl]carbonyl}piperidin-4-yl)-L-alanine;
N-[2-(1-{[2,4-dihydroxy-5-(propan-2-yl)phenyl]carbonyl}piperidin-4-yl)ethyl]-L-phenylalanine;
N-[(1-{[2,4-dihydroxy-5-(propan-2-yl)phenyl]carbonyl}piperidin-4-yl)methyl]-L-valine;
(2S)-cyclohexyl[(1-{[2,4-dihydroxy-5-(propan-2-yl)phenyl]carbonyl}piperidin-4-yl)amino]ethanoic acid;
N-[2-(1-{[2,4-dihydroxy-5-(propan-2-yl)phenyl]carbonyl}piperidin-4-yl)ethyl]-2-methylalanine;
O-tert-butyl-N-[2-(1-{[2,4-dihydroxy-5-(propan-2-yl)phenyl]carbonyl}piperidin-4-yl)ethyl]-L-serine;

(2S)-cyclohexyl{[(1-{[2,4-dihydroxy-5-(propan-2-yl)phenyl]carbonyl}piperidin-4-yl)methyl]amino}ethanoic acid;

N-[(1-{[2,4-dihydroxy-5-(propan-2-yl)phenyl]carbonyl}piperidin-4-yl)methyl]-2-methylalanine;

N-[(1-{[2,4-dihydroxy-5-(propan-2-yl)phenyl]carbonyl}piperidin-4-yl)methyl]-L-serine;

O-tert-butyl-N-[(1-{[2,4-dihydroxy-5-(propan-2-yl)phenyl]carbonyl}piperidin-4-yl)methyl]-L-serine;

(2S)-{[(1-{[2,4-dihydroxy-5-(propan-2-yl)phenyl]carbonyl}piperidin-4-yl)methyl]amino}(phenyl)ethanoic acid;

N-[2-(1-{[2,4-dihydroxy-5-(propan-2-yl)phenyl]carbonyl}piperidin-4-yl)ethyl]-L-valine;

O-tert-butyl-N-(1-{[2,4-dihydroxy-5-(propan-2-yl)phenyl]carbonyl}piperidin-4-yl)-L-serine;

(2S)-cyclohexyl{[2-(1-{[2,4-dihydroxy-5-(propan-2-yl)phenyl]carbonyl}piperidin-4-yl)ethyl]amino}ethanoic acid;

(2S)-{[2-(1-{[2,4-dihydroxy-5-(propan-2-yl)phenyl]carbonyl}piperidin-4-yl)ethyl]amino}(phenyl)ethanoic acid;

N-(1-{[2,4-dihydroxy-5-(propan-2-yl)phenyl]carbonyl}piperidin-4-yl)-L-serine;

cyclopentyl N-{3-[(1-{[2,4-dihydroxy-5-(propan-2-yl)phenyl]carbonyl}piperidin-4-yl)amino]propyl}-L-leucinate; and N-{3-[(1-{[2,4-dihydroxy-5-(propan-2-yl)phenyl]carbonyl}piperidin-4-yl)amino]propyl}-L-leucine.

9. A pharmaceutical composition which comprises a compound as defined in claim 1 and a pharmaceutically acceptable carrier or diluent.

* * * * *